US007923236B2

(12) United States Patent
Gusakov et al.

(10) Patent No.: US 7,923,236 B2
(45) Date of Patent: Apr. 12, 2011

(54) FUNGAL ENZYMES

(75) Inventors: Alexander Vasilievich Gusakov, Moscow (RU); Peter J. Punt, Houten (NL); Jan Cornelis Verdoes, Bennekom (NL); Jacoba Van der Meij, legal representative, Bennekom (NL); Arkady Panteleimonovich Sinitsyn, Moscow (RU); Elena Vlasenko, Davis, CA (US); Sandra Wihelmina Agnes Hinz, Wageningen (NL); Mark Gosink, Wellington, FL (US); Zhijie Jiang, West Palm Beach, FL (US)

(73) Assignee: Dyadic International (USA), Inc., Jupiter, FL (US)

(*) Notice: Subject to any disclaimer, the term of this patent is extended or adjusted under 35 U.S.C. 154(b) by 519 days.

(21) Appl. No.: 11/833,133

(22) Filed: Aug. 2, 2007

(65) Prior Publication Data
US 2009/0280105 A1 Nov. 12, 2009

(51) Int. Cl.
*C12N 9/42* (2006.01)
*C12N 1/20* (2006.01)
*C12N 1/00* (2006.01)
*C12N 15/00* (2006.01)
*C12P 21/06* (2006.01)
*C12P 19/00* (2006.01)
*C12P 13/00* (2006.01)
*C12P 7/26* (2006.01)
*C12P 7/06* (2006.01)
*C12P 7/08* (2006.01)
*C07K 14/00* (2006.01)
*C07H 21/04* (2006.01)

(52) U.S. Cl. ............... 435/209; 435/252.3; 435/254.11; 435/254.5; 435/254.6; 435/320.1; 435/69.1; 435/72; 435/128; 435/148; 435/161; 435/163; 162/174; 162/72; 8/107; 8/159; 8/636; 510/392; 530/350; 536/23.2

(58) Field of Classification Search .................. 435/209, 435/252.3, 254.11, 254.5, 254.6, 320.1, 69.1, 435/72, 128, 148, 161, 163; 536/23.2; 530/350; 510/392; 162/174, 72; 8/107, 159, 636
See application file for complete search history.

(56) References Cited

U.S. PATENT DOCUMENTS

| | | | |
|---|---|---|---|
| 2,974,001 | A | 5/1957 | Carter |
| 4,435,307 | A | 3/1984 | Barbesgaard et al. |
| 4,443,355 | A | 4/1984 | Murata et al. |
| 4,661,289 | A | 4/1987 | Parslow et al. |
| 5,120,463 | A | 6/1992 | Bjork et al. |
| 6,015,707 | A | 1/2000 | Emalfarb et al. |
| 6,573,086 | B1 | 6/2003 | Emalfrab et al. |
| 7,244,605 | B2 * | 7/2007 | Harris et al. .................. 435/201 |
| 2003/0157595 | A1 | 8/2003 | Emalfarb et al. |
| 2004/0002136 | A1 | 1/2004 | Emalfarb et al. |
| 2005/0214920 | A1 * | 9/2005 | Harris et al. .................. 435/209 |
| 2006/0053514 | A1 | 3/2006 | Wu et al. |
| 2006/0134747 | A1 | 6/2006 | Baldwin et al. |
| 2006/0218671 | A1 | 9/2006 | Brown et al. |
| 2007/0077630 | A1 | 4/2007 | Harris et al. |
| 2007/0238155 | A1 * | 10/2007 | Gusakov et al. .............. 435/101 |

FOREIGN PATENT DOCUMENTS

| GB | 2094826 | 9/1982 |
|---|---|---|
| JP | 50-132269 | 10/1975 |

OTHER PUBLICATIONS

Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Bajpai et al., "Deinking with enzymes: a review." TAPPI Journal. 1998. 81(12), 111-117.
Barnett et al., "Cloning and amplification of the gene encoding an extracellular B-glucosidase from *Trichoderma reesei*: Evidence for improved rates of saccharification of cellulosic substrates", Biotechnol., 9:562 (1991).
Bauer et al., "Development and application of a suite of polysacchardie-degrading enzymes for analyzing plant cell walls", Proc. Natl. Acad. Sci. U.S.A. 103:11417 (2006).
Beldman et al., "The cellulase of *Trichoderma viride*: Purification, characterization and comparison of all detectable endoglucanases, exoglucanases and B-glucosidases," 1985, Eur. J. Biochem. 146, 301-308.
Bhatawadekar, "Studies on Optimum conditions of Enzymatic desizing of LTKP sized fabric by cellulase—steeping and cellulase-padding methods," (May 1983) Journal of the Textile Association, pp. 83-86.
Blum et al., "Enzymic Degradation Of Cellulose Fibers;" Reports of the Shizuoka Prefectural Hamamatsu Textile Industrial Research Institute No. 24 (1985) Textile Research Journal, vol. 22, No. 3, 178-192 (1952).
Crepin et al., "Functional classification of the microbial feruloyl esterases," 2004, Appl. Microbiol. Biotechnol. 63, 647-652.
De Vries et al., "The *Aspergillus niger* faeB gene encodes a second feruloyl esterase involved in pectin and xyland degradation and is specifically induced in the presence of aromatic compounds," 2002, Biochem J. 363, 377-386.

(Continued)

*Primary Examiner* — Ganapathirama Raghu
(74) *Attorney, Agent, or Firm* — McDermott, Will & Emery; Nicole R. Sullivan; Michael J. Keller

(57) ABSTRACT

This invention relates to enzymes and methods for producing the same. More specifically this invention relates to a variety of fungal enzymes. Nucleic acid molecules encoding such enzymes, compositions, recombinant and genetically modified host cells, and methods of use are described. The invention also relates to a method to convert lignocellulosic biomass to fermentable sugars with enzymes that degrade the lignocellulosic material and novel combinations of enzymes, including those that provide a synergistic release of sugars from plant biomass. The invention also relates to methods to use the novel enzymes and compositions of such enzymes in a variety of other processes, including washing of clothing, detergent processes, deinking and biobleaching of paper and pulp, and treatment of waste streams.

58 Claims, 26 Drawing Sheets

OTHER PUBLICATIONS

Egana et al., "Purification and Characterization of two acetyl xylan esterases from *Penicillium purpurogenum*," Biotechnol. Appl. Biochem. 24(1):33 (1996) abstract only.

Faulds et al., "Release of ferulic acid from wheat bran by a ferulic acid esterase (Fae-III) frin *Asoergillus niger*," 1995, J. Appl. Microbiol. Biotechnol. 43, 1082-1087.

Flipphi et al., "Molecular cloning, expression and structure of the endo-1,5-a-L-arabinase gene of *Aspergillus niger*," Appl. Microbiol. Biotechnol. 40:318 (1993).

Foreman et al., "Transcriptional Regulation of Biomass-degrading Enzymes in the Filamentous Fungus *Trichoderma reesei*," 2003, J. Biol. Chem. 278, 31988-31997.

Galante et al., "Enzyme applications in detergency and in manufacturing industries." Current Organic Chemistry. 2003, 7, 1399-1422.

Gordillo et al., "*Penicillium purpurogenum* produces a family 1 acetyl xylan esterase containing a carbohydrate-binding module: characterization of the protein and its gene," Mycol. Res. 110:1129 (2006).

Gusakov et al., "Design of highly efficient cellulase mixtures for enzymatic hydrolysis of cellulose," Biotechnol. Bioeng. vol. 97, No. 5, 2007, pp. 1028-1038.

Gusakov, "Microassays to control the results of cellulase treatment of denim fabrics," Textile Chemist and Colorist and American Dyestuff Reporter, (2000), V.32, N. 5, p. 42.

Hahn-Hagerdal et al., "Bio-ethanol—the fuel of tomorrow from the residues of today." Trends in Biotechnology. 2006, 24 (12), 549-556.

Helmut Uhlig. Industrial enzymes and their applications. Translated and updated by Elfriede M. Linsmaier-Bednar. John Wiley & Sons, Inc 1998, p. 454 (in particular, chapters 5.1, 5.2, 5.3, 5.4, 5.5, 5.6, 5.7, 5.9, 5.10, 5.11, and 5.13).

Himmel et al., "Cellulase for commodity products from cellulosic biomass." Current Opinion in Biotechnology. 1999, 10, 358-364.

Kormelink et al., "Degradation of different [(glucurono)arabino]xylans by a combination of purified xylan-degrading enzymes," 1993d, Appl. Micr. Biotechnol. 38, 688-695.

Kormelink et al., "Purification and Characterization of an acetyl xylan esterase from *Aspergillus niger*," 1993c, J. Biotechnol. 27, 267-282.

Kormelink et al., "Purification and characterization of three endo-(1,4)-B-xylanases and one B-xylosidase from *Aspergillus awamori*," 1993b, J. Biotechnol. 27:249-265.

Kramer et al., "Insect Chitinases: Molecular Biology and Potential Use as Biopesticides," Insect Biochem Mol Biol. 27:887 (1997).

Leisola et al., "Determination of the Solubilizing Activity of a Cellulase Complex with Dyed Substrates," (1976) Analytical Biochemistry, v. 70, p. 592.

Margolles-Clark et al., "Acetyle xylan esterase from *Trichoderma reesei* contains active-site serine residue and a cellulose-binding domain," Eur. J. Biochem. 237:553 (1996).

Martinez, D. et al., "Genome sequencing and analysis of the biomass-degrading fungus *Trichoderma reesei* (syn. *Hypocrea jecorina*)," 2008 Nature Biotechnol. 26, 553-560.

Mielenz, "Ethanol production from biomass: technology and commercialization status." Current Opinion in Microbiology. 2001, 4, 324-329.

Poutanen et al., "Deacetylation of xylans by acetyl esterases of *Trichoderma reesei*," 1990, J. Appl. Microbiol. Biotechnol. 33, 506-510.

Ralet et al., "Degradation of feruloylated oligosaccharides from sugar-beet pulp and wheat bran by ferulic acid esterases from *Aspergillus niger*," 1994, Carbohydr. Res. 257-269.

Reese et al., "Chitin induces accummulation in tissue of innate immune cells associated with allergy," Nature 447:92 (2007).

Roller et al., "Biotechnology in the production and modification of biopolymers for foods." Critical Reviews in Biotechnology. 1992, 12(3), 261-277.

Sheehan et al., "Energy, and the environment: a strategic perspective on the U.S. Department of Energy's Research and Development Activities for Bioethanol." Biotechnology Progress. 1999, 15, 817-827.

Sorensen et al., "Efficiencies of designed enzyme combinations in releasing arabinose and xylose from wheat arabinoxylari in an industrial ethanol fermentation residue," 2005, Enzyme Microb. Technol. 36, 773-784.

Sorensen et al., "Enzymatic Hydrolysis of Wheat Arabinoxylan by a recombinant "Minimal" Enzyme cocktail containing B-Xylosidase and novel endo-1,4-B-Xylanase and a-L-Arabinofuranosidase activities," 2007, Biotechnol. Progr. 23, 100-107.

Tenkanen 1998, "Action of *Trichoderma reesei* and *Aspergillus oryzae* esterases in the deacetylation of hemicelluloses," Biotechnol. Appl. Biochem. 27, 19-24 (abstract only).

Tsujibo et al., "Cloning and Expression of an a-L-arabinofuranosidase gene (stxlV) from *Streptomyces thermoviolaceus* OPC-520, and characterization of the enzyme," Biosci. Biotechnol. Biochem. 66:434 (2002).

Viikari et al., Use of cellulases in pulp and paper applications. In: "Carbohydrates from *Trichoderma reesei* and other microorganisms. Structure, Biochemistry, Genetics and Applications." Editors: Mark Claessens, Wim Nerinckx, and Kathleen Piens. The Royal Society of Chemistry 1998, 245-254.

Yano et al., "Cloning and Expression of an a-1,3-Glucanase Gene from Bacillus circulans KA-304: The Enzyme Participates in Protoplast Formation of Schizophyllum commune," Biosci Biotechnol Biochem. 70:1754 (2006).

International Search Report for International (PCT) Application No. PCT/US08/71982, mailed Mar. 5, 2009.

Written Opinion for International (PCT) Application No. PCT/US08/71982, mailed Mar. 5, 2009.

Birren et al., Database UniProt:Q2GZ45, XP002594851, Mar. 21, 2006, Nucleotide Sequence, "Annotation of the *Chaetomium globosum* CBS 148.51 genome," (1 page).

* cited by examiner

SEQUENCE LISTING

```
<160> NUMBER OF SEQ ID NOS: 94

<210> SEQ ID NO 1
<211> LENGTH: 1836
<212> TYPE: DNA
<213> ORGANISM: Chrysosporium lucknowense
<220> FEATURE:
<221> NAME/KEY: CDS
<222> LOCATION: (98)..(506)
<220> FEATURE:
<221> NAME/KEY: CDS
<222> LOCATION: (574)..(1742)

<400> SEQUENCE: 1
atataaattg ggtgattccc agctcttgat gggcgtgtct tctgcctggc agccctcgtc      60
ttcagatcaa gcaactgtgt gctgatcctc ttccgcc atg tac gcc aag ttc gcg     115
                                          Met Tyr Ala Lys Phe Ala
                                           1               5 acc ctc gcc gcc ctt gtg gct ggc gcc gct gct cag aac gcc tgc act     163
Thr Leu Ala Ala Leu Val Ala Gly Ala Ala Ala Gln Asn Ala Cys Thr
             10                  15                  20 ctg acc gct gag aac cac ccc tcg ctg acg tgg tcc aag tgc acg tct     211
Leu Thr Ala Glu Asn His Pro Ser Leu Thr Trp Ser Lys Cys Thr Ser
         25                  30                  35 ggc ggc agc tgc acc agc gtc cag ggt tcc atc acc atc gac gcc aac     259
Gly Gly Ser Cys Thr Ser Val Gln Gly Ser Ile Thr Ile Asp Ala Asn
     40                  45                  50
```

-continued

| | |
|---|---|
| tgg cgg tgg act cac cgg acc gat agc gcc acc aac tgc tac gag ggc<br>Trp Arg Trp Thr His Arg Thr Asp Ser Ala Thr Asn Cys Tyr Glu Gly<br>55                  60                65                70 | 307 |
| aac aag tgg gat act tcg tac tgc agc gat ggt cct tct tgc gcc tcc<br>Asn Lys Trp Asp Thr Ser Tyr Cys Ser Asp Gly Pro Ser Cys Ala Ser<br>                75                80                85 | 355 |
| aag tgc tgc atc gac ggc gct gac tac tcg agc acc tat ggc atc acc<br>Lys Cys Cys Ile Asp Gly Ala Asp Tyr Ser Ser Thr Tyr Gly Ile Thr<br>                90                95                100 | 403 |
| acg agc ggt aac tcc ctg aac ctc aag ttc gtc acc aag ggc cag tac<br>Thr Ser Gly Asn Ser Leu Asn Leu Lys Phe Val Thr Lys Gly Gln Tyr<br>            105              110              115 | 451 |
| tcg acc aac atc ggc tcg cgt acc tac ctg atg gag agc gac acc aag<br>Ser Thr Asn Ile Gly Ser Arg Thr Tyr Leu Met Glu Ser Asp Thr Lys<br>120                125              130 | 499 |
| tac cag a gtaagttcct ctcgcacccg ccgccggga gatgatggcg cccagcccgc<br>Tyr Gln<br>135 | 556 |
| tgacgcgaat gacacag tg  ttc cag ctc ctc ggc aac gag ttc acc ttc<br>                                  Met Phe Gln Leu Leu Gly Asn Glu Phe Thr Phe<br>                                          140                  145 | 605 |
| gat gtc gac gtc tcc aac ctc ggc tgc ggc ctc aat ggc gcc ctc tac<br>Asp Val Asp Val Ser Asn Leu Gly Cys Gly Leu Asn Gly Ala Leu Tyr<br>            150              155              160 | 653 |
| ttc gtg tcc atg gat gcc gat ggt ggc atg tcc aag tac tcg ggc aac<br>Phe Val Ser Met Asp Ala Asp Gly Gly Met Ser Lys Tyr Ser Gly Asn<br>165                170              175 | 701 |
| aag gca ggt gcc aag tac ggt acc ggc tac tgt gat tct cag tgc ccc<br>Lys Ala Gly Ala Lys Tyr Gly Thr Gly Tyr Cys Asp Ser Gln Cys Pro<br>180                185              190              195 | 749 |
| cgc gac ctc aag ttc atc aac ggc gag gcc aac gta gag aac tgg cag<br>Arg Asp Leu Lys Phe Ile Asn Gly Glu Ala Asn Val Glu Asn Trp Gln<br>            200              205              210 | 797 |
| agc tcg acc aac gat gcc aac gcc ggc acg ggc aag tac ggc agc tgc<br>Ser Ser Thr Asn Asp Ala Asn Ala Gly Thr Gly Lys Tyr Gly Ser Cys<br>                215              220              225 | 845 |
| tgc tcc gag atg gac gtc tgg gag gcc aac aac atg gcc gcc gcc ttc<br>Cys Ser Glu Met Asp Val Trp Glu Ala Asn Asn Met Ala Ala Ala Phe<br>            230              235              240 | 893 |
| act ccc cac cct tgc acc gtg atc ggc cag tcg cgc tgc gag ggc gac<br>Thr Pro His Pro Cys Thr Val Ile Gly Gln Ser Arg Cys Glu Gly Asp<br>245                250              255 | 941 |
| tcg tgc ggc ggt acc tac agc acc gac cgc tat gcc ggc atc tgc gac<br>Ser Cys Gly Gly Thr Tyr Ser Thr Asp Arg Tyr Ala Gly Ile Cys Asp<br>260                265              270              275 | 989 |
| ccc gac gga tgc gac ttc aac tcg tac cgc cag ggc aac aag acc ttc<br>Pro Asp Gly Cys Asp Phe Asn Ser Tyr Arg Gln Gly Asn Lys Thr Phe<br>                280              285              290 | 1037 |
| tac ggc aag ggc atg acg gtc gac acg acc aag aag atc acg gtc gtc<br>Tyr Gly Lys Gly Met Thr Val Asp Thr Thr Lys Lys Ile Thr Val Val<br>            295              300              305 | 1085 |
| acc cag ttc ctc aag aac tcg gcc ggc gag ctc tcc gag atc aag cgg<br>Thr Gln Phe Leu Lys Asn Ser Ala Gly Glu Leu Ser Glu Ile Lys Arg<br>310                315              320 | 1133 |
| ttc tac gtc cag aac ggc aag gtc atc ccc aac tcc gag tcc acc atc<br>Phe Tyr Val Gln Asn Gly Lys Val Ile Pro Asn Ser Glu Ser Thr Ile<br>325                330              335 | 1181 |
| ccg ggc gtc gag ggc aac tcc atc acc cag gac tgg tgc gac cgc cag<br>Pro Gly Val Glu Gly Asn Ser Ile Thr Gln Asp Trp Cys Asp Arg Gln<br>340                345              350              355 | 1229 |

-continued

```
aag gcc gcc ttc ggc gac gtg acc gac ttc cag gac aag ggc ggc atg      1277
Lys Ala Ala Phe Gly Asp Val Thr Asp Phe Gln Asp Lys Gly Gly Met
                360                 365                 370 gtc cag atg ggc aag gcc ctc gcg ggg ccc atg gtc ctc gtc atg tcc      1325
Val Gln Met Gly Lys Ala Leu Ala Gly Pro Met Val Leu Val Met Ser
            375                 380                 385 atc tgg gac gac cac gcc gtc aac atg ctc tgg ctc gac tcc acc tgg      1373
Ile Trp Asp Asp His Ala Val Asn Met Leu Trp Leu Asp Ser Thr Trp
        390                 395                 400 ccc atc gac ggc gcc ggc aag ccg ggc gcc gag cgc ggt gcc tgc ccc      1421
Pro Ile Asp Gly Ala Gly Lys Pro Gly Ala Glu Arg Gly Ala Cys Pro
    405                 410                 415 acc acc tcg ggc gtc ccc gct gag gtc gag gcc gag gcc ccc aac tcc      1469
Thr Thr Ser Gly Val Pro Ala Glu Val Glu Ala Glu Ala Pro Asn Ser
420                 425                 430                 435 aac gtc atc ttc tcc aac atc cgc ttc ggc ccc atc ggc tcc acc gtc      1517
Asn Val Ile Phe Ser Asn Ile Arg Phe Gly Pro Ile Gly Ser Thr Val
                440                 445                 450 tcc ggc ctg ccc gac ggc ggc agc ggc aac ccc aac ccg ccc gtc agc      1565
Ser Gly Leu Pro Asp Gly Gly Ser Gly Asn Pro Asn Pro Pro Val Ser
            455                 460                 465 tcg tcc acc ccg gtc ccc tcc tcg tcc acc aca tcc tcc ggt tcc tcc      1613
Ser Ser Thr Pro Val Pro Ser Ser Ser Thr Thr Ser Ser Gly Ser Ser
        470                 475                 480 ggc ccg act ggc ggc acg ggt gtc gct aag cac tat gag caa tgc gga      1661
Gly Pro Thr Gly Gly Thr Gly Val Ala Lys His Tyr Glu Gln Cys Gly
    485                 490                 495 gga atc ggg ttc act ggc cct acc cag tgc gag agc ccc tac act tgc      1709
Gly Ile Gly Phe Thr Gly Pro Thr Gln Cys Glu Ser Pro Tyr Thr Cys
500                 505                 510                 515 acc aaa ctg aat gac tgg tac tcg cag tgc ctg taaacgaacc tctctgaagg   1762
Thr Lys Leu Asn Asp Trp Tyr Ser Gln Cys Leu
                520                 525 aggttctgag acacgcgcga ttcttctgta tatagtttta tttttcactc tggagtgctt   1822
cgctccacca gtac                                                       1836

<210> SEQ ID NO 2
<211> LENGTH: 526
<212> TYPE: PRT
<213> ORGANISM: Chrysosporium lucknowense

<400> SEQUENCE: 2

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125
```

Met Glu Ser Asp Thr Lys Tyr Gln Met Phe Gln Leu Leu Gly Asn Glu
130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
                180                 185                 190

Gln Cys Pro Arg Asp Leu Lys Phe Ile Asn Gly Glu Ala Asn Val Glu
            195                 200                 205

Asn Trp Gln Ser Ser Thr Asn Asp Ala Asn Ala Gly Thr Gly Lys Tyr
210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
                260                 265                 270

Ile Cys Asp Pro Asp Gly Cys Asp Phe Asn Ser Tyr Arg Gln Gly Asn
            275                 280                 285

Lys Thr Phe Tyr Gly Lys Gly Met Thr Val Asp Thr Thr Lys Lys Ile
290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
                340                 345                 350

Asp Arg Gln Lys Ala Ala Phe Gly Asp Val Thr Asp Phe Gln Asp Lys
            355                 360                 365

Gly Gly Met Val Gln Met Gly Lys Ala Leu Ala Gly Pro Met Val Leu
370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
                420                 425                 430

Pro Asn Ser Asn Val Ile Phe Ser Asn Ile Arg Phe Gly Pro Ile Gly
            435                 440                 445

Ser Thr Val Ser Gly Leu Pro Asp Gly Gly Ser Gly Asn Pro Asn Pro
450                 455                 460

Pro Val Ser Ser Ser Thr Pro Val Pro Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
                515                 520                 525

<210> SEQ ID NO 3
<211> LENGTH: 1578
<212> TYPE: DNA
<213> ORGANISM: Chrysosporium lucknowense

<400> SEQUENCE: 3
atgtacgcca agttcgcgac cctcgccgcc cttgtggctg gcgccgctgc tcagaacgcc 60
tgcactctga ccgctgagaa ccacccctcg ctgacgtggt ccaagtgcac gtctggcggc 120
agctgcacca gcgtccaggg ttccatcacc atcgacgcca actggcggtg gactcaccgg 180
accgatagcg ccaccaactg ctacgagggc aacaagtggg atacttcgta ctgcagcgat 240
ggtccttctt gcgcctccaa gtgctgcatc gacggcgctg actactcgag cacctatggc 300
atcaccacga gcggtaactc cctgaacctc aagttcgtca ccaagggcca gtactcgacc 360
aacatcggct cgcgtaccta cctgatggag agcgacacca agtaccagat gttccagctc 420
ctcggcaacg agttcacctt cgatgtcgac gtctccaacc tcggctgcgg cctcaatggc 480
gccctctact tcgtgtccat ggatgccgat ggtggcatgt ccaagtactc gggcaacaag 540
gcaggtgcca agtacggtac cggctactgt gattctcagt gcccccgcga cctcaagttc 600
atcaacggcg aggccaacgt agagaactgg cagagctcga ccaacgatgc caacgccggc 660
acgggcaagt acggcagctg ctgctccgag atggacgtct gggaggccaa caacatggcc 720
gccgccttca ctccccaccc ttgcaccgtg atcggccagt cgcgctgcga gggcgactcg 780
tgcggcggta cctacagcac cgaccgctat gccggcatct gcgaccccga cggatgcgac 840
ttcaactcgt accgccaggg caacaagacc ttctacggca agggcatgac ggtcgacacg 900
accaagaaga tcacggtcgt cacccagttc ctcaagaact cggccggcga gctctccgag 960
atcaagcggt tctacgtcca gaacggcaag gtcatcccca actccgagtc caccatcccg 1020
ggcgtcgagg gcaactccat cacccaggac tggtgcgacc gccagaaggc cgccttcggc 1080
gacgtgaccg acttccagga caagggcggc atggtccaga tgggcaaggc cctcgcgggg 1140
cccatggtcc tcgtcatgtc catctgggac gaccacgccg tcaacatgct ctggctcgac 1200
tccacctggc ccatcgacgg cgccggcaag ccgggcgccg agcgcggtgc ctgccccacc 1260
acctcgggcg tccccgctga ggtcgaggcc gaggccccca actccaacgt catcttctcc 1320
aacatccgct tcggccccat cggctccacc gtctccggcc tgcccgacgg cggcagcggc 1380
aaccccaacc cgcccgtcag ctcgtccacc ccggtcccct cctcgtccac cacatcctcc 1440
ggttcctccg gcccgactgg cggcacgggt gtcgctaagc actatgagca atgcggagga 1500
atcgggttca ctggccctac ccagtgcgag agcccctaca cttgcaccaa actgaatgac 1560
tggtactcgc agtgcctg 1578

<210> SEQ ID NO 4
<211> LENGTH: 2029
<212> TYPE: DNA
<213> ORGANISM: Chrysosporium lucknowense
<220> FEATURE:
<221> NAME/KEY: CDS
<222> LOCATION: (108)..(674)
<220> FEATURE:
<221> NAME/KEY: CDS
<222> LOCATION: (762)..(898)
<220> FEATURE:
<221> NAME/KEY: CDS
<222> LOCATION: (974)..(1186)
<220> FEATURE:
<221> NAME/KEY: CDS
<222> LOCATION: (1284)..(1530)
<220> FEATURE:
<221> NAME/KEY: CDS
<222> LOCATION: (1638)..(1768)
<220> FEATURE:
<221> NAME/KEY: CDS
<222> LOCATION: (1836)..(1890)

<400> SEQUENCE: 4

```
atataaaaag gcaaatgagg cggcgccttg gacaggtcca ttctcccacc gctcaaccag       60
cctccaattc ctcagaagtc tgttgctctc tcgcagtcgc agtcaag atg aag cag       116
                                                    Met Lys Gln
                                                      1 tac ctc cag tac ctc gcg gcg acc ctg ccc ctg gtg ggc ctg gcc acg       164
Tyr Leu Gln Tyr Leu Ala Ala Thr Leu Pro Leu Val Gly Leu Ala Thr
  5                  10                  15 gcc cag cag gcg ggt aac ctg cag acc gag act cac ccc aag ctc act       212
Ala Gln Gln Ala Gly Asn Leu Gln Thr Glu Thr His Pro Lys Leu Thr
 20                  25                  30                  35 tgg tcg aag tgc acg gcc ccg gga tcc tgc caa cag gtc aac ggc gag       260
Trp Ser Lys Cys Thr Ala Pro Gly Ser Cys Gln Gln Val Asn Gly Glu
                 40                  45                  50 gtc gtc atc gac tcc aac tgg cgc tgg gtg cac gac gag aac gcg cag       308
Val Val Ile Asp Ser Asn Trp Arg Trp Val His Asp Glu Asn Ala Gln
             55                  60                  65 aac tgc tac gac ggc aac cag tgg acc aac gct tgc agc tct gcc acc       356
Asn Cys Tyr Asp Gly Asn Gln Trp Thr Asn Ala Cys Ser Ser Ala Thr
         70                  75                  80 gac tgc gcc gag aat tgc gcg ctc gag ggt gcc gac tac cag ggc acc       404
Asp Cys Ala Glu Asn Cys Ala Leu Glu Gly Ala Asp Tyr Gln Gly Thr
     85                  90                  95 tat ggc gcc tcg acc agc ggc aat gcc ctg acg ctc acc ttc gtc act       452
Tyr Gly Ala Ser Thr Ser Gly Asn Ala Leu Thr Leu Thr Phe Val Thr
100                 105                 110                 115 aag cac gag tac ggc acc aac att ggt tcg cgc ctc tac ctc atg aac       500
Lys His Glu Tyr Gly Thr Asn Ile Gly Ser Arg Leu Tyr Leu Met Asn
                120                 125                 130 ggc gcg aac aag tac cag atg ttc acc ctc aag ggc aac gag ctg gcc       548
Gly Ala Asn Lys Tyr Gln Met Phe Thr Leu Lys Gly Asn Glu Leu Ala
            135                 140                 145 ttc gac gtc gac ctc tcg gcc gtc gag tgc ggc ctc aac agc gcc ctc       596
Phe Asp Val Asp Leu Ser Ala Val Glu Cys Gly Leu Asn Ser Ala Leu
        150                 155                 160 tac ttc gtg gcc atg gag gag gat ggc ggt gtg tcg agc tac ccg acc       644
Tyr Phe Val Ala Met Glu Glu Asp Gly Gly Val Ser Ser Tyr Pro Thr
    165                 170                 175 aac acg gcc ggt gct aag ttc ggc act ggg gtaagttcaa cgacccgaga          694
Asn Thr Ala Gly Ala Lys Phe Gly Thr Gly
180                 185 cgggtgccct tattatctgc tgcgaaaacg gacggtcccc ttttgctaac taccctcctc      754 caaacag tac tgc gac gcc caa tgc gca cgc gac ctc aag ttc gtc ggc       803
        Tyr Cys Asp Ala Gln Cys Ala Arg Asp Leu Lys Phe Val Gly
            190                 195                 200 ggc aag ggc aac atc gag ggc tgg aag ccg tcc acc aac gat gcc aat       851
Gly Lys Gly Asn Ile Glu Gly Trp Lys Pro Ser Thr Asn Asp Ala Asn
        205                 210                 215 gcc ggt gtc ggt cct tat ggc ggg tgc tgc gct gag atc gac gtc tg        898
Ala Gly Val Gly Pro Tyr Gly Gly Cys Cys Ala Glu Ile Asp Val Trp
    220                 225                 230 gtaagttttg ttgcctgggc agcaatggta tattagctcg agtggttccc gtcgttgctg      958
accctctctt accag g gag tcg aac aag tat gct ttc gct ttc acc ccg       1007
              Glu Ser Asn Lys Tyr Ala Phe Ala Phe Thr Pro
                                240                 245 cac ggt tgc gag aac cct aaa tac cac gtc tgc gag acc acc aac tgc      1055
His Gly Cys Glu Asn Pro Lys Tyr His Val Cys Glu Thr Thr Asn Cys
            250                 255                 260
```

```
ggt ggc acc tac tcc gag gac cgc ttc gct ggt gac tgc gat gcc aac    1103
Gly Gly Thr Tyr Ser Glu Asp Arg Phe Ala Gly Asp Cys Asp Ala Asn
        265                 270                 275 ggc tgc gac tac aac ccc tac cgc atg ggc aac cag gac ttc tac ggt    1151
Gly Cys Asp Tyr Asn Pro Tyr Arg Met Gly Asn Gln Asp Phe Tyr Gly
    280                 285                 290 ccc ggc ttg acg gtc gat acc agc aag aag ttc ac  gtgagtacac         1196
Pro Gly Leu Thr Val Asp Thr Ser Lys Lys Phe Thr
295                 300                 305 cgtgcttgaa gcccctccc ccccccccc caaaaaaaaa aagaaaaaag aagtcaaatg    1256
attgatgcta accaaatcaa ataacag c gtc gtc agc cag ttc gag gag aac    1308
                               Val Val Ser Gln Phe Glu Glu Asn
                                               310 aag ctc acc cag ttc ttc gtc cag gac ggc aag aag att gag atc ccc    1356
Lys Leu Thr Gln Phe Phe Val Gln Asp Gly Lys Lys Ile Glu Ile Pro
315                 320                 325                 330 ggc ccc aag gtc gag ggc atc gat gcg gac agc gcc gct atc acc cct    1404
Gly Pro Lys Val Glu Gly Ile Asp Ala Asp Ser Ala Ala Ile Thr Pro
                335                 340                 345 gag ctg tgc agt gcc ctg ttc aag gcc ttc gat gac cgt gac cgc ttc    1452
Glu Leu Cys Ser Ala Leu Phe Lys Ala Phe Asp Asp Arg Asp Arg Phe
            350                 355                 360 tcg gag gtt ggc ggc ttc gat gcc atc aac acg gcc ctc agc act ccc    1500
Ser Glu Val Gly Gly Phe Asp Ala Ile Asn Thr Ala Leu Ser Thr Pro
        365                 370                 375 atg gtc ctc gtc atg tcc atc tgg gat gat gtacgttacc taaccccccc     1550
Met Val Leu Val Met Ser Ile Trp Asp Asp
    380                 385 ccctttttt tttcccgctt ctctcccga aactgccact acttatatac gtcccgcgtc    1610
catgatgctt accttttctc cttccag cac tac gcc aat atg ctc tgg ctc gac 1664
                               His Tyr Ala Asn Met Leu Trp Leu Asp
                                                390                 395 tcg agc tac ccc cct gag aag gct ggc cag cct ggc ggt gac cgt ggc    1712
Ser Ser Tyr Pro Pro Glu Lys Ala Gly Gln Pro Gly Gly Asp Arg Gly
            400                 405                 410 ccg tgt cct cag gac tct ggc gtc ccg gcc gac gtt gag gct cag tac    1760
Pro Cys Pro Gln Asp Ser Gly Val Pro Ala Asp Val Glu Ala Gln Tyr
        415                 420                 425 cct aat gc  gtgagtcgaa accgtaaaat gtcgggcaaa aaaaagatcg             1808
Pro Asn Ala
430 ctcaagctaa cgaaataata tgattag c aag gtc atc tgg tcc aac atc cgc    1860
                                 Lys Val Ile Trp Ser Asn Ile Arg
                                                 435                 440 ttc ggc ccc atc ggc tcg act gtc aac gtc taaactgcaa cctgaccggg      1910
Phe Gly Pro Ile Gly Ser Thr Val Asn Val
                445                 450 ccctttctct ccaccccac ccctctcaag ttctctctgg tggagccctc gtgtccttct   1970
tttcctaggt tcgcgaacct ttgagcttgt gtatcgtagg gtcattgtgt acatacaca   2029

<210> SEQ ID NO 5
<211> LENGTH: 450
<212> TYPE: PRT
<213> ORGANISM: Chrysosporium lucknowense

<400> SEQUENCE: 5

Met Lys Gln Tyr Leu Gln Tyr Leu Ala Ala Thr Leu Pro Leu Val Gly
1               5                   10                  15
```

```
Leu Ala Thr Ala Gln Ala Gly Asn Leu Gln Thr Glu His Pro
            20              25              30

Lys Leu Thr Trp Ser Lys Cys Thr Ala Pro Gly Ser Cys Gln Gln Val
            35              40              45

Asn Gly Glu Val Val Ile Asp Ser Asn Trp Arg Trp Val His Asp Glu
 50              55              60

Asn Ala Gln Asn Cys Tyr Asp Gly Asn Gln Trp Thr Asn Ala Cys Ser
 65              70              75              80

Ser Ala Thr Asp Cys Ala Glu Asn Cys Ala Leu Gly Ala Asp Tyr
            85              90              95

Gln Gly Thr Tyr Gly Ala Ser Thr Ser Gly Asn Ala Leu Thr Leu Thr
            100             105             110

Phe Val Thr Lys His Glu Tyr Gly Thr Asn Ile Gly Ser Arg Leu Tyr
            115             120             125

Leu Met Asn Gly Ala Asn Lys Tyr Gln Met Phe Thr Leu Lys Gly Asn
    130             135             140

Glu Leu Ala Phe Asp Val Asp Leu Ser Ala Val Glu Cys Gly Leu Asn
145             150             155             160

Ser Ala Leu Tyr Phe Val Ala Met Glu Glu Asp Gly Gly Val Ser Ser
            165             170             175

Tyr Pro Thr Asn Thr Ala Gly Ala Lys Phe Gly Thr Gly Tyr Cys Asp
            180             185             190

Ala Gln Cys Ala Arg Asp Leu Lys Phe Val Gly Gly Lys Gly Asn Ile
            195             200             205

Glu Gly Trp Lys Pro Ser Thr Asn Asp Ala Asn Ala Gly Val Gly Pro
210             215             220

Tyr Gly Gly Cys Cys Ala Glu Ile Asp Val Trp Glu Ser Asn Lys Tyr
225             230             235             240

Ala Phe Ala Phe Thr Pro His Gly Cys Glu Asn Pro Lys Tyr His Val
            245             250             255

Cys Glu Thr Thr Asn Cys Gly Gly Thr Tyr Ser Glu Asp Arg Phe Ala
            260             265             270

Gly Asp Cys Asp Ala Asn Gly Cys Asp Tyr Asn Pro Tyr Arg Met Gly
            275             280             285

Asn Gln Asp Phe Tyr Gly Pro Gly Leu Thr Val Asp Thr Ser Lys Lys
    290             295             300

Phe Thr Val Val Ser Gln Phe Glu Glu Asn Lys Leu Thr Gln Phe Phe
305             310             315             320

Val Gln Asp Gly Lys Lys Ile Glu Ile Pro Gly Pro Lys Val Glu Gly
            325             330             335

Ile Asp Ala Asp Ser Ala Ala Ile Thr Pro Glu Leu Cys Ser Ala Leu
            340             345             350

Phe Lys Ala Phe Asp Asp Arg Asp Arg Phe Ser Glu Val Gly Gly Phe
            355             360             365

Asp Ala Ile Asn Thr Ala Leu Ser Thr Pro Met Val Leu Val Met Ser
    370             375             380

Ile Trp Asp Asp His Tyr Ala Asn Met Leu Trp Leu Asp Ser Ser Tyr
385             390             395             400

Pro Pro Glu Lys Ala Gly Gln Pro Gly Gly Asp Arg Gly Pro Cys Pro
            405             410             415

Gln Asp Ser Gly Val Pro Ala Asp Val Glu Ala Gln Tyr Pro Asn Ala
            420             425             430

Lys Val Ile Trp Ser Asn Ile Arg Phe Gly Pro Ile Gly Ser Thr Val
            435             440             445
```

Asn Val
   450

<210> SEQ ID NO 6
<211> LENGTH: 1350
<212> TYPE: DNA
<213> ORGANISM: Chrysosporium lucknowense

<400> SEQUENCE: 6

```
atgaagcagt acctccagta cctcgcggcg accctgcccc tggtgggcct ggccacggcc     60
cagcaggcgg gtaacctgca gaccgagact caccccaagc tcacttggtc gaagtgcacg    120
gccccgggat cctgccaaca ggtcaacggc gaggtcgtca tcgactccaa ctggcgctgg    180
gtgcacgacg agaacgcgca gaactgctac gacggcaacc agtggaccaa cgcttgcagc    240
tctgccaccg actgcgccga gaattgcgcg ctcgagggtg ccgactacca gggcacctat    300
ggcgcctcga ccagcggcaa tgccctgacg ctcaccttcg tcactaagca cgagtacggc    360
accaacattg gttcgcgcct ctacctcatg aacggcgcga acaagtacca gatgttcacc    420
ctcaagggca cgagctggc cttcgacgtc gacctctcgg ccgtcgagtg cggcctcaac    480
agcgccctct acttcgtggc catggaggag gatggcggtg tgtcgagcta cccgaccaac    540
acggccggtg ctaagttcgg cactgggtac tgcgacgccc aatgcgcacg cgacctcaag    600
ttcgtcggcg gcaagggcaa catcgagggc tggaagccgt ccaccaacga tgccaatgcc    660
ggtgtcggtc cttatggcgg tgctgcgct gagatcgacg tctgggagtc gaacaagtat    720
gctttcgctt tcacccccgca cggttgcgag aaccctaaat accacgtctg cgagaccacc    780
aactgcggtg gcacctactc cgaggaccgc ttcgctggtg actgcgatgc caacggctgc    840
gactacaacc cctaccgcat gggcaaccag gacttctacg gtcccggctt gacggtcgat    900
accagcaaga agttcaccgt cgtcagccag ttcgaggaga acaagctcac ccagttcttc    960
gtccaggacg gcaagaagat tgagatcccc ggccccaagg tcgagggcat cgatgcggac   1020
agcgccgcta tcaccctga gctgtgcagt gccctgttca aggccttcga tgaccgtgac   1080
cgcttctcgg aggttggcgg cttcgatgcc atcaacacgg ccctcagcac tcccatggtc   1140
ctcgtcatgt ccatctggga tgatcactac gccaatatgc tctggctcga ctcgagctac   1200
ccccctgaga aggctggcca gcctggcggt gaccgtggcc cgtgtcctca ggactctggc   1260
gtcccggccg acgttgaggc tcagtaccct aatgccaagg tcatctggtc caacatccgc   1320
ttcggcccca tcggctcgac tgtcaacgtc                                   1350
```

<210> SEQ ID NO 7
<211> LENGTH: 1592
<212> TYPE: DNA
<213> ORGANISM: Chrysosporium lucknowense
<220> FEATURE:
<221> NAME/KEY: CDS
<222> LOCATION: (78)..(519)
<220> FEATURE:
<221> NAME/KEY: CDS
<222> LOCATION: (630)..(954)
<220> FEATURE:
<221> NAME/KEY: CDS
<222> LOCATION: (1048)..(1465)

<400> SEQUENCE: 7

```
tgcttgggaa gaaaggatct ctcgaccatg caccacagcc tagctctaac ccagcttgtc     60
gtgtgttgtt gcccagc atg aag ttc gtg cag tcc gcc acc ctg gcg ttc      110
                   Met Lys Phe Val Gln Ser Ala Thr Leu Ala Phe
                    1               5                  10
```

| | | |
|---|---|---|
| gcc gcc acg gcc ctc gct gcg ccc tcg cgc acg act ccc cag aag ccc<br>Ala Ala Thr Ala Leu Ala Ala Pro Ser Arg Thr Thr Pro Gln Lys Pro<br>              15                   20                   25 | 158 |
| cgc cag gcc tcg gcg ggc tgc gcg tcg gcc gtg acg ctc gat gcc agc<br>Arg Gln Ala Ser Ala Gly Cys Ala Ser Ala Val Thr Leu Asp Ala Ser<br>         30                   35                   40 | 206 |
| acc aac gtg ttc cag cag tac acg ctg cac ccc aac aac ttc tac cgt<br>Thr Asn Val Phe Gln Gln Tyr Thr Leu His Pro Asn Asn Phe Tyr Arg<br>45                   50                   55 | 254 |
| gcc gag gtc gag gct gcc gcc gag gcc atc tcc gac tcg gcg ctg gcc<br>Ala Glu Val Glu Ala Ala Ala Glu Ala Ile Ser Asp Ser Ala Leu Ala<br>60                   65                   70                   75 | 302 |
| gag aag gcc cgc aag gtc gcc gac gtc ggt acc ttc ctg tgg ctc gac<br>Glu Lys Ala Arg Lys Val Ala Asp Val Gly Thr Phe Leu Trp Leu Asp<br>         80                   85                   90 | 350 |
| acc atc gag aac att ggc cgg ctg gag ccc gcg ctc gag gac gtg ccc<br>Thr Ile Glu Asn Ile Gly Arg Leu Glu Pro Ala Leu Glu Asp Val Pro<br>              95                  100                 105 | 398 |
| tgc gag aac atc gtg ggt ctc gtc atc tac gac ctc ccg ggc cgt gac<br>Cys Glu Asn Ile Val Gly Leu Val Ile Tyr Asp Leu Pro Gly Arg Asp<br>         110                  115                 120 | 446 |
| tgc gcg gcc aag gcc tcc aac ggc gag ctc aag gtc ggc gag ctc gac<br>Cys Ala Ala Lys Ala Ser Asn Gly Glu Leu Lys Val Gly Glu Leu Asp<br>         125                  130                 135 | 494 |
| agg tac aag acc gag tac atc gac a gtgagttaac cctttgtggc<br>Arg Tyr Lys Thr Glu Tyr Ile Asp<br>140                  145 | 539 |
| cccttctttt cccccgagag agcgtctggt tgagtggggt tgtgagagag aaaatggggc | 599 |
| gagcttaaag actgacgtgt tggctcgcag ag atc gcc gag atc ctc aag gcc<br>                                            Lys Ile Ala Glu Ile Leu Lys Ala<br>                                             150                 155 | 652 |
| cac tcc aac acg gcc ttc gcc ctc gtc atc gag ccc gac tcg ctc ccc<br>His Ser Asn Thr Ala Phe Ala Leu Val Ile Glu Pro Asp Ser Leu Pro<br>                   160                 165                 170 | 700 |
| aac ctg gtc acc aat agc gac ctg cag acg tgc cag cag agc gct tcc<br>Asn Leu Val Thr Asn Ser Asp Leu Gln Thr Cys Gln Gln Ser Ala Ser<br>         175                  180                 185 | 748 |
| ggc tac cgc gag ggt gtc gcc tat gcc ctc aag cag ctc aac ctc ccc<br>Gly Tyr Arg Glu Gly Val Ala Tyr Ala Leu Lys Gln Leu Asn Leu Pro<br>         190                  195                 200 | 796 |
| aac gtg gtc atg tac atc gat gcc ggc cac ggt ggc tgg ctc ggc tgg<br>Asn Val Val Met Tyr Ile Asp Ala Gly His Gly Gly Trp Leu Gly Trp<br>         205                  210                 215 | 844 |
| gac gcc aac ctc aag ccc ggc gcc cag gag ctc gcc agc gtc tac aag<br>Asp Ala Asn Leu Lys Pro Gly Ala Gln Glu Leu Ala Ser Val Tyr Lys<br>220                   225                   230                 235 | 892 |
| tct gct ggt tcg ccc tcg caa gtc cgc ggt atc tcc acc aac gtg gct<br>Ser Ala Gly Ser Pro Ser Gln Val Arg Gly Ile Ser Thr Asn Val Ala<br>         240                  245                 250 | 940 |
| ggt tgg aac gcc tg gtaagacact ctatgtcccc ctcgtcggtc aatggcgagc<br>Gly Trp Asn Ala Trp<br>         255 | 994 |
| ggaatggcgt gaaatgcatg gtgctgacct ttgatctttt cccctccta tag g gac<br>                                                                                                                                             Asp | 1051 |
| cag gag ccc ggt gag ttc tcg gac gcc tcg gat gcc cag tac aac aag<br>Gln Glu Pro Gly Glu Phe Ser Asp Ala Ser Asp Ala Gln Tyr Asn Lys<br>         260                  265                 270 | 1099 |
| tgc cag aac gag aag atc tac atc aac acc ttt ggc gct gag ctc aag<br>Cys Gln Asn Glu Lys Ile Tyr Ile Asn Thr Phe Gly Ala Glu Leu Lys | 1147 |

-continued

```
                275                 280                 285
tct gcc ggc atg ccc aac cac gcc atc atc gac act ggc cgc aac ggt     1195
Ser Ala Gly Met Pro Asn His Ala Ile Ile Asp Thr Gly Arg Asn Gly
290                 295                 300                 305 gtc acc ggt ctc cgc gac gag tgg ggt gac tgg tgc aac gtc aac ggc     1243
Val Thr Gly Leu Arg Asp Glu Trp Gly Asp Trp Cys Asn Val Asn Gly
                310                 315                 320 gcc ggc ttc ggt gtg cgc ccg act gcc aac act ggc gac gag ctc gcc     1291
Ala Gly Phe Gly Val Arg Pro Thr Ala Asn Thr Gly Asp Glu Leu Ala
            325                 330                 335 gac gcc ttc gtg tgg gtc aag ccc ggt ggc gag tcc gac ggc acc agc     1339
Asp Ala Phe Val Trp Val Lys Pro Gly Gly Glu Ser Asp Gly Thr Ser
        340                 345                 350 gac tcg tcg gcg gcg cgc tac gac agc ttc tgc ggc aag ccc gac gcc     1387
Asp Ser Ser Ala Ala Arg Tyr Asp Ser Phe Cys Gly Lys Pro Asp Ala
    355                 360                 365 ttc aag ccc agc ccc gag gcc ggt acc tgg aac cag gcc tac ttc gag     1435
Phe Lys Pro Ser Pro Glu Ala Gly Thr Trp Asn Gln Ala Tyr Phe Glu
370                 375                 380                 385 atg ctc ctc aag aac gcc aac ccg tcc ttc taagctcctc gacggcttct       1485
Met Leu Leu Lys Asn Ala Asn Pro Ser Phe
                390                 395 tgctgtcagt cgctctgacg gtggtgtgct ggtggtgccc ctgctcctgc tgctgctgct  1545
ccgcggggag gggaggcaac gaaaatgaag tcctgcttca aaacaaa                 1592

<210> SEQ ID NO 8
<211> LENGTH: 395
<212> TYPE: PRT
<213> ORGANISM: Chrysosporium lucknowense

<400> SEQUENCE: 8

Met Lys Phe Val Gln Ser Ala Thr Leu Ala Phe Ala Ala Thr Ala Leu
1               5                   10                  15

Ala Ala Pro Ser Arg Thr Thr Pro Gln Lys Pro Arg Gln Ala Ser Ala
                20                  25                  30

Gly Cys Ala Ser Ala Val Thr Leu Asp Ala Ser Thr Asn Val Phe Gln
            35                  40                  45

Gln Tyr Thr Leu His Pro Asn Asn Phe Tyr Arg Ala Glu Val Glu Ala
        50                  55                  60

Ala Ala Glu Ala Ile Ser Asp Ser Ala Leu Ala Glu Lys Ala Arg Lys
65                  70                  75                  80

Val Ala Asp Val Gly Thr Phe Leu Trp Leu Asp Thr Ile Glu Asn Ile
                85                  90                  95

Gly Arg Leu Glu Pro Ala Leu Glu Asp Val Pro Cys Glu Asn Ile Val
            100                 105                 110

Gly Leu Val Ile Tyr Asp Leu Pro Gly Arg Asp Cys Ala Ala Lys Ala
        115                 120                 125

Ser Asn Gly Glu Leu Lys Val Gly Glu Leu Asp Arg Tyr Lys Thr Glu
    130                 135                 140

Tyr Ile Asp Lys Ile Ala Glu Ile Leu Lys Ala His Ser Asn Thr Ala
145                 150                 155                 160

Phe Ala Leu Val Ile Glu Pro Asp Ser Leu Pro Asn Leu Val Thr Asn
                165                 170                 175

Ser Asp Leu Gln Thr Cys Gln Gln Ser Ala Ser Gly Tyr Arg Glu Gly
            180                 185                 190

Val Ala Tyr Ala Leu Lys Gln Leu Asn Leu Pro Asn Val Val Met Tyr
        195                 200                 205
```

```
Ile Asp Ala Gly His Gly Gly Trp Leu Gly Trp Asp Ala Asn Leu Lys
    210                 215                 220
Pro Gly Ala Gln Glu Leu Ala Ser Val Tyr Lys Ser Ala Gly Ser Pro
225                 230                 235                 240
Ser Gln Val Arg Gly Ile Ser Thr Asn Val Ala Gly Trp Asn Ala Trp
                245                 250                 255
Asp Gln Glu Pro Gly Glu Phe Ser Asp Ala Ser Asp Ala Gln Tyr Asn
            260                 265                 270
Lys Cys Gln Asn Glu Lys Ile Tyr Ile Asn Thr Phe Gly Ala Glu Leu
        275                 280                 285
Lys Ser Ala Gly Met Pro Asn His Ala Ile Ile Asp Thr Gly Arg Asn
    290                 295                 300
Gly Val Thr Gly Leu Arg Asp Glu Trp Gly Asp Trp Cys Asn Val Asn
305                 310                 315                 320
Gly Ala Gly Phe Gly Val Arg Pro Thr Ala Asn Thr Gly Asp Glu Leu
                325                 330                 335
Ala Asp Ala Phe Val Trp Val Lys Pro Gly Gly Glu Ser Asp Gly Thr
            340                 345                 350
Ser Asp Ser Ser Ala Ala Arg Tyr Asp Ser Phe Cys Gly Lys Pro Asp
        355                 360                 365
Ala Phe Lys Pro Ser Pro Glu Ala Gly Thr Trp Asn Gln Ala Tyr Phe
    370                 375                 380
Glu Met Leu Leu Lys Asn Ala Asn Pro Ser Phe
385                 390                 395

<210> SEQ ID NO 9
<211> LENGTH: 1185
<212> TYPE: DNA
<213> ORGANISM: Chrysosporium lucknowense

<400> SEQUENCE: 9
atgaagttcg tgcagtccgc caccctggcg ttcgccgcca cggccctcgc tgcgccctcg     60
cgcacgactc cccagaagcc ccgccaggcc tcggcgggct gcgcgtcggc cgtgacgctc    120
gatgccagca ccaacgtgtt ccagcagtac acgctgcacc ccaacaactt ctaccgtgcc    180
gaggtcgagg ctgccgccga ggccatctcc gactcggcgc tggccgagaa ggcccgcaag    240
gtcgccgacg tcggtacctt cctgtggctc gacaccatcg agaacattgg ccggctggag    300
cccgcgctcg aggacgtgcc ctgcgagaac atcgtgggtc tcgtcatcta cgacctcccg    360
ggccgtgact gcgcggccaa ggcctccaac ggcgagctca aggtcggcga gctcgacagg    420
tacaagaccg agtacatcga caagatcgcc gagatcctca aggcccactc caacacggcc    480
ttcgccctcg tcatcgagcc cgactcgctc cccaacctgg tcaccaatag cgacctgcag    540
acgtgccagc agagcgcttc cggctaccgc gagggtgtcg cctatgccct caagcagctc    600
aacctcccca acgtggtcat gtacatcgat gccggccacg gtggctggct cggctgggac    660
gccaacctca agcccggcgc ccaggagctc gccagcgtct acaagtctgc tggttcgccc    720
tcgcaagtcc gcggtatctc caccaacgtg gctggttgga acgcctggga ccaggagccc    780
ggtgagttct cggacgcctc ggatgcccag tacaacaagt gccagaacga gaagatctac    840
atcaacacct ttggcgctga gctcaagtct gccggcatgc ccaaccacgc catcatcgac    900
actggccgca acggtgtcac cggtctccgc gacgagtggg gtgactggtg caacgtcaac    960
ggcgccggct tcggtgtgcg cccgactgcc aacactggcg acgagctcgc cgacgccttc   1020
gtgtgggtca agcccggtgg cgagtccgac ggcaccagcg actcgtcggc ggcgcgctac   1080
```

```
gacagcttct gcggcaagcc cgacgccttc aagcccagcc ccgaggccgg tacctggaac    1140
caggcctact tcgagatgct cctcaagaac gccaacccgt ccttc                    1185

<210> SEQ ID NO 10
<211> LENGTH: 2115
<212> TYPE: DNA
<213> ORGANISM: Chrysosporium lucknowense
<220> FEATURE:
<221> NAME/KEY: CDS
<222> LOCATION: (90)..(181)
<220> FEATURE:
<221> NAME/KEY: CDS
<222> LOCATION: (278)..(786)
<220> FEATURE:
<221> NAME/KEY: CDS
<222> LOCATION: (871)..(1455)
<220> FEATURE:
<221> NAME/KEY: CDS
<222> LOCATION: (1629)..(1888)

<400> SEQUENCE: 10
tgtgtggttt ctctccctcg tgccaaacca ctcccacctc ccgccccgag atagttgctt    60
gtttcgctcc gtgagaggga cacacacca atg gcc aag aag ctt ttc atc acc     113
                                 Met Ala Lys Lys Leu Phe Ile Thr
                                  1               5 gcc gcg ctt gcg gct gcc gtg ttg gcg gcc ccc gtc att gag gag cgc     161
Ala Leu Ala Ala Ala Val Leu Ala Ala Pro Val Ile Glu Glu Arg
     10              15                  20 cag aac tgc ggc gct gtg tg gtaagaaagc ccggtccgag tctcccatga        211
Gln Asn Cys Gly Ala Val Trp
 25              30 ttttctcgtc gagtaatggc ataagggcca cccttcgac tgaccgtgag aatcgatcaa    271 atccag g act caa tgc ggc ggt aac ggg tgg caa ggt ccc aca tgc tgc    320
        Thr Gln Cys Gly Gly Asn Gly Trp Gln Gly Pro Thr Cys Cys
                35                  40                  45 gcc tcg ggc tcg acc tgc gtt gcg cag aac gag tgg tac tct cag tgc    368
Ala Ser Gly Ser Thr Cys Val Ala Gln Asn Glu Trp Tyr Ser Gln Cys
         50                  55                  60 ctg ccc aac agc cag gtg acg agt tcc acc act ccg tcg tcg act tcc    416
Leu Pro Asn Ser Gln Val Thr Ser Ser Thr Thr Pro Ser Ser Thr Ser
         65                  70                  75 acc tcg cag cgc agc acc agc acc tcc agc agc acc acc agg agc ggc    464
Thr Ser Gln Arg Ser Thr Ser Thr Ser Ser Ser Thr Thr Arg Ser Gly
         80                  85                  90 agc tcc tcc tcc tcc tcc acc acg ccc ccg ccc gtc tcc agc ccc gtg    512
Ser Ser Ser Ser Ser Ser Thr Thr Pro Pro Pro Val Ser Ser Pro Val
         95                 100                 105 acc agc att ccc ggc ggt gcg acc tcc acg gcg agc tac tct ggc aac    560
Thr Ser Ile Pro Gly Gly Ala Thr Ser Thr Ala Ser Tyr Ser Gly Asn
110                 115                 120                 125 ccc ttc tcg ggc gtc cgg ctc ttc gcc aac gac tac tac agg tcc gag    608
Pro Phe Ser Gly Val Arg Leu Phe Ala Asn Asp Tyr Tyr Arg Ser Glu
                130                 135                 140 gtc cac aat ctc gcc att cct agc atg act ggt act ctg gcg gcc aag    656
Val His Asn Leu Ala Ile Pro Ser Met Thr Gly Thr Leu Ala Ala Lys
                145                 150                 155 gct tcc gcc gtc gcc gaa gtc cct agc ttc cag tgg ctc gac cgg aac    704
Ala Ser Ala Val Ala Glu Val Pro Ser Phe Gln Trp Leu Asp Arg Asn
                160                 165                 170 gtc acc atc gac acc ctg atg gtc cag act ctg tcc cag gtc cgg gct    752
Val Thr Ile Asp Thr Leu Met Val Gln Thr Leu Ser Gln Val Arg Ala
            175                 180                 185
```

```
ctc aat aag gcc ggt gcc aat cct ccc tat gct g gtgagttaca              796
Leu Asn Lys Ala Gly Ala Asn Pro Pro Tyr Ala
190             195             200 tggcgacttg ccttctcgtc ccctacctttt cttgacggga tcggttacct gacctggagg   856
caaaacaaca acag cc  caa ctc gtc gtc tac gac ctc ccc gac cgt gac      905
                    Ala Gln Leu Val Val Tyr Asp Leu Pro Asp Arg Asp
                                    205                 210 tgt gcc gcc gct gcg tcc aac ggc gag ttt tcg att gca aac ggc ggc      953
Cys Ala Ala Ala Ala Ser Asn Gly Glu Phe Ser Ile Ala Asn Gly Gly
                215                 220                 225 gcc gcc aac tac agg agc tac atc gac gct atc cgc aag cac atc att     1001
Ala Ala Asn Tyr Arg Ser Tyr Ile Asp Ala Ile Arg Lys His Ile Ile
        230                 235                 240 gag tac tcg gac atc cgg atc atc ctg gtt atc gag ccc gac tcg atg     1049
Glu Tyr Ser Asp Ile Arg Ile Ile Leu Val Ile Glu Pro Asp Ser Met
245                 250                 255                 260 gcc aac atg gtg acc aac atg aac gtg gcc aag tgc agc aac gcc gcg     1097
Ala Asn Met Val Thr Asn Met Asn Val Ala Lys Cys Ser Asn Ala Ala
                265                 270                 275 tcg acg tac cac gag ttg acc gtg tac gcg ctc aag cag ctg aac ctg     1145
Ser Thr Tyr His Glu Leu Thr Val Tyr Ala Leu Lys Gln Leu Asn Leu
            280                 285                 290 ccc aac gtc gcc atg tat ctc gac gcc ggc cac gcc ggc tgg ctc ggc     1193
Pro Asn Val Ala Met Tyr Leu Asp Ala Gly His Ala Gly Trp Leu Gly
            295                 300                 305 tgg ccc gcc aac atc cag ccc gcc gcc gag ctg ttt gcc ggc atc tac     1241
Trp Pro Ala Asn Ile Gln Pro Ala Ala Glu Leu Phe Ala Gly Ile Tyr
310                 315                 320 aat gat gcc ggc aag ccg gct gcc gtc cgc ggc ctg gcc act aac gtc     1289
Asn Asp Ala Gly Lys Pro Ala Ala Val Arg Gly Leu Ala Thr Asn Val
325                 330                 335                 340 gcc aac tac aac gcc tgg agc atc gct tcg gcc ccg tcg tac acg tcg     1337
Ala Asn Tyr Asn Ala Trp Ser Ile Ala Ser Ala Pro Ser Tyr Thr Ser
                345                 350                 355 cct aac cct aac tac gac gag aag cac tac atc gag gcc ttc agc ccg     1385
Pro Asn Pro Asn Tyr Asp Glu Lys His Tyr Ile Glu Ala Phe Ser Pro
            360                 365                 370 ctc ttg aac tcg gcc ggc ttc ccc gca cgc ttc att gtc gac act ggc     1433
Leu Leu Asn Ser Ala Gly Phe Pro Ala Arg Phe Ile Val Asp Thr Gly
        375                 380                 385 cgc aac ggc aaa caa cct acc g gtatgttttt ttttcttttg tctctgtccc      1485
Arg Asn Gly Lys Gln Pro Thr
390             395 cccctttttct cccccttcag ttggcgtcca caaggtctct tagtcctgct tcatctgtga  1545
ccaacctccc cccccccggc accgcccaca accgtttgac tctatactct tgggaatggg  1605
cgccgaaact gaccgttcca cag gc  caa caa cag tgg ggt gac tgg tgc aat  1657
                             Gly Gln Gln Gln Trp Gly Asp Trp Cys Asn
                                             400                 405 gtc aag ggc acc ggc ttt ggc gtg cgc ccg acg gcc aac acg ggc cac     1705
Val Lys Gly Thr Gly Phe Gly Val Arg Pro Thr Ala Asn Thr Gly His
                410                 415                 420 gag ctg gtc gat gcc ttt gtc tgg gtc aag ccc ggc ggc gag tcc gac     1753
Glu Leu Val Asp Ala Phe Val Trp Val Lys Pro Gly Gly Glu Ser Asp
            425                 430                 435 ggc aca agc gac acc agc gcc gcc cgc tac gac tac cac tgc ggc ctg     1801
Gly Thr Ser Asp Thr Ser Ala Ala Arg Tyr Asp Tyr His Cys Gly Leu
        440                 445                 450 tcc gat gcc ctg cag cct gcc ccc gag gct gga cag tgg ttc cag gcc     1849
```

```
Ser Asp Ala Leu Gln Pro Ala Pro Glu Ala Gly Gln Trp Phe Gln Ala
    455                 460                 465 tac ttc gag cag ctg ctc acc aac gcc aac ccg ccc ttc taaacctcgt      1898
Tyr Phe Glu Gln Leu Leu Thr Asn Ala Asn Pro Pro Phe
            470                 475                 480 cataaagaga gagagatggc gggcatgggc ctgattgggt tcattgacca tgcggctctt   1958 ctggggtac atattttacc tacctaccta taaataaggc ggcctatcgg gctctcgctt    2018
cgtttattag gtacttgttc ttgtacatac tttgtttata catacagcag ttagcatcca  2078
ctattcgttt cgacaaagcg aactttcca gaaaaaa                             2115

<210> SEQ ID NO 11
<211> LENGTH: 482
<212> TYPE: PRT
<213> ORGANISM: Chrysosporium lucknowense

<400> SEQUENCE: 11

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300
```

-continued

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
            325                 330                 335

Ala Thr Asn Val Ala Asn Tyr Asn Ala Trp Ser Ile Ala Ser Ala Pro
        340                 345                 350

Ser Tyr Thr Ser Pro Asn Pro Asn Tyr Asp Glu Lys His Tyr Ile Glu
    355                 360                 365

Ala Phe Ser Pro Leu Leu Asn Ser Ala Gly Phe Pro Ala Arg Phe Ile
370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
            405                 410                 415

Ala Asn Thr Gly His Glu Leu Val Asp Ala Phe Val Trp Val Lys Pro
        420                 425                 430

Gly Gly Glu Ser Asp Gly Thr Ser Asp Thr Ser Ala Ala Arg Tyr Asp
    435                 440                 445

Tyr His Cys Gly Leu Ser Asp Ala Leu Gln Pro Ala Pro Glu Ala Gly
450                 455                 460

Gln Trp Phe Gln Ala Tyr Phe Glu Gln Leu Leu Thr Asn Ala Asn Pro
465                 470                 475                 480

Pro Phe

<210> SEQ ID NO 12
<211> LENGTH: 1446
<212> TYPE: DNA
<213> ORGANISM: Chrysosporium lucknowense

<400> SEQUENCE: 12
atggccaaga agcttttcat caccgccgcg cttgcggctg ccgtgttggc ggccccgtc      60
attgaggagc gccagaactg cggcgctgtg tggactcaat gcggcggtaa cgggtggcaa    120
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300
acgcccccgc ccgtctccag ccccgtgacc agcattcccg gcggtgcgac ctccacggcg    360
agctactctg gcaaccccct tcgggcgtc cggctcttcg ccaacgacta ctacaggtcc    420
gaggtccaca atctcgccat tcctagcatg actggtactc tggcggccaa ggcttccgcc    480
gtcgccgaag tccctagctt ccagtggctc gaccggaacg tcaccatcga cacctgatg    540
gtccagactc tgtcccaggt ccgggctctc aataaggccg gtgccaatcc tccctatgct    600
gcccaactcg tcgtctacga cctccccgac cgtgactgtg ccgccgctgc gtccaacggc    660
gagttttcga ttgcaaacgg cggcgccgcc aactacagga gctacatcga cgctatccgc    720
aagcacatca ttgagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgtcgcc taaccctaac   1080
tacgacgaga agcactacat cgaggccttc agcccgctct tgaactcggc cggcttcccc   1140

-continued

```
gcacgcttca ttgtcgacac tggccgcaac ggcaaacaac ctaccggcca acaacagtgg    1200
ggtgactggt gcaatgtcaa gggcaccggc tttggcgtgc gcccgacggc caacacgggc    1260
cacgagctgg tcgatgcctt tgtctgggtc aagcccggcg cgagtccga cggcacaagc    1320 gacaccagcg ccgcccgcta cgactaccac tgcggcctgt ccgatgccct gcagcctgcc    1380
cccgaggctg acagtggtt ccaggcctac ttcgagcagc tgctcaccaa cgccaacccg    1440
cccttc                                                              1446

<210> SEQ ID NO 13
<211> LENGTH: 2507
<212> TYPE: DNA
<213> ORGANISM: Chrysosporium lucknowense
<220> FEATURE:
<221> NAME/KEY: CDS
<222> LOCATION: (967)..(1572)
<220> FEATURE:
<221> NAME/KEY: CDS
<222> LOCATION: (1666)..(2427)

<400> SEQUENCE: 13
ctatataaag gtacttacag ataaaatccc caggttgaca gcccttttcga gcataagaat    60 ccaggtccta tagtggccgg ctcgaagccc agatttgagc cctattgaga ataactatat   120
ggcactggat gaaggattgg cttgaacatc gctacgatgt ttaatcgctg agtcttacag   180
ggcttcgact ggctgttctg gaggcgtggg aggcagtccc ccccgagttt cttcagtgcc   240
tggcacactc aatgcctcga cggctagcaa aaaccagggg ggagagactg ggtattgata   300
cttctgtatt atagaaattt gtattgggtt ggttgtacct agacttcttg gctacttttc   360
tgatttgcgt tagttgtggg gcatgtatcg cactaggatt aataatgctg gaagaggtgt   420
agagatgttg cgtcgcatgg ccaccgagat ccggcctggc gtcgtgcctt gcagctcgca   480
cgatgcgcgc gacgatgcgg gacacccctc cccccctccc cctccccct acattaggag   540 gggatccggg gccgctgccc gttttccgtc ttggtattcc cggctgacac aacggttctc   600
cagagtgata accgaggcac accagtagca gtccacgatg gcacggcagg ggatacattc   660
cgcccggaac aacccaagat ctgggaatcc cagtgacgac cccggggtcc tccggggtcc   720
cccgatttcg tctgaaccga cgaactggaa ggaggcgagc cttggaacga tgggggatat   780
gatatatatt aagatgcaac attctctccc tccctcctct ctctctccct ccccccctct   840
ctcctcctct tccctcctc cccgccgttc tctctccatg agcctcaatt cttgctccga   900
gcgcggtgta tttcccccac gaggaattga caaaagaaaa agaaaaagac aagactctcg   960 agaacg atg ggt cgc ggc gct gct ttc cta ggc ctc gcc tcg ctc ctc    1008
       Met Gly Arg Gly Ala Ala Phe Leu Gly Leu Ala Ser Leu Leu
       1               5                  10 gtg ggc gcg gcc aag gcc cag acg ccc ggc gag ggc gag gag gtg cac    1056
Val Gly Ala Ala Lys Ala Gln Thr Pro Gly Glu Gly Glu Glu Val His
15              20                  25                  30 ccg cag atc acg acg tac cgc tgc acc aag gcg gac ggg tgc gag gag    1104
Pro Gln Ile Thr Thr Tyr Arg Cys Thr Lys Ala Asp Gly Cys Glu Glu
                35                  40                  45 aag acc aac tac atc gtg ctg gac gcc cta tcg cac ccg gtc cac cag    1152
Lys Thr Asn Tyr Ile Val Leu Asp Ala Leu Ser His Pro Val His Gln
            50                  55                  60 gtc gac aac ccg tac aac tgc ggc gac tgg ggc cag aag ccc aac gag    1200
Val Asp Asn Pro Tyr Asn Cys Gly Asp Trp Gly Gln Lys Pro Asn Glu
        65                  70                  75 acg gcc tgc ccg gac ctc gag tcg tgc gcc agg aac tgc atc atg gac    1248
```

```
                Thr Ala Cys Pro Asp Leu Glu Ser Cys Ala Arg Asn Cys Ile Met Asp
                    80              85                  90 ccg gtc tcg gac tac ggc cgg cac ggg gtc tcg acc gac ggc acc tcg        1296
Pro Val Ser Asp Tyr Gly Arg His Gly Val Ser Thr Asp Gly Thr Ser
 95             100                 105                 110 ctg cgc ctc aag cag cta gtc ggc ggc aac gtc gtc agc ccg cgc gtc        1344
Leu Arg Leu Lys Gln Leu Val Gly Gly Asn Val Val Ser Pro Arg Val
            115                 120                 125 tac ctg ctc gac gag acc aag gag cgc tac gag atg ctc aag ctg acc        1392
Tyr Leu Leu Asp Glu Thr Lys Glu Arg Tyr Glu Met Leu Lys Leu Thr
                130                 135                 140 ggc aac gag ttc acc ttt gac gtc gac gcc acc aag ctg ccc tgc ggc        1440
Gly Asn Glu Phe Thr Phe Asp Val Asp Ala Thr Lys Leu Pro Cys Gly
            145                 150                 155 atg aac agc gcc ctc tac ctc tcc gag atg gac gcc acc ggc gcc cgg        1488
Met Asn Ser Ala Leu Tyr Leu Ser Glu Met Asp Ala Thr Gly Ala Arg
        160                 165                 170 agc gag ctc aac ccg ggc ggc gcc acc ttt ggc acc ggc tac tgc gac        1536
Ser Glu Leu Asn Pro Gly Gly Ala Thr Phe Gly Thr Gly Tyr Cys Asp
175                 180                 185                 190 gcc cag tgc tac gtc acc ccc ttc atc aac ggc ctc gtacgtattc             1582
Ala Gln Cys Tyr Val Thr Pro Phe Ile Asn Gly Leu
                195                 200 tcctattaat cttgtttctt ttttcctttt cttttttga tataatagaa ttaagaagaa       1642
ctcggtgggc tgacatgaca cag ggc aac atc gag ggc aag ggc gcg tgc tgc      1695
                        Gly Asn Ile Glu Gly Lys Gly Ala Cys Cys
                                    205                 210 aac gag atg gat atc tgg gag gcc aac gcg cgg gcg cag cac atc gcg        1743
Asn Glu Met Asp Ile Trp Glu Ala Asn Ala Arg Ala Gln His Ile Ala
            215                 220                 225 ccg cac ccg tgc agc aag gcg ggg ccg tac ctg tgc gag ggc gcc gag        1791
Pro His Pro Cys Ser Lys Ala Gly Pro Tyr Leu Cys Glu Gly Ala Glu
        230                 235                 240 tgc gag ttc gac ggc gtg tgc gac aag aac ggc tgc gcc tgg aac ccg        1839
Cys Glu Phe Asp Gly Val Cys Asp Lys Asn Gly Cys Ala Trp Asn Pro
245                 250                 255                 260 tac cgg gtc aac gtg acg gac tac tac ggc gag ggc gcc gag ttc agg        1887
Tyr Arg Val Asn Val Thr Asp Tyr Tyr Gly Glu Gly Ala Glu Phe Arg
                265                 270                 275 gtg gac acg acc cgg ccc ttc tcg gtc gtc acg cag ttc cgc gcc ggc        1935
Val Asp Thr Thr Arg Pro Phe Ser Val Val Thr Gln Phe Arg Ala Gly
            280                 285                 290 ggc gac gcg ggg ggc ggc aag ctc gag agc atc tac cgg ctc ttc gtc        1983
Gly Asp Ala Gly Gly Gly Lys Leu Glu Ser Ile Tyr Arg Leu Phe Val
        295                 300                 305 cag gac ggc agg gtg atc gag tcg tac gtc gtc gac aag ccc ggc ctg        2031
Gln Asp Gly Arg Val Ile Glu Ser Tyr Val Val Asp Lys Pro Gly Leu
310                 315                 320 ccc ccg acg gac cgc atg acg gac gag ttc tgc gcc gcc acc ggc gcc        2079
Pro Pro Thr Asp Arg Met Thr Asp Glu Phe Cys Ala Ala Thr Gly Ala
325                 330                 335                 340 gcc cgc ttc acg gag ctc ggc gcc atg gag gcc atg ggc gac gcc ctg        2127
Ala Arg Phe Thr Glu Leu Gly Ala Met Glu Ala Met Gly Asp Ala Leu
                345                 350                 355 acg cgc ggc atg gtc ctc gcc ctc agc atc tgg tgg agc gag ggc gac        2175
Thr Arg Gly Met Val Leu Ala Leu Ser Ile Trp Trp Ser Glu Gly Asp
            360                 365                 370 aac atg aac tgg ctc gac tcg ggc gag gcc ggc ccc tgc gac ccg gac        2223
Asn Met Asn Trp Leu Asp Ser Gly Glu Ala Gly Pro Cys Asp Pro Asp
        375                 380                 385
```

```
gag ggc aac ccg tcc aac atc atc cgc gtc cag ccc gac ccg gag gtc      2271
Glu Gly Asn Pro Ser Asn Ile Ile Arg Val Gln Pro Asp Pro Glu Val
    390                 395                 400 gtc ttc agc aac ctg cgc tgg ggc gag atc ggc tca acc tac gag tcc      2319
Val Phe Ser Asn Leu Arg Trp Gly Glu Ile Gly Ser Thr Tyr Glu Ser
405                 410                 415                 420 gcc gtc gac ggg ccc gtc ggc aag ggc aag ggc aag ggc aag ggc aag      2367
Ala Val Asp Gly Pro Val Gly Lys Gly Lys Gly Lys Gly Lys Gly Lys
                425                 430                 435 gct ccc gcc ggc gac ggc aac ggg aag gag aag agc aat ggc aag cgc      2415
Ala Pro Ala Gly Asp Gly Asn Gly Lys Glu Lys Ser Asn Gly Lys Arg
            440                 445                 450 ttc agg agg ttc tgagcaacct tgatattatt tttttctttc tttccttcac          2467
Phe Arg Arg Phe
        455 cagttaatta gttgcctttg attagaaaga gagagagaaa                          2507

<210> SEQ ID NO 14
<211> LENGTH: 456
<212> TYPE: PRT
<213> ORGANISM: Chrysosporium lucknowense

<400> SEQUENCE: 14

Met Gly Arg Gly Ala Ala Phe Leu Gly Leu Ala Ser Leu Leu Val Gly
1               5                   10                  15

Ala Ala Lys Ala Gln Thr Pro Gly Glu Gly Glu Glu Val His Pro Gln
            20                  25                  30

Ile Thr Thr Tyr Arg Cys Thr Lys Ala Asp Gly Cys Glu Glu Lys Thr
        35                  40                  45

Asn Tyr Ile Val Leu Asp Ala Leu Ser His Pro Val His Gln Val Asp
    50                  55                  60

Asn Pro Tyr Asn Cys Gly Asp Trp Gly Gln Lys Pro Asn Glu Thr Ala
65                  70                  75                  80

Cys Pro Asp Leu Glu Ser Cys Ala Arg Asn Cys Ile Met Asp Pro Val
                85                  90                  95

Ser Asp Tyr Gly Arg His Gly Val Ser Thr Asp Gly Thr Ser Leu Arg
            100                 105                 110

Leu Lys Gln Leu Val Gly Gly Asn Val Val Ser Pro Arg Val Tyr Leu
        115                 120                 125

Leu Asp Glu Thr Lys Glu Arg Tyr Glu Met Leu Lys Leu Thr Gly Asn
    130                 135                 140

Glu Phe Thr Phe Asp Val Asp Ala Thr Lys Leu Pro Cys Gly Met Asn
145                 150                 155                 160

Ser Ala Leu Tyr Leu Ser Glu Met Asp Ala Thr Gly Ala Arg Ser Glu
                165                 170                 175

Leu Asn Pro Gly Gly Ala Thr Phe Gly Thr Gly Tyr Cys Asp Ala Gln
            180                 185                 190

Cys Tyr Val Thr Pro Phe Ile Asn Gly Leu Gly Asn Ile Glu Gly Lys
        195                 200                 205

Gly Ala Cys Cys Asn Glu Met Asp Ile Trp Glu Ala Asn Ala Arg Ala
    210                 215                 220

Gln His Ile Ala Pro His Pro Cys Ser Lys Ala Gly Pro Tyr Leu Cys
225                 230                 235                 240

Glu Gly Ala Glu Cys Glu Phe Asp Gly Val Cys Asp Lys Asn Gly Cys
                245                 250                 255

Ala Trp Asn Pro Tyr Arg Val Asn Val Thr Asp Tyr Tyr Gly Glu Gly
```

-continued

```
            260                 265                 270

Ala Glu Phe Arg Val Asp Thr Thr Arg Pro Phe Ser Val Val Thr Gln
        275                 280                 285
Phe Arg Ala Gly Gly Asp Ala Gly Gly Gly Lys Leu Glu Ser Ile Tyr
    290                 295                 300

Arg Leu Phe Val Gln Asp Gly Arg Val Ile Glu Ser Tyr Val Val Asp
305                 310                 315                 320
Lys Pro Gly Leu Pro Pro Thr Asp Arg Met Thr Asp Glu Phe Cys Ala
                325                 330                 335
Ala Thr Gly Ala Ala Arg Phe Thr Glu Leu Gly Ala Met Glu Ala Met
            340                 345                 350

Gly Asp Ala Leu Thr Arg Gly Met Val Leu Ala Leu Ser Ile Trp Trp
        355                 360                 365

Ser Glu Gly Asp Asn Met Asn Trp Leu Asp Ser Gly Glu Ala Gly Pro
    370                 375                 380

Cys Asp Pro Asp Glu Gly Asn Pro Ser Asn Ile Ile Arg Val Gln Pro
385                 390                 395                 400
Asp Pro Glu Val Val Phe Ser Asn Leu Arg Trp Gly Glu Ile Gly Ser
                405                 410                 415

Thr Tyr Glu Ser Ala Val Asp Gly Pro Val Gly Lys Gly Lys Gly Lys
            420                 425                 430

Gly Lys Gly Lys Ala Pro Ala Gly Asp Gly Asn Gly Lys Glu Lys Ser
        435                 440                 445

Asn Gly Lys Arg Phe Arg Arg Phe
    450                 455

<210> SEQ ID NO 15
<211> LENGTH: 1368
<212> TYPE: DNA
<213> ORGANISM: Chrysosporium lucknowense

<400> SEQUENCE: 15
atgggtcgcg gcgctgcttt cctaggcctc gcctcgctcc tcgtgggcgc ggccaaggcc      60
cagacgcccg gcgagggcga ggaggtgcac ccgcagatca cgacgtaccg ctgcaccaag     120
gcggacgggt gcgaggagaa gaccaactac atcgtgctgg acgccctatc gcacccggtc     180
caccaggtcg acaacccgta caactgcggc gactggggcc agaagcccaa cgagacggcc     240
tgcccggacc tcgagtcgtg cgccaggaac tgcatcatgg acccggtctc ggactacggc     300
cggcacgggg tctcgaccga cggcacctcg ctgcgcctca agcagctagt cggcggcaac     360
gtcgtcagcc cgcgcgtcta cctgctcgac gagaccaagg agcgctacga gatgctcaag     420
ctgaccggca acgagttcac ctttgacgtc gacgccacca agctgccctg cggcatgaac     480
agcgccctct acctctccga gatggacgcc accggcgccc ggagcgagct caacccgggc     540
ggcgccacct ttggcaccgg ctactgcgac gcccagtgct acgtcacccc cttcatcaac     600
ggcctcggca acatcgaggg caagggcgcg tgctgcaacg agatggatat ctgggaggcc     660
aacgcgcggg cgcagcacat cgcgccgcac ccgtgcagca aggcggggcc gtacctgtgc     720
gagggcgccg agtgcgagtt cgacggcgtg tgcgacaaga acggctgcgc ctggaacccg     780
taccgggtca acgtgacgga ctactacggc gagggcgccg agttcagggt ggacacgacc     840
cggcccttct cggtcgtcac gcagttccgc gccggcggcg acgcgggggg cggcaagctc     900
gagagcatct accggctctt cgtccaggac ggcagggtga tcgagtcgta cgtcgtcgac     960
aagcccggcc tgcccccgac ggaccgcatg acggacgagt tctgcgccgc caccggcgcc    1020
```

-continued

```
gcccgcttca cggagctcgg cgccatggag gccatgggcg acgccctgac gcgcggcatg    1080
gtcctcgccc tcagcatctg gtggagcgag ggcgacaaca tgaactggct cgactcgggc    1140
gaggccggcc cctgcgaccc ggacgagggc aacccgtcca acatcatccg cgtccagccc    1200
gacccggagg tcgtcttcag caacctgcgc tggggcgaga tcggctcaac ctacgagtcc    1260
gccgtcgacg ggcccgtcgg caagggcaag ggcaagggca agggcaaggc tcccgccggc    1320
gacggcaacg ggaaggagaa gagcaatggc aagcgcttca ggaggttc                 1368
```

<210> SEQ ID NO 16
<211> LENGTH: 1305
<212> TYPE: DNA
<213> ORGANISM: Chrysosporium lucknowense
<220> FEATURE:
<221> NAME/KEY: CDS
<222> LOCATION: (103)..(545)
<220> FEATURE:
<221> NAME/KEY: CDS
<222> LOCATION: (683)..(903)
<220> FEATURE:
<221> NAME/KEY: CDS
<222> LOCATION: (986)..(1062)

<400> SEQUENCE: 16

```
cgacaaagac ccgtcagtga ttaataataa ttagtagcag tttctttctt tcaagactca     60
agaatactcc tttccgccat cgtggcagcg tttagattca tc atg cag ccg ttt       114
                                              Met Gln Pro Phe
                                                1 ctg ctc ttg ttc ctc tcg tcg gtc acg gcg gcg agc ccc ctg acg gcg      162
Leu Leu Leu Phe Leu Ser Ser Val Thr Ala Ala Ser Pro Leu Thr Ala
  5                  10                  15                  20 ctc gac aag cgg cag cag gcg acg ttg tgc gag cag tac ggc tac tgg      210
Leu Asp Lys Arg Gln Gln Ala Thr Leu Cys Glu Gln Tyr Gly Tyr Trp
             25                  30                  35 tcg ggc aac ggt tac gag gtc aac aac aac aac tgg ggc aag gat tcg      258
Ser Gly Asn Gly Tyr Glu Val Asn Asn Asn Asn Trp Gly Lys Asp Ser
         40                  45                  50 gcc tcg ggc ggc cat cag tgc acc tac gtc gac agc agc agc tcc agc      306
Ala Ser Gly Gly His Gln Cys Thr Tyr Val Asp Ser Ser Ser Ser Ser
     55                  60                  65 ggc gtc gcc tgg cac acg acc tgg cag tgg gaa gga ggc cag aac cag      354
Gly Val Ala Trp His Thr Thr Trp Gln Trp Glu Gly Gly Gln Asn Gln
 70                  75                  80 gtc aag agc ttc gcc aac tgc ggc ctg cag gtg ccc aag ggc agg acc      402
Val Lys Ser Phe Ala Asn Cys Gly Leu Gln Val Pro Lys Gly Arg Thr
85                  90                  95                 100 atc tcg tcc atc agc aac ctg cag acc tcc atc tcg tgg tcc tac agc      450
Ile Ser Ser Ile Ser Asn Leu Gln Thr Ser Ile Ser Trp Ser Tyr Ser
                105                 110                 115 aac acc aac atc cgc gcc aac gtg gcc tac gac ctc ttc acc gcg gca      498
Asn Thr Asn Ile Arg Ala Asn Val Ala Tyr Asp Leu Phe Thr Ala Ala
            120                 125                 130 gac ccg aac cac gcg acc agc agc ggc gac tac gag ctc atg atc tg      545
Asp Pro Asn His Ala Thr Ser Ser Gly Asp Tyr Glu Leu Met Ile Trp
        135                 140                 145 gtcagttttt tttttctttt tcttttcttt ctctttcttt ttcttttcct ttctcctgtt    605
ttattttctt atccattgct tcgccctctt tccttaaccc tgctgactct ctcttcttgt    665
caatgatact gtaatag g ctg gcg aga ttc ggc gac gtc tac ccc atc ggc    716
                    Leu Ala Arg Phe Gly Asp Val Tyr Pro Ile Gly
                                    150                 155 tcg tcc cag ggc cac gtc aac gtg gcc ggc cag gac tgg gag ctg tgg      764
```

```
Ser Ser Gln Gly His Val Asn Val Ala Gly Gln Asp Trp Glu Leu Trp
160                 165                 170                 175 acg ggc ttc aac ggc aac atg cgg gtc tac agc ttc gta gcg ccc agc       812
Thr Gly Phe Asn Gly Asn Met Arg Val Tyr Ser Phe Val Ala Pro Ser
                    180                 185                 190 ccc cgc aac agc ttc agc gcc aac gtc aag gac ttc ttc aac tat ctc       860
Pro Arg Asn Ser Phe Ser Ala Asn Val Lys Asp Phe Phe Asn Tyr Leu
                195                 200                 205 cag tcc aac cag ggc ttc ccg gcc agc agc caa tac ctt ctc a             903
Gln Ser Asn Gln Gly Phe Pro Ala Ser Ser Gln Tyr Leu Leu
            210                 215                 220 gtaaggagac gagatctcga acagcatacc atatatgcgt gcggtacaag tgcactaacc     963
cccttttttt tcccgttcgc ag tc  ttc cag gcg ggc acc gag ccc ttc acc    1014
                        Ile Phe Gln Ala Gly Thr Glu Pro Phe Thr
                                225                 230 ggc ggc gag acc acc ctt acc gtc aac aac tac tct gca agg gtt gct      1062
Gly Gly Glu Thr Thr Leu Thr Val Asn Asn Tyr Ser Ala Arg Val Ala
                235                 240                 245 taaacaggaa ggccgaggat ggcccccaag gccgttgcgg gttcacgagc tctcttcttt    1122
tcaagtgctg tacatacata attagcgtac caagtcatag ctgtttgtca gcttcaaact    1182
aagtgctcgc ccacaaaaga gggggaggg gaaaataaca aattgccgaa cgcagtgata     1242
agcttctggg agcgttgaaa gcagtctaca gtaggtggct gtacgaagga aaagagtgcc    1302
tta                                                                 1305

<210> SEQ ID NO 17
<211> LENGTH: 247
<212> TYPE: PRT
<213> ORGANISM: Chrysosporium lucknowense

<400> SEQUENCE: 17

Met Gln Pro Phe Leu Leu Leu Phe Leu Ser Ser Val Thr Ala Ala Ser
1               5                   10                  15

Pro Leu Thr Ala Leu Asp Lys Arg Gln Gln Ala Thr Leu Cys Glu Gln
                20                  25                  30

Tyr Gly Tyr Trp Ser Gly Asn Gly Tyr Glu Val Asn Asn Asn Trp
            35                  40                  45

Gly Lys Asp Ser Ala Ser Gly Gly His Gln Cys Thr Tyr Val Asp Ser
        50                  55                  60

Ser Ser Ser Ser Gly Val Ala Trp His Thr Thr Trp Gln Trp Glu Gly
65                  70                  75                  80

Gly Gln Asn Gln Val Lys Ser Phe Ala Asn Cys Gly Leu Gln Val Pro
                85                  90                  95

Lys Gly Arg Thr Ile Ser Ser Ile Ser Asn Leu Gln Thr Ser Ile Ser
                100                 105                 110

Trp Ser Tyr Ser Asn Thr Asn Ile Arg Ala Asn Val Ala Tyr Asp Leu
            115                 120                 125

Phe Thr Ala Ala Asp Pro Asn His Ala Thr Ser Ser Gly Asp Tyr Glu
        130                 135                 140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
                165                 170                 175

Gly Phe Asn Gly Asn Met Arg Val Tyr Ser Phe Val Ala Pro Ser Pro
            180                 185                 190

Arg Asn Ser Phe Ser Ala Asn Val Lys Asp Phe Phe Asn Tyr Leu Gln
```

```
        195                 200                 205

Ser Asn Gln Gly Phe Pro Ala Ser Ser Gln Tyr Leu Leu Ile Phe Gln
    210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245

<210> SEQ ID NO 18
<211> LENGTH: 741
<212> TYPE: DNA
<213> ORGANISM: Chrysosporium lucknowense

<400> SEQUENCE: 18
atgcagccgt ttctgctctt gttcctctcg tcggtcacgg cggcgagccc cctgacggcg      60
ctcgacaagc ggcagcaggc gacgttgtgc gagcagtacg gctactggtc gggcaacggt     120
tacgaggtca acaacaacaa ctggggcaag gattcggcct cgggcggcca tcagtgcacc     180
tacgtcgaca gcagcagctc cagcggcgtc gcctggcaca cgacctggca gtgggaagga     240
ggccagaacc aggtcaagag cttcgccaac tgcggcctgc aggtgcccaa gggcaggacc     300
atctcgtcca tcagcaacct gcagacctcc atctcgtggt cctacagcaa caccaacatc     360
cgcgccaacg tggcctacga cctcttcacc gcggcagacc cgaaccacgc gaccagcagc     420
ggcgactacg agctcatgat ctggctggcg agattcggcg acgtctaccc catcggctcg     480
tcccagggcc acgtcaacgt ggccggccag gactgggagc tgtggacggg cttcaacggc     540
aacatgcggg tctacagctt cgtagcgccc agcccccgca acagcttcag cgccaacgtc     600
aaggacttct tcaactatct ccagtccaac cagggcttcc cggccagcag ccaatacctt     660
ctcatcttcc aggcgggcac cgagcccttc accggcggcg agaccaccct taccgtcaac     720
aactactctg caagggttgc t                                               741

<210> SEQ ID NO 19
<211> LENGTH: 1448
<212> TYPE: DNA
<213> ORGANISM: Chrysosporium lucknowense
<220> FEATURE:
<221> NAME/KEY: CDS
<222> LOCATION: (166)..(597)
<220> FEATURE:
<221> NAME/KEY: CDS
<222> LOCATION: (708)..(738)
<220> FEATURE:
<221> NAME/KEY: CDS
<222> LOCATION: (846)..(972)
<220> FEATURE:
<221> NAME/KEY: CDS
<222> LOCATION: (1074)..(1158)

<400> SEQUENCE: 19
atatataagt gagagtgttt tttgactgcc ccgggttctg gtagttgaag ggaagttcga      60
tgctctctgc tgtcgtcgct ctcgtcgctc tcgtcggcat cctccatccg tccgcctttg     120
ataacccgct ccccgactca gtcaagacga cgcatacttg gcacc atg cat ctc tcc     177
                                                  Met His Leu Ser
                                                  1 gcc acc acc ggg ttc ctc gcc ctc ccg gcc ctg gcc ctg gcc cag ctc       225
Ala Thr Thr Gly Phe Leu Ala Leu Pro Ala Leu Ala Leu Ala Gln Leu
5                   10                  15                  20 tcg ggc agc ggc cag acg acc cgg tac tgg gac tgc tgc aag ccg agc       273
Ser Gly Ser Gly Gln Thr Thr Arg Tyr Trp Asp Cys Cys Lys Pro Ser
                25                  30                  35
```

```
tgc gcc tgg ccc ggc aag ggc ccc tcg tct ccg gtg cag gcc tgc gac      321
Cys Ala Trp Pro Gly Lys Gly Pro Ser Ser Pro Val Gln Ala Cys Asp
         40                  45                  50 aag aac gac aac ccg ctc aac gac ggc ggc tcc acc cgg tcc ggc tgc      369
Lys Asn Asp Asn Pro Leu Asn Asp Gly Gly Ser Thr Arg Ser Gly Cys
 55                  60                  65 gac gcg ggc ggc agc gcc tac atg tgc tcc tcc cag agc ccc tgg gcc      417
Asp Ala Gly Gly Ser Ala Tyr Met Cys Ser Ser Gln Ser Pro Trp Ala
         70                  75                  80 gtc agc gac gag ctg tcg tac ggc tgg gcg gcc gtc aag ctc gcc ggc      465
Val Ser Asp Glu Leu Ser Tyr Gly Trp Ala Ala Val Lys Leu Ala Gly
 85                  90                  95                 100 agc tcc gag tcg cag tgg tgc tgc gcc tgc tac gag ctg acc ttc acc      513
Ser Ser Glu Ser Gln Trp Cys Cys Ala Cys Tyr Glu Leu Thr Phe Thr
                105                 110                 115 agc ggg ccg gtc gcg ggc aag aag atg att gtg cag gcg acc aac acc      561
Ser Gly Pro Val Ala Gly Lys Lys Met Ile Val Gln Ala Thr Asn Thr
        120                 125                 130 ggt ggc gac ctg ggc gac aac cac ttt gac ctg gcc gtgagttgcc           607
Gly Gly Asp Leu Gly Asp Asn His Phe Asp Leu Ala
        135                 140 tccccttctc cccggaccgc tcagattaga tgagattaga ctttgctcgt aaatcggtcc    667
aagattcccg ttgactgacc aacaaacatc atacgggcag atc ccc ggt ggc ggt      722
                                            Ile Pro Gly Gly Gly
                                                145 gtc ggt att ttc aac g gtaagctggt gccccggac ccctcccgg accccctccc      778
Val Gly Ile Phe Asn
150 cttttcctcc agcgagccga gttgggatcg ccgagatcga gaactcacac aacttctctc    838 tcgacag cc tgc acc gac cag tac ggc gct ccc ccg aac ggc tgg ggc       886
           Ala Cys Thr Asp Gln Tyr Gly Ala Pro Pro Asn Gly Trp Gly
                            160                 165 gac cgc tac ggc ggc atc cat tcc aag gaa gag tgc gaa tcc ttc ccg      934
Asp Arg Tyr Gly Gly Ile His Ser Lys Glu Glu Cys Glu Ser Phe Pro
170                 175                 180 gag gcc ctc aag ccc ggc tgc aac tgg cgc ttc gac tg  gtacgttgct       982
Glu Ala Leu Lys Pro Gly Cys Asn Trp Arg Phe Asp Trp
185                 190                 195 ttgacatacc ggaacccaat tcctccaacc cccccctttt ctcccccaa ctccggggt     1042 agtcggaatg tcgcgactga ccctatttca g g ttc caa aac gcc gac aac ccg    1095
                                    Phe Gln Asn Ala Asp Asn Pro
                                                    200 tcg gtc acc ttc cag gag gtg gcc tgc ccg tcg gag ctc acg tcc aag     1143
Ser Val Thr Phe Gln Glu Val Ala Cys Pro Ser Glu Leu Thr Ser Lys
205                 210                 215                 220 agc ggc tgc tcc cgt taagagggaa gagaggggc tggaaggacc gaaagattca      1198
Ser Gly Cys Ser Arg
                225 acctctgctc ctgctgggga agctcgggcg cgagtgtgaa actggtgtaa atattgtggc   1258 acacacaagc tactacagtc cgtctcgccg tccggctaac tagccttgct gcggatctgt   1318 ccatcttcgg tccgaactgt ccgttgctgt tttggctcgg tgcctcatct tctcccaacc   1378 tagtcaagaa tgaatcgtga gagaggctga gagagataag atcgacttca gaaatccagg   1438 gttgaaagca                                                          1448

<210> SEQ ID NO 20
<211> LENGTH: 225
```

<212> TYPE: PRT
<213> ORGANISM: Chrysosporium lucknowense

<400> SEQUENCE: 20

```
Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225
```

<210> SEQ ID NO 21
<211> LENGTH: 675
<212> TYPE: DNA
<213> ORGANISM: Chrysosporium lucknowense

<400> SEQUENCE: 21

```
atgcatctct ccgccaccac cgggttcctc gccctcccgg ccctggccct ggcccagctc     60
tcgggcagcg gccagacgac ccggtactgg gactgctgca agccgagctg cgcctggccc    120
ggcaagggcc cctcgtctcc ggtgcaggcc tgcgacaaga acgacaaccc gctcaacgac    180
ggcggctcca cccggtccgg ctgcgacgcg ggcggcagcg cctacatgtg ctcctcccag    240
agcccctggg ccgtcagcga cgagctgtcg tacggctggg cggccgtcaa gctcgccggc    300
agctccgagt cgcagtggtg ctgcgcctgc tacgagctga ccttcaccag cgggccggtc    360
gcgggcaaga agatgattgt gcaggcgacc aacaccggtg gcgacctggg cgacaaccac    420
tttgacctgg ccatccccgg tggcggtgtc ggtattttca acgcctgcac cgaccagtac    480
ggcgctcccc cgaacggctg gggcgaccgc tacggcggca tccattccaa ggaagagtgc    540
gaatccttcc cggaggccct caagcccggc tgcaactggc gcttcgactg gttccaaaac    600
gccgacaacc cgtcggtcac cttccaggag gtggcctgcc cgtcggagct cacgtccaag    660
```

```
                                                      -continued agcggctgct cccgt                                                675

<210> SEQ ID NO 22
<211> LENGTH: 1658
<212> TYPE: DNA
<213> ORGANISM: Chrysosporium lucknowense
<220> FEATURE:
<221> NAME/KEY: CDS
<222> LOCATION: (211)..(1139)
<220> FEATURE:
<221> NAME/KEY: CDS
<222> LOCATION: (1217)..(1430)

<400> SEQUENCE: 22
aggaacgggg aggaggaggg cttggttagg gtcgcgttcg tttggagatt gctgagctct    60
gagccttcgg tccttggatc cctgcggtcc ccggtctcct ctctctctct ctctctctct   120
ctctctctct cttcttccca cgctcgttcg acagacgcct cccttcttc gctctccttt    180 ccctcgcacg tagcacacta atagtgcacc atg cgc gtc tct agt ttg gtc gcg   234
                                   Met Arg Val Ser Ser Leu Val Ala
                                     1               5 gcc ctt gct acc ggt ggt ctt gtc gcc gcc acg cct aag ccc aag ggg    282
Ala Leu Ala Thr Gly Gly Leu Val Ala Ala Thr Pro Lys Pro Lys Gly
         10                  15                  20 tcg tcg ccc cct ggg gcc gtg gac gcg aac cct ttc aag ggc aag acg    330
Ser Ser Pro Pro Gly Ala Val Asp Ala Asn Pro Phe Lys Gly Lys Thr
 25                  30                  35                  40 cag ttc gtc aac ccg gca tgg gcg gcc aag ctg gaa cag acc aaa aag    378
Gln Phe Val Asn Pro Ala Trp Ala Ala Lys Leu Glu Gln Thr Lys Lys
                 45                  50                  55 gcg ttc ctg gcc agg aac gac acc gtc aat gcc gcc aag acg gag aag    426
Ala Phe Leu Ala Arg Asn Asp Thr Val Asn Ala Ala Lys Thr Glu Lys
             60                  65                  70 gtc cag cag acc agc tcg ttc gtc tgg gtc tcg agg atc gcc gag ctc    474
Val Gln Gln Thr Ser Ser Phe Val Trp Val Ser Arg Ile Ala Glu Leu
         75                  80                  85 tcc aac atc gac gac gcc atc gcg gct gcc cgc aag gcg cag aag aag    522
Ser Asn Ile Asp Asp Ala Ile Ala Ala Ala Arg Lys Ala Gln Lys Lys
 90                  95                 100 acg ggc agg agg cag atc gtc ggc ctg gtg ctc tac aac ctt ccg gac    570
Thr Gly Arg Arg Gln Ile Val Gly Leu Val Leu Tyr Asn Leu Pro Asp
105                 110                 115                 120 cgc gac tgc agc gcg ggc gag agc gcg ggc gag ctc agc agc gac aag    618
Arg Asp Cys Ser Ala Gly Glu Ser Ala Gly Glu Leu Ser Ser Asp Lys
                125                 130                 135 aac ggg ctc gag atc tac aag act gag ttc gtc aag ccc ttc gcc gac    666
Asn Gly Leu Glu Ile Tyr Lys Thr Glu Phe Val Lys Pro Phe Ala Asp
            140                 145                 150 aag gtg gcg gcc gca aag gac ctc gac ttc gcc atc gtc ctg gag ccc    714
Lys Val Ala Ala Ala Lys Asp Leu Asp Phe Ala Ile Val Leu Glu Pro
        155                 160                 165 gac tcg ctg gcc aac ctg gtc acc aac ctg ggc atc gag ttc tgc gcc    762
Asp Ser Leu Ala Asn Leu Val Thr Asn Leu Gly Ile Glu Phe Cys Ala
    170                 175                 180 aac gcc gcc ccc gtc tac cgc gag ggc atc gcc tat gcc atc tcc agc    810
Asn Ala Ala Pro Val Tyr Arg Glu Gly Ile Ala Tyr Ala Ile Ser Ser
185                 190                 195                 200 ctt cag cag cca aac gtg cac ttg tac atc gat gct gcc cac ggc ggc    858
Leu Gln Gln Pro Asn Val His Leu Tyr Ile Asp Ala Ala His Gly Gly
                205                 210                 215 tgg ctc ggc tgg gac gac aac ctg ccg ctg gcc gcc aag gag ttt gcc    906
Trp Leu Gly Trp Asp Asp Asn Leu Pro Leu Ala Ala Lys Glu Phe Ala
```

-continued

```
            220                 225                 230 gag gtg gtc aag ctt gcc ggc gag ggc aag aag atc cgc ggc ttc gtc      954
Glu Val Val Lys Leu Ala Gly Glu Gly Lys Lys Ile Arg Gly Phe Val
        235                 240                 245 acc aac gtg tcc aac tac aac ccc ttc cac gcc gtc gtg cgc gag aac     1002
Thr Asn Val Ser Asn Tyr Asn Pro Phe His Ala Val Val Arg Glu Asn
    250                 255                 260 ttt acc gag tgg agc aac tcg tgg gac gag tct cac tac gcc tcc tcg     1050
Phe Thr Glu Trp Ser Asn Ser Trp Asp Glu Ser His Tyr Ala Ser Ser
265                 270                 275                 280 ctc aca ccg ttc ctc gag aaa gag ggg ctg ccg gca cgc ttc atc gtc     1098
Leu Thr Pro Phe Leu Glu Lys Glu Gly Leu Pro Ala Arg Phe Ile Val
                285                 290                 295 gac cag ggt cgc gtt gcc ctc ccg gga gcc cgc aag gag tg              1139
Asp Gln Gly Arg Val Ala Leu Pro Gly Ala Arg Lys Glu Trp
            300                 305 gtgagtttcg accagattga ccctcgaccc atgcgaccga gattgctgac gattgaattg   1199
cgtgtcccgt cccccag g ggt gaa tgg tgc aac gtg gca ccc gcc gga ttt    1250
                     Gly Glu Trp Cys Asn Val Ala Pro Ala Gly Phe
                                     315                 320 ggc ccc gcg ccc acg acc agg gtc aac aac acc gtc gtc gat gct ctc     1298
Gly Pro Ala Pro Thr Thr Arg Val Asn Asn Thr Val Val Asp Ala Leu
            325                 330                 335 gtc tgg gtc aag cct ggc ggc gag agc gac ggc gag tgt ggc ttg gct     1346
Val Trp Val Lys Pro Gly Gly Glu Ser Asp Gly Glu Cys Gly Leu Ala
        340                 345                 350 ggc gcc ccc aag gcc ggc cag tgg ttc gac gag tac gcc cag atg ctg     1394
Gly Ala Pro Lys Ala Gly Gln Trp Phe Asp Glu Tyr Ala Gln Met Leu
    355                 360                 365 gtc gag aat gcc cac ccg tct gtc gtc cac aag tgg tagataaatt          1440
Val Glu Asn Ala His Pro Ser Val Val His Lys Trp
370                 375                 380 ttggagtccg agaagggtcc cagatagact tttgttttaa aacaaaatgc aaggtgtcga   1500
cagatactgg cttaacatta accaagcacc atgaacatga cttgtcaaca tattgataca   1560
ttccgctgct ttcccatacg tgctctcagg tctcagggat caaatggata ggtcggtaat   1620
gcaaaacgat ccattggata tccagaagag agaaaaaa                           1658

<210> SEQ ID NO 23
<211> LENGTH: 381
<212> TYPE: PRT
<213> ORGANISM: Chrysosporium lucknowense

<400> SEQUENCE: 23

Met Arg Val Ser Ser Leu Val Ala Ala Leu Ala Thr Gly Gly Leu Val
1               5                   10                  15

Ala Ala Thr Pro Lys Pro Lys Gly Ser Ser Pro Pro Gly Ala Val Asp
            20                  25                  30

Ala Asn Pro Phe Lys Gly Lys Thr Gln Phe Val Asn Pro Ala Trp Ala
        35                  40                  45

Ala Lys Leu Glu Gln Thr Lys Lys Ala Phe Leu Ala Arg Asn Asp Thr
    50                  55                  60

Val Asn Ala Ala Lys Thr Glu Lys Val Gln Gln Thr Ser Ser Phe Val
65                  70                  75                  80

Trp Val Ser Arg Ile Ala Glu Leu Ser Asn Ile Asp Asp Ala Ile Ala
                85                  90                  95

Ala Ala Arg Lys Ala Gln Lys Lys Thr Gly Arg Arg Gln Ile Val Gly
            100                 105                 110
```

```
Leu Val Leu Tyr Asn Leu Pro Asp Arg Asp Cys Ser Ala Gly Glu Ser
            115                 120                 125

Ala Gly Glu Leu Ser Ser Asp Lys Asn Gly Leu Glu Ile Tyr Lys Thr
        130                 135                 140

Glu Phe Val Lys Pro Phe Ala Asp Lys Val Ala Ala Lys Asp Leu
145                 150                 155                 160

Asp Phe Ala Ile Val Leu Glu Pro Asp Ser Leu Ala Asn Leu Val Thr
                165                 170                 175

Asn Leu Gly Ile Glu Phe Cys Ala Asn Ala Ala Pro Val Tyr Arg Glu
            180                 185                 190

Gly Ile Ala Tyr Ala Ile Ser Ser Leu Gln Gln Pro Asn Val His Leu
        195                 200                 205

Tyr Ile Asp Ala Ala His Gly Gly Trp Leu Gly Trp Asp Asp Asn Leu
    210                 215                 220

Pro Leu Ala Ala Lys Glu Phe Ala Glu Val Val Lys Leu Ala Gly Glu
225                 230                 235                 240

Gly Lys Lys Ile Arg Gly Phe Val Thr Asn Val Ser Asn Tyr Asn Pro
            245                 250                 255

Phe His Ala Val Val Arg Glu Asn Phe Thr Glu Trp Ser Asn Ser Trp
        260                 265                 270

Asp Glu Ser His Tyr Ala Ser Ser Leu Thr Pro Phe Leu Glu Lys Glu
    275                 280                 285

Gly Leu Pro Ala Arg Phe Ile Val Asp Gln Gly Arg Val Ala Leu Pro
290                 295                 300

Gly Ala Arg Lys Glu Trp Gly Glu Trp Cys Asn Val Ala Pro Ala Gly
305                 310                 315                 320

Phe Gly Pro Ala Pro Thr Thr Arg Val Asn Asn Thr Val Val Asp Ala
            325                 330                 335

Leu Val Trp Val Lys Pro Gly Gly Glu Ser Asp Gly Glu Cys Gly Leu
        340                 345                 350

Ala Gly Ala Pro Lys Ala Gly Gln Trp Phe Asp Glu Tyr Ala Gln Met
    355                 360                 365

Leu Val Glu Asn Ala His Pro Ser Val Val His Lys Trp
370                 375                 380

<210> SEQ ID NO 24
<211> LENGTH: 1143
<212> TYPE: DNA
<213> ORGANISM: Chrysosporium lucknowense

<400> SEQUENCE: 24
atgcgcgtct ctagtttggt cgcggcccct tgctaccggtg gtcttgtcgc cgccacgcct      60
aagcccaagg ggtcgtcgcc cctgggggcc gtggacgcga accctttcaa gggcaagacg     120
cagttcgtca acccggcatg gcggccaag ctggaacaga ccaaaaaggc gttcctggcc     180
aggaacgaca ccgtcaatgc cgccaagacg gagaaggtcc agcagaccag ctcgttcgtc     240
tgggtctcga ggatcgccga gctctccaac atcgacgacg ccatcgcggc tgcccgcaag     300
gcgcagaaga agacgggcag gaggcagatc gtcggcctgg tgctctacaa ccttccggac     360
cgcgactgca gcgcgggcga gagcgcgggc gagctcagca gcgacaagaa cgggctcgag     420
atctacaaga ctgagttcgt caagcccttc gccgacaagg tggcggccgc aaaggacctc     480
gacttcgcca tcgtcctgga gcccgactcg ctggccaacc tggtcaccaa cctgggcatc     540
gagttctgcg ccaacgccgc ccccgtctac cgcgagggca tcgcctatgc catctccagc     600
```

-continued

```
cttcagcagc caaacgtgca cttgtacatc gatgctgccc acggcggctg gctcggctgg     660
gacgacaacc tgccgctggc cgccaaggag tttgccgagg tggtcaagct tgccggcgag     720
ggcaagaaga tccgcggctt cgtcaccaac gtgtccaact acaaccccct ccacgccgtc     780
gtgcgcgaga actttaccga gtggagcaac tcgtgggacg agtctcacta cgcctcctcg     840
ctcacaccgt tcctcgagaa agaggggctg ccggcacgct tcatcgtcga ccagggtcgc     900
gttgccctcc cgggagcccg caaggagtgg ggtgaatggt gcaacgtggc acccgccgga     960
tttggccccg cgcccacgac cagggtcaac aacaccgtcg tcgatgctct cgtctgggtc    1020
aagcctggcg gcgagagcga cggcgagtgt ggcttggctg gcgccccaa ggccggccag     1080 tggttcgacg agtacgccca gatgctggtc gagaatgccc acccgtctgt cgtccacaag    1140
tgg                                                                  1143
```

<210> SEQ ID NO 25
<211> LENGTH: 1683
<212> TYPE: DNA
<213> ORGANISM: Chrysosporium lucknowense
<220> FEATURE:
<221> NAME/KEY: CDS
<222> LOCATION: (76)..(148)
<220> FEATURE:
<221> NAME/KEY: CDS
<222> LOCATION: (223)..(286)
<220> FEATURE:
<221> NAME/KEY: CDS
<222> LOCATION: (438)..(700)
<220> FEATURE:
<221> NAME/KEY: CDS
<222> LOCATION: (780)..(1531)

<400> SEQUENCE: 25

```
atctgccggt tgcccacgtc gccgtcgact gcttgtccgc ttcctacctg cagcctcttt      60
cagagaccat caaac atg cgt act ctt acg ttc gtg ctg gca gcc gcc ccg     111
                 Met Arg Thr Leu Thr Phe Val Leu Ala Ala Ala Pro
                  1               5                  10 gtg gct gtg ctt gcc caa tct cct ctg tgg ggc cag t gtatgtaatt         158
Val Ala Val Leu Ala Gln Ser Pro Leu Trp Gly Gln
        15                  20 gccttactcg gaaatagtc accactagag ggacttaagc tcactacttc ctgtttcaca     218 atag gc  ggc ggt caa ggc tgg aca ggt ccc acg acc tgc gtt tct ggc     266
     Cys Gly Gly Gln Gly Trp Thr Gly Pro Thr Thr Cys Val Ser Gly
                    30                  35 gca gta tgc caa ttc gtc aa  gtcagtaact gcttttattt cttttctctc        316
Ala Val Cys Gln Phe Val Asn
40                  45 tgggattacg atttcgtttt gcacttagct tggttctgca tttcattgtt gtattgttct     376 cttttgtgt gtgagaggtt ttattaccac ctaaaggcca tttgctaaca aatctcccca      436 g t gac tgg tac tcc caa tgc gtg ccc gga tcg agc aac cct cct acg       483
  Asp Trp Tyr Ser Gln Cys Val Pro Gly Ser Ser Asn Pro Pro Thr
           50                  55                  60 ggc acc acc agc agc acc act gga agc acc ccg gct cct act ggc ggc       531
Gly Thr Thr Ser Ser Thr Thr Gly Ser Thr Pro Ala Pro Thr Gly Gly
            65                  70                  75 ggc ggc agc gga acc ggc ctc cac gac aaa ttc aag gcc aag ggc aag       579
Gly Gly Ser Gly Thr Gly Leu His Asp Lys Phe Lys Ala Lys Gly Lys
        80                  85                  90 ctc tac ttc gga acc gag atc gat cac tac cat ctc aac aac aat gcc       627
Leu Tyr Phe Gly Thr Glu Ile Asp His Tyr His Leu Asn Asn Asn Ala
    95                  100                 105
```

```
ttg acc aac att gtc aag aaa gac ttt ggt caa gtc act cac gag aac      675
Leu Thr Asn Ile Val Lys Lys Asp Phe Gly Gln Val Thr His Glu Asn
110                 115                 120                 125 agc ttg aag tgg gat gct act gag c gtgagtgacc tctcctcctt               720
Ser Leu Lys Trp Asp Ala Thr Glu
                130 ctcccgaaca ataatagata attacgagcc ggttcgaggc tgacattgcg cgattctag      779 cg agc cgc aat caa ttc aac ttt gcc aac gcc gac gcg gtt gtc aac        826
   Pro Ser Arg Asn Gln Phe Asn Phe Ala Asn Ala Asp Ala Val Val Asn
       135                 140                 145 ttt gcc cag gcc aac ggc aag ctc atc cgc ggc cac acc ctc ctc tgg       874
Phe Ala Gln Ala Asn Gly Lys Leu Ile Arg Gly His Thr Leu Leu Trp
150                 155                 160                 165 cac tct cag ctg ccg cag tgg gtg cag aac atc aac gac cgc aac acc       922
His Ser Gln Leu Pro Gln Trp Val Gln Asn Ile Asn Asp Arg Asn Thr
                170                 175                 180 ttg acc cag gtc atc gag aac cac gtc acc acc ctt gtc act cgc tac       970
Leu Thr Gln Val Ile Glu Asn His Val Thr Thr Leu Val Thr Arg Tyr
                185                 190                 195 aag ggc aag atc ctc cac tgg gac gtc gtt aac gag atc ttt gcc gag      1018
Lys Gly Lys Ile Leu His Trp Asp Val Val Asn Glu Ile Phe Ala Glu
                200                 205                 210 gac ggc tcg ctc cgc gac agc gtc ttc agc cgc gtc ctc ggc gag gac      1066
Asp Gly Ser Leu Arg Asp Ser Val Phe Ser Arg Val Leu Gly Glu Asp
                215                 220                 225 ttt gtc ggc atc gcc ttc cgc gcc gcc cgc gcc gcc gat ccc aac gcc      1114
Phe Val Gly Ile Ala Phe Arg Ala Ala Arg Ala Ala Asp Pro Asn Ala
230                 235                 240                 245 aag ctc tac atc aac gac tac aac ctc gac att gcc aac tac gcc aag      1162
Lys Leu Tyr Ile Asn Asp Tyr Asn Leu Asp Ile Ala Asn Tyr Ala Lys
                250                 255                 260 gtg acc cgg ggc atg gtc gag aag gtc aac aag tgg atc gcc cag ggc      1210
Val Thr Arg Gly Met Val Glu Lys Val Asn Lys Trp Ile Ala Gln Gly
                265                 270                 275 atc ccg atc gac ggc atc ggc acc cag tgc cac ctg gcc ggg ccc ggc      1258
Ile Pro Ile Asp Gly Ile Gly Thr Gln Cys His Leu Ala Gly Pro Gly
                280                 285                 290 ggg tgg aac acg gcc gcc ggc gtc ccc gac gcc ctc aag gcc ctc gcc      1306
Gly Trp Asn Thr Ala Ala Gly Val Pro Asp Ala Leu Lys Ala Leu Ala
295                 300                 305 gcg gcc aac gtc aag gag atc gcc atc acc gag ctc gac atc gcc ggc      1354
Ala Ala Asn Val Lys Glu Ile Ala Ile Thr Glu Leu Asp Ile Ala Gly
310                 315                 320                 325 gcc tcc gcc aac gac tac ctc acc gtc atg aac gcc tgc ctc cag gtc      1402
Ala Ser Ala Asn Asp Tyr Leu Thr Val Met Asn Ala Cys Leu Gln Val
                330                 335                 340 tcc aag tgc gtc ggc atc acc gtc tgg ggc gtc tct gac aag gac agc      1450
Ser Lys Cys Val Gly Ile Thr Val Trp Gly Val Ser Asp Lys Asp Ser
                345                 350                 355 tgg agg tcg agc agc aac ccg ctc ctc ttc gac agc aac tac cag cca      1498
Trp Arg Ser Ser Ser Asn Pro Leu Leu Phe Asp Ser Asn Tyr Gln Pro
                360                 365                 370 aag gcg gca tac aat gct ctg att aat gcc ttg taagaggagg tatattattt    1551
Lys Ala Ala Tyr Asn Ala Leu Ile Asn Ala Leu
375                 380 ttagaggcaa tgaagctagg aggaaagagg ggaagtgagg taattagcta ggacaggcaa    1611
atctagcagc aattataagt caacactata taaatattc ctataatggc ttgtgcttcg     1671
gtgtgcaaaa aa                                                        1683
```

<210> SEQ ID NO 26
<211> LENGTH: 384
<212> TYPE: PRT
<213> ORGANISM: Chrysosporium lucknowense

<400> SEQUENCE: 26

```
Met Arg Thr Leu Thr Phe Val Leu Ala Ala Ala Pro Val Ala Val Leu
1               5                   10                  15

Ala Gln Ser Pro Leu Trp Gly Gln Cys Gly Gly Gln Gly Trp Thr Gly
            20                  25                  30

Pro Thr Thr Cys Val Ser Gly Ala Val Cys Gln Phe Val Asn Asp Trp
        35                  40                  45

Tyr Ser Gln Cys Val Pro Gly Ser Ser Asn Pro Pro Thr Gly Thr Thr
    50                  55                  60

Ser Ser Thr Thr Gly Ser Thr Pro Ala Pro Thr Gly Gly Gly Gly Ser
65                  70                  75                  80

Gly Thr Gly Leu His Asp Lys Phe Lys Ala Lys Gly Lys Leu Tyr Phe
                85                  90                  95

Gly Thr Glu Ile Asp His Tyr His Leu Asn Asn Asn Ala Leu Thr Asn
            100                 105                 110

Ile Val Lys Lys Asp Phe Gly Gln Val Thr His Glu Asn Ser Leu Lys
        115                 120                 125

Trp Asp Ala Thr Glu Pro Ser Arg Asn Gln Phe Asn Phe Ala Asn Ala
    130                 135                 140

Asp Ala Val Val Asn Phe Ala Gln Ala Asn Gly Lys Leu Ile Arg Gly
145                 150                 155                 160

His Thr Leu Leu Trp His Ser Gln Leu Pro Gln Trp Val Gln Asn Ile
                165                 170                 175

Asn Asp Arg Asn Thr Leu Thr Gln Val Ile Glu Asn His Val Thr Thr
            180                 185                 190

Leu Val Thr Arg Tyr Lys Gly Lys Ile Leu His Trp Asp Val Val Asn
        195                 200                 205

Glu Ile Phe Ala Glu Asp Gly Ser Leu Arg Asp Ser Val Phe Ser Arg
    210                 215                 220

Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
                245                 250                 255

Ala Asn Tyr Ala Lys Val Thr Arg Gly Met Val Glu Lys Val Asn Lys
            260                 265                 270

Trp Ile Ala Gln Gly Ile Pro Ile Asp Gly Ile Gly Thr Gln Cys His
        275                 280                 285

Leu Ala Gly Pro Gly Gly Trp Asn Thr Ala Ala Gly Val Pro Asp Ala
    290                 295                 300

Leu Lys Ala Leu Ala Ala Ala Asn Val Lys Glu Ile Ala Ile Thr Glu
305                 310                 315                 320

Leu Asp Ile Ala Gly Ala Ser Ala Asn Asp Tyr Leu Thr Val Met Asn
                325                 330                 335

Ala Cys Leu Gln Val Ser Lys Cys Val Gly Ile Thr Val Trp Gly Val
            340                 345                 350

Ser Asp Lys Asp Ser Trp Arg Ser Ser Ser Asn Pro Leu Leu Phe Asp
        355                 360                 365

Ser Asn Tyr Gln Pro Lys Ala Ala Tyr Asn Ala Leu Ile Asn Ala Leu
    370                 375                 380
```

<210> SEQ ID NO 27
<211> LENGTH: 1152
<212> TYPE: DNA
<213> ORGANISM: Chrysosporium lucknowense

<400> SEQUENCE: 27

```
atgcgtactc ttacgttcgt gctggcagcc gccccggtgg ctgtgcttgc ccaatctcct     60
ctgtggggcc agtgcggcgg tcaaggctgg acaggtccca cgacctgcgt ttctggcgca    120
gtatgccaat tcgtcaatga ctggtactcc caatgcgtgc ccggatcgag caaccctcct    180
acgggcacca ccagcagcac cactggaagc accccggctc ctactggcgg cggcggcagc    240
ggaaccggcc tccacgacaa attcaaggcc aagggcaagc tctacttcgg aaccgagatc    300
gatcactacc atctcaacaa caatgccttg accaacattg tcaagaaaga ctttggtcaa    360
gtcactcacg agaacagctt gaagtgggat gctactgagc cgagccgcaa tcaattcaac    420
tttgccaacg ccgacgcggt tgtcaacttt gcccaggcca acggcaagct catccgcggc    480
cacaccctcc tctggcactc tcagctgccg cagtgggtgc agaacatcaa cgaccgcaac    540
accttgaccc aggtcatcga gaaccacgtc accaccctt g tcactcgcta caagggcaag    600
atcctccact gggacgtcgt taacgagatc tttgccgagg acggctcgct ccgcgacagc    660
gtcttcagcc gcgtcctcgg cgaggacttt gtcggcatcg ccttccgcgc cgcccgcgcc    720
gccgatccca cgccaagct c tacatcaac gactacaacc tcgacattgc caactacgcc    780
aaggtgaccc ggggcatggt cgagaaggtc aacaagtgga tcgcccaggg catcccgatc    840
gacggcatcg gcacccagtg ccacctggcc gggcccggcg ggtggaacac ggccgccggc    900
gtccccgacg ccctcaaggc cctcgccgcg ccaacgtca aggagatcgc catcaccgag    960
ctcgacatcg ccggcgcctc cgccaacgac tacctcaccg tcatgaacgc ctgcctccag   1020
gtctccaagt gcgtcggcat caccgtctgg ggcgtctctg acaaggacag ctggaggtcg   1080
agcagcaacc cgctcctctt cgacagcaac taccagccaa aggcggcata caatgctctg   1140
attaatgcct tg                                                       1152
```

<210> SEQ ID NO 28
<211> LENGTH: 1194
<212> TYPE: DNA
<213> ORGANISM: Chrysosporium lucknowense
<220> FEATURE:
<221> NAME/KEY: CDS
<222> LOCATION: (76)..(367)
<220> FEATURE:
<221> NAME/KEY: CDS
<222> LOCATION: (480)..(850)

<400> SEQUENCE: 28

```
atgaatcaga agacgacact gggcaactaa acagcttgca gcagagtttt gtgccttgca     60
taggccctcg atatc atg gtc tcg ttc act ctc ctc ctc acg gtc atc gcc    111
                Met Val Ser Phe Thr Leu Leu Leu Thr Val Ile Ala
                 1               5                  10 gct gcg gtg acg acg gcc agc cct ctc gag gtg gtc aag cgc ggc atc    159
Ala Ala Val Thr Thr Ala Ser Pro Leu Glu Val Val Lys Arg Gly Ile
         15                  20                  25 cag ccg ggc acg ggc acc cac gag ggg tac ttc tac tcg ttc tgg acc    207
Gln Pro Gly Thr Gly Thr His Glu Gly Tyr Phe Tyr Ser Phe Trp Thr
     30                  35                  40 gac ggc cgt ggc tcg gtc gac ttc aac ccc ggg ccc cgc ggc tcg tac    255
Asp Gly Arg Gly Ser Val Asp Phe Asn Pro Gly Pro Arg Gly Ser Tyr
 45                  50                  55                  60
```

-continued

```
agc gtc acc tgg aac aac gtc aac aac tgg gtt ggc ggc aag ggc tgg      303
Ser Val Thr Trp Asn Asn Val Asn Asn Trp Val Gly Gly Lys Gly Trp
                65                  70                  75 aac ccg ggc ccg ccg cgc aag att gcg tac aac ggc acc tgg aac aac      351
Asn Pro Gly Pro Pro Arg Lys Ile Ala Tyr Asn Gly Thr Trp Asn Asn
            80                  85                  90 tac aac gtg aac agc t gtgcgttgtc ctcctctttc tccctttcgc ttgttttcct    407
Tyr Asn Val Asn Ser
        95 tgatgattgg gatccatttt aaaagagaag gaaaaaaaaa acaaaggaaa atagaagata    467 actaacgcca ag ct  ctg gca gac ctc gcc ctg tac ggc tgg act cgc aac    517
              Ser Leu Ala Asp Leu Ala Leu Tyr Gly Trp Thr Arg Asn
                      100                 105                 110 ccg ctg gtc gag tat tac atc gtg gag gca tac ggc acg tac aac ccc      565
Pro Leu Val Glu Tyr Tyr Ile Val Glu Ala Tyr Gly Thr Tyr Asn Pro
                115                 120                 125 tcg tcg ggc acg gcg cgg ctg ggc acc atc gag gac gac ggc ggc gtg      613
Ser Ser Gly Thr Ala Arg Leu Gly Thr Ile Glu Asp Asp Gly Gly Val
            130                 135                 140 tac gac atc tac aag acg acg cgg tac aac cag ccg tcc atc gag ggg      661
Tyr Asp Ile Tyr Lys Thr Thr Arg Tyr Asn Gln Pro Ser Ile Glu Gly
        145                 150                 155 acc tcc acc ttc gac cag tac tgg tcc gtc cgc cgc cag aag cgc gtc      709
Thr Ser Thr Phe Asp Gln Tyr Trp Ser Val Arg Arg Gln Lys Arg Val
    160                 165                 170 ggc ggc act atc gac acg ggc aag cac ttt gac gag tgg aag cgc cag      757
Gly Gly Thr Ile Asp Thr Gly Lys His Phe Asp Glu Trp Lys Arg Gln
175                 180                 185                 190 ggc aac ctc cag ctc ggc acc tgg aac tac atg atc atg gcc acc gag      805
Gly Asn Leu Gln Leu Gly Thr Trp Asn Tyr Met Ile Met Ala Thr Glu
                195                 200                 205 ggc tac cag agc tct ggt tcg gcc act atc gag gtc cgg gag gcc          850
Gly Tyr Gln Ser Ser Gly Ser Ala Thr Ile Glu Val Arg Glu Ala
            210                 215                 220 taaagaagcc aggcgccttt cttttgtttt gcaggagggg gtagaggggg ggggggaggg    910
aaaacgaaaa gtagcagggt ggttttatgc cggcagccgt gggccattcg agtgcaacct    970
gtatctctct ctctcccaag tctccgggct ccttctcaga gaacttcaat atgtctgggg   1030
acaaaccacc ttgtgaaata caacggtaat tatctaagtt tgagtgccct atcgtatgct   1090
tctgaaaatt tcctgctcct tgatacaagt cggtttgagc cgagccaatg agactgtgtc   1150
gattgataga ggccctgaag gatcaagcgc gatgcaacaa ttaa                    1194

<210> SEQ ID NO 29
<211> LENGTH: 221
<212> TYPE: PRT
<213> ORGANISM: Chrysosporium lucknowense

<400> SEQUENCE: 29

Met Val Ser Phe Thr Leu Leu Leu Thr Val Ile Ala Ala Ala Val Thr
1               5                   10                  15

Thr Ala Ser Pro Leu Glu Val Val Lys Arg Gly Ile Gln Pro Gly Thr
            20                  25                  30

Gly Thr His Glu Gly Tyr Phe Tyr Ser Phe Trp Thr Asp Gly Arg Gly
        35                  40                  45

Ser Val Asp Phe Asn Pro Gly Pro Arg Gly Ser Tyr Ser Val Thr Trp
    50                  55                  60

Asn Asn Val Asn Asn Trp Val Gly Gly Lys Gly Trp Asn Pro Gly Pro
65                  70                  75                  80
```

```
Pro Arg Lys Ile Ala Tyr Asn Gly Thr Trp Asn Asn Tyr Asn Val Asn
                85                  90                  95

Ser Ser Leu Ala Asp Leu Ala Leu Tyr Gly Trp Thr Arg Asn Pro Leu
            100                 105                 110

Val Glu Tyr Tyr Ile Val Glu Ala Tyr Gly Thr Tyr Asn Pro Ser Ser
        115                 120                 125

Gly Thr Ala Arg Leu Gly Thr Ile Glu Asp Asp Gly Gly Val Tyr Asp
    130                 135                 140

Ile Tyr Lys Thr Thr Arg Tyr Asn Gln Pro Ser Ile Glu Gly Thr Ser
145                 150                 155                 160

Thr Phe Asp Gln Tyr Trp Ser Val Arg Arg Gln Lys Arg Val Gly Gly
                165                 170                 175

Thr Ile Asp Thr Gly Lys His Phe Asp Glu Trp Lys Arg Gln Gly Asn
            180                 185                 190

Leu Gln Leu Gly Thr Trp Asn Tyr Met Ile Met Ala Thr Glu Gly Tyr
        195                 200                 205

Gln Ser Ser Gly Ser Ala Thr Ile Glu Val Arg Glu Ala
    210                 215                 220

<210> SEQ ID NO 30
<211> LENGTH: 663
<212> TYPE: DNA
<213> ORGANISM: Chrysosporium lucknowense

<400> SEQUENCE: 30
atggtctcgt tcactctcct cctcacggtc atcgccgctg cggtgacgac ggccagccct     60
ctcgaggtgg tcaagcgcgg catccagccg ggcacgggca cccacagggg gtacttctac    120
tcgttctgga ccgacggccg tgctcggtc gacttcaacc ccgggccccg cggctcgtac    180
agcgtcacct ggaacaacgt caacaactgg gttgcggca agggctggaa cccgggcccg    240
ccgcgcaaga ttgcgtacaa cggcacctgg aacaactaca acgtgaacag ctctctggca    300
gacctcgccc tgtacggctg gactcgcaac ccgctggtcg agtattacat cgtggaggca    360
tacggcacgt acaaccccctc gtcgggcacg gcgcggctgg gcaccatcga ggacgacggc    420
ggcgtgtacg acatctacaa gacgacgcgg tacaaccagc cgtccatcga ggggacctcc    480
accttcgacc agtactggtc cgtccgccgc cagaagcgcg tcggcggcac tatcgacacg    540
ggcaagcact tgacgagtg gaagcgccag ggcaacctcc agctcggcac ctggaactac    600
atgatcatgg ccaccgaggg ctaccagagc tctggttcgg ccactatcga ggtccgggag    660
gcc                                                                 663

<210> SEQ ID NO 31
<211> LENGTH: 1598
<212> TYPE: DNA
<213> ORGANISM: Chrysosporium lucknowense
<220> FEATURE:
<221> NAME/KEY: CDS
<222> LOCATION: (69)..(398)
<220> FEATURE:
<221> NAME/KEY: CDS
<222> LOCATION: (467)..(1375)

<400> SEQUENCE: 31
tggctctcca acaccccctgc ccctcagcct ccgctcgtc agtgttgtat cctcttctgg     60 ccggtatc atg cac tcc aaa gct ttc ttg gca gcg ctt ctt gcg cct gcc    110
         Met His Ser Lys Ala Phe Leu Ala Ala Leu Leu Ala Pro Ala
         1               5                   10
```

```
gtc tca ggg caa ctg aac gac ctc gcc gtc agg gct gga ctc aag tac      158
Val Ser Gly Gln Leu Asn Asp Leu Ala Val Arg Ala Gly Leu Lys Tyr
 15              20                  25                  30 ttt ggt act gct ctt agc gag agc gtc atc aac agt gat act cgg tat      206
Phe Gly Thr Ala Leu Ser Glu Ser Val Ile Asn Ser Asp Thr Arg Tyr
                 35                  40                  45 gct gcc atc ctc agc gac aag agc atg ttc ggc cag ctc gtc ccc gag      254
Ala Ala Ile Leu Ser Asp Lys Ser Met Phe Gly Gln Leu Val Pro Glu
                     50                  55                  60 aat ggc atg aag tgg gat gct act gag ccg tcc cgt ggc cag ttc aac      302
Asn Gly Met Lys Trp Asp Ala Thr Glu Pro Ser Arg Gly Gln Phe Asn
                 65                  70                  75 tac gcc tcg ggc gac atc acg gcc aac acg gcc aag aag aat ggc cag      350
Tyr Ala Ser Gly Asp Ile Thr Ala Asn Thr Ala Lys Lys Asn Gly Gln
     80                  85                  90 ggc atg cgt tgc cac acc atg gtc tgg tac agc cag ctc ccg agc tgg      398
Gly Met Arg Cys His Thr Met Val Trp Tyr Ser Gln Leu Pro Ser Trp
 95                 100                 105                 110 gtgagtgcag ccccctcat cacatccacc agtctgcagt catactcacg agtataataa     458 caccgcag gtc tcc tcg ggc tcg tgg acc agg gac tcg ctc acc tcg gtc     508
         Val Ser Ser Gly Ser Trp Thr Arg Asp Ser Leu Thr Ser Val
                         115                 120 atc gag acg cac atg aac aac gtc atg ggc cac tac aag ggc caa tgc      556
Ile Glu Thr His Met Asn Asn Val Met Gly His Tyr Lys Gly Gln Cys
125                 130                 135                 140 tac gcc tgg gat gtc atc aac gag gcc atc aat gac gac ggc aac tcc      604
Tyr Ala Trp Asp Val Ile Asn Glu Ala Ile Asn Asp Asp Gly Asn Ser
                 145                 150                 155 tgg cgc gac aac gtc ttt ctc cgg acc ttt ggg acc gac tac ttc gcc      652
Trp Arg Asp Asn Val Phe Leu Arg Thr Phe Gly Thr Asp Tyr Phe Ala
             160                 165                 170 ctg tcc ttc aac cta gcc aag aag gcc gat ccc gat acc aag ctg tac      700
Leu Ser Phe Asn Leu Ala Lys Lys Ala Asp Pro Asp Thr Lys Leu Tyr
         175                 180                 185 tac aac gac tac aac ctc gag tac aac cag gcc aag acg gac cgc gct      748
Tyr Asn Asp Tyr Asn Leu Glu Tyr Asn Gln Ala Lys Thr Asp Arg Ala
     190                 195                 200 gtt gag ctc gtc aag atg gtc cag gcc gcc ggc gcg ccc atc gac ggt      796
Val Glu Leu Val Lys Met Val Gln Ala Ala Gly Ala Pro Ile Asp Gly
205                 210                 215                 220 gtc ggc ttc cag ggc cac ctc att gtc ggc tcg acc ccg acg cgc tcg      844
Val Gly Phe Gln Gly His Leu Ile Val Gly Ser Thr Pro Thr Arg Ser
                 225                 230                 235 cag ctg gcc acc gcc ctc cag cgc ttc acc gcg ctc ggc ctc gag gtc      892
Gln Leu Ala Thr Ala Leu Gln Arg Phe Thr Ala Leu Gly Leu Glu Val
             240                 245                 250 gcc tac acc gag ctc gac atc cgc cac tcg agc ctg ccg gcc tct tcg      940
Ala Tyr Thr Glu Leu Asp Ile Arg His Ser Ser Leu Pro Ala Ser Ser
         255                 260                 265 tcg gcg ctc gcg acc cag ggc aac gac ttc gcc aac gtg gtc ggc tct      988
Ser Ala Leu Ala Thr Gln Gly Asn Asp Phe Ala Asn Val Val Gly Ser
     270                 275                 280 tgc ctc gac acc gcc ggc tgc gtc ggc gtc acc gtc tgg ggc ttc acc     1036
Cys Leu Asp Thr Ala Gly Cys Val Gly Val Thr Val Trp Gly Phe Thr
285                 290                 295                 300 gat gcg cac tcg tgg atc ccg aac acg ttc ccc ggc cag ggc gac gcc     1084
Asp Ala His Ser Trp Ile Pro Asn Thr Phe Pro Gly Gln Gly Asp Ala
                 305                 310                 315 ctg atc tac gac agc aac tac aac aag aag ccc gcg tgg acc tcg atc     1132
Leu Ile Tyr Asp Ser Asn Tyr Asn Lys Lys Pro Ala Trp Thr Ser Ile
```

```
            320                 325                 330 tcg tcc gtc ctg gcc gcc aag gcc acc ggc gcc ccg ccc gcc tcg tcc      1180
Ser Ser Val Leu Ala Ala Lys Ala Thr Gly Ala Pro Pro Ala Ser Ser
        335                 340                 345 tcc acc acc ctc gtc acc atc acc acc cct ccg ccg gca tcc acc acc      1228
Ser Thr Thr Leu Val Thr Ile Thr Thr Pro Pro Pro Ala Ser Thr Thr
    350                 355                 360 gcc tcc tcc tcc tcc agt gcc acg ccc acg agc gtc ccg acg cag acg      1276
Ala Ser Ser Ser Ser Ser Ala Thr Pro Thr Ser Val Pro Thr Gln Thr
365                 370                 375                 380 agg tgg gga cag tgc ggc ggc atc gga tgg acg ggg ccg acc cag tgc      1324
Arg Trp Gly Gln Cys Gly Gly Ile Gly Trp Thr Gly Pro Thr Gln Cys
                385                 390                 395 gag agc cca tgg acc tgc cag aag ctg aac gac tgg tac tgg cag tgc      1372
Glu Ser Pro Trp Thr Cys Gln Lys Leu Asn Asp Trp Tyr Trp Gln Cys
            400                 405                 410 ctg taagggacga ggtcccgctg agggcgagtc ttctggattg ttgaagttgg          1425
Leu cagcataatt tggtgaggtt cctagacaga gaccatcggg ggccgatcca ggaaacactg   1485
gctgcatccg accgggattt tctgacttct tctgcatgta ttgaaggttg tgttgagaac   1545
caactgtaaa taagggacca gcagatcaaa gctggaggtt caagcagaat aaa          1598

<210> SEQ ID NO 32
<211> LENGTH: 413
<212> TYPE: PRT
<213> ORGANISM: Chrysosporium lucknowense
<400> SEQUENCE: 32

Met His Ser Lys Ala Phe Leu Ala Ala Leu Leu Ala Pro Ala Val Ser
1               5                   10                  15

Gly Gln Leu Asn Asp Leu Ala Val Arg Ala Gly Leu Lys Tyr Phe Gly
            20                  25                  30

Thr Ala Leu Ser Glu Ser Val Ile Asn Ser Asp Thr Arg Tyr Ala Ala
        35                  40                  45

Ile Leu Ser Asp Lys Ser Met Phe Gly Gln Leu Val Pro Glu Asn Gly
    50                  55                  60

Met Lys Trp Asp Ala Thr Glu Pro Ser Arg Gly Gln Phe Asn Tyr Ala
65                  70                  75                  80

Ser Gly Asp Ile Thr Ala Asn Thr Ala Lys Lys Asn Gly Gln Gly Met
                85                  90                  95

Arg Cys His Thr Met Val Trp Tyr Ser Gln Leu Pro Ser Trp Val Ser
            100                 105                 110

Ser Gly Ser Trp Thr Arg Asp Ser Leu Thr Ser Val Ile Glu Thr His
        115                 120                 125

Met Asn Asn Val Met Gly His Tyr Lys Gly Gln Cys Tyr Ala Trp Asp
    130                 135                 140

Val Ile Asn Glu Ala Ile Asn Asp Asp Gly Asn Ser Trp Arg Asp Asn
145                 150                 155                 160

Val Phe Leu Arg Thr Phe Gly Thr Asp Tyr Phe Ala Leu Ser Phe Asn
                165                 170                 175

Leu Ala Lys Lys Ala Asp Pro Asp Thr Lys Leu Tyr Tyr Asn Asp Tyr
            180                 185                 190

Asn Leu Glu Tyr Asn Gln Ala Lys Thr Asp Arg Ala Val Glu Leu Val
        195                 200                 205

Lys Met Val Gln Ala Ala Gly Ala Pro Ile Asp Gly Val Gly Phe Gln
    210                 215                 220
```

```
Gly His Leu Ile Val Gly Ser Thr Pro Thr Arg Ser Gln Leu Ala Thr
225                 230                 235                 240

Ala Leu Gln Arg Phe Thr Ala Leu Gly Leu Glu Val Ala Tyr Thr Glu
            245                 250                 255

Leu Asp Ile Arg His Ser Ser Leu Pro Ala Ser Ser Ala Leu Ala
        260                 265                 270

Thr Gln Gly Asn Asp Phe Ala Asn Val Val Gly Ser Cys Leu Asp Thr
        275                 280                 285

Ala Gly Cys Val Gly Val Thr Val Trp Gly Phe Thr Asp Ala His Ser
290                 295                 300

Trp Ile Pro Asn Thr Phe Pro Gly Gln Gly Asp Ala Leu Ile Tyr Asp
305                 310                 315                 320

Ser Asn Tyr Asn Lys Lys Pro Ala Trp Thr Ser Ile Ser Ser Val Leu
            325                 330                 335

Ala Ala Lys Ala Thr Gly Ala Pro Pro Ala Ser Ser Ser Thr Thr Leu
            340                 345                 350

Val Thr Ile Thr Thr Pro Pro Ala Ser Thr Thr Ala Ser Ser Ser
        355                 360                 365

Ser Ser Ala Thr Pro Thr Ser Val Pro Thr Gln Thr Arg Trp Gly Gln
    370                 375                 380

Cys Gly Gly Ile Gly Trp Thr Gly Pro Thr Gln Cys Glu Ser Pro Trp
385                 390                 395                 400

Thr Cys Gln Lys Leu Asn Asp Trp Tyr Trp Gln Cys Leu
            405                 410

<210> SEQ ID NO 33
<211> LENGTH: 1239
<212> TYPE: DNA
<213> ORGANISM: Chrysosporium lucknowense

<400> SEQUENCE: 33
atgcactcca aagctttctt ggcagcgctt cttgcgcctg ccgtctcagg gcaactgaac      60
gacctcgccg tcagggctgg actcaagtac tttggtactg ctcttagcga gagcgtcatc     120
aacagtgata ctcggtatgc tgccatcctc agcgacaaga gcatgttcgg ccagctcgtc     180
cccgagaatg gcatgaagtg ggatgctact gagccgtccc gtggccagtt caactacgcc     240
tcgggcgaca tcacggccaa cacggccaag aagaatggcc agggcatgcg ttgccacacc     300
atggtctggt acagccagct cccgagctgg gtctcctcgg gctcgtggac cagggactcg     360
ctcacctcgg tcatcgagac gcacatgaac aacgtcatgg ccactacaa gggccaatgc     420 tacgcctggg atgtcatcaa cgaggccatc aatgacgacg gcaactcctg cgcgacaaac     480
gtctttctcc ggacctttgg gaccgactac ttcgccctgt ccttcaacct agccaagaag     540
gccgatcccg ataccaagct gtactacaac gactacaacc tcgagtacaa ccaggccaag     600
acggaccgcg ctgttgagct cgtcaagatg gtccaggccg ccgcgcgcc catcgacggt     660 gtcggcttcc agggccacct cattgtcggc tcgaccccga cgcgctcgca gctggccacc     720
gccctccagc gcttcaccgc gctcggcctc gaggtcgcct acaccgagct cgacatccgc     780
cactcgagcc tgccggcctc ttcgtcggcg ctcgcgaccc agggcaacga cttcgccaac     840
gtggtcggct cttgcctcga caccgccggc tgcgtcggcg tcaccgtctg gggcttcacc     900
gatgcgcact cgtggatccc gaacacgttc cccggccagg gcgacgccct gatctacgac     960
agcaactaca acaagaagcc cgcgtggacc tcgatctcgt ccgtcctggc cgccaaggcc    1020
accggcgccc cgcccgcctc gtcctccacc accctcgtca ccatcaccac ccctccgccg    1080
```

```
gcatccacca ccgcctcctc ctcctccagt gccacgccca cgagcgtccc gacgcagacg    1140
aggtggggac agtgcggcgg catcggatgg acggggccga cccagtgcga gagcccatgg    1200
acctgccaga agctgaacga ctggtactgg cagtgcctg                           1239

<210> SEQ ID NO 34
<211> LENGTH: 1664
<212> TYPE: DNA
<213> ORGANISM: Chrysosporium lucknowense
<220> FEATURE:
<221> NAME/KEY: CDS
<222> LOCATION: (136)..(393)
<220> FEATURE:
<221> NAME/KEY: CDS
<222> LOCATION: (496)..(1131)
<220> FEATURE:
<221> NAME/KEY: CDS
<222> LOCATION: (1256)..(1486)

<400> SEQUENCE: 34
gattaaatag ggtcgctctg ctcgccgctc tcttgggttt gctctcgtca agcatcctcc     60
cccacctcgc gccgcaagta cggtacaggc ctgcaaccga ggatcgagcc cgtcaaagaa    120
cgagtcaaaa tcaag atg cat ctc tcc tcg tct ctc ctc ctc ctc gcc gcc    171
                 Met His Leu Ser Ser Ser Leu Leu Leu Leu Ala Ala
                  1               5                  10 ttg ccc ctg ggc atc gcc ggc aag ggc aag ggc cac ggc cac ggc ccc    219
Leu Pro Leu Gly Ile Ala Gly Lys Gly Lys Gly His Gly His Gly Pro
         15                  20                  25 cat acc ggg ctc cac acc ctc gcc aag cag gcc ggc ctc aag tac ttc    267
His Thr Gly Leu His Thr Leu Ala Lys Gln Ala Gly Leu Lys Tyr Phe
     30                  35                  40 ggc tct gcc acc gac tct ccc ggc cag cgt gag cgc gcc ggc tac gag    315
Gly Ser Ala Thr Asp Ser Pro Gly Gln Arg Glu Arg Ala Gly Tyr Glu
 45                  50                  55                  60 gac aag tac gcc cag tac gac cag atc atg tgg aag tcg ggc gag ttc    363
Asp Lys Tyr Ala Gln Tyr Asp Gln Ile Met Trp Lys Ser Gly Glu Phe
                 65                  70                  75 ggc ctg acg acc ccg acc aac ggc caa aag gttcgacatt agacctcctg       413
Gly Leu Thr Thr Pro Thr Asn Gly Gln Lys
             80                  85 cctgcgctcc cttcttaacc ctagacctgc tttcgccccg ggaaggccgc ctcgttgcta    473
accagttctc ggctcattct ag tgg ctg ttt act gag ccc gag cgt ggc gtg    525
                        Trp Leu Phe Thr Glu Pro Glu Arg Gly Val
                                     90                  95 ttc aac ttc acc gag ggt gac atc gtg acg aac ctg gcc cgg aag cac    573
Phe Asn Phe Thr Glu Gly Asp Ile Val Thr Asn Leu Ala Arg Lys His
                 100                 105                 110 ggt ttc atg cag cgg tgc cac gcg ctc gtc tgg cac agc cag ctc gcc    621
Gly Phe Met Gln Arg Cys His Ala Leu Val Trp His Ser Gln Leu Ala
            115                 120                 125 cct tgg gtc gag tcg acc gag tgg acg ccc gag gag ctg cgc cag gtc    669
Pro Trp Val Glu Ser Thr Glu Trp Thr Pro Glu Glu Leu Arg Gln Val
        130                 135                 140 att gtc aac cac atc acc cac gtg gcc ggc tac tac aag ggc aag tgc    717
Ile Val Asn His Ile Thr His Val Ala Gly Tyr Tyr Lys Gly Lys Cys
145                 150                 155                 160 tat gcc tgg gac gtc gtc aac gag gcc ctg aac gag gac ggc acc tac    765
Tyr Ala Trp Asp Val Val Asn Glu Ala Leu Asn Glu Asp Gly Thr Tyr
                165                 170                 175 cgc gag tcc gtc ttc tac aag gtg ctc ggc gag gac tac atc aag ctg    813
Arg Glu Ser Val Phe Tyr Lys Val Leu Gly Glu Asp Tyr Ile Lys Leu
```

-continued

```
            180                 185                 190 gcc ttc gag acg gcc gcc aag gtc gac ccc cac gcc aag ctc tac tac      861
Ala Phe Glu Thr Ala Ala Lys Val Asp Pro His Ala Lys Leu Tyr Tyr
        195                 200                 205 aac gac tac aac ctc gag tcc ccc agc gcc aag acc gag ggc gcc aag      909
Asn Asp Tyr Asn Leu Glu Ser Pro Ser Ala Lys Thr Glu Gly Ala Lys
    210                 215                 220 cgc atc gtc aag atg ctc aag gac gcc ggc atc cgc atc gac ggc gtc      957
Arg Ile Val Lys Met Leu Lys Asp Ala Gly Ile Arg Ile Asp Gly Val
225                 230                 235                 240 ggc ctg cag gcc cac ctc gtc gcc gag agc cac ccg acc ctc gac gag     1005
Gly Leu Gln Ala His Leu Val Ala Glu Ser His Pro Thr Leu Asp Glu
                245                 250                 255 cac atc gat gcc atc aag ggc ttc acc gag ctc ggc gtc gag gtc gcc     1053
His Ile Asp Ala Ile Lys Gly Phe Thr Glu Leu Gly Val Glu Val Ala
            260                 265                 270 ctg acc gag ctc gac atc cgc ctc tcc atc ccg gcc aac gcc acc aac     1101
Leu Thr Glu Leu Asp Ile Arg Leu Ser Ile Pro Ala Asn Ala Thr Asn
        275                 280                 285 ctc gcc cag cag agg gag gcg tac aag aac gtgagttttt tttattttat       1151
Leu Ala Gln Gln Arg Glu Ala Tyr Lys Asn
    290                 295 ttttatcttc cctcttgttc ttccatccaa cccccccccc ttttgacggt gcccagtcag   1211
attgctcttg atcgatgcta acctttgttc cttctctttg atag gtc gtc ggc gct    1267
                                                 Val Val Gly Ala
                                                     300 tgc gtc cag gtt cgc ggc tgc att ggc gtg gag atc tgg gac ttc tat     1315
Cys Val Gln Val Arg Gly Cys Ile Gly Val Glu Ile Trp Asp Phe Tyr
        305                 310                 315 gac ccc ttc agc tgg gtc cct gcc acc ttc ccc ggc cag ggc gcc ccc     1363
Asp Pro Phe Ser Trp Val Pro Ala Thr Phe Pro Gly Gln Gly Ala Pro
    320                 325                 330 ctg ctc tgg ttc gag gac ttt tcc aag cac ccc gcc tac gac ggc gtc     1411
Leu Leu Trp Phe Glu Asp Phe Ser Lys His Pro Ala Tyr Asp Gly Val
335                 340                 345                 350 gtc gag gcc ctg acc aac agg acc acg ggc ggg tgc aag ggc aag ggc     1459
Val Glu Ala Leu Thr Asn Arg Thr Thr Gly Gly Cys Lys Gly Lys Gly
                355                 360                 365 aag ggc aag ggc aag gtt tgg aag gcc taataagtgg tgttgtgcgg          1506
Lys Gly Lys Gly Lys Val Trp Lys Ala
            370                 375 gtcgtgtaga gatttaggga gaggattggg tccttcggtt cttgtatcta attattattc   1566
cgtactatta attgcatttc gatctaaagt tagtgttgag cgggtcgccg cagtcatgcg   1626
acatgcatgg cacgctaagc tcggccgagc tctcggga                           1664

<210> SEQ ID NO 35
<211> LENGTH: 375
<212> TYPE: PRT
<213> ORGANISM: Chrysosporium lucknowense

<400> SEQUENCE: 35

Met His Leu Ser Ser Ser Leu Leu Leu Leu Ala Ala Leu Pro Leu Gly
1               5                   10                  15

Ile Ala Gly Lys Gly Lys Gly His Gly His Gly Pro His Thr Gly Leu
            20                  25                  30

His Thr Leu Ala Lys Gln Ala Gly Leu Lys Tyr Phe Gly Ser Ala Thr
        35                  40                  45

Asp Ser Pro Gly Gln Arg Glu Arg Ala Gly Tyr Glu Asp Lys Tyr Ala
```

```
    50                  55                  60

Gln Tyr Asp Gln Ile Met Trp Lys Ser Gly Glu Phe Gly Leu Thr Thr
65                  70                  75                  80

Pro Thr Asn Gly Gln Lys Trp Leu Phe Thr Glu Pro Glu Arg Gly Val
                85                  90                  95

Phe Asn Phe Thr Glu Gly Asp Ile Val Thr Asn Leu Ala Arg Lys His
            100                 105                 110

Gly Phe Met Gln Arg Cys His Ala Leu Val Trp His Ser Gln Leu Ala
        115                 120                 125

Pro Trp Val Glu Ser Thr Glu Trp Thr Pro Glu Glu Leu Arg Gln Val
    130                 135                 140

Ile Val Asn His Ile Thr His Val Ala Gly Tyr Tyr Lys Gly Lys Cys
145                 150                 155                 160

Tyr Ala Trp Asp Val Val Asn Glu Ala Leu Asn Glu Asp Gly Thr Tyr
                165                 170                 175

Arg Glu Ser Val Phe Tyr Lys Val Leu Gly Glu Asp Tyr Ile Lys Leu
            180                 185                 190

Ala Phe Glu Thr Ala Ala Lys Val Asp Pro His Ala Lys Leu Tyr Tyr
        195                 200                 205

Asn Asp Tyr Asn Leu Glu Ser Pro Ser Ala Lys Thr Glu Gly Ala Lys
    210                 215                 220

Arg Ile Val Lys Met Leu Lys Asp Ala Gly Ile Arg Ile Asp Gly Val
225                 230                 235                 240

Gly Leu Gln Ala His Leu Val Ala Glu Ser His Pro Thr Leu Asp Glu
                245                 250                 255

His Ile Asp Ala Ile Lys Gly Phe Thr Glu Leu Gly Val Glu Val Ala
            260                 265                 270

Leu Thr Glu Leu Asp Ile Arg Leu Ser Ile Pro Ala Asn Ala Thr Asn
        275                 280                 285

Leu Ala Gln Gln Arg Glu Ala Tyr Lys Asn Val Val Gly Ala Cys Val
    290                 295                 300

Gln Val Arg Gly Cys Ile Gly Val Glu Ile Trp Asp Phe Tyr Asp Pro
305                 310                 315                 320

Phe Ser Trp Val Pro Ala Thr Phe Pro Gly Gln Gly Ala Pro Leu Leu
                325                 330                 335

Trp Phe Glu Asp Phe Ser Lys His Pro Ala Tyr Asp Gly Val Val Glu
            340                 345                 350

Ala Leu Thr Asn Arg Thr Thr Gly Gly Cys Lys Gly Lys Gly Lys Gly
        355                 360                 365

Lys Gly Lys Val Trp Lys Ala
    370                 375
```

<210> SEQ ID NO 36
<211> LENGTH: 1125
<212> TYPE: DNA
<213> ORGANISM: Chrysosporium lucknowense

<400> SEQUENCE: 36

```
atgcatctct cctcgtctct cctcctcctc gccgccttgc ccctgggcat cgccggcaag      60
ggcaagggcc acggccacgg cccccatacc gggctccaca ccctcgccaa gcaggccggc     120
ctcaagtact tcggctctgc caccgactct cccggccagc gtgagcgcgc cggctacgag     180
gacaagtacg cccagtacga ccagatcatg tggaagtcgg gcgagttcgg cctgacgacc     240
ccgaccaacg gccaaaagtg gctgtttact gagcccgagc gtggcgtgtt caacttcacc     300
```

```
gagggtgaca tcgtgacgaa cctggcccgg aagcacggtt tcatgcagcg gtgccacgcg    360
ctcgtctggc acagccagct cgccccttgg gtcgagtcga ccgagtggac gcccgaggag    420
ctgcgccagg tcattgtcaa ccacatcacc cacgtggccg gctactacaa gggcaagtgc    480
tatgcctggg acgtcgtcaa cgaggccctg aacgaggacg gcacctaccg cgagtccgtc    540
ttctacaagg tgctcggcga ggactacatc aagctggcct tcgagacggc cgccaaggtc    600 gaccccacg ccaagctcta ctacaacgac tacaacctcg agtcccccag cgccaagacc    660
gagggcgcca agcgcatcgt caagatgctc aaggacgccg gcatccgcat cgacggcgtc    720
ggcctgcagg cccacctcgt cgccgagagc caccccgaccc tcgacgagca catcgatgcc    780
atcaagggct tcaccgagct cggcgtcgag gtcgccctga ccgagctcga catccgcctc    840
tccatcccgg ccaacgccac caacctcgcc cagcagaggg aggcgtacaa gaacgtcgtc    900
ggcgcttgcg tccaggttcg cggctgcatt ggcgtggaga tctgggactt ctatgacccc    960
ttcagctggg tccctgccac cttccccggc cagggcgccc ccctgctctg gttcgaggac    1020
ttttccaagc accccgccta cgacggcgtc gtcgaggccc tgaccaacag gaccacgggc    1080
gggtgcaagg gcaagggcaa gggcaagggc aaggtttgga aggcc    1125
```

```
<210> SEQ ID NO 37
<211> LENGTH: 1192
<212> TYPE: DNA
<213> ORGANISM: Chrysosporium lucknowense
<220> FEATURE:
<221> NAME/KEY: CDS
<222> LOCATION: (121)..(386)
<220> FEATURE:
<221> NAME/KEY: CDS
<222> LOCATION: (531)..(942)

<400> SEQUENCE: 37
acataaatag agccactggc tcccctcaag ggattggcgt tcgaagcatc gtcagaaccg    60
caatatacat attagtgtaa tatcttgcac ctcattagat ccacaatcat catcagcatc    120 atg gtt acc ctc act cgc ctg gcg gtc gcc gcg gcc atg atc tcc         168
Met Val Thr Leu Thr Arg Leu Ala Val Ala Ala Ala Met Ile Ser
1               5                  10                  15 agc act ggc ctg gct gcc ccg acg ccc gaa gct ggc ccc gac ctt ccc     216
Ser Thr Gly Leu Ala Ala Pro Thr Pro Glu Ala Gly Pro Asp Leu Pro
            20                  25                  30 gac ttt gag ctc ggg gtc aac aac ctc gcc cgc cgc gcg ctg gac tac     264
Asp Phe Glu Leu Gly Val Asn Asn Leu Ala Arg Arg Ala Leu Asp Tyr
        35                  40                  45 aac cag aac tac agg acc agc ggc aac gtc aac tac tcg ccc acc gac     312
Asn Gln Asn Tyr Arg Thr Ser Gly Asn Val Asn Tyr Ser Pro Thr Asp
    50                  55                  60 aac ggc tac tcg gtc agc ttc tcc aac gcg gga gat ttt gtc gtc ggg     360
Asn Gly Tyr Ser Val Ser Phe Ser Asn Ala Gly Asp Phe Val Val Gly
65                  70                  75                  80 aag ggc tgg agg acg gga gcc acc ag  gtaagacagc agcgtacaat           406
Lys Gly Trp Arg Thr Gly Ala Thr Arg
                85 cgtcagggtt attggttata tggttatcca gacttgagcc gtggatttct tttatttcat    466 ttttcctttc ctccactctt aaacacgctt cgggcagcgt tgacaaacct tctaatatct    526 tcag a aac atc acc ttc tcg gga tcg aca cag cat acc tcg ggc acc      573
       Asn Ile Thr Phe Ser Gly Ser Thr Gln His Thr Ser Gly Thr
                90                  95                 100 gtg ctc gtc tcc gtc tac ggc tgg acc cgg aac ccg ctg atc gag tac     621
Val Leu Val Ser Val Tyr Gly Trp Thr Arg Asn Pro Leu Ile Glu Tyr
```

```
               105                 110                 115
tac gtg cag gag tac acg tcc aac ggg gcc ggc tcc gct cag ggc gag    669
Tyr Val Gln Glu Tyr Thr Ser Asn Gly Ala Gly Ser Ala Gln Gly Glu
120                 125                 130                 135 aag ctg ggc acg gtc gag agc gac ggg ggc acg tac gag atc tgg cgg    717
Lys Leu Gly Thr Val Glu Ser Asp Gly Gly Thr Tyr Glu Ile Trp Arg
                140                 145                 150 cac cag cag gtc aac cag ccg tcg atc gag ggc acc tcg acc ttc tgg    765
His Gln Gln Val Asn Gln Pro Ser Ile Glu Gly Thr Ser Thr Phe Trp
                155                 160                 165 cag tac atc tcg aac cgc gtg tcc ggc cag cgg ccc aac ggc ggc acc    813
Gln Tyr Ile Ser Asn Arg Val Ser Gly Gln Arg Pro Asn Gly Gly Thr
                170                 175                 180 gtc acc ctc gcc aac cac ttc gcc gcc tgg cag aag ctc ggc ctg aac    861
Val Thr Leu Ala Asn His Phe Ala Ala Trp Gln Lys Leu Gly Leu Asn
            185                 190                 195 ctg ggc cag cac gac tac cag gtc ctg gcc acc gag ggc tgg ggc aac    909
Leu Gly Gln His Asp Tyr Gln Val Leu Ala Thr Glu Gly Trp Gly Asn
200                 205                 210                 215 gcc ggc ggc agc tcc cag tac acc gtc agc ggc tgaccgttgg gtggtggggg    962
Ala Gly Gly Ser Ser Gln Tyr Thr Val Ser Gly
                    220                 225 gcaaagagct ggtcttagaa ccatccaacg atccttacca tgaaagagct tgtgacttag   1022
tcgctgttca tgaaaacatg tctgttttac acagacaaga tttaccaatt gcaatgaagc   1082
atacgtcaac tcgaacgtgt ttgtgtttct cgtgcctctc gtatgaatat gctatgctga   1142
tggagtatca ctcttgatgt caaacatgct atattaacga cataactata              1192

<210> SEQ ID NO 38
<211> LENGTH: 226
<212> TYPE: PRT
<213> ORGANISM: Chrysosporium lucknowense

<400> SEQUENCE: 38

Met Val Thr Leu Thr Arg Leu Ala Val Ala Ala Ala Met Ile Ser
1               5                   10                  15

Ser Thr Gly Leu Ala Ala Pro Thr Pro Glu Ala Gly Pro Asp Leu Pro
                20                  25                  30

Asp Phe Gl

```
                180               185              190
Trp Gln Lys Leu Gly Leu Asn Leu Gly Gln His Asp Tyr Gln Val Leu
        195                 200                 205

Ala Thr Glu Gly Trp Gly Asn Ala Gly Gly Ser Ser Gln Tyr Thr Val
    210                 215                 220

Ser Gly
225

<210> SEQ ID NO 39
<211> LENGTH: 678
<212> TYPE: DNA
<213> ORGANISM: Chrysosporium lucknowense

<400> SEQUENCE: 39
atggttaccc tcactcgcct ggcggtcgcc gcggcggcca tgatctccag cactggcctg      60
gctgccccga cgcccgaagc tggccccgac cttcccgact ttgagctcgg ggtcaacaac     120
ctcgcccgcc gcgcgctgga ctacaaccag aactacagga ccagcggcaa cgtcaactac     180
tcgcccaccg acaacggcta ctcggtcagc ttctccaacg cgggagattt tgtcgtcggg     240
aagggctgga ggacgggagc caccagaaac atcaccttct cgggatcgac acagcatacc     300
tcgggcaccg tgctcgtctc cgtctacggc tggacccgga accgctgat cgagtactac      360 gtgcaggagt acacgtccaa cggggccggc tccgctcagg cgagaagct gggcacggtc      420 gagagcgacg ggggcacgta cgagatctgg cggcaccagc aggtcaacca gccgtcgatc     480
gagggcacct cgaccttctg gcagtacatc tcgaaccgcg tgtccggcca gcggcccaac     540
ggcggcaccg tcaccctcgc caaccacttc gccgcctggc agaagctcgg cctgaacctg     600
ggccagcacg actaccaggt cctggccacc gagggctggg gcaacgccgg cggcagctcc     660
cagtacaccg tcagcggc                                                  678

<210> SEQ ID NO 40
<211> LENGTH: 1194
<212> TYPE: DNA
<213> ORGANISM: Chrysosporium lucknowense
<220> FEATURE:
<221> NAME/KEY: CDS
<222> LOCATION: (205)..(485)
<220> FEATURE:
<221> NAME/KEY: CDS
<222> LOCATION: (584)..(986)

<400> SEQUENCE: 40
gtataaatgc atcaaggagc gactgccccc ccatcaataa ccacccggtt gcttgagtct      60
ctcgcactcg cggccccttc ttctctgctt cgcacgcatc tcgctgtctc gctgtctcgc     120
tgtctcactg tctcgctgtc tcactgtctc gctgtctcac tgtctcgctg tctcactgtc     180
tcactcgtcc atcagagcaa aacc atg gtc tcg ctc aag tcc ctc ctc ctc      231
                              Met Val Ser Leu Lys Ser Leu Leu Leu
                                1               5 gcc gcg gcg gcg acg ttg acg gcg gtg acg gcg cgc ccg ttc gac ttt      279
Ala Ala Ala Ala Thr Leu Thr Ala Val Thr Ala Arg Pro Phe Asp Phe
 10                  15                  20                  25 gac gac ggc aac tcg acc gag gcg ctg gcc aag cgc cag gtc acg ccc      327
Asp Asp Gly Asn Ser Thr Glu Ala Leu Ala Lys Arg Gln Val Thr Pro
                 30                  35                  40 aac gcg cag ggc tac cac tcg ggc tac ttc tac tcg tgg tgg tcc gac      375
Asn Ala Gln Gly Tyr His Ser Gly Tyr Phe Tyr Ser Trp Trp Ser Asp
             45                  50                  55 ggc ggc ggc cag gcc acc ttc acc ctg ctc gag ggc agc cac tac cag      423
```

```
Gly Gly Gly Gln Ala Thr Phe Thr Leu Leu Glu Gly Ser His Tyr Gln
        60                  65                  70 gtc aac tgg agg aac acg ggc aac ttt gtc ggt ggc aag ggc tgg aac      471
Val Asn Trp Arg Asn Thr Gly Asn Phe Val Gly Gly Lys Gly Trp Asn
    75                  80                  85 ccg ggt acc ggc cg  gtaagttgtg tttcttttct tgaactattg actactaatt      525
Pro Gly Thr Gly Arg
90 atcgtatctt tccagtcaac ggggttgaaa ggttggttgg ctgactgccg gatcgcag g    584 acc atc aac tac ggc ggc tcg ttc aac ccg agc ggc aac ggc tac ctg      632
Thr Ile Asn Tyr Gly Gly Ser Phe Asn Pro Ser Gly Asn Gly Tyr Leu
95                  100                 105                 110 gcc gtc tac ggc tgg acg cac aac ccg ctg atc gag tac tac gtg gtc      680
Ala Val Tyr Gly Trp Thr His Asn Pro Leu Ile Glu Tyr Tyr Val Val
                115                 120                 125 gag tcg tac ggg acc tac aac ccg ggc agc cag gcc cag tac aag ggc      728
Glu Ser Tyr Gly Thr Tyr Asn Pro Gly Ser Gln Ala Gln Tyr Lys Gly
            130                 135                 140 agc ttc cag agc gac ggc ggc acc tac aac atc tac gtc tcg acc cgc      776
Ser Phe Gln Ser Asp Gly Gly Thr Tyr Asn Ile Tyr Val Ser Thr Arg
        145                 150                 155 tac aac gcg ccc tcg atc gag ggc acc cgc acc ttc cag cag tac tgg      824
Tyr Asn Ala Pro Ser Ile Glu Gly Thr Arg Thr Phe Gln Gln Tyr Trp
    160                 165                 170 tcc atc cgc acc tcc aag cgc gtc ggc ggc tcc gtc acc atg cag aac      872
Ser Ile Arg Thr Ser Lys Arg Val Gly Gly Ser Val Thr Met Gln Asn
175                 180                 185                 190 cac ttc aac gcc tgg gcc cag cac ggc atg ccc ctc ggc tcc cac gac      920
His Phe Asn Ala Trp Ala Gln His Gly Met Pro Leu Gly Ser His Asp
                195                 200                 205 tac cag atc gtc gcc acc gag ggc tac cag agc agc ggc tcc tcc gac      968
Tyr Gln Ile Val Ala Thr Glu Gly Tyr Gln Ser Ser Gly Ser Ser Asp
            210                 215                 220 atc tac gtc cag act cac taggtacctt aggtattcaa gcgatccagt            1016
Ile Tyr Val Gln Thr His
        225 cggtcagaca gactcttcca ggcacgccgc tgtccatcag tgggtagtat tatcccatga   1076 tgggcgccgg cggtgacggg aaaaggggcc attcgtctgc agtaccttat tttactatta   1136 atactgccta tctgccagca taacaatagg tagcacgcgt gcacttacca ggaattca     1194

<210> SEQ ID NO 41
<211> LENGTH: 228
<212> TYPE: PRT
<213> ORGANISM: Chrysosporium lucknowense

<400> SEQUENCE: 41

Met Val Ser Leu Lys Ser Leu Leu Leu Ala Ala Ala Ala Thr Leu Thr
1               5                   10                  15

Ala Val Thr Ala Arg Pro Phe Asp Phe Asp Asp Gly Asn Ser Thr Glu
            20                  25                  30

Ala Leu Ala Lys Arg Gln Val Thr Pro Asn Ala Gln Gly Tyr His Ser
        35                  40                  45

Gly Tyr Phe Tyr Ser Trp Trp Ser Asp Gly Gly Gly Gln Ala Thr Phe
    50                  55                  60

Thr Leu Leu Glu Gly Ser His Tyr Gln Val Asn Trp Arg Asn Thr Gly
65                  70                  75                  80

Asn Phe Val Gly Gly Lys Gly Trp Asn Pro Gly Thr Gly Arg Thr Ile
                85                  90                  95
```

```
Asn Tyr Gly Gly Ser Phe Asn Pro Ser Gly Asn Gly Tyr Leu Ala Val
            100                 105                 110

Tyr Gly Trp Thr His Asn Pro Leu Ile Glu Tyr Tyr Val Val Glu Ser
        115                 120                 125

Tyr Gly Thr Tyr Asn Pro Gly Ser Gln Ala Gln Tyr Lys Gly Ser Phe
    130                 135                 140

Gln Ser Asp Gly Gly Thr Tyr Asn Ile Tyr Val Ser Thr Arg Tyr Asn
145                 150                 155                 160

Ala Pro Ser Ile Glu Gly Thr Arg Thr Phe Gln Gln Tyr Trp Ser Ile
                165                 170                 175

Arg Thr Ser Lys Arg Val Gly Ser Val Thr Met Gln Asn His Phe
                180                 185                 190

Asn Ala Trp Ala Gln His Gly Met Pro Leu Gly Ser His Asp Tyr Gln
                195                 200                 205

Ile Val Ala Thr Glu Gly Tyr Gln Ser Ser Gly Ser Ser Asp Ile Tyr
            210                 215                 220

Val Gln Thr His
225
```

<210> SEQ ID NO 42
<211> LENGTH: 684
<212> TYPE: DNA
<213> ORGANISM: Chrysosporium lucknowense

<400> SEQUENCE: 42

```
atggtctcgc tcaagtccct cctcctcgcc gcggcggcga cgttgacggc ggtgacggcg      60
cgcccgttcg actttgacga cggcaactcg accgaggcgc tggccaagcg ccaggtcacg     120
cccaacgcgc agggctacca ctcgggctac ttctactcgt ggtggtccga cggcggcggc     180
caggccacct tcaccctgct cgagggcagc cactaccagg tcaactggag gaacacgggc     240
aactttgtcg gtggcaaggg ctggaacccg ggtaccggcc ggaccatcaa ctacggcggc     300
tcgttcaacc cgagcggcaa cggctacctg gccgtctacg ctggacgca caacccgctg      360
atcgagtact acgtggtcga gtcgtacggg acctacaacc cggcagcca ggcccagtac      420
aagggcagct ccagagcga cggcggcacc tacaacatct acgtctcgac ccgctacaac     480
gcgccctcga tcgagggcac ccgcaccttc agcagtact ggtccatccg cacctccaag      540
cgcgtcggcg gctccgtcac catgcagaac cacttcaacg cctgggccca gcacggcatg     600
cccctcggct ccacgacta ccagatcgtc gccaccgagg gctaccagag cagcggctcc     660
tccgacatct acgtccagac tcac                                             684
```

<210> SEQ ID NO 43
<211> LENGTH: 2740
<212> TYPE: DNA
<213> ORGANISM: Chrysosporium lucknowense
<220> FEATURE:
<221> NAME/KEY: CDS
<222> LOCATION: (1)..(230)
<220> FEATURE:
<221> NAME/KEY: CDS
<222> LOCATION: (294)..(682)
<220> FEATURE:
<221> NAME/KEY: CDS
<222> LOCATION: (744)..(2737)

<400> SEQUENCE: 43

```
atg caa ctt cca gcc gca gcc caa tgg ctg ctc acg ctt ccc gcg aaa       48
Met Gln Leu Pro Ala Ala Ala Gln Trp Leu Leu Thr Leu Pro Ala Lys
1               5                  10                  15
```

| | | |
|---|---|---|
| gcc tca ctt gct gac aat cat cgt cag gtt cac cag aag ccc ctc gcg<br>Ala Ser Leu Ala Asp Asn His Arg Gln Val His Gln Lys Pro Leu Ala<br>20                        25                      30 | | 96 |
| aga tct gaa cct ttt tac ccg tcg cca tgg atg aat ccc aac gcc gac<br>Arg Ser Glu Pro Phe Tyr Pro Ser Pro Trp Met Asn Pro Asn Ala Asp<br>    35                      40                      45 | | 144 |
| ggc tgg gcg gag gcc tat gcc cag gcc aag tcc ttt gtc tcc caa atg<br>Gly Trp Ala Glu Ala Tyr Ala Gln Ala Lys Ser Phe Val Ser Gln Met<br>50                        55                      60 | | 192 |
| act ctg cta gag aag gtc aac ttg acc acg gga gtc gg  gtaagtttg<br>Thr Leu Leu Glu Lys Val Asn Leu Thr Thr Gly Val Gly<br>65                      70                      75 | | 240 |
| tcattttgtc caggtaacat gcaaatggtt ctgctaacaa taacttaccg tag c tgg<br>                                                                     Trp | | 297 |
| ggg gct gag cag tgc gtc ggc caa gtg ggc gcg atc cct cgc ctt gga<br>Gly Ala Glu Gln Cys Val Gly Gln Val Gly Ala Ile Pro Arg Leu Gly<br>    80                      85                      90 | | 345 |
| ctt cgc agt ctg tgc atg cat gac tcc cct ctc ggc atc cga gga gcc<br>Leu Arg Ser Leu Cys Met His Asp Ser Pro Leu Gly Ile Arg Gly Ala<br>95                        100                   105              110 | | 393 |
| gac tac aac tca gcg ttc ccc tct ggc cag acc gtt gct gct acc tgg<br>Asp Tyr Asn Ser Ala Phe Pro Ser Gly Gln Thr Val Ala Ala Thr Trp<br>                  115                   120                   125 | | 441 |
| gat cgc ggt ctg atg tac cgt cgc ggc tac gca atg ggc cag gag gcc<br>Asp Arg Gly Leu Met Tyr Arg Arg Gly Tyr Ala Met Gly Gln Glu Ala<br>         130                   135                   140 | | 489 |
| aaa ggc aag ggc atc aat gtc ctt ctc gga cca gtc gcc ggc ccc ctt<br>Lys Gly Lys Gly Ile Asn Val Leu Leu Gly Pro Val Ala Gly Pro Leu<br>                  145                   150                   155 | | 537 |
| ggc cgc atg ccc gag ggc ggt cgt aac tgg gaa ggc ttc gct ccg gat<br>Gly Arg Met Pro Glu Gly Gly Arg Asn Trp Glu Gly Phe Ala Pro Asp<br>160                      165                   170 | | 585 |
| ccc gtc ctt acc ggc atc ggc atg tcc gag acg atc aag ggc att cag<br>Pro Val Leu Thr Gly Ile Gly Met Ser Glu Thr Ile Lys Gly Ile Gln<br>175                      180                   185              190 | | 633 |
| gat gct ggc gtc atc gct tgt gcg aag cac ttt att gga aac gag cag g<br>Asp Ala Gly Val Ile Ala Cys Ala Lys His Phe Ile Gly Asn Glu Gln<br>                   195                   200                   205 | | 682 |
| gtgagtagtc aaagacgggc cgtctcggac ccgcggcttc aagctgctga ctctgctgca | | 742 |
| g ag  cac ttc aga cag gtg cca gaa gcc cag gga tac ggt tac aac atc<br>    Glu His Phe Arg Gln Val Pro Glu Ala Gln Gly Tyr Gly Tyr Asn Ile<br>                   210                   215                   220 | | 790 |
| agc gaa acc ctc tcc tcc aac att gac gac aag acc atg cac gag ctc<br>Ser Glu Thr Leu Ser Ser Asn Ile Asp Asp Lys Thr Met His Glu Leu<br>             225                   230                   235 | | 838 |
| tac ctt tgg ccg ttt gcc gat gcc gtc cgg gcc ggc gtc ggc tct gtc<br>Tyr Leu Trp Pro Phe Ala Asp Ala Val Arg Ala Gly Val Gly Ser Val<br>240                      245                   250 | | 886 |
| atg tgc tcg tac cag cag gtc aac aac tcg tac gcc tgc cag aac tcg<br>Met Cys Ser Tyr Gln Gln Val Asn Asn Ser Tyr Ala Cys Gln Asn Ser<br>255                      260                   265              270 | | 934 |
| aag ctg ctg aac gac ctc ctc aag aac gag ctt ggg ttt cag ggc ttc<br>Lys Leu Leu Asn Asp Leu Leu Lys Asn Glu Leu Gly Phe Gln Gly Phe<br>                  275                   280                   285 | | 982 |
| gtc atg agc gac tgg cag gca cag cac act ggc gca gca agc gcc gtg<br>Val Met Ser Asp Trp Gln Ala Gln His Thr Gly Ala Ala Ser Ala Val<br>         290                   295                   300 | | 1030 |
| gct ggt ctc gat atg tcc atg ccg ggc gac acc cag ttc aac act ggc<br>Ala Gly Leu Asp Met Ser Met Pro Gly Asp Thr Gln Phe Asn Thr Gly | | 1078 |

```
                305                 310                 315
gtc agt ttc tgg ggc gcc aat ctc acc ctc gcc gtc ctc aac ggc aca    1126
Val Ser Phe Trp Gly Ala Asn Leu Thr Leu Ala Val Leu Asn Gly Thr
    320                 325                 330 gtc cct gcc tac cgt ctc gac gac atg gcc atg cgc atc atg gcc gcc    1174
Val Pro Ala Tyr Arg Leu Asp Asp Met Ala Met Arg Ile Met Ala Ala
335                 340                 345                 350 ctc ttc aag gtc acc aag acc acc cac ctg gaa ccc atc aac ttc tcc    1222
Leu Phe Lys Val Thr Lys Thr Thr His Leu Glu Pro Ile Asn Phe Ser
                355                 360                 365 ttc tgg acc gac gac act tat ggc ccg atc cac tgg gcc gcc aag cat    1270
Phe Trp Thr Asp Asp Thr Tyr Gly Pro Ile His Trp Ala Ala Lys His
            370                 375                 380 ggc tac cag aag att aat tcc cac gtt gac gtc cgc gcc gac cac ggc    1318
Gly Tyr Gln Lys Ile Asn Ser His Val Asp Val Arg Ala Asp His Gly
        385                 390                 395 aac ctc atc cgg gag att gcc gcc aag ggt acg gtg ctg ctg aag aat    1366
Asn Leu Ile Arg Glu Ile Ala Ala Lys Gly Thr Val Leu Leu Lys Asn
    400                 405                 410 acc ggc tct cta ccc ctg aac aag cca aag ttc gtg gcc gtc atc ggc    1414
Thr Gly Ser Leu Pro Leu Asn Lys Pro Lys Phe Val Ala Val Ile Gly
415                 420                 425                 430 gag gat gct ggg tcg agc ccc aac ggg ccc aac ggc tgc agc gac cgc    1462
Glu Asp Ala Gly Ser Ser Pro Asn Gly Pro Asn Gly Cys Ser Asp Arg
                435                 440                 445 ggc tgt aac gaa ggc acg ctc gcc atg ggc tgg gga tcc ggc aca gcc    1510
Gly Cys Asn Glu Gly Thr Leu Ala Met Gly Trp Gly Ser Gly Thr Ala
            450                 455                 460 aac tat ccg tac ctc gtt tcc ccc gac gcc gcg ctc cag gcc cgg gcc    1558
Asn Tyr Pro Tyr Leu Val Ser Pro Asp Ala Ala Leu Gln Ala Arg Ala
        465                 470                 475 atc cag gac ggc acg agg tac gag agc gtc ctg tcc aac tac gcc gag    1606
Ile Gln Asp Gly Thr Arg Tyr Glu Ser Val Leu Ser Asn Tyr Ala Glu
    480                 485                 490 gaa aag aca aag gct ctg gtc tcg cag gcc aat gca acc gcc atc gtc    1654
Glu Lys Thr Lys Ala Leu Val Ser Gln Ala Asn Ala Thr Ala Ile Val
495                 500                 505                 510 ttc gtc aat gcc gac tca ggc gag ggc tac atc aac gtg gac ggt aac    1702
Phe Val Asn Ala Asp Ser Gly Glu Gly Tyr Ile Asn Val Asp Gly Asn
                515                 520                 525 gag ggc gac cgt aag aac ctg act ctc tgg aac aac ggt gat act ctg    1750
Glu Gly Asp Arg Lys Asn Leu Thr Leu Trp Asn Asn Gly Asp Thr Leu
            530                 535                 540 gtc aag aac gtc tcg agc tgg tgc agc aac acc atc gtc gtc atc cac    1798
Val Lys Asn Val Ser Ser Trp Cys Ser Asn Thr Ile Val Val Ile His
        545                 550                 555 tcg gtc ggc ccg gtc ctc ctg acc gat tgg tac gac aac ccc aac atc    1846
Ser Val Gly Pro Val Leu Leu Thr Asp Trp Tyr Asp Asn Pro Asn Ile
    560                 565                 570 acg gcc att ctc tgg gct ggt ctt ccg ggc cag gag tcg ggc aac tcc    1894
Thr Ala Ile Leu Trp Ala Gly Leu Pro Gly Gln Glu Ser Gly Asn Ser
575                 580                 585                 590 atc acc gac gtg ctt tac ggc aag gtc aac ccc gcc gcc cgc tcg ccc    1942
Ile Thr Asp Val Leu Tyr Gly Lys Val Asn Pro Ala Ala Arg Ser Pro
                595                 600                 605 ttc act tgg ggc aag acc cgc gaa agc tat ggc gcg gac gtc ctg tac    1990
Phe Thr Trp Gly Lys Thr Arg Glu Ser Tyr Gly Ala Asp Val Leu Tyr
            610                 615                 620 aag ccg aat aat ggc aat ggt gcg ccc caa cag gac ttc acc gag ggc    2038
Lys Pro Asn Asn Gly Asn Gly Ala Pro Gln Gln Asp Phe Thr Glu Gly
```

-continued 625 630 635 gtc ttc atc gac tac cgc tac ttc gac aag gtt gac gat gac tcg gtc 2086
Val Phe Ile Asp Tyr Arg Tyr Phe Asp Lys Val Asp Asp Asp Ser Val
640 645 650 atc tac gag ttc ggc cac ggc ctg agc tac acc acc ttc gag tac agc 2134
Ile Tyr Glu Phe Gly His Gly Leu Ser Tyr Thr Thr Phe Glu Tyr Ser
655 660 665 670 aac atc cgc gtc gtc aag tcc aac gtc agc gag tac cgg ccc acg acg 2182
Asn Ile Arg Val Val Lys Ser Asn Val Ser Glu Tyr Arg Pro Thr Thr
675 680 685 ggc acc acg gcc cag gcc ccg acg ttt ggc aac ttc tcc acc gac ctc 2230
Gly Thr Thr Ala Gln Ala Pro Thr Phe Gly Asn Phe Ser Thr Asp Leu
690 695 700 gag gac tat ctc ttc ccc aag gac gag ttc ccc tac atc tac cag tac 2278
Glu Asp Tyr Leu Phe Pro Lys Asp Glu Phe Pro Tyr Ile Tyr Gln Tyr
705 710 715 atc tac ccg tac ctc aac acg acc gac ccc cgg agg gcc tcg gcc gat 2326
Ile Tyr Pro Tyr Leu Asn Thr Thr Asp Pro Arg Arg Ala Ser Ala Asp
720 725 730 ccc cac tac ggc cag acc gcc gag gag ttc ctc ccg ccc cac gcc acc 2374
Pro His Tyr Gly Gln Thr Ala Glu Glu Phe Leu Pro Pro His Ala Thr
735 740 745 750 gat gac gac ccc cag ccg ctc ctc cgg tcc tcg ggc gga aac tcc ccc 2422
Asp Asp Asp Pro Gln Pro Leu Leu Arg Ser Ser Gly Gly Asn Ser Pro
755 760 765 ggc ggc aac cgc cag ctg tac gac att gtc tac aca atc acg gcc gac 2470
Gly Gly Asn Arg Gln Leu Tyr Asp Ile Val Tyr Thr Ile Thr Ala Asp
770 775 780 atc acg aat acg ggc tcc gtt gta ggc gag gag gta ccg cag ctc tac 2518
Ile Thr Asn Thr Gly Ser Val Val Gly Glu Glu Val Pro Gln Leu Tyr
785 790 795 gtc tcg ctg ggc ggt ccc gag gat ccc aag gtg cag ctg cgc gac ttt 2566
Val Ser Leu Gly Gly Pro Glu Asp Pro Lys Val Gln Leu Arg Asp Phe
800 805 810 gac agg atg cgg atc gaa ccc ggc gag acg agg cag ttc acc ggc cgc 2614
Asp Arg Met Arg Ile Glu Pro Gly Glu Thr Arg Gln Phe Thr Gly Arg
815 820 825 830 ctg acg cgc aga gat ctg agc aac tgg gac gtc acg gtg cag gac tgg 2662
Leu Thr Arg Arg Asp Leu Ser Asn Trp Asp Val Thr Val Gln Asp Trp
835 840 845 gtc atc agc agg tat ccc aag acg gca tat gtt ggg agg agc agc cgg 2710
Val Ile Ser Arg Tyr Pro Lys Thr Ala Tyr Val Gly Arg Ser Ser Arg
850 855 860 aag ttg gat ctc aag att gag ctt cct tga 2740
Lys Leu Asp Leu Lys Ile Glu Leu Pro
865 870

<210> SEQ ID NO 44
<211> LENGTH: 871
<212> TYPE: PRT
<213> ORGANISM: Chrysosporium lucknowense

<400> SEQUENCE: 44

Met Gln Leu Pro Ala Ala Ala Gln Trp Leu Leu Thr Leu Pro Ala Lys
1 5 10 15

Ala Ser Leu Ala Asp Asn His Arg Gln Val His Gln Lys Pro Leu Ala
20 25 30

Arg Ser Glu Pro Phe Tyr Pro Ser Pro Trp Met Asn Pro Asn Ala Asp
35 40 45

Gly Trp Ala Glu Ala Tyr Ala Gln Ala Lys Ser Phe Val Ser Gln Met

```
              50                  55                  60
Thr Leu Leu Glu Lys Val Asn Leu Thr Thr Gly Val Gly Trp Gly Ala
 65                  70                  75                  80

Glu Gln Cys Val Gly Gln Val Gly Ala Ile Pro Arg Leu Gly Leu Arg
                     85                  90                  95

Ser Leu Cys Met His Asp Ser Pro Leu Gly Ile Arg Gly Ala Asp Tyr
                    100                 105                 110

Asn Ser Ala Phe Pro Ser Gly Gln Thr Val Ala Ala Thr Trp Asp Arg
                115                 120                 125

Gly Leu Met Tyr Arg Arg Gly Tyr Ala Met Gly Gln Glu Ala Lys Gly
            130                 135                 140

Lys Gly Ile Asn Val Leu Leu Gly Pro Val Ala Gly Pro Leu Gly Arg
145                 150                 155                 160

Met Pro Glu Gly Gly Arg Asn Trp Glu Gly Phe Ala Pro Asp Pro Val
                    165                 170                 175

Leu Thr Gly Ile Gly Met Ser Glu Thr Ile Lys Gly Ile Gln Asp Ala
                180                 185                 190

Gly Val Ile Ala Cys Ala Lys His Phe Ile Gly Asn Glu Gln Glu His
                195                 200                 205

Phe Arg Gln Val Pro Glu Ala Gln Gly Tyr Gly Tyr Asn Ile Ser Glu
210                 215                 220

Thr Leu Ser Ser Asn Ile Asp Asp Lys Thr Met His Glu Leu Tyr Leu
225                 230                 235                 240

Trp Pro Phe Ala Asp Ala Val Arg Ala Gly Val Gly Ser Val Met Cys
                245                 250                 255

Ser Tyr Gln Gln Val Asn Asn Ser Tyr Ala Cys Gln Asn Ser Lys Leu
                260                 265                 270

Leu Asn Asp Leu Leu Lys Asn Glu Leu Gly Phe Gln Gly Phe Val Met
            275                 280                 285

Ser Asp Trp Gln Ala Gln His Thr Gly Ala Ala Ser Ala Val Ala Gly
            290                 295                 300

Leu Asp Met Ser Met Pro Gly Asp Thr Gln Phe Asn Thr Gly Val Ser
305                 310                 315                 320

Phe Trp Gly Ala Asn Leu Thr Leu Ala Val Leu Asn Gly Thr Val Pro
                325                 330                 335

Ala Tyr Arg Leu Asp Asp Met Ala Met Arg Ile Met Ala Ala Leu Phe
                340                 345                 350

Lys Val Thr Lys Thr Thr His Leu Glu Pro Ile Asn Phe Ser Phe Trp
                355                 360                 365

Thr Asp Asp Thr Tyr Gly Pro Ile His Trp Ala Ala Lys His Gly Tyr
370                 375                 380

Gln Lys Ile Asn Ser His Val Asp Val Arg Ala Asp His Gly Asn Leu
385                 390                 395                 400

Ile Arg Glu Ile Ala Ala Lys Gly Thr Val Leu Leu Lys Asn Thr Gly
                405                 410                 415

Ser Leu Pro Leu Asn Lys Pro Lys Phe Val Ala Val Ile Gly Glu Asp
                420                 425                 430

Ala Gly Ser Ser Pro Asn Gly Pro Asn Gly Cys Ser Asp Arg Gly Cys
            435                 440                 445

Asn Glu Gly Thr Leu Ala Met Gly Trp Gly Ser Gly Thr Ala Asn Tyr
            450                 455                 460

Pro Tyr Leu Val Ser Pro Asp Ala Ala Leu Gln Ala Arg Ala Ile Gln
465                 470                 475                 480
```

Asp Gly Thr Arg Tyr Glu Ser Val Leu Ser Asn Tyr Ala Glu Glu Lys
                485                 490                 495

Thr Lys Ala Leu Val Ser Gln Ala Asn Ala Thr Ala Ile Val Phe Val
            500                 505                 510

Asn Ala Asp Ser Gly Glu Gly Tyr Ile Asn Val Asp Gly Asn Glu Gly
            515                 520                 525

Asp Arg Lys Asn Leu Thr Leu Trp Asn Asn Gly Asp Thr Leu Val Lys
            530                 535                 540

Asn Val Ser Ser Trp Cys Ser Asn Thr Ile Val Ile His Ser Val
545                 550                 555                 560

Gly Pro Val Leu Leu Thr Asp Trp Tyr Asp Pro Asn Ile Thr Ala
                565                 570                 575

Ile Leu Trp Ala Gly Leu Pro Gly Gln Glu Ser Gly Asn Ser Ile Thr
            580                 585                 590

Asp Val Leu Tyr Gly Lys Val Asn Pro Ala Ala Arg Ser Pro Phe Thr
            595                 600                 605

Trp Gly Lys Thr Arg Glu Ser Tyr Gly Ala Asp Val Leu Tyr Lys Pro
610                 615                 620

Asn Asn Gly Asn Gly Ala Pro Gln Gln Asp Phe Thr Glu Gly Val Phe
625                 630                 635                 640

Ile Asp Tyr Arg Tyr Phe Asp Lys Val Asp Asp Ser Val Ile Tyr
            645                 650                 655

Glu Phe Gly His Gly Leu Ser Tyr Thr Thr Phe Glu Tyr Ser Asn Ile
            660                 665                 670

Arg Val Val Lys Ser Asn Val Ser Glu Tyr Arg Pro Thr Thr Gly Thr
            675                 680                 685

Thr Ala Gln Ala Pro Thr Phe Gly Asn Phe Ser Thr Asp Leu Glu Asp
            690                 695                 700

Tyr Leu Phe Pro Lys Asp Glu Phe Pro Tyr Ile Tyr Gln Tyr Ile Tyr
705                 710                 715                 720

Pro Tyr Leu Asn Thr Thr Asp Pro Arg Arg Ala Ser Ala Asp Pro His
            725                 730                 735

Tyr Gly Gln Thr Ala Glu Glu Phe Leu Pro Pro His Ala Thr Asp Asp
            740                 745                 750

Asp Pro Gln Pro Leu Leu Arg Ser Ser Gly Gly Asn Ser Pro Gly Gly
            755                 760                 765

Asn Arg Gln Leu Tyr Asp Ile Val Tyr Thr Ile Thr Ala Asp Ile Thr
            770                 775                 780

Asn Thr Gly Ser Val Val Gly Glu Glu Val Pro Gln Leu Tyr Val Ser
785                 790                 795                 800

Leu Gly Gly Pro Glu Asp Pro Lys Val Gln Leu Arg Asp Phe Asp Arg
                805                 810                 815

Met Arg Ile Glu Pro Gly Glu Thr Arg Gln Phe Thr Gly Arg Leu Thr
            820                 825                 830

Arg Arg Asp Leu Ser Asn Trp Asp Val Thr Val Gln Asp Trp Val Ile
            835                 840                 845

Ser Arg Tyr Pro Lys Thr Ala Tyr Val Gly Arg Ser Ser Arg Lys Leu
            850                 855                 860

Asp Leu Lys Ile Glu Leu Pro
865                 870

<210> SEQ ID NO 45
<211> LENGTH: 2613
<212> TYPE: DNA
<213> ORGANISM: Chrysosporium lucknowense

<400> SEQUENCE: 45

```
atgcaacttc cagccgcagc ccaatggctg ctcacgcttc ccgcgaaagc ctcacttgct        60
gacaatcatc gtcaggttca ccagaagccc ctcgcgagat ctgaaccttt ttacccgtcg       120
ccatggatga atcccaacgc cgacggctgg gcggaggcct atgcccaggc caagtccttt       180
gtctcccaaa tgactctgct agagaaggtc aacttgacca cgggagtcgg ctgggggct        240
gagcagtgcg tcggccaagt gggcgcgatc cctcgccttg acttcgcag tctgtgcatg        300
catgactccc ctctcggcat ccgaggagcc gactacaact cagcgttccc ctctggccag       360
accgttgctg ctacctggga tcgcggtctg atgtaccgtc gcggctacgc aatgggccag       420
gaggccaaag gcaagggcat caatgtcctt ctcggaccag tcgccggccc ccttggccgc       480
atgcccgagg gcggtcgtaa ctgggaaggc ttcgctccgg atcccgtcct taccggcatc       540
ggcatgtccg agacgatcaa gggcattcag gatgctggcg tcatcgcttg tgcgaagcac       600
tttattggaa acgagcagga gcacttcaga caggtgccaa aagcccaggg atacggttac       660
aacatcagcg aaaccctctc ctccaacatt gacgacaaga ccatgcacga gctctacctt       720
tggccgtttg ccgatgccgt ccgggccggc gtcggctctg tcatgtgctc gtaccagcag       780
gtcaacaact cgtacgcctg ccagaactcg aagctgctga cgacctcct caagaacgag        840
cttgggtttc agggcttcgt catgagcgac tggcaggcac agcacactgg cgcagcaagc       900
gccgtggctg gtctcgatat gtccatgccg ggcgacaccc agttcaacac tggcgtcagt       960
ttctggggcg ccaatctcac cctcgccgtc ctcaacggca cagtccctgc ctaccgtctc      1020
gacgacatgg ccatgcgcat catggccgcc ctcttcaagg tcaccaagac cacccacctg      1080
gaacccatca acttctcctt ctggaccgac gacacttatg ccccgatcca ctgggccgcc      1140
aagcatggct accagaagat taattcccac gttgacgtcc gcgccgacca cggcaacctc      1200
atccgggaga ttgccgccaa gggtacggtg ctgctgaaga ataccggctc tctacccctg      1260
aacaagccaa agttcgtggc cgtcatcggc gaggatgctg ggtcgagccc caacgggccc      1320
aacggctgca cgaccgcgg ctgtaacgaa ggcacgctcg ccatgggctg gggatccggc       1380
acagccaact atccgtacct cgtttccccc gacgccgcgc tccaggcccg gccatccag       1440
gacggcacga ggtacgagag cgtcctgtcc aactacgccg aggaaaagac aaaggctctg      1500
gtctcgcagg ccaatgcaac cgccatcgtc ttcgtcaatg ccgactcagg cgagggctac      1560
atcaacgtgg acggtaacga gggcgaccgt aagaacctga ctctctggaa caacggtgat      1620
actctggtca agaacgtctc gagctggtgc agcaacacca tcgtcgtcat ccactcggtc      1680
ggcccggtcc tcctgaccga ttggtacgac aaccccaaca tcacggccat tctctgggct      1740
ggtcttccgg gccaggagtc gggcaactcc atcaccgacg tgctttacgg caaggtcaac      1800
cccgccgccc gctcgccctt cacttggggc aagacccgcg aaagctatgg cgcggacgtc      1860
ctgtacaagc cgaataatgg caatggtgcg ccccaacagg acttcaccga gggcgtcttc      1920
atcgactacc gctacttcga caaggttgac gatgactcgg tcatctacga gttcggccac      1980
ggcctgagct acaccacctt cgagtacagc aacatccgcg tcgtcaagtc caacgtcagc      2040
gagtaccggc ccacgacggg caccacggcc caggccccga cgtttggcaa cttctccacc      2100
gacctcgagg actatctctt ccccaaggac gagttcccct acatctacca gtacatctac      2160
ccgtacctca acacgaccga cccccggagg gcctcggccg atccccacta cggccagacc      2220
gccgaggagt tcctcccgcc ccacgccacc gatgacgacc cccagccgct cctccggtcc      2280
tcgggcggaa actcccccgg cggcaaccgc cagctgtacg acattgtcta cacaatcacg      2340
```

```
gccgacatca cgaatacggg ctccgttgta ggcgaggagg taccgcagct ctacgtctcg    2400
ctgggcggtc ccgaggatcc caaggtgcag ctgcgcgact ttgacaggat gcggatcgaa    2460
cccggcgaga cgaggcagtt caccggccgc ctgacgcgca gagatctgag caactgggac    2520
gtcacggtgc aggactgggt catcagcagg tatcccaaga cggcatatgt tgggaggagc    2580
agccggaagt tggatctcaa gattgagctt cct                                 2613

<210> SEQ ID NO 46
<211> LENGTH: 1226
<212> TYPE: DNA
<213> ORGANISM: Chrysosporium lucknowense
<220> FEATURE:
<221> NAME/KEY: CDS
<222> LOCATION: (89)..(690)
<220> FEATURE:
<221> NAME/KEY: CDS
<222> LOCATION: (776)..(1223)

<400> SEQUENCE: 46
agacagcttg agagacctcc taatcctaga tctcgaggct caacctgagg agagacggtc    60
tgtaattacc cgctgcacga caccaaag atg atg ctc aca cgc ttc gtg gct     112
                               Met Met Leu Thr Arg Phe Val Ala
                                1               5 ggc ctg ctc ggc atc tcc gcc gcg gat gcc gcc ctc acc tac aga ggc    160
Gly Leu Leu Gly Ile Ser Ala Ala Asp Ala Ala Leu Thr Tyr Arg Gly
         10                  15                  20 gtg gat tgg tcc tca gtg gtg gtt gag gaa cgg gcc ggc gtc tcg tac    208
Val Asp Trp Ser Ser Val Val Val Glu Glu Arg Ala Gly Val Ser Tyr
 25                  30                  35                  40 aag aac acc aac ggg aat gcc caa ccg ctt gag aac atc ctg gct gcc    256
Lys Asn Thr Asn Gly Asn Ala Gln Pro Leu Glu Asn Ile Leu Ala Ala
                 45                  50                  55 aat ggc gtc aac acg gtg cgg cag cga gtc tgg gtt aac ccc gcg gac    304
Asn Gly Val Asn Thr Val Arg Gln Arg Val Trp Val Asn Pro Ala Asp
             60                  65                  70 ggc aac tac aac ctc gac tac aac atc gcg atc gcg aag agg gcg aag    352
Gly Asn Tyr Asn Leu Asp Tyr Asn Ile Ala Ile Ala Lys Arg Ala Lys
         75                  80                  85 gct gcc ggg ctt ggc gtg tac atc gac ttc cac tac agc gac acc tgg    400
Ala Ala Gly Leu Gly Val Tyr Ile Asp Phe His Tyr Ser Asp Thr Trp
 90                  95                 100 gcc gat cct gct cat cag acc atg ccc gct ggg tgg ccg agc gac att    448
Ala Asp Pro Ala His Gln Thr Met Pro Ala Gly Trp Pro Ser Asp Ile
105                 110                 115                 120 gac aac ctc tcc tgg aag ctc tac aac tac act ctg gac gcc gcc aac    496
Asp Asn Leu Ser Trp Lys Leu Tyr Asn Tyr Thr Leu Asp Ala Ala Asn
                125                 130                 135 aag ctc cag aac gcg ggt atc cag ccc acc atc gtg tcc atc ggt aac    544
Lys Leu Gln Asn Ala Gly Ile Gln Pro Thr Ile Val Ser Ile Gly Asn
            140                 145                 150 gag atc cgg gcc ggt ctg cta tgg ccc aca ggg aga acc gag aac tgg    592
Glu Ile Arg Ala Gly Leu Leu Trp Pro Thr Gly Arg Thr Glu Asn Trp
        155                 160                 165 gcc aac att gcc cgg ttg ttg cac tcc gct gct tgg ggt atc aag gac    640
Ala Asn Ile Ala Arg Leu Leu His Ser Ala Ala Trp Gly Ile Lys Asp
    170                 175                 180 tcg tcg ctc agc ccg aag cca aag atc atg atc cac ctc gac aac gga    688
Ser Ser Leu Ser Pro Lys Pro Lys Ile Met Ile His Leu Asp Asn Gly
185                 190                 195                 200 tg  gtgagttata tcatcctttc cttgtccgat aacctgttcc tcagcctggt          740
```

-continued

```
Trp cgatgtggag agctgatggc gggggatcca aacag g gac tgg ggt acc cag aat      794
                                         Asp Trp Gly Thr Gln Asn
                                                     205 tgg tgg tac acg aat gtc ttg aag cag ggt aca ctt gag ctg tcc gac      842
Trp Trp Tyr Thr Asn Val Leu Lys Gln Gly Thr Leu Glu Leu Ser Asp
        210                 215                 220 ttt gac atg atg ggc gtc tcg ttc tac ccc ttt tac tcg tcg tcg gca      890
Phe Asp Met Met Gly Val Ser Phe Tyr Pro Phe Tyr Ser Ser Ser Ala
    225                 230                 235 acc ttg agc gcc ctg aaa tcg agc ttg gac aac atg gcc aaa acc tgg      938
Thr Leu Ser Ala Leu Lys Ser Ser Leu Asp Asn Met Ala Lys Thr Trp
240                 245                 250                 255 aac aag gag att gcc gtg gtc gag acc aat tgg cca atc tct tgt ccc      986
Asn Lys Glu Ile Ala Val Val Glu Thr Asn Trp Pro Ile Ser Cys Pro
                260                 265                 270 aac cca agg tac agt ttc ccc tcg gac gtc aag aac atc ccc ttc tcg     1034
Asn Pro Arg Tyr Ser Phe Pro Ser Asp Val Lys Asn Ile Pro Phe Ser
            275                 280                 285 ccg gaa gga cag acg acc ttc atc acc aac gtg gcc aac atc gtg tcc     1082
Pro Glu Gly Gln Thr Thr Phe Ile Thr Asn Val Ala Asn Ile Val Ser
        290                 295                 300 tcg gta agc cgc ggc gta ggc ctg ttt tat tgg gaa ccc gct tgg att     1130
Ser Val Ser Arg Gly Val Gly Leu Phe Tyr Trp Glu Pro Ala Trp Ile
    305                 310                 315 cac aat gca aac ctg ggc tcg tcg tgc gcc gac aac acc atg ttt tcg     1178
His Asn Ala Asn Leu Gly Ser Ser Cys Ala Asp Asn Thr Met Phe Ser
320                 325                 330                 335 caa tcc ggg cag gct ttg tcc agc ttg tcc gtt ttc cag aga atc tga     1226
Gln Ser Gly Gln Ala Leu Ser Ser Leu Ser Val Phe Gln Arg Ile
                340                 345                 350

<210> SEQ ID NO 47
<211> LENGTH: 350
<212> TYPE: PRT
<213> ORGANISM: Chrysosporium lucknowense
<400> SEQUENCE: 47

Met Met Leu Thr Arg Phe Val Ala Gly Leu Leu Gly Ile Ser Ala Ala
1               5                   10                  15

Asp Ala Ala Leu Thr Tyr Arg Gly Val Asp Trp Ser Ser Val Val Val
            20                  25                  30

Glu Glu Arg Ala Gly Val Ser Tyr Lys Asn Thr Asn Gly Asn Ala Gln
        35                  40                  45

Pro Leu Glu Asn Ile Leu Ala Ala Asn Gly Val Asn Thr Val Arg Gln
    50                  55                  60

Arg Val Trp Val Asn Pro Ala Asp Gly Asn Tyr Asn Leu Asp Tyr Asn
65                  70                  75                  80

Ile Ala Ile Ala Lys Arg Ala Lys Ala Ala Gly Leu Gly Val Tyr Ile
                85                  90                  95

Asp Phe His Tyr Ser Asp Thr Trp Ala Asp Pro Ala His Gln Thr Met
            100                 105                 110

Pro Ala Gly Trp Pro Ser Asp Ile Asp Asn Leu Ser Trp Lys Leu Tyr
        115                 120                 125

Asn Tyr Thr Leu Asp Ala Ala Asn Lys Leu Gln Asn Ala Gly Ile Gln
    130                 135                 140

Pro Thr Ile Val Ser Ile Gly Asn Glu Ile Arg Ala Gly Leu Leu Trp
145                 150                 155                 160
```

```
Pro Thr Gly Arg Thr Glu Asn Trp Ala Asn Ile Ala Arg Leu Leu His
                165                 170                 175

Ser Ala Ala Trp Gly Ile Lys Asp Ser Ser Leu Ser Pro Lys Pro Lys
            180                 185                 190

Ile Met Ile His Leu Asp Asn Gly Trp Asp Trp Gly Thr Gln Asn Trp
        195                 200                 205

Trp Tyr Thr Asn Val Leu Lys Gln Gly Thr Leu Glu Leu Ser Asp Phe
    210                 215                 220

Asp Met Met Gly Val Ser Phe Tyr Pro Phe Tyr Ser Ser Ser Ala Thr
225                 230                 235                 240
Leu Ser Ala Leu Lys Ser Ser Leu Asp Asn Met Ala Lys Thr Trp Asn
                245                 250                 255
Lys Glu Ile Ala Val Val Glu Thr Asn Trp Pro Ile Ser Cys Pro Asn
            260                 265                 270
Pro Arg Tyr Ser Phe Pro Ser Asp Val Lys Asn Ile Pro Phe Ser Pro
        275                 280                 285
Glu Gly Gln Thr Thr Phe Ile Thr Asn Val Ala Asn Ile Val Ser Ser
    290                 295                 300
Val Ser Arg Gly Val Gly Leu Phe Tyr Trp Glu Pro Ala Trp Ile His
305                 310                 315                 320
Asn Ala Asn Leu Gly Ser Ser Cys Ala Asp Asn Thr Met Phe Ser Gln
                325                 330                 335
Ser Gly Gln Ala Leu Ser Ser Leu Ser Val Phe Gln Arg Ile
            340                 345                 350

<210> SEQ ID NO 48
<211> LENGTH: 1050
<212> TYPE: DNA
<213> ORGANISM: Chrysosporium lucknowense
<400> SEQUENCE: 48
atgatgctca cacgcttcgt ggctggcctg ctcggcatct ccgccgcgga tgccgccctc      60
acctacagag gcgtggattg gtcctcagtg gtggttgagg aacgggccgg cgtctcgtac     120
aagaacacca acgggaatgc ccaaccgctt gagaacatcc tggctgccaa tggcgtcaac     180
acggtgcggc agcgagtctg ggttaacccc gcggacggca actacaacct cgactacaac     240
atcgcgatcg cgaagagggc gaaggctgcc gggcttggcg tgtacatcga cttccactac     300
agcgacacct gggccgatcc tgctcatcag accatgcccg ctgggtggcc gagcgacatt     360
gacaacctct cctggaagct ctacaactac actctggacg ccgccaacaa gctccagaac     420
gcgggtatcc agcccaccat cgtgtccatc ggtaacgaga tccgggccgg tctgctatgg     480
cccacaggga gaaccgagaa ctgggccaac attgcccggt tgttgcactc cgctgcttgg     540
ggtatcaagg actcgtcgct cagcccgaag ccaaagatca tgatccacct cgacaacgga     600
tgggactggg gtacccagaa ttggtggtac acgaatgtct tgaagcaggg tacacttgag     660
ctgtccgact ttgacatgat gggcgtctcg ttctacccct tttactcgtc gtcggcaacc     720
ttgagcgccc tgaaatcgag cttggacaac atggccaaaa cctggaacaa ggagattgcc     780
gtggtcgaga ccaattggcc aatctcttgt cccaacccaa ggtacagttt cccctcggac     840
gtcaagaaca tccccttctc gccggaagga cagacgacct tcatcaccaa cgtggccaac     900
atcgtgtcct cggtaagccg cggcgtaggc ctgttttatt gggaacccgc ttggattcac     960
aatgcaaacc tgggctcgtc gtgcgccgac aacaccatgt tttcgcaatc cgggcaggct    1020
ttgtccagct tgtccgtttt ccagagaatc                                     1050
```

```
<210> SEQ ID NO 49
<211> LENGTH: 2344
<212> TYPE: DNA
<213> ORGANISM: Chrysosporium lucknowense
<220> FEATURE:
<221> NAME/KEY: CDS
<222> LOCATION: (54)..(276)
<220> FEATURE:
<221> NAME/KEY: CDS
<222> LOCATION: (348)..(717)
<220> FEATURE:
<221> NAME/KEY: CDS
<222> LOCATION: (814)..(887)
<220> FEATURE:
<221> NAME/KEY: CDS
<222> LOCATION: (947)..(1078)
<220> FEATURE:
<221> NAME/KEY: CDS
<222> LOCATION: (1144)..(2228)

<400> SEQUENCE: 49
```

| | | |
|---|---|---|
| agctccagga ccacctccca tccgtaaacg atctggcct cgtcacgccc gcc atg<br>                                                                                     Met<br>                                                                                    1 | 56 |

```
cac gct ctc tcg tcg ctc gct gtc ctc ggc gcc tgg gcc gtc cag acg      104
His Ala Leu Ser Ser Leu Ala Val Leu Gly Ala Trp Ala Val Gln Thr
            5                  10                  15 gtc ttg ggc cgt ccg gcc acc ctc tca aag cgg gcc acc gac tcc ttc      152
Val Leu Gly Arg Pro Ala Thr Leu Ser Lys Arg Ala Thr Asp Ser Phe
         20                  25                  30 atc gag acc gag acg cct atc gca tgg gaa aag ctg cgg tgc aac atc      200
Ile Glu Thr Glu Thr Pro Ile Ala Trp Glu Lys Leu Arg Cys Asn Ile
 35                  40                  45 ggc gct aac ggc tgt gcg gct tcc gga gcc gct gcc ggt gtg gtc att      248
Gly Ala Asn Gly Cys Ala Ala Ser Gly Ala Ala Ala Gly Val Val Ile
 50                  55                  60                  65 gcc agc ccg tcc aag tcg gat cca gac t gtgcgttgac agcggcccct         296
Ala Ser Pro Ser Lys Ser Asp Pro Asp
                 70 acccctt att atcgcaactt cggtcggtgt tgagatgctg agacgcgaca g ac ttc    352
                                                            Tyr Phe tac acc tgg act cga gat gcc ggc ctg gtc ctg acg ggt atc gtg gac      400
Tyr Thr Trp Thr Arg Asp Ala Gly Leu Val Leu Thr Gly Ile Val Asp
            80                  85                  90 gcc ctg tcc caa aac tac tcg gcg gcc ctg cag acc aac att cag gac      448
Ala Leu Ser Gln Asn Tyr Ser Ala Ala Leu Gln Thr Asn Ile Gln Asp
         95                 100                 105 tac atc atc gcc cag gcc aag ctc cag ggt gtt tcg aac ccc tcc ggt      496
Tyr Ile Ile Ala Gln Ala Lys Leu Gln Gly Val Ser Asn Pro Ser Gly
110                 115                 120 agc ctc tcg gac ggc acc ggt ctt ggc gag ccc aag ttc aat gtc gat      544
Ser Leu Ser Asp Gly Thr Gly Leu Gly Glu Pro Lys Phe Asn Val Asp
125                 130                 135                 140 ctc acc cag ttc acg ggc gac tgg ggc cgg ccg cag cgc gac ggt ccg      592
Leu Thr Gln Phe Thr Gly Asp Trp Gly Arg Pro Gln Arg Asp Gly Pro
                145                 150                 155 cct ctc cgg gcc atc gcc ctc atc cgc tac gcc aag tgg ctg gct tcc      640
Pro Leu Arg Ala Ile Ala Leu Ile Arg Tyr Ala Lys Trp Leu Ala Ser
            160                 165                 170 aac ggt tac aag gac acg gcc aac agc gtc gtc tgg ccc gtc atc aag      688
Asn Gly Tyr Lys Asp Thr Ala Asn Ser Val Val Trp Pro Val Ile Lys
         175                 180                 185 aac gac ctg gcc tat gcc gct cag tat tg gtgagtgccc cttctacttc        737
Asn Asp Leu Ala Tyr Ala Ala Gln Tyr Trp
```

```
                190                 195
tcgcccttgg gggagtttct tcccgtcctg acgccggagg cacgctaaca cacgccacac    797
acacacgcac atacag g aac gag act ggt ttc gac ctg tgg gag gag gtt      847
                    Asn Glu Thr Gly Phe Asp Leu Trp Glu Glu Val
                        200                 205 ccc ggc agc tcg ttc ttc acc att gcc agc acg cac cga g gtgggtggtc     897
Pro Gly Ser Ser Phe Phe Thr Ile Ala Ser Thr His Arg
210             215                 220 cccgttgtac atatgggt tgatcaacga attactgacg cagcgacag cc  ttg gta      954
                                                       Ala Leu Val
                                                               225 gag gga gct gcc ctc gct gcc cag ctc ggc acc gaa tgc agc gcc tgc     1002
Glu Gly Ala Ala Leu Ala Ala Gln Leu Gly Thr Glu Cys Ser Ala Cys
                230                 235                 240 atc acc gtc gcg ccc caa gtc ctc tgc ttc cag cag agc ttc tgg aac     1050
Ile Thr Val Ala Pro Gln Val Leu Cys Phe Gln Gln Ser Phe Trp Asn
                245                 250                 255 ccg tcg ggc ggt tac gtt gtc tcg aac a gtaagtctct tctcgtggtg         1098
Pro Ser Gly Gly Tyr Val Val Ser Asn
                260             265 gtgccgctcc cagcctcaat ttccacacaa ctaaacaacg gcaag tc  aac ggc ggc   1154
                                                     Ile Asn Gly Gly
                                                                270 aac aac cgg tcc ggc aag gat ctc aac tcg gtc ctg gcc tcc atc cac     1202
Asn Asn Arg Ser Gly Lys Asp Leu Asn Ser Val Leu Ala Ser Ile His
                275                 280                 285 acc ttt gac ccg gcg gtc ggc tgc gac tcg gtc acc ttc cag ccc tgc     1250
Thr Phe Asp Pro Ala Val Gly Cys Asp Ser Val Thr Phe Gln Pro Cys
                290                 295                 300 agc gac aag gcc ctc tcc aac cac aag gcc tac gtc gac tcc ttc cgc     1298
Ser Asp Lys Ala Leu Ser Asn His Lys Ala Tyr Val Asp Ser Phe Arg
                305                 310                 315 agc gtc tac gcc atc aac tcg ggc att gcc cag ggc aag gcc gtc gcc     1346
Ser Val Tyr Ala Ile Asn Ser Gly Ile Ala Gln Gly Lys Ala Val Ala
                320                 325                 330 gtg ggc cgc tac tcg gag gac gtc tac tac aac ggc aac ccg tgg tac     1394
Val Gly Arg Tyr Ser Glu Asp Val Tyr Tyr Asn Gly Asn Pro Trp Tyr
335                 340                 345                 350 ctg gcc aac ttc gcg gcc gcc gag cag ctc tac gac gcc gtc ttc gtc     1442
Leu Ala Asn Phe Ala Ala Ala Glu Gln Leu Tyr Asp Ala Val Phe Val
                355                 360                 365 tgg aag aag cag cag tcc atc gag gtc acc cag ctg tcc ctc ccc ttc     1490
Trp Lys Lys Gln Gln Ser Ile Glu Val Thr Gln Leu Ser Leu Pro Phe
                370                 375                 380 ttc aag gac ctg ctc ccc ggc atc tcc acc ggc acc tac acc ccg tcg     1538
Phe Lys Asp Leu Leu Pro Gly Ile Ser Thr Gly Thr Tyr Thr Pro Ser
                385                 390                 395 tcg tcg acg tac cag cag atc ctc gac gcc gtc tcg gcc tac gcc gac     1586
Ser Ser Thr Tyr Gln Gln Ile Leu Asp Ala Val Ser Ala Tyr Ala Asp
                400                 405                 410 ggc ttc atc gac gtc gcg gcc aag tac acc ccc tcg gac ggc tcc ctg     1634
Gly Phe Ile Asp Val Ala Ala Lys Tyr Thr Pro Ser Asp Gly Ser Leu
415                 420                 425                 430 gcc gag cag tac acg cgc gac tcg ggc cag ccg atc tcg gcc aag gac     1682
Ala Glu Gln Tyr Thr Arg Asp Ser Gly Gln Pro Ile Ser Ala Lys Asp
                435                 440                 445 ctg acc tgg tcc tac gcc gcc ttc ctc tcg gcc gcc gac cgc cgc gcg     1730
Leu Thr Trp Ser Tyr Ala Ala Phe Leu Ser Ala Ala Asp Arg Arg Ala
                450                 455                 460
```

```
ggc atc gtc ccg gcc ggc tgg tcc gcc gag cac ggc aag acg ctg ccc     1778
Gly Ile Val Pro Ala Gly Trp Ser Ala Glu His Gly Lys Thr Leu Pro
        465                 470                 475 ggc tcg tgc tcg gcc gtc cag gtc gcc ggc acc tac acc cag gcc acc     1826
Gly Ser Cys Ser Ala Val Gln Val Ala Gly Thr Tyr Thr Gln Ala Thr
    480                 485                 490 gcc acc tcc ttc ccg ccc ggc cag acg ccc aac ccg acc agc gac acc     1874
Ala Thr Ser Phe Pro Pro Gly Gln Thr Pro Asn Pro Thr Ser Asp Thr
495                 500                 505                 510 ccg gcc ccg ttc ccc acg gcc tgc gcc gac tcc acc cag gtc ttc gtc     1922
Pro Ala Pro Phe Pro Thr Ala Cys Ala Asp Ser Thr Gln Val Phe Val
                515                 520                 525 acc ttc cgc gcc gag gtg acc acc cag tgg ggc cag tcg gtc aag gtc     1970
Thr Phe Arg Ala Glu Val Thr Thr Gln Trp Gly Gln Ser Val Lys Val
            530                 535                 540 gtc ggc agc tcg tcc gag ctc ggc aac tgg gac gtc tcc aag gcc ccg     2018
Val Gly Ser Ser Ser Glu Leu Gly Asn Trp Asp Val Ser Lys Ala Pro
        545                 550                 555 cgc ctg tcc gcg tcg gcc tac acg gcg tcg gac ccg ctc tgg gcc atc     2066
Arg Leu Ser Ala Ser Ala Tyr Thr Ala Ser Asp Pro Leu Trp Ala Ile
    560                 565                 570 acg gtg ccc atg aag gcc ggc cag tcg gtg cag tac aag ttc gtc aag     2114
Thr Val Pro Met Lys Ala Gly Gln Ser Val Gln Tyr Lys Phe Val Lys
575                 580                 585                 590 gtc aac ggg gac ggg tcg atc cag tgg gag tcg gac ccg aac cgc cag     2162
Val Asn Gly Asp Gly Ser Ile Gln Trp Glu Ser Asp Pro Asn Arg Gln
                595                 600                 605 ttc acg gtc agc tct tcc tcc acg gcc agc ggc tgt gcc tgg cag acc     2210
Phe Thr Val Ser Ser Ser Ser Thr Ala Ser Gly Cys Ala Trp Gln Thr
            610                 615                 620 atc gag gcg acc tgg cgg tagatatggg agtactggag caaaagcctc            2258
Ile Glu Ala Thr Trp Arg
        625 attcggagcc ttcggtggct cttgggtggg gggggggtg gaaaagaggg gaggtaatag   2318 gatgatcatg agcgtttggg aaaaaa                                        2344

<210> SEQ ID NO 50
<211> LENGTH: 628
<212> TYPE: PRT
<213> ORGANISM: Chrysosporium lucknowense

<400> SEQUENCE: 50

Met His Ala Leu Ser Ser Leu Ala Val Leu Gly Ala Trp Ala Val Gln
1               5                   10                  15

Thr Val Leu Gly Arg Pro Ala Thr Leu Ser Lys Arg Ala Thr Asp Ser
            20                  25                  30

Phe Ile Glu Thr Glu Thr Pro Ile Ala Trp Glu Lys Leu Arg Cys Asn
        35                  40                  45

Ile Gly Ala Asn Gly Cys Ala Ala Ser Gly Ala Ala Ala Gly Val Val
    50                  55                  60

Ile Ala Ser Pro Ser Lys Ser Asp Pro Asp Tyr Phe Tyr Thr Trp Thr
65                  70                  75                  80

Arg Asp Ala Gly Leu Val Leu Thr Gly Ile Val Asp Ala Leu Ser Gln
                85                  90                  95

Asn Tyr Ser Ala Ala Leu Gln Thr Asn Ile Gln Asp Tyr Ile Ile Ala
            100                 105                 110

Gln Ala Lys Leu Gln Gly Val Ser Asn Pro Ser Gly Ser Leu Ser Asp
        115                 120                 125
```

```
Gly Thr Gly Leu Gly Glu Pro Lys Phe Asn Val Asp Leu Thr Gln Phe
130                 135                 140

Thr Gly Asp Trp Gly Arg Pro Gln Arg Asp Gly Pro Pro Leu Arg Ala
145                 150                 155                 160

Ile Ala Leu Ile Arg Tyr Ala Lys Trp Leu Ala Ser Asn Gly Tyr Lys
                165                 170                 175

Asp Thr Ala Asn Ser Val Val Trp Pro Val Ile Lys Asn Asp Leu Ala
                180                 185                 190

Tyr Ala Ala Gln Tyr Trp Asn Glu Thr Gly Phe Asp Leu Trp Glu Glu
            195                 200                 205

Val Pro Gly Ser Ser Phe Phe Thr Ile Ala Ser Thr His Arg Ala Leu
210                 215                 220

Val Glu Gly Ala Ala Leu Ala Ala Gln Leu Gly Thr Glu Cys Ser Ala
225                 230                 235                 240

Cys Ile Thr Val Ala Pro Gln Val Leu Cys Phe Gln Gln Ser Phe Trp
                245                 250                 255

Asn Pro Ser Gly Gly Tyr Val Val Ser Asn Ile Asn Gly Gly Asn Asn
                260                 265                 270

Arg Ser Gly Lys Asp Leu Asn Ser Val Leu Ala Ser Ile His Thr Phe
            275                 280                 285

Asp Pro Ala Val Gly Cys Asp Ser Val Thr Phe Gln Pro Cys Ser Asp
290                 295                 300

Lys Ala Leu Ser Asn His Lys Ala Tyr Val Asp Ser Phe Arg Ser Val
305                 310                 315                 320

Tyr Ala Ile Asn Ser Gly Ile Ala Gln Gly Lys Ala Val Ala Val Gly
                325                 330                 335

Arg Tyr Ser Glu Asp Val Tyr Tyr Asn Gly Asn Pro Trp Tyr Leu Ala
            340                 345                 350

Asn Phe Ala Ala Ala Glu Gln Leu Tyr Asp Ala Val Phe Val Trp Lys
            355                 360                 365

Lys Gln Gln Ser Ile Glu Val Thr Gln Leu Ser Leu Pro Phe Phe Lys
370                 375                 380

Asp Leu Leu Pro Gly Ile Ser Thr Gly Thr Tyr Thr Pro Ser Ser Ser
385                 390                 395                 400

Thr Tyr Gln Gln Ile Leu Asp Ala Val Ser Ala Tyr Ala Asp Gly Phe
                405                 410                 415

Ile Asp Val Ala Ala Lys Tyr Thr Pro Ser Asp Gly Ser Leu Ala Glu
                420                 425                 430

Gln Tyr Thr Arg Asp Ser Gly Gln Pro Ile Ser Ala Lys Asp Leu Thr
            435                 440                 445

Trp Ser Tyr Ala Ala Phe Leu Ser Ala Ala Asp Arg Arg Ala Gly Ile
450                 455                 460

Val Pro Ala Gly Trp Ser Ala Glu His Gly Lys Thr Leu Pro Gly Ser
465                 470                 475                 480

Cys Ser Ala Val Gln Val Ala Gly Thr Tyr Thr Gln Ala Thr Ala Thr
                485                 490                 495

Ser Phe Pro Pro Gly Gln Thr Pro Asn Pro Thr Ser Asp Thr Pro Ala
            500                 505                 510

Pro Phe Pro Thr Ala Cys Ala Asp Ser Thr Gln Val Phe Val Thr Phe
            515                 520                 525

Arg Ala Glu Val Thr Thr Gln Trp Gly Gln Ser Val Lys Val Val Gly
            530                 535                 540

Ser Ser Ser Glu Leu Gly Asn Trp Asp Val Ser Lys Ala Pro Arg Leu
545                 550                 555                 560
```

```
Ser Ala Ser Ala Tyr Thr Ala Ser Asp Pro Leu Trp Ala Ile Thr Val
            565                 570                 575
Pro Met Lys Ala Gly Gln Ser Val Gln Tyr Lys Phe Val Lys Val Asn
            580                 585                 590
Gly Asp Gly Ser Ile Gln Trp Glu Ser Asp Pro Asn Arg Gln Phe Thr
            595                 600                 605
Val Ser Ser Ser Thr Ala Ser Gly Cys Ala Trp Gln Thr Ile Glu
    610                 615                 620
Ala Thr Trp Arg
625

<210> SEQ ID NO 51
<211> LENGTH: 1884
<212> TYPE: DNA
<213> ORGANISM: Chrysosporium lucknowense

<400> SEQUENCE: 51
atgcacgctc tctcgtcgct cgctgtcctc ggcgcctggg ccgtccagac ggtcttgggc        60
cgtccggcca ccctctcaaa gcgggccacc gactccttca tcgagaccga dacgcctatc       120
gcatgggaaa agctgcggtg caacatcggc gctaacggct gtgcggcttc cggagccgct       180
gccggtgtgg tcattgccag cccgtccaag tcggatccag actacttcta cacctggact       240
cgagatgccg gcctggtcct gacgggtatc gtggacgccc tgtcccaaaa ctactcggcg       300
gccctgcaga ccaacattca ggactacatc atcgcccagg ccaagctcca gggtgtttcg       360
aaccccctccg gtagcctctc ggacggcacc ggtcttggcg agcccaagtt caatgtcgat       420
ctcacccagt tcacgggcga ctggggccgg ccgcagcgcg acggtccgcc tctccgggcc       480
atcgccctca tccgctacgc caagtggctg gcttccaacg gttacaagga cacggccaac       540
agcgtcgtct ggcccgtcat caagaacgac ctggcctatg ccgctcagta ttggaacgag       600
actggttttcg acctgtggga ggaggttccc ggcagctcgt tcttcaccat tgccagcacg       660
caccgagcct tggtagaggg agctgccctc gctgcccagc tcggcaccga atgcagcgcc       720
tgcatcaccg tcgcgcccca agtcctctgc ttccagcaga gcttctggaa cccgtcgggc       780
ggttacgttg tctcgaacat caacggcggc aacaaccggt ccggcaagga tctcaactcg       840
gtcctggcct ccatccacac ctttgacccg gcggtcggct gcgactcggt caccttccag       900
ccctgcagcg acaaggcgct ctccaaccac aaggcctacg tcgactcctt ccgcagcgtc       960
tacgccatca actcgggcat tgcccagggc aaggccgtcg ccgtgggccg ctactcggag      1020
gacgtctact acaacggcaa cccgtggtac ctggccaact cgcggccgc cgagcagctc      1080
tacgacgccc tcttcgtctg gaagaagcag cagtccatcg aggtcaccca gctgtccctc      1140
cccttcttca aggacctgct ccccggcatc tccaccggca cctacacccc gtcgtcgtcg      1200
acgtaccagc agatcctcga cgccgtctcg gcctacgccg acggcttcat cgacgtcgcg      1260
gccaagtaca ccccctcgga cggctccctg gccgagcagt acacgcgcga ctcgggccag      1320
ccgatctcgg ccaaggacct gacctggtcc tacgccgcct cctctcggc cgccgaccgc      1380
cgcgcgggca tcgtcccggc cggctggtcc gccgagcacg gcaagacgct gcccggctcg      1440
tgctcggccg tccaggtcgc cggcacctac acccaggcca ccgccacctc cttcccgccc      1500
ggccagacgc ccaacccgac cagcgacacc ccggccccgt tccccacggc ctgcgccgac      1560
tccacccagg tcttcgtcac cttccgcgcc gaggtgacca cccagtgggg ccagtcggtc      1620
aaggtcgtcg gcagctcgtc cgagctcggc aactgggacg tctccaaggc cccgcgcctg      1680
```

-continued

```
tccgcgtcgg cctacacggc gtcggacccg ctctgggcca tcacggtgcc catgaaggcc    1740
ggccagtcgg tgcagtacaa gttcgtcaag gtcaacgggg acgggtcgat ccagtgggag    1800
tcggacccga accgccagtt cacggtcagc tcttcctcca cggccagcgg ctgtgcctgg    1860
cagaccatcg aggcgacctg gcgg                                           1884
```

```
<210> SEQ ID NO 52
<211> LENGTH: 1637
<212> TYPE: DNA
<213> ORGANISM: Chrysosporium lucknowense
<220> FEATURE:
<221> NAME/KEY: CDS
<222> LOCATION: (148)..(864)
<220> FEATURE:
<221> NAME/KEY: CDS
<222> LOCATION: (1194)..(1601)

<400> SEQUENCE: 52
```

```
gtataagatt gacgacgatc cgggtagaca aaccgacttg cagatctttg caacccatat      60
ttgtactagc ctccaggttc atcctgccca ggtctcctgg cctagagttg tatacatttg     120
ctttgttaac ggagcctttt cctcgtc atg aga tcc tcc gcc atc tgg tcc acc    174
                                Met Arg Ser Ser Ala Ile Trp Ser Thr
                                 1               5 gcc ttc gcg gcg ttg gca cac act gcc gcc gcc gtc act ggt gct gcc       222
Ala Phe Ala Ala Leu Ala His Thr Ala Ala Ala Val Thr Gly Ala Ala
 10              15                  20                  25 gag ggc ttc gcc aaa ggg gtc acg gga ggt ggc aat gcg act ccc gtc       270
Glu Gly Phe Ala Lys Gly Val Thr Gly Gly Gly Asn Ala Thr Pro Val
                 30                  35                  40 tat ccc aaa acc acg gcc gag ctg gtc tcg tac ctg ggt gac tcg gag       318
Tyr Pro Lys Thr Thr Ala Glu Leu Val Ser Tyr Leu Gly Asp Ser Glu
             45                  50                  55 cct cgt gtc atc atg ctg gac cgg aca ttc gac ttc acc gga acc gag       366
Pro Arg Val Ile Met Leu Asp Arg Thr Phe Asp Phe Thr Gly Thr Glu
 60                  65                  70 ggc acc gcg acc gag acg ggc tgc gcc ccc tgg ggc acc ggc tcg ggc       414
Gly Thr Ala Thr Glu Thr Gly Cys Ala Pro Trp Gly Thr Gly Ser Gly
             75                  80                  85 tgc cag ctg gcc ctg aac aag aac gac tgg tgc acc cgg gag cag ccg       462
Cys Gln Leu Ala Leu Asn Lys Asn Asp Trp Cys Thr Arg Glu Gln Pro
 90                  95                 100                 105 aac gcg ccc aaa gtg agc atc acg tac gac aag gcc ggc att ctc ggc       510
Asn Ala Pro Lys Val Ser Ile Thr Tyr Asp Lys Ala Gly Ile Leu Gly
                110                 115                 120 atc acc gtc aag tcc aac aag tcc ctc atc ggc gtc ggc aac aag ggc       558
Ile Thr Val Lys Ser Asn Lys Ser Leu Ile Gly Val Gly Asn Lys Gly
            125                 130                 135 gtc atc aag ggc aaa ggc atc cgc atg gtc agc ggc acc agc aac gtc       606
Val Ile Lys Gly Lys Gly Ile Arg Met Val Ser Gly Thr Ser Asn Val
        140                 145                 150 atc atc cag aac atc cac atc acc aac ctc aac ccg cag tac gtc tgg       654
Ile Ile Gln Asn Ile His Ile Thr Asn Leu Asn Pro Gln Tyr Val Trp
    155                 160                 165 ggc ggc gac gcc atc acg ctc gac aat acc gag atg atc tgg atc gac       702
Gly Gly Asp Ala Ile Thr Leu Asp Asn Thr Glu Met Ile Trp Ile Asp
170                 175                 180                 185 cac gtc acc acc tcc ctc atc ggc cgc cag cac gtc gtc ctg ggt aac       750
His Val Thr Thr Ser Leu Ile Gly Arg Gln His Val Val Leu Gly Asn
                190                 195                 200 aac ccg agc ggc cgc gtc acc atc tcc aac agc aag ttc gac ggc cag       798
Asn Pro Ser Gly Arg Val Thr Ile Ser Asn Ser Lys Phe Asp Gly Gln
```

```
                     205                 210                 215
acc tcc tgg tcc gcc acc tgc aac acc tac cac tac tgg ggc ctg tac        846
Thr Ser Trp Ser Ala Thr Cys Asn Thr Tyr His Tyr Trp Gly Leu Tyr
            220                 225                 230 ttt aca ggg tcc aac gac gtgagttttc accctccttt tcttcttccc               894
Phe Thr Gly Ser Asn Asp
    235 agcataagtc ataaatcaaa aaaagaaaaa aaagaaaaa agaaaaaaag caaaagaaa         954 aaaagaaaa aagaaaaaa aagaaaaaaa gaaaaaaag aaaaaagaa aaaagataa           1014 aaagaagaa agaaaaaag aaaaaagaa aaaaagaaa aaaaaaaag aaaaaagaa            1074 aaaaaaaga aaaaaagaa gaacagaaca aagaaacga agaaaaagga aaataaaaaa         1134 gaatagaata atgcctaaat aggtacagat gctaacggaa ttgcttccac ccaatccag       1193 atg atc acc ttc aag aac aac ctc atc acc cac atg tcg ggc cgc agc       1241
Met Ile Thr Phe Lys Asn Asn Leu Ile Thr His Met Ser Gly Arg Ser
240                 245                 250                 255 ccc aag gtg gcg ggc aac acg ctg ctg cac gcg gtc aac aac tac tgg       1289
Pro Lys Val Ala Gly Asn Thr Leu Leu His Ala Val Asn Asn Tyr Trp
            260                 265                 270 tac gac agc aag ggc cac aac ttc gag ctg gac gcg ggg gcc atg gtg       1337
Tyr Asp Ser Lys Gly His Asn Phe Glu Leu Asp Ala Gly Ala Met Val
        275                 280                 285 ctc gtc gag ggc agc gtg ttc cag aac gtc gag gcg ccg ctc cag tcc       1385
Leu Val Glu Gly Ser Val Phe Gln Asn Val Glu Ala Pro Leu Gln Ser
    290                 295                 300 ggc ggc gcc ggc cgg ctc ttc gcc agc tcc ggc acc gcc tcg gcc tgc       1433
Gly Gly Ala Gly Arg Leu Phe Ala Ser Ser Gly Thr Ala Ser Ala Cys
305                 310                 315 gcc ccg tac ctc ggc cgc gtg tgc cag gcc aac ggc ttc ggc agc tcc       1481
Ala Pro Tyr Leu Gly Arg Val Cys Gln Ala Asn Gly Phe Gly Ser Ser
320                 325                 330                 335 ggc tcc ctc tcc ggc tcc gac acc tcc ttc ctg cag tac ttc cag aac       1529
Gly Ser Leu Ser Gly Ser Asp Thr Ser Phe Leu Gln Tyr Phe Gln Asn
            340                 345                 350 aag aac atc gcc ggc gcg aca gac tac aac acg gcc aag aac gtc ctc       1577
Lys Asn Ile Ala Gly Ala Thr Asp Tyr Asn Thr Ala Lys Asn Val Leu
        355                 360                 365 gac acc gcc gga ttt ggc aca atc tgatcgatcg tgttgcgttt ccttggaaaa      1631
Asp Thr Ala Gly Phe Gly Thr Ile
            370                 375 ggtgga                                                                1637

<210> SEQ ID NO 53
<211> LENGTH: 375
<212> TYPE: PRT
<213> ORGANISM: Chrysosporium lucknowense

<400> SEQUENCE: 53

Met Arg Ser Ser Ala Ile Trp Ser Thr Ala Phe Ala Ala Leu Ala His
1               5                   10                  15

Thr Ala Ala Val Thr Gly Ala Ala Glu Gly Phe Ala Lys Gly Val
            20                  25                  30

Thr Gly Gly Gly Asn Ala Thr Pro Val Tyr Pro Lys Thr Thr Ala Glu
        35                  40                  45

Leu Val

Cys Ala Pro Trp Gly Thr Gly Ser Gly Cys Gln Leu Ala Leu Asn Lys
                85                  90                  95

Asn Asp Trp Cys Thr Arg Glu Gln Pro Asn Ala Pro Lys Val Ser Ile
            100                 105                 110

Thr Tyr Asp Lys Ala Gly Ile Leu Gly Ile Thr Val Lys Ser Asn Lys
        115                 120                 125

Ser Leu Ile Gly Val Gly Asn Lys Gly Val Ile Lys Gly Lys Gly Ile
130                 135                 140

Arg Met Val Ser Gly Thr Ser Asn Val Ile Ile Gln Asn Ile His Ile
145                 150                 155                 160

Thr Asn Leu Asn Pro Gln Tyr Val Trp Gly Asp Ala Ile Thr Leu
                165                 170                 175

Asp Asn Thr Glu Met Ile Trp Ile Asp His Val Thr Thr Ser Leu Ile
            180                 185                 190

Gly Arg Gln His Val Val Leu Gly Asn Asn Pro Ser Gly Arg Val Thr
        195                 200                 205

Ile Ser Asn Ser Lys Phe Asp Gly Gln Thr Ser Trp Ser Ala Thr Cys
210                 215                 220

Asn Thr Tyr His Tyr Trp Gly Leu Tyr Phe Thr Gly Ser Asn Asp Met
225                 230                 235                 240

Ile Thr Phe Lys Asn Asn Leu Ile Thr His Met Ser Gly Arg Ser Pro
                245                 250                 255

Lys Val Ala Gly Asn Thr Leu Leu His Ala Val Asn Asn Tyr Trp Tyr
            260                 265                 270

Asp Ser Lys Gly His Asn Phe Glu Leu Asp Ala Gly Ala Met Val Leu
        275                 280                 285

Val Glu Gly Ser Val Phe Gln Asn Val Glu Ala Pro Leu Gln Ser Gly
290                 295                 300

Gly Ala Gly Arg Leu Phe Ala Ser Ser Gly Thr Ala Ser Ala Cys Ala
305                 310                 315                 320

Pro Tyr Leu Gly Arg Val Cys Gln Ala Asn Gly Phe Gly Ser Ser Gly
                325                 330                 335

Ser Leu Ser Gly Ser Asp Thr Ser Phe Leu Gln Tyr Phe Gln Asn Lys
            340                 345                 350

Asn Ile Ala Gly Ala Thr Asp Tyr Asn Thr Ala Lys Asn Val Leu Asp
        355                 360                 365

Thr Ala Gly Phe Gly Thr Ile
370                 375

<210> SEQ ID NO 54
<211> LENGTH: 1125
<212> TYPE: DNA
<213> ORGANISM: Chrysosporium lucknowense

<400> SEQUENCE: 54
atgagatcct ccgccatctg tccaccgcc ttcgcggcgt tggcacacac tgccgccgcc    60
gtcactggtg ctgccgaggg cttcgccaaa ggggtcacgg aggtggcaa tgcgactccc   120 gtctatccca aaaccacggc cgagctggtc tcgtacctgg gtgactcgga gcctcgtgtc   180
atcatgctgg accggacatt cgacttcacc ggaaccgagg caccgcgac cgagacgggc   240 tgcgccccct ggggcaccgg ctcgggctgc cagctggccc tgaacaagaa cgactggtgc   300
acccgggagc agccgaacgc gcccaaagtg agcatcacgt acgacaaggc cggcattctc   360
ggcatcaccg tcaagtccaa caagtccctc atcggcgtcg gcaacaaggg cgtcatcaag   420

-continued

```
ggcaaaggca tccgcatggt cagcggcacc agcaacgtca tcatccagaa catccacatc    480
accaacctca acccgcagta cgtctggggc ggcgacgcca tcacgctcga caataccgag    540
atgatctgga tcgaccacgt caccacctcc ctcatcggcc gccagcacgt cgtcctgggt    600
aacaacccga gcgccgcgt caccatctcc aacagcaagt cgacggcca gacctcctgg      660 tccgccacct gcaacaccta ccactactgg ggcctgtact ttacagggtc aacgacatg     720 atcaccttca agaacaacct catcccccac atgtcgggcc gcagcccaa ggtggcgggc     780 aacacgctgc tgcacgcggt caacaactac tggtacgaca gcaagggcca aacttcgag     840 ctggacgcgg gggccatggt gctcgtcgag ggcagcgtgt ccagaacgt cgaggcgccg     900 ctccagtccg gcggcgccgg ccggctcttc gccagctccg gcaccgcctc ggcctgcgcc    960
ccgtacctcg gccgcgtgtg ccaggccaac ggcttcggca gctccggctc cctctccggc    1020
tccgacacct ccttcctgca gtacttccag aacaagaaca tcgccggcgc gacagactac    1080
aacacggcca agaacgtcct cgacaccgcc ggatttggca caatc                    1125
```

```
<210> SEQ ID NO 55
<211> LENGTH: 1904
<212> TYPE: DNA
<213> ORGANISM: Chrysosporium lucknowense
<220> FEATURE:
<221> NAME/KEY: CDS
<222> LOCATION: (179)..(330)
<220> FEATURE:
<221> NAME/KEY: CDS
<222> LOCATION: (443)..(591)
<220> FEATURE:
<221> NAME/KEY: CDS
<222> LOCATION: (732)..(1708)

<400> SEQUENCE: 55
```

```
gtataagagc actgtgatcg ttcacaaagc cggcgtactc ctctagagca tctatcatca    60
acatcaccag aaaggtcaag accaggtggt tgccatatcc agtcgcaaaa gagccaaaga    120
gcgaaggagc acgaaagcac agcccaatca ttccctgctt tgctacttct ctccacc       178 atg gtg act ccc tct ctg aag aag gca gct ctg gct gcc ctg tcc ctc    226
Met Val Thr Pro Ser Leu Lys Lys Ala Ala Leu Ala Ala Leu Ser Leu
1               5                   10                  15 ttc ccg ctc ctc tcc cta gct tcg ccg gtg cca gca aca gcc gaa gct    274
Phe Pro Leu Leu Ser Leu Ala Ser Pro Val Pro Ala Thr Ala Glu Ala
            20                  25                  30 agc gta cag acc cgg cag tca tcg gga tac aag aac atc gtg tac ttt    322
Ser Val Gln Thr Arg Gln Ser Ser Gly Tyr Lys Asn Ile Val Tyr Phe
        35                  40                  45 acc aac tg gtatgtacgc ccggccgtca acccctccgc cctccgctcc               370
Thr Asn Trp
    50 ctctctccac cgtttccggg ccagacgaac cactcaagac tttacttaat tactcactgg    430 ccaatcgaac ag g ggt att tac ggc cgc aac tac cag cca gac cag ctg    479
              Gly Ile Tyr Gly Arg Asn Tyr Gln Pro Asp Gln Leu
                      55                  60 ccc gcg tct cag ctc acc cac gtg ctc tat tcc ttt gcc aac atc agg    527
Pro Ala Ser Gln Leu Thr His Val Leu Tyr Ser Phe Ala Asn Ile Arg
65                  70                  75 tcc aac ggc gag gta ttc ctc tcc gac acg tat gcg gac cta gag aag    575
Ser Asn Gly Glu Val Phe Leu Ser Asp Thr Tyr Ala Asp Leu Glu Lys
80                  85                  90                  95 cac tat ccc aac gac t gtaagattaa ttatatccct cttccatcca cccatgtact    631
His Tyr Pro Asn Asp
                100
```

```
cccaacccaa caaccagtca tccattttat ccaccccctt tctttgtaat cttctctctt      691 cccccttct gttccactga cagcacggct ccccggcag ca tgg aat gac gtc           745
                                              Ser Trp Asn Asp Val
                                                               105 gga aac aac gtg tac ggc tgc gtc aag cag ctc ttc ctg ctc aag aag       793
Gly Asn Asn Val Tyr Gly Cys Val Lys Gln Leu Phe Leu Leu Lys Lys
                    110             115                 120 gcg aac cgc cag ctc aag acg ctg ctc tcc atc ggc ggc tgg acc tac       841
Ala Asn Arg Gln Leu Lys Thr Leu Leu Ser Ile Gly Gly Trp Thr Tyr
                125             130             135 tcg gcc acc ttc ccc gcg gcg gcc agc aca gcc gag agc cga gcc ctc       889
Ser Ala Thr Phe Pro Ala Ala Ala Ser Thr Ala Glu Ser Arg Ala Leu
                140             145             150 ttc gcg tcg tcg gcg gtc cgg ctc ctg gcc gac ctg ggc ttc gac ggc       937
Phe Ala Ser Ser Ala Val Arg Leu Leu Ala Asp Leu Gly Phe Asp Gly
            155             160             165 ctc gac atc gac tgg gag tac ccg gcc aac gag cag gag gcg gcc aac       985
Leu Asp Ile Asp Trp Glu Tyr Pro Ala Asn Glu Gln Glu Ala Ala Asn
170             175             180             185 ttc gtc ctc ctg ctc aag gcg gtc cgc tcg gcc ctg gac gac tac gcg      1033
Phe Val Leu Leu Leu Lys Ala Val Arg Ser Ala Leu Asp Asp Tyr Ala
                190             195             200 gcc cag cac gcg ccc ggc tac cac ttc ctc ctc acc atc gcc tcg ccg      1081
Ala Gln His Ala Pro Gly Tyr His Phe Leu Leu Thr Ile Ala Ser Pro
            205             210             215 gcc ggc ccg agc aac tac ggg cac ctg ccg ctg cgc gac atc gcc ggc      1129
Ala Gly Pro Ser Asn Tyr Gly His Leu Pro Leu Arg Asp Ile Ala Gly
                220             225             230 gtg atc gac ttc ttc aac ttc atg ggc tac gac tac gcc ggc tcg tgg      1177
Val Ile Asp Phe Phe Asn Phe Met Gly Tyr Asp Tyr Ala Gly Ser Trp
235             240             245 agc acc gcg gcg gga cac cag gcc aac ctg tac ccg acc gcc gac gcg      1225
Ser Thr Ala Ala Gly His Gln Ala Asn Leu Tyr Pro Thr Ala Asp Ala
250             255             260             265 ggc agg acg ccc ttc tcg acc gac aag gcc ctg tcc gac tac gtc gcc      1273
Gly Arg Thr Pro Phe Ser Thr Asp Lys Ala Leu Ser Asp Tyr Val Ala
                270             275             280 gcc ggc gtc gac ccg gcc aag atc gtg ctc ggc atg ccc atc tac ggc      1321
Ala Gly Val Asp Pro Ala Lys Ile Val Leu Gly Met Pro Ile Tyr Gly
            285             290             295 cgc tcc ttc gag gcc acc gac ggc ctg ggc aag ccc ttc acc ggc gtc      1369
Arg Ser Phe Glu Ala Thr Asp Gly Leu Gly Lys Pro Phe Thr Gly Val
            300             305             310 ggc cag ggc agc tgg gag agc ggc gtg tgg gac tac aag gtg ctg ccc      1417
Gly Gln Gly Ser Trp Glu Ser Gly Val Trp Asp Tyr Lys Val Leu Pro
315             320             325 cgg gcc ggc gcc acc gtc cag tac gac gag gag gcc ggc gcg acc tac      1465
Arg Ala Gly Ala Thr Val Gln Tyr Asp Glu Glu Ala Gly Ala Thr Tyr
330             335             340             345 agc tac gac ccg gcc acg cgc gag ctc atc agc ttc gac acg gtc gac      1513
Ser Tyr Asp Pro Ala Thr Arg Glu Leu Ile Ser Phe Asp Thr Val Asp
                350             355             360 atg gtc aag aag aag gtc gac tac gtc aag cag aag ggc ttc gcc ggc      1561
Met Val Lys Lys Lys Val Asp Tyr Val Lys Gln Lys Gly Phe Ala Gly
                365             370             375 agc atg ttc tgg gag gcc tcc gcc gac cgc acc ggc gac cag agc ctc      1609
Ser Met Phe Trp Glu Ala Ser Ala Asp Arg Thr Gly Asp Gln Ser Leu
            380             385             390 atc ggc gcc agc ttc ggc gcc ctc ggc ggc atc gac cag tcc cag aac      1657
```

-continued

| | | | | | | | | | | | | |
|---|---|---|---|---|---|---|---|---|---|---|---|---|
| Ile | Gly | Ala | Ser | Phe | Gly | Ala | Leu | Gly | Gly | Ile | Asp | Gln | Ser | Gln | Asn |
| | | 395 | | | | 400 | | | | 405 | | | | cag ctg tcg tac ccg gac agc aag tat gat aac ctc agg gcc ggc ttc   1705
Gln Leu Ser Tyr Pro Asp Ser Lys Tyr Asp Asn Leu Arg Ala Gly Phe
410             415                 420                 425 ccg tgaggcccta tgacctcccg agtcctggtc gagagagggg agctggagag   1758
Pro agagagagag agagagagag agagggagcc tgaagccgta ctgattcggc aaaccatttt   1818
gaagcctgga catgttttacc ttcgtttttct cttcttggat ggtttgcatt attattagcc   1878
gcttttcttt tttctctcca ttcgtt   1904

<210> SEQ ID NO 56
<211> LENGTH: 426
<212> TYPE: PRT
<213> ORGANISM: Chrysosporium lucknowense

<400> SEQUENCE: 56

Met Val Thr Pro Ser Leu Lys Lys Ala Ala Leu Ala Ala Leu Ser Leu
1               5                   10                  15

Phe Pro Leu Leu Ser Leu Ala Ser Pro Val Pro Ala Thr Ala Glu Ala
                20                  25                  30

Ser Val Gln Thr Arg Gln Ser Ser Gly Tyr Lys Asn Ile Val Tyr Phe
            35                  40                  45

Thr Asn Trp Gly Ile Tyr Gly Arg Asn Tyr Gln Pro Asp Gln Leu Pro
        50                  55                  60

Ala Ser Gln Leu Thr His Val Leu Tyr Ser Phe Ala Asn Ile Arg Ser
65                  70                  75                  80

Asn Gly Glu Val Phe Leu Ser Asp Thr Tyr Ala Asp Leu Glu Lys His
                85                  90                  95

Tyr Pro Asn Asp Ser Trp Asn Asp Val Gly Asn Asn Val Tyr Gly Cys
            100                 105                 110

Val Lys Gln Leu Phe Leu Leu Lys Ala Asn Arg Gln Leu Lys Thr
        115                 120                 125

Leu Leu Ser Ile Gly Gly Trp Thr Tyr Ser Ala Thr Phe Pro Ala Ala
    130                 135                 140

Ala Ser Thr Ala Glu Ser Arg Ala Leu Phe Ala Ser Ser Ala Val Arg
145                 150                 155                 160

Leu Leu Ala Asp Leu Gly Phe Asp Gly Leu Asp Ile Asp Trp Glu Tyr
                165                 170                 175

Pro Ala Asn Glu Gln Glu Ala Ala Asn Phe Val Leu Leu Leu Lys Ala
            180                 185                 190

Val Arg Ser Ala Leu Asp Asp Tyr Ala Ala Gln His Ala Pro Gly Tyr
        195                 200                 205

His Phe Leu Leu Thr Ile Ala Ser Pro Ala Gly Pro Ser Asn Tyr Gly
    210                 215                 220

His Leu Pro Leu Arg Asp Ile Ala Gly Val Ile Asp Phe Phe Asn Phe
225                 230                 235                 240

Met Gly Tyr Asp Tyr Ala Gly Ser Trp Ser Thr Ala Ala Gly His Gln
                245                 250                 255

Ala Asn Leu Tyr Pro Thr Ala Asp Ala Gly Arg Thr Pro Phe Ser Thr
            260                 265                 270

Asp Lys Ala Leu Ser Asp Tyr Val Ala Ala Gly Val Asp Pro Ala Lys
        275                 280                 285

Ile Val Leu Gly Met Pro Ile Tyr Gly Arg Ser Phe Glu Ala Thr Asp
    290                 295                 300

```
Gly Leu Gly Lys Pro Phe Thr Gly Val Gly Gln Gly Ser Trp Glu Ser
305                 310                 315                 320

Gly Val Trp Asp Tyr Lys Val Leu Pro Arg Ala Gly Ala Thr Val Gln
            325                 330                 335

Tyr Asp Glu Glu Ala Gly Ala Thr Tyr Ser Tyr Asp Pro Ala Thr Arg
        340                 345                 350

Glu Leu Ile Ser Phe Asp Thr Val Asp Met Val Lys Lys Lys Val Asp
    355                 360                 365

Tyr Val Lys Gln Lys Gly Phe Ala Gly Ser Met Phe Trp Glu Ala Ser
370                 375                 380

Ala Asp Arg Thr Gly Asp Gln Ser Leu Ile Gly Ala Ser Phe Gly Ala
385                 390                 395                 400

Leu Gly Gly Ile Asp Gln Ser Gln Asn Gln Leu Ser Tyr Pro Asp Ser
                405                 410                 415

Lys Tyr Asp Asn Leu Arg Ala Gly Phe Pro
            420                 425

<210> SEQ ID NO 57
<211> LENGTH: 1278
<212> TYPE: DNA
<213> ORGANISM: Chrysosporium lucknowense

<400> SEQUENCE: 57
atggtgactc cctctctgaa gaaggcagct ctggctgccc tgtccctctt cccgctcctc     60
tccctagctt cgccggtgcc agcaacagcc gaagctagcg tacagacccg gcagtcatcg    120
ggatacaaga acatcgtgta ctttaccaac tggggtattt acggccgcaa ctaccagcca    180
gaccagctgc ccgcgtctca gctcacccac gtgctctatt cctttgccaa catcaggtcc    240
aacggcgagg tattcctctc cgacacgtat gcggacctag agaagcacta tcccaacgac    300
tcatggaatg acgtcggaaa caacgtgtac ggctgcgtca agcagctctt cctgctcaag    360
aaggcgaacc gccagctcaa gacgctgctc tccatcggcg gctggaccta ctcggccacc    420
ttccccgcgg cggccagcac agccgagagc cgagccctct tcgcgtcgtc ggcggtccgg    480
ctcctggccg acctgggctt cgacggcctc gacatcgact gggagtaccc ggccaacgag    540
caggaggcgg ccaacttcgt cctcctgctc aaggcggtcc gctcggccct ggacgactac    600
gcggcccagc acgcgcccgg ctaccacttc ctcctcacca tcgcctcgcc ggccggcccg    660
agcaactacg gcacctgcc gctgcgcgac atcgccggcg tgatcgactt cttcaacttc    720
atgggctacg actacgccgg ctcgtggagc accgcggcgg acaccaggc caacctgtac    780 ccgaccgccg acgcgggcag gacgcccttc tcgaccgaca aggccctgtc cgactacgtc    840
gccgccggcg tcgacccggc caagatcgtg ctcggcatgc ccatctacgg ccgctccttc    900
gaggccaccg acggcctggg caagcccttc accggcgtcg gccagggcag ctgggagagc    960
ggcgtgtggg actacaaggt gctgccccgg gccgcgccca cgtccagta cgacgaggag   1020 gccggcgcga cctacagcta cgaccccggc acgcgcgagc tcatcagctt cgacacggtc   1080
gacatggtca agaagaaggt cgactacgtc aagcagaagg gcttcgccgg cagcatgttc   1140
tgggaggcct ccgccgaccg caccggcgac cagagcctca tcggcgccag cttcggcgcc   1200
ctcggcggca tcgaccagtc ccagaaccag ctgtcgtacc cggacagcaa gtatgataac   1260
ctcagggccg gcttcccg                                                1278

<210> SEQ ID NO 58
<211> LENGTH: 3200
```

<212> TYPE: DNA
<213> ORGANISM: Chrysosporium lucknowense
<220> FEATURE:
<221> NAME/KEY: CDS
<222> LOCATION: (118)..(2838)

<400> SEQUENCE: 58

```
aggcccttcc cttgtgccta ttaccttacc cgaattgtta attatgtgtc taccaggcac      60
ccaggagggc attgtactca ctcactctcc gagagaacat cgaatccgga aaacaga       117
```

| | | | | | | | | | | | | | | | | |
|---|---|---|---|---|---|---|---|---|---|---|---|---|---|---|

-continued

| | | |
|---|---|---|
| acc tgg cac cga acg tac acg ctc cca ccc ctt tcc acc acc gag ctc<br>Thr Trp His Arg Thr Tyr Thr Leu Pro Pro Leu Ser Thr Thr Glu Leu<br>275                      280                      285 | | 981 |
| gcc ctc tcc gcg acc att gcc gac ccc cag atc tgg tgg ccc cgc caa<br>Ala Leu Ser Ala Thr Ile Ala Asp Pro Gln Ile Trp Trp Pro Arg Gln<br>          290                     295                    300 | | 1029 |
| tgg ggt ggt caa ccg ctc tac acc gcc gcc ttg acc gtc acc acg cgc<br>Trp Gly Gly Gln Pro Leu Tyr Thr Ala Ala Leu Thr Val Thr Thr Arg<br>305                      310                      315            320 | | 1077 |
| ggc acc acc acg ccg tcc gac cgg tcc acg gcc acc ttc ggc ctg cgc<br>Gly Thr Thr Thr Pro Ser Asp Arg Ser Thr Ala Thr Phe Gly Leu Arg<br>                         325                      330                    335 | | 1125 |
| acc gtc gag gcg agg ctg aac ccg acc tac aac gac acc acc ttc cac<br>Thr Val Glu Ala Arg Leu Asn Pro Thr Tyr Asn Asp Thr Thr Phe His<br>                         340                      345                  350 | | 1173 |
| gtc aac tcg cgc ccc ttc cag gtc ctg ggc gcc ggc tac tcc ccc aac<br>Val Asn Ser Arg Pro Phe Gln Val Leu Gly Ala Gly Tyr Ser Pro Asn<br>         355                      360                    365 | | 1221 |
| gtc ttc ctc cgc gcg ccg cca cgg acc gcc gcg gcc gac tac acg gcc<br>Val Phe Leu Arg Ala Pro Pro Arg Thr Ala Ala Ala Asp Tyr Thr Ala<br>370                      375                      380 | | 1269 |
| acg ctc cag tac gta ctc gac ctg ggc ctg aac acg atc cgg ctc gag<br>Thr Leu Gln Tyr Val Leu Asp Leu Gly Leu Asn Thr Ile Arg Leu Glu<br>385                      390                      395            400 | | 1317 |
| ggc aag gac gag cac tcg gaa ctg tac gcg gcg gac cgg ctg ggc<br>Gly Lys Asp Glu His Ser Glu Leu Tyr Ala Ala Ala Asp Arg Leu Gly<br>                         405                      410                  415 | | 1365 |
| gtc atg atc ctt gcc ggc tgg gag tgc tgc gac aag tgg gag gcg tgg<br>Val Met Ile Leu Ala Gly Trp Glu Cys Cys Asp Lys Trp Glu Ala Trp<br>                  420                      425                    430 | | 1413 |
| agc tac aac ggc gac ctg gcc atc gac ccg gtg ccg gtc tgg gac gac<br>Ser Tyr Asn Gly Asp Leu Ala Ile Asp Pro Val Pro Val Trp Asp Asp<br>         435                      440                    445 | | 1461 |
| gcc gac tac gcc gtc gcg cgt gcc gcc atg gcc cac gag gcc cgc atg<br>Ala Asp Tyr Ala Val Ala Arg Ala Ala Met Ala His Glu Ala Arg Met<br>450                      455                      460 | | 1509 |
| ctc cag ccc cat ccc agc ctg ctg ggc ttc ctc atc ggc agc gac ttc<br>Leu Gln Pro His Pro Ser Leu Leu Gly Phe Leu Ile Gly Ser Asp Phe<br>465                      470                      475            480 | | 1557 |
| tgg ccc gac gac cgc gcc acc gcc gcc tac ctc gat gcc ctg gaa gcc<br>Trp Pro Asp Asp Arg Ala Thr Ala Ala Tyr Leu Asp Ala Leu Glu Ala<br>                         485                      490                  495 | | 1605 |
| gcc gac tgg gcc gcc ccc gtg ctg gcc tcg gcc tcg aag cgc ggg tac<br>Ala Asp Trp Ala Ala Pro Val Leu Ala Ser Ala Ser Lys Arg Gly Tyr<br>                  500                      505                    510 | | 1653 |
| ccc gag cgg acc ggt ccg gga ggg ctc aag atg gac ggg ccg tac gac<br>Pro Glu Arg Thr Gly Pro Gly Gly Leu Lys Met Asp Gly Pro Tyr Asp<br>         515                      520                    525 | | 1701 |
| tgg gtg cca ccg ggg tac tgg tgg gac acg gag ccg acc ggg gag agg<br>Trp Val Pro Pro Gly Tyr Trp Trp Asp Thr Glu Pro Thr Gly Glu Arg<br>530                      535                      540 | | 1749 |
| ctc gga gcc gcg ttc ggt ttt ggg tcc gag ctg ggc gcg ggc gtg ggc<br>Leu Gly Ala Ala Phe Gly Phe Gly Ser Glu Leu Gly Ala Gly Val Gly<br>545                      550                      555            560 | | 1797 |
| acg ccg gag ctg ggg tcg ctg agg cgg ttc ctg agc gag ggg gac ctg<br>Thr Pro Glu Leu Gly Ser Leu Arg Arg Phe Leu Ser Glu Gly Asp Leu<br>                         565                      570                  575 | | 1845 |
| gag gcc ctg tgg aag cgg ccg aac gtg agc cta ttc cac atg tcg agg<br>Glu Ala Leu Trp Lys Arg Pro Asn Val Ser Leu Phe His Met Ser Arg<br>                  580                      585                    590 | | 1893 |

-continued

| | | |
|---|---|---|
| gag acc tcc caa ttt acg acg agg gtg atc tac aac gcc ggg ctc tgg<br>Glu Thr Ser Gln Phe Thr Thr Arg Val Ile Tyr Asn Ala Gly Leu Trp<br>595                    600                  605 | 1941 |
| aac cgg tgg ggc gcc ccc gcg agc ctg gaa gac tac ctg atg aag gcg<br>Asn Arg Trp Gly Ala Pro Ala Ser Leu Glu Asp Tyr Leu Met Lys Ala<br>610                    615                  620 | 1989 |
| cag ctg atg gac tac gag gcc acg cgg gct cag ttc gac gcc tac acg<br>Gln Leu Met Asp Tyr Glu Ala Thr Arg Ala Gln Phe Asp Ala Tyr Thr<br>625                    630                  635                  640 | 2037 |
| gcc atg tgg aac gcc gag agg ccg gcc acg ggc ctg ata tac tgg atg<br>Ala Met Trp Asn Ala Glu Arg Pro Ala Thr Gly Leu Ile Tyr Trp Met<br>                  645                  650                  655 | 2085 |
| ctc aac aac gcc tgg ccg agc ctg cac tgg aac ctg tgg gac tac tac<br>Leu Asn Asn Ala Trp Pro Ser Leu His Trp Asn Leu Trp Asp Tyr Tyr<br>                  660                  665                  670 | 2133 |
| atg cgt cct gcc ggt agt tac ttt ggg gca aag gcc ggc agc agg gtg<br>Met Arg Pro Ala Gly Ser Tyr Phe Gly Ala Lys Ala Gly Ser Arg Val<br>                  675                  680                  685 | 2181 |
| gaa aat gtc gtg ttt gac tac gtc agg agg gcg gtc tgg ctg gtc aac<br>Glu Asn Val Val Phe Asp Tyr Val Arg Arg Ala Val Trp Leu Val Asn<br>690                    695                  700 | 2229 |
| cgg tcc ctg gac aag agc ggg acg agg aga gtg cag gtg gac gtc atg<br>Arg Ser Leu Asp Lys Ser Gly Thr Arg Arg Val Gln Val Asp Val Met<br>705                    710                  715                  720 | 2277 |
| gat aag cat ggt aaa gtc cta tac aag gac acg acc gtc acc acg act<br>Asp Lys His Gly Lys Val Leu Tyr Lys Asp Thr Thr Val Thr Thr Thr<br>                  725                  730                  735 | 2325 |
| gtt cca aac acg agc aag gac att ctt tca cta gcg gga cct ctg ggc<br>Val Pro Asn Thr Ser Lys Asp Ile Leu Ser Leu Ala Gly Pro Leu Gly<br>                  740                  745                  750 | 2373 |
| aac atc acc gac gtg gtg ttt ttg cgg ctg gtc ctc tac gat gca caa<br>Asn Ile Thr Asp Val Val Phe Leu Arg Leu Val Leu Tyr Asp Ala Gln<br>                  755                  760                  765 | 2421 |
| cgg caa ggg cat gcg ctg agt cga aac gtg tac tgg gtt gcg aag gag<br>Arg Gln Gly His Ala Leu Ser Arg Asn Val Tyr Trp Val Ala Lys Glu<br>770                    775                  780 | 2469 |
| cca gat gtg ctg gac tgg gac gag tcg gat tgg tac ttc acg ccg gtg<br>Pro Asp Val Leu Asp Trp Asp Glu Ser Asp Trp Tyr Phe Thr Pro Val<br>785                    790                  795                  800 | 2517 |
| acc agc tac tcg gac tac act gca cta aac aac atg gct cag gca gac<br>Thr Ser Tyr Ser Asp Tyr Thr Ala Leu Asn Asn Met Ala Gln Ala Asp<br>                  805                  810                  815 | 2565 |
| gtc acg gtt cac aat gtc tgg cac ggc tca ggg gtt gac atg acg ctg<br>Val Thr Val His Asn Val Trp His Gly Ser Gly Val Asp Met Thr Leu<br>820                    825                  830 | 2613 |
| gag aac aaa tct aag gtg cca gcg ttc ttt gtc agc ttg acg ctg gtg<br>Glu Asn Lys Ser Lys Val Pro Ala Phe Phe Val Ser Leu Thr Leu Val<br>835                    840                  845 | 2661 |
| gat gta cac ggg aac gag gtc ctg ccg gtg acg tgg gag gac aac tat<br>Asp Val His Gly Asn Glu Val Leu Pro Val Thr Trp Glu Asp Asn Tyr<br>850                    855                  860 | 2709 |
| gtc acc cta tgg ccg ggt gag aaa ttg aca ctt cgg gga agg tca atg<br>Val Thr Leu Trp Pro Gly Glu Lys Leu Thr Leu Arg Gly Arg Ser Met<br>865                    870                  875                  880 | 2757 |
| ggg gta gat gca aag ccg tgg gag gtc att gtg aga gga aag aac gtt<br>Gly Val Asp Ala Lys Pro Trp Glu Val Ile Val Arg Gly Lys Asn Val<br>                  885                  890                  895 | 2805 |
| gaa gca aag aga gtc cgt cac cgg tgg cat gta tgagagaaga ccaacattac<br>Glu Ala Lys Arg Val Arg His Arg Trp His Val<br>                  900                  905 | 2858 |

```
atggatagcc ttaatggtat agatcctacc gaatgaaatc actcattagc gaggaagtac    2918
tttgtgagtt gggtgagcat attccctaaa ttcattctac tgggggttgc attagaggca    2978
cctcacgtgg aacaactgtt aggattcaat ttcgcagcaa gaaccgtagt cccactcgtt    3038
ttcaaatatc catgtgagac atgtgatctg tctgtataac ggggcggcta cttgcccact    3098
tcacccaaca cggaagacct aggtttggtg ggccaccata ttgcctttgc atgactattt    3158
cacaccccaa cgtgaaacga tgctctaaaa ccaacgaaaa aa                       3200
```

<210> SEQ ID NO 59
<211> LENGTH: 907
<212> TYPE: PRT
<213> ORGANISM: Chrysosporium lucknowense

<400> SEQUENCE: 59

```
Met Arg Ala Lys Arg Ala Ala Ile Ala Leu Phe Leu Ala Trp Pro Ala
1               5                  10                  15

Ile Thr Arg Ala Ala Ser Leu Val Ser Phe Pro Gly Asn Thr Ala Ala
            20                  25                  30

Ile Pro Ser Trp Glu Leu Gln Ser Ser Val Glu Ala Gly Thr Asp Leu
        35                  40                  45

Glu G

-continued

```
Gly Thr Thr Thr Pro Ser Asp Arg Ser Thr Ala Thr Phe Gly Leu Arg
            325                 330                 335

Thr Val Glu Ala Arg Leu Asn Pro Thr Tyr Asn Asp Thr Thr Phe His
        340                 345                 350

Val Asn Ser Arg Pro Phe Gln Val Leu Gly Ala Gly Tyr Ser Pro Asn
            355                 360                 365

Val Phe Leu Arg Ala Pro Pro Arg Thr Ala Ala Asp Tyr Thr Ala
    370                 375                 380

Thr Leu Gln Tyr Val Leu Asp Leu Gly Leu Asn Thr Ile Arg Leu Glu
385                 390                 395                 400

Gly Lys Asp Glu His Ser Glu Leu Tyr Ala Ala Ala Asp Arg Leu Gly
                405                 410                 415

Val Met Ile Leu Ala Gly Trp Glu Cys Cys Asp Lys Trp Glu Ala Trp
                420                 425                 430

Ser Tyr Asn Gly Asp Leu Ala Ile Asp Pro Val Pro Val Trp Asp Asp
            435                 440                 445

Ala Asp Tyr Ala Val Ala Arg Ala Ala Met Ala His Glu Ala Arg Met
        450                 455                 460

Leu Gln Pro His Pro Ser Leu Leu Gly Phe Leu Ile Gly Ser Asp Phe
465                 470                 475                 480

Trp Pro Asp Asp Arg Ala Thr Ala Ala Tyr Leu Asp Ala Leu Glu Ala
                485                 490                 495

Ala Asp Trp Ala Ala Pro Val Leu Ala Ser Ala Ser Lys Arg Gly Tyr
            500                 505                 510

Pro Glu Arg Thr Gly Pro Gly Gly Leu Lys Met Asp Gly Pro Tyr Asp
        515                 520                 525

Trp Val Pro Pro Gly Tyr Trp Trp Asp Thr Glu Pro Thr Gly Glu Arg
    530                 535                 540

Leu Gly Ala Ala Phe Gly Phe Gly Ser Glu Leu Gly Ala Gly Val Gly
545                 550                 555                 560

Thr Pro Glu Leu Gly Ser Leu Arg Arg Phe Leu Ser Glu Gly Asp Leu
                565                 570                 575

Glu Ala Leu Trp Lys Arg Pro Asn Val Ser Leu Phe His Met Ser Arg
            580                 585                 590

Glu Thr Ser Gln Phe Thr Thr Arg Val Ile Tyr Asn Ala Gly Leu Trp
        595                 600                 605

Asn Arg Trp Gly Ala Pro Ala Ser Leu Glu Asp Tyr Leu Met Lys Ala
    610                 615                 620

Gln Leu Met Asp Tyr Glu Ala Thr Arg Ala Gln Phe Asp Ala Tyr Thr
625                 630                 635                 640

Ala Met Trp Asn Ala Glu Arg Pro Ala Thr Gly Leu Ile Tyr Trp Met
                645                 650                 655

Leu Asn Asn Ala Trp Pro Ser Leu His Trp Asn Leu Trp Asp Tyr Tyr
            660                 665                 670

Met Arg Pro Ala Gly Ser Tyr Phe Gly Ala Lys Ala Gly Ser Arg Val
        675                 680                 685

Glu Asn Val Val Phe Asp Tyr Val Arg Arg Ala Val Trp Leu Val Asn
    690                 695                 700

Arg Ser Leu Asp Lys Ser Gly Thr Arg Arg Val Gln Val Asp Val Met
705                 710                 715                 720

Asp Lys His Gly Lys Val Leu Tyr Lys Asp Thr Val Thr Thr Thr
                725                 730                 735

Val Pro Asn Thr Ser Lys Asp Ile Leu Ser Leu Ala Gly Pro Leu Gly
            740                 745                 750
```

```
Asn Ile Thr Asp Val Val Phe Leu Arg Leu Val Leu Tyr Asp Ala Gln
            755                 760                 765
Arg Gln Gly His Ala Leu Ser Arg Asn Val Tyr Trp Val Ala Lys Glu
        770                 775                 780
Pro Asp Val Leu Asp Trp Asp Glu Ser Asp Trp Tyr Phe Thr Pro Val
785                 790                 795                 800
Thr Ser Tyr Ser Asp Tyr Thr Ala Leu Asn Asn Met Ala Gln Ala Asp
            805                 810                 815
Val Thr Val His Asn Val Trp His Gly Ser Gly Val Asp Met Thr Leu
        820                 825                 830
Glu Asn Lys Ser Lys Val Pro Ala Phe Phe Val Ser Leu Thr Leu Val
        835                 840                 845
Asp Val His Gly Asn Glu Val Leu Pro Val Thr Trp Glu Asp Asn Tyr
    850                 855                 860
Val Thr Leu Trp Pro Gly Glu Lys Leu Thr Leu Arg Gly Arg Ser Met
865                 870                 875                 880
Gly Val Asp Ala Lys Pro Trp Glu Val Ile Val Arg Gly Lys Asn Val
            885                 890                 895
Glu Ala Lys Arg Val Arg His Arg Trp His Val
        900                 905
```

<210> SEQ ID NO 60
<211> LENGTH: 2721
<212> TYPE: DNA
<213> ORGANISM: Chrysosporium lucknowense

<400> SEQUENCE: 60

```
atgcgggcga aagggcggc cattgccctt ttcctagctt ggccggccat aacacgggcc     60
gcgtccctcg tctcttttcc gggaaacacg gccgcgattc catcgtggga actgcagtct    120
tctgtggagg ccggcactga cctcgaaggt ctttcacaag ttggggtcga tacaaagtca    180
tggcaccaca tcaaaacatg gagatgtacg ctcatgggct gcctgatcga ggccggcgtc    240
tacaatgaag atcaactctt ctactcggag aacctgcgca aagtcaacga gacgcaattc    300
ctggtgccat ggatttatcg caacgagttc tccctgcatc ccggcccggg caggcacttc    360
ttcctgcaga cacacggcat ctcttcgcga gccgacatct ttctgaacgg caaacgagtg    420
gccaattctt cggagcaggc gggttcgtac gttggccgga tttacgacat caccaaacag    480
gttcacagag aaaatgcgct ggcaattcag gtgtacccga ccaactacta ctacgacctg    540
gcgctcggat gggtggattg gaacccatgg ccggccgaca acggcaccgg cgtctggcgg    600
gacgtcgaga tcaagcagac cggggcggtc atgctggagc cgttgcgggt tgtgacgcac    660
ttggggccga cgctcggaga tgagccagca aacgtgaccc tcaaggccca agcacataac    720
cttgaaaaact acaccgtcac catcacggcc accggccaca tcgccctgga cccccactct    780
gataaccaac aacaccatca ccaccaccac cctattacct ggcaccgaac gtacacgctc    840
ccaccccttt ccaccaccga gctcgcccct ccgcgaccca ttgccgaccc ccagatctgg    900
tggccccgcc aatggggtgg tcaaccgctc tacaccgccg ccttgaccgt caccacgcgc    960
ggcaccacca cgccgtccga ccggtccacg gccaccttcg gcctgcgcac cgtcgaggcg   1020
aggctgaacc cgacctacaa cgacaccacc ttccacgtca actcgcgccc cttccaggtc   1080
ctgggcgccg gctactcccc caacgtcttc ctccgcgcgc cgccacggac cgccgcggcc   1140
gactacacgg ccacgctcca gtacgtactc gacctgggcc tgaacacgat ccggctcgag   1200
ggcaaggacg agcactcgga actgtacgcg gcggcggacc ggctgggcgt catgatcctt   1260
```

-continued

```
gccggctggg agtgctgcga caagtgggag gcgtggagct acaacggcga cctggccatc    1320
gacccggtgc cggtctggga cgacgccgac tacgccgtcg cgcgtgccgc catggcccac    1380
gaggcccgca tgctccagcc ccatcccagc ctgctgggct tcctcatcgg cagcgacttc    1440
tggcccgacg accgcgccac cgccgcctac ctcgatgccc tggaagccgc cgactgggcc    1500
gcccccgtgc tggcctcggc ctcgaagcgc gggtaccccg agcggaccgg tccgggaggg    1560
ctcaagatgg acgggccgta cgactgggtg ccaccggggt actggtggga cacggagccg    1620
accggggaga ggctcggagc cgcgttcggt tttgggtccg agctgggcgc gggcgtgggc    1680
acgccggagc tggggtcgct gaggcggttc ctgagcgagg gggacctgga ggccctgtgg    1740
aagcggccga acgtgagcct attccacatg tcgaggdaga cctcccaatt tacgacgagg    1800
gtgatctaca acgccgggct ctggaaccgg tggggcgccc ccgcgagcct ggaagactac    1860
ctgatgaagg cgcagctgat ggactacgag gccacgcggg ctcagttcga cgcctacacg    1920
gccatgtgga acgccgagag gccggccacg ggcctgatat actggatgct caacaacgcc    1980 tggcccgagcc tgcactggaa cctgtgggac tactacatgc gtcctgccgg tagttacttt    2040
ggggcaaagg ccggcagcag ggtggaaaat gtcgtgtttg actacgtcag gagggcggtc    2100
tggctggtca accggtcccct ggacaagagc gggacgagga gagtgcaggt ggacgtcatg    2160
gataagcatg gtaaagtcct atacaaggac acgaccgtca ccacgactgt tccaaacacg    2220
agcaaggaca ttctttcact agcgggacct ctgggcaaca tcaccgacgt ggtgttttg    2280 cggctggttc tctacgatgc acaacggcaa gggcatgcgc tgagtcgaaa cgtgtactgg    2340
gttgcgaagg agccagatgt gctggactgg gacgagtcgg attggtactt cacgccggtg    2400
accagctact cggactacac tgcactaaac aacatggctc aggcagacgt cacggttcac    2460
aatgtctggc acggctcagg ggttgacatg acgctggaga acaaatctaa ggtgccagcg    2520
ttctttgtca gcttgacgct ggtggatgta cacgggaacg aggtcctgcc ggtgacgtgg    2580
gaggacaact atgtcacccct atggccgggt gagaaattga cacttcgggg aaggtcaatg    2640
ggggtagatg caaagccgtg ggaggtcatt gtgagaggaa agaacgttga agcaaagaga    2700
gtccgtcacc ggtggcatgt a                                              2721
```

<210> SEQ ID NO 61
<211> LENGTH: 1275
<212> TYPE: DNA
<213> ORGANISM: Chrysosporium lucknowense
<220> FEATURE:
<221> NAME/KEY: CDS
<222> LOCATION: (180)..(668)
<220> FEATURE:
<221> NAME/KEY: CDS
<222> LOCATION: (776)..(1225)

<400> SEQUENCE: 61

```
gtataattct acgtcatccc ctccgttccc ttcccagctc ccctctccta ctgctgagtg     60
atgttaataa tagtacgagt cgtggaattt gtggatactg atccaggata aagtctcttc    120
cattcggccc gacctcctaa aactcccgac aaagctaaac cgcccgtgt gacgacaag     179 atg aag ctc ctg ggc aaa ctc tcg gcg gca ctc gcc ctc gcg ggc agc     227
Met Lys Leu Leu Gly Lys Leu Ser Ala Ala Leu Ala Leu Ala Gly Ser
1               5                   10                  15 agg ctg gct gcc gcg cac ccg gtc ttc gac gag ctg atg cgg ccg acg     275
Arg Leu Ala Ala Ala His Pro Val Phe Asp Glu Leu Met Arg Pro Thr
            20                  25                  30 gcg ccg ctg gtg cgc ccg cgg gcg gcc ctg cag cag gtg acc aac ttt     323
```

```
                Ala Pro Leu Val Arg Pro Arg Ala Leu Gln Gln Val Thr Asn Phe
                         35                  40                  45 ggc agc aac ccg tcc aac acg aag atg ttc atc tac gtg ccc gac aag         371
Gly Ser Asn Pro Ser Asn Thr Lys Met Phe Ile Tyr Val Pro Asp Lys
 50                  55                  60 ctg gcc ccc aac ccg ccc atc ata gtg gcc atc cac tac tgc acc ggc         419
Leu Ala Pro Asn Pro Pro Ile Ile Val Ala Ile His Tyr Cys Thr Gly
 65                  70                  75                  80 acc gcc cag gcc tac tac tcg ggc tcc cct tac gcc cgc ctc gcc gac         467
Thr Ala Gln Ala Tyr Tyr Ser Gly Ser Pro Tyr Ala Arg Leu Ala Asp
                 85                  90                  95 cag aag ggc ttc atc gtc atc tac ccg gag tcc ccc tac agc ggc acc         515
Gln Lys Gly Phe Ile Val Ile Tyr Pro Glu Ser Pro Tyr Ser Gly Thr
            100                 105                 110 tgt tgg gac gtc tcg tcg cgc gcc gcc ctg acc cac aac ggc ggc ggc         563
Cys Trp Asp Val Ser Ser Arg Ala Ala Leu Thr His Asn Gly Gly Gly
            115                 120                 125 gac agc aac tcg atc gcc aac atg gtc acc tac acc ctc gaa aag tac         611
Asp Ser Asn Ser Ile Ala Asn Met Val Thr Tyr Thr Leu Glu Lys Tyr
130                 135                 140 aat ggc gac gcc agc aag gtc ttt gtc acc ggc tcg tcg tcc ggc gcc         659
Asn Gly Asp Ala Ser Lys Val Phe Val Thr Gly Ser Ser Ser Gly Ala
145                 150                 155                 160 atg atg acg gtgcgttcta attacccctc ccactccttt ttttttttt                  708
Met Met Thr tttgttttcc ttcctttct tttcccagg agcgtcttgg ttgattgact gacttgttca         768 aatccag aac gtg atg gcc gcc gcg tac ccg gaa ctg ttc gcg gca gga         817
        Asn Val Met Ala Ala Ala Tyr Pro Glu Leu Phe Ala Ala Gly
            165                 170                 175 atc gcc tac tcg ggc gtg ccc gcc ggc tgc ttc tac agc cag tcc gga         865
Ile Ala Tyr Ser Gly Val Pro Ala Gly Cys Phe Tyr Ser Gln Ser Gly
            180                 185                 190 ggc acc aac gcg agg aac agc tcg tgc gcc aac ggg cag atc aac tcg         913
Gly Thr Asn Ala Arg Asn Ser Ser Cys Ala Asn Gly Gln Ile Asn Ser
            195                 200                 205 acg ccc cag gtg tgg gcc aag atg gtc ttc gac atg tac ccg gaa tac         961
Thr Pro Gln Val Trp Ala Lys Met Val Phe Asp Met Tyr Pro Glu Tyr
210                 215                 220                 225 gac ggc ccg cgc ccc aag atg cag atc tac cac ggc tcg gcc gac ggc        1009
Asp Gly Pro Arg Pro Lys Met Gln Ile Tyr His Gly Ser Ala Asp Gly
                230                 235                 240 acg ctc aga ccc agc aac tac aac gag acc atc aag cag tgg tgc ggc        1057
Thr Leu Arg Pro Ser Asn Tyr Asn Glu Thr Ile Lys Gln Trp Cys Gly
            245                 250                 255 gtc ttc ggc ttc gac tac acc cgc ccc gac acc acc cag gcc aac tcc        1105
Val Phe Gly Phe Asp Tyr Thr Arg Pro Asp Thr Thr Gln Ala Asn Ser
            260                 265                 270 ccg cag gcc ggc tac acc acc tac acc tgg ggc gag cag cag ctc gtc        1153
Pro Gln Ala Gly Tyr Thr Thr Tyr Thr Trp Gly Glu Gln Gln Leu Val
            275                 280                 285 ggc atc tac gcc cag ggc gtc gga cac acg gtc ccc atc cgc ggc agc        1201
Gly Ile Tyr Ala Gln Gly Val Gly His Thr Val Pro Ile Arg Gly Ser
290                 295                 300                 305 gac gac atg gcc ttc ttt ggc ctg tgatgatgag aggttcggtg ggctgggaac       1255
Asp Asp Met Ala Phe Phe Gly Leu
                310 cagagcggaa gtacggttta                                                  1275

<210> SEQ ID NO 62
```

```
<211> LENGTH: 313
<212> TYPE: PRT
<213> ORGANISM: Chrysosporium lucknowense

<400> SEQUENCE: 62

Met Lys Leu Leu Gly Lys Leu Ser Ala Leu Ala Leu Ala Gly Ser
1               5                   10                  15

Arg Leu Ala Ala Ala His Pro Val Phe Asp Glu Leu Met Arg Pro Thr
            20                  25                  30

Ala Pro Leu Val Arg Pro Arg Ala Ala Leu Gln Gln Val Thr Asn Phe
        35                  40                  45

Gly Ser Asn Pro

-continued

```
gtgcccgaca agctggcccc caacccgccc atcatagtgg ccatccacta ctgcaccggc      240 accgccagg  cctactactc gggctcccct tacgcccgcc tcgccgacca gaagggcttc      300
atcgtcatct accccggagtc ccctacagc  ggcacctgtt gggacgtctc gtcgcgcgcc     360
gccctgaccc acaacggcgg cggcgacagc aactcgatcg ccaacatggt cacctacacc      420
ctcgaaaagt acaatggcga cgccagcaag gtctttgtca ccggctcctc gtccggcgcc      480
atgatgacga cgtgatggc  cgccgcgtac ccggaactgt cgcggcagg  aatcgcctac      540 tcgggcgtgc cgccggctg  cttctacagc cagtccggag gcaccaacgc gaggaacagc      600
tcgtgcgcca acgggcagat caactcgacg ccccaggtgt gggccaagat ggtcttcgac      660
atgtacccgg aatacgacgg cccgcgcccc aagatgcaga tctaccacgg ctcggccgac      720
ggcacgctca gcccagcaa  ctacaacgag accatcaagc agtggtgcgg cgtcttcggc      780
ttcgactaca cccgccccga caccacccag gccaactccc cgcaggccgg ctacaccacc      840
tacacctggg gcgagcagca gctcgtcggc atctacgccc agggcgtcgg acacacggtc      900
cccatccgcg gcagcgacga catggccttc tttggcctg                            939
```

<210> SEQ ID NO 64
<211> LENGTH: 1182
<212> TYPE: DNA
<213> ORGANISM: Chrysosporium lucknowense
<220> FEATURE:
<221> NAME/KEY: CDS
<222> LOCATION: (162)..(621)
<220> FEATURE:
<221> NAME/KEY: CDS
<222> LOCATION: (793)..(1169)

<400> SEQUENCE: 64

```
atataaataa gccgggaggg catcaggaca tgacctctac ctctctgtaa tcagacgctg       60
gtggcttcct cccacatatc ggggttaata tttattagct cgtcattgtc tctgcgcgcc     120
ttgccgcaaa acatcacccg tatattgcgt atcagcaaac a atg atc tcg gtt cct    176
                                             Met Ile Ser Val Pro
                                              1               5 gct ctc gct ctg gcc ctt ctg gcc gcc gtc cag gtc gtc gag tct gcc       224
Ala Leu Ala Leu Ala Leu Leu Ala Ala Val Gln Val Val Glu Ser Ala
         10                  15                  20 tcg gct ggc tgt ggc aag gcg ccc cct tcc tcg ggc acc aag tcg atg       272
Ser Ala Gly Cys Gly Lys Ala Pro Pro Ser Ser Gly Thr Lys Ser Met
     25                  30                  35 acg gtc aac ggc aag cag cgc cag tac att ctc cag ctg ccc aac aac       320
Thr Val Asn Gly Lys Gln Arg Gln Tyr Ile Leu Gln Leu Pro Asn Asn
 40                  45                  50 tac gac gcc aac aag gcc cac agg gtg gtg atc ggg tac cac tgg cgc       368
Tyr Asp Ala Asn Lys Ala His Arg Val Val Ile Gly Tyr His Trp Arg
 55                  60                  65 gac gga tcc atg aac gac gtg gcc aac ggc ggc ttc tac gat ctg cgg       416
Asp Gly Ser Met Asn Asp Val Ala Asn Gly Gly Phe Tyr Asp Leu Arg
 70                  75                  80                  85 tcc cgg gcg ggc gac agc acc atc ttc gtt gcc ccc aac ggc ctc aat       464
Ser Arg Ala Gly Asp Ser Thr Ile Phe Val Ala Pro Asn Gly Leu Asn
             90                  95                 100 gcc gga tgg gcc aac gtg ggc ggc gag gac atc acc ttt acg gac cag       512
Ala Gly Trp Ala Asn Val Gly Gly Glu Asp Ile Thr Phe Thr Asp Gln
        105                 110                 115 atc gta gac atg ctc aag aac gac ctc tgc gtg gac gag acc cag ttc       560
Ile Val Asp Met Leu Lys Asn Asp Leu Cys Val Asp Glu Thr Gln Phe
    120                 125                 130
```

-continued

```
ttt gct acg ggc tgg agc tat ggc ggt gcc atg agc cat agc gtg gct      608
Phe Ala Thr Gly Trp Ser Tyr Gly Gly Ala Met Ser His Ser Val Ala
    135                 140                 145 tgt tct cgg cca g gtaatattga ttttgtcatc ctgtcttttt tcttcttctt        661
Cys Ser Arg Pro
150 cttctctttc ttccctctgg cattcttctc ttctcttctc ttctcttctc ctcttttatt    721 tccccgtcat ttcccccac aaagaaacac ctggacaagc caatgacatc cattaatata     781 tataaatgca g ac  gtc ttc aag gcc gtc gcg gtc atc gcc ggg gcc cag     830
             Asp Val Phe Lys Ala Val Ala Val Ile Ala Gly Ala Gln
                 155                 160                 165 ctg tcc ggc tgc gcc ggc ggc acg acg ccc gtg gcg tac cta ggc atc      878
Leu Ser Gly Cys Ala Gly Gly Thr Thr Pro Val Ala Tyr Leu Gly Ile
            170                 175                 180 cac gga gcc gcc gac aac gtc ctg ccc atc gac ctc ggc cgc cag ctg      926
His Gly Ala Ala Asp Asn Val Leu Pro Ile Asp Leu Gly Arg Gln Leu
        185                 190                 195 cgc gac aag tgg ctg cag acc aac ggc tgc aac tac cag ggc gcc cag      974
Arg Asp Lys Trp Leu Gln Thr Asn Gly Cys Asn Tyr Gln Gly Ala Gln
    200                 205                 210 gac ccc gcg ccg ggc cag cag gcc cac atc aag acc acc tac agc tgc     1022
Asp Pro Ala Pro Gly Gln Gln Ala His Ile Lys Thr Thr Tyr Ser Cys
215                 220                 225                 230 tcc cgc gcg ccc gtc acc tgg atc ggc cac ggg ggc ggc cac gtc ccc     1070
Ser Arg Ala Pro Val Thr Trp Ile Gly His Gly Gly Gly His Val Pro
                235                 240                 245 gac ccc acg ggc aac aac ggc gtc aag ttt gcg ccc cag gag acc tgg     1118
Asp Pro Thr Gly Asn Asn Gly Val Lys Phe Ala Pro Gln Glu Thr Trp
            250                 255                 260 gac ttc ttt gat gcc gcc gtc gga gcg gcc ggc gcg cag agc ccg atg     1166
Asp Phe Phe Asp Ala Ala Val Gly Ala Ala Gly Ala Gln Ser Pro Met
        265                 270                 275 aca taagcccgaa gga                                                  1182
Thr

<210> SEQ ID NO 65
<211> LENGTH: 279
<212> TYPE: PRT
<213> ORGANISM: Chrysosporium lucknowense

<400> SEQUENCE: 65

Met Ile Ser Val Pro Ala Leu Ala Leu Ala Leu Leu Ala Ala Val Gln
1               5                   10                  15

Val Val Glu Ser Ala Ser Ala Gly Cys Gly Lys Ala Pro Pro Ser Ser
            20                  25                  30

Gly Thr Lys Ser Met Thr Val Asn Gly Lys Gln Arg Gln Tyr Ile Leu
        35                  40                  45

Gln Leu Pro Asn Asn Tyr Asp Ala Asn Lys Ala His Arg Val Val Ile
    50                  55                  60

Gly Tyr His Trp Arg Asp Gly Ser Met Asn Asp Val Ala Asn Gly Gly
65                  70                  75                  80

Phe Tyr Asp Leu Arg Ser Arg Ala Gly Asp Ser Thr Ile Phe Val Ala
                85                  90                  95

Pro Asn Gly Leu Asn Ala Gly Trp Ala Asn Val Gly Gly Glu Asp Ile
            100                 105                 110

Thr Phe Thr Asp Gln Ile Val Asp Met Leu Lys Asn Asp Leu Cys Val
        115                 120                 125

Asp Glu Thr Gln Phe Phe Ala Thr Gly Trp Ser Tyr Gly Gly Ala Met
```

```
                130             135             140
Ser His Ser Val Ala Cys Ser Arg Pro Asp Val Phe Lys Ala Val Ala
145                 150                 155                 160

Val Ile Ala Gly Ala Gln Leu Ser Gly Cys Ala Gly Gly Thr Thr Pro
                165                 170                 175

Val Ala Tyr Leu Gly Ile His Gly Ala Ala Asp Asn Val Leu Pro Ile
            180                 185                 190

Asp Leu Gly Arg Gln Leu Arg Asp Lys Trp Leu Gln Thr Asn Gly Cys
                195                 200                 205

Asn Tyr Gln Gly Ala Gln Asp Pro Ala Pro Gly Gln Gln Ala His Ile
        210                 215                 220

Lys Thr Thr Tyr Ser Cys Ser Arg Ala Pro Val Thr Trp Ile Gly His
225                 230                 235                 240

Gly Gly Gly His Val Pro Asp Pro Thr Gly Asn Asn Gly Val Lys Phe
                245                 250                 255

Ala Pro Gln Glu Thr Trp Asp Phe Phe Asp Ala Ala Val Gly Ala Ala
            260                 265                 270

Gly Ala Gln Ser Pro Met Thr
            275

<210> SEQ ID NO 66
<211> LENGTH: 837
<212> TYPE: DNA
<213> ORGANISM: Chrysosporium lucknowense

<400> SEQUENCE: 66
atgatctcgg ttcctgctct cgctctggcc cttctggccg ccgtccaggt cgtcgagtct     60
gcctcggctg ctgtggcaa ggcgcccct tcctcgggca ccaagtcgat gacggtcaac      120
ggcaagcagc gccagtacat tctccagctg cccaacaact acgacgccaa caaggcccac    180
agggtggtga tcgggtacca ctggcgcgac ggatccatga cgacgtggc caacggcggc    240 ttctacgatc tgcggtcccg gcgggcgac agcaccatct tcgttgcccc caacggcctc    300
aatgccggat gggccaacgt gggcggcgag gacatcaccc ttacggacca gatcgtagac    360
atgctcaaga cgacctctg cgtggacgag acccagttct ttgctacggg ctggagctat    420
ggcggtgcca tgagccatag cgtggcttgt tctcggccag acgtcttcaa ggccgtcgcg    480
gtcatcgccg gggcccagct gtccggctgc gccggcggca cgacgcccgt ggcgtaccta    540
ggcatccacg gagccgccga caacgtcctg cccatcgacc tcggccgcca gctgcgcgac    600
aagtggctgc agaccaacgg ctgcaactac cagggcgccc aggaccccgc gccgggccag    660
caggcccaca tcaagaccac ctacagctgc tcccgcgcgc ccgtcacctg gatcggccac    720
gggggcggcc acgtccccga ccccacgggc aacaacggcg tcaagtttgc gccccaggag    780
acctgggact cttttgatgc cgccgtcgga gcggccggcg cgcagagccc gatgaca       837

<210> SEQ ID NO 67
<211> LENGTH: 1537
<212> TYPE: DNA
<213> ORGANISM: Chrysosporium lucknowense
<220> FEATURE:
<221> NAME/KEY: CDS
<222> LOCATION: (394)..(1299)

<400> SEQUENCE: 67
ccttccgagt cccaatgccg agtaattaac ccaaacaaca accccagtca ctttagccca     60
ggttttgcgg cattcgttag agtaccgtta cagccaagcg ttgaaatatg ctagagaaac    120
```

```
cggaggatgt tccccaggtt ggttctcagc ggagagagca attgcaaccc tggaagaaaa        180
cgtccgtggc acttcggcaa ctattcttat catatagcac cgtcaatcct tcaccagcat        240
gccaaaggac tgtataatat ctttgacata aacttgggcc accattcttg aacacgagg         300 atgggctgaa ccctttgttt ccctcttgcc caccatttaa ttacgttcta caaccaatct        360
ttggcaacat agcaaggacc aagagaagca aag atg tcc cgg tac ctt ctc ggt         414
                                     Met Ser Arg Tyr Leu Leu Gly
                                      1               5 cga cta ata gtg gcc aca gtg gcc atc acg gtg gcc tct ctc cgc ggc          462
Arg Leu Ile Val Ala Thr Val Ala Ile Thr Val Ala Ser Leu Arg Gly
         10                  15                  20 gtg acg gcc gcc acg ccg tcg ccg gga tgc ggg aag acg ccg acg ctg          510
Val Thr Ala Ala Thr Pro Ser Pro Gly Cys Gly Lys Thr Pro Thr Leu
 25                  30                  35 atc acg gac ggg tcc gcc acg act ccc ctg acg ctg acc tcc aac ggc          558
Ile Thr Asp Gly Ser Ala Thr Thr Pro Leu Thr Leu Thr Ser Asn Gly
40                  45                  50                  55 aag acg cgg cgg ttc tac gtc aag ctt ccc gac gac tac gac aac agc          606
Lys Thr Arg Arg Phe Tyr Val Lys Leu Pro Asp Asp Tyr Asp Asn Ser
                 60                  65                  70 cac ccg tac cgg ctc atc ttc gcg ctg cac gcc ctc ggg ggg acc gcc          654
His Pro Tyr Arg Leu Ile Phe Ala Leu His Ala Leu Gly Gly Thr Ala
             75                  80                  85 cag cag gtc acc acc ggg acg ggc ggc tac ctg ccg tgg tac ggg atc          702
Gln Gln Val Thr Thr Gly Thr Gly Gly Tyr Leu Pro Trp Tyr Gly Ile
         90                  95                 100 ccc gac ctc gcg gcc aac gac acg gtg ggc gcc gtc tac gtg gcg ccc          750
Pro Asp Leu Ala Ala Asn Asp Thr Val Gly Ala Val Tyr Val Ala Pro
    105                 110                 115 gac ggg ctc aac aac ggc tgg gcc aac cag ggg ggc gag gac gtg gcc          798
Asp Gly Leu Asn Asn Gly Trp Ala Asn Gln Gly Gly Glu Asp Val Ala
120                 125                 130                 135 ttc ctg gag gcc gtg atg gag acg gtg gag cag gac gtg tgc gtc gac          846
Phe Leu Glu Ala Val Met Glu Thr Val Glu Gln Asp Val Cys Val Asp
                140                 145                 150 cgg gac ctg cgc ttc tcg acc ggc ttc agc tac ggc gcc gcc atg tcg          894
Arg Asp Leu Arg Phe Ser Thr Gly Phe Ser Tyr Gly Ala Ala Met Ser
            155                 160                 165 tac acg ctc gcg tgc gcg ctc ggc cgc cgc atc cgg gcc gtc gcc gtg          942
Tyr Thr Leu Ala Cys Ala Leu Gly Arg Arg Ile Arg Ala Val Ala Val
        170                 175                 180 ctc tcg ggc agc ccc gtc atc agc ggc ggc tgc gcc ggc gcc ggc tcc          990
Leu Ser Gly Ser Pro Val Ile Ser Gly Gly Cys Ala Gly Ala Gly Ser
185                 190                 195 ggc gcc tcc gag ccc gtc gcc tac tac ggc cag cac ggc atg tcc gac         1038
Gly Ala Ser Glu Pro Val Ala Tyr Tyr Gly Gln His Gly Met Ser Asp
200                 205                 210                 215 ccg gtc ctc ccc gtc gcc ggc ggc cgc gag atg cgc gac cac ttc gtc         1086
Pro Val Leu Pro Val Ala Gly Gly Arg Glu Met Arg Asp His Phe Val
                220                 225                 230 cgc acc aac ggc tgc gac gcc ggc cgg ggc ccc ccg gag ccc gcc              1134
Arg Thr Asn Gly Cys Asp Ala Gly Arg Gly Pro Pro Arg Glu Pro Ala
            235                 240                 245 cgc ggc agc ggc acc cac gtc aag acg gtc tac gac ggc tgc gac ccg         1182
Arg Gly Ser Gly Thr His Val Lys Thr Val Tyr Asp Gly Cys Asp Pro
        250                 255                 260 gac tac ccc gtc gtg tgg aac gcg ttc gac ggc gac cac acc ccg cag         1230
Asp Tyr Pro Val Val Trp Asn Ala Phe Asp Gly Asp His Thr Pro Gln
265                 270                 275
```

```
ccc gtc gac cgg ggc gcc acc acc act ttc tcg gcc gtc gag acc tgg    1278
Pro Val Asp Arg Gly Ala Thr Thr Thr Phe Ser Ala Val Glu Thr Trp
280                 285                 290                 295 gag ttc ttc tcg cag ttc aag taattaagcc cgagaggaat ccctgagca        1329
Glu Phe Phe Ser Gln Phe Lys
                300 ttccctttg gcacaatatg tgaacccgtc tcgcaacttc ggttcggttt ccgatgatgt    1389
taggtatttt acgttccgtt catgaccgct gccctgatat tcttgatcgt gtttcaatct   1449
ggacaagtaa agaacattcg acctttgtgc ctgactgact tcggggccga tgtgccgcgc   1509
ctgatcacca ggttgtaagt aattaatt                                     1537

<210> SEQ ID NO 68
<211> LENGTH: 302
<212> TYPE: PRT
<213> ORGANISM: Chrysosporium lucknowense

<400> SEQUENCE: 68
```

Met Ser Arg Tyr Leu Leu Gly Arg Leu Ile Val Ala Thr Val Ala Ile
1               5                   10                  15

Thr Val Ala Ser Leu Arg Gly Val Thr Ala Ala Thr Pro Ser Pro Gly
            20                  25                  30

Cys Gly Lys Thr Pro Thr Leu Ile Thr Asp Gly Ser Ala Thr Thr Pro
        35                  40                  45

Leu Thr Leu Thr Ser Asn Gly Lys Thr Arg Arg Phe Tyr Val Lys Leu
    50                  55                  60

Pro Asp Asp Tyr Asp Asn Ser His Pro Tyr Arg Leu Ile Phe Ala Leu
65                  70                  75                  80

His Ala Leu Gly Gly Thr Ala Gln Gln Val Thr Thr Gly Thr Gly Gly
                85                  90                  95

Tyr Leu Pro Trp Tyr Gly Ile Pro Asp Leu Ala Ala Asn Asp Thr Val
            100                 105                 110

Gly Ala Val Tyr Val Ala Pro Asp Gly Leu Asn Asn Gly Trp Ala Asn
        115                 120                 125

Gln Gly Gly Glu Asp Val Ala Phe Leu Glu Ala Val Met Glu Thr Val
    130                 135                 140

Glu Gln Asp Val Cys Val Asp Arg Asp Leu Arg Phe Ser Thr Gly Phe
145                 150                 155                 160

Ser Tyr Gly Ala Ala Met Ser Tyr Thr Leu Ala Cys Ala Leu Gly Arg
                165                 170                 175

Arg Ile Arg Ala Val Ala Val Leu Ser Gly Ser Pro Val Ile Ser Gly
            180                 185                 190

Gly Cys Ala Gly Ala Gly Ser Gly Ala Ser Glu Pro Val Ala Tyr Tyr
        195                 200                 205

Gly Gln His Gly Met Ser Asp Pro Val Leu Pro Val Ala Gly Gly Arg
    210                 215                 220

Glu Met Arg Asp His Phe Val Arg Thr Asn Gly Cys Asp Ala Gly Arg
225                 230                 235                 240

Gly Pro Pro Arg Glu Pro Ala Arg Gly Ser Gly Thr His Val Lys Thr
                245                 250                 255

Val Tyr Asp Gly Cys Asp Pro Asp Tyr Pro Val Val Trp Asn Ala Phe
            260                 265                 270

Asp Gly Asp His Thr Pro Gln Pro Val Asp Arg Gly Ala Thr Thr Thr
        275                 280                 285

Phe Ser Ala Val Glu Thr Trp Glu Phe Phe Ser Gln Phe Lys
    290                 295                 300

<210> SEQ ID NO 69
<211> LENGTH: 906
<212> TYPE: DNA
<213> ORGANISM: Chrysosporium lucknowense

<400> SEQUENCE: 69

```
atgtcccggt accttctcgg tcgactaata gtggccacag tggccatcac ggtggcctct      60
ctccgcggcg tgacggccgc cacgccgtcg ccgggatgcg ggaagacgcc gacgctgatc     120
acggacgggt ccgccacgac tcccctgacg ctgacctcca acggcaagac gcggcggttc     180
tacgtcaagc ttcccgacga ctacgacaac agccacccgt accggctcat cttcgcgctg     240
cacgccctcg gcgggaccgc ccagcaggtc accaccggga cgggcggcta cctgccgtgg     300
tacgggatcc ccgacctcgc ggccaacgac acggtgggcg ccgtctacgt ggcgcccgac     360
gggctcaaca acggctgggc caaccagggg ggcgaggacg tggccttcct ggaggccgtg     420
atggagacgg tggagcagga cgtgtgcgtc gaccgggacc tgcgcttctc gaccggcttc     480
agctacggcg ccgccatgtc gtacacgctc gcgtgcgcgc tcggccgccg catccgggcc     540
gtcgccgtgc tctcgggcag ccccgtcatc agcggcggct gcgccggcgc cggctccggc     600
gcctccgagc ccgtcgccta ctacggccag cacggcatgt ccgacccggt cctccccgtc     660
gccggcggcc gcgagatgcg cgaccacttc gtccgcacca acggctgcga cgccggccgg     720
ggcccccccc gggagcccgc ccgcggcagc ggcacccacg tcaagacggt ctacgacggc     780
tgcgacccgg actaccccgt cgtgtggaac gcgttcgacg gcgaccacac cccgcagccc     840
gtcgaccggg gcgccaccac cactttctcg gccgtcgaga cctgggagtt cttctcgcag     900
ttcaag                                                                906
```

<210> SEQ ID NO 70
<211> LENGTH: 1919
<212> TYPE: DNA
<213> ORGANISM: Chrysosporium lucknowense
<220> FEATURE:
<221> NAME/KEY: CDS
<222> LOCATION: (279)..(340)
<220> FEATURE:
<221> NAME/KEY: CDS
<222> LOCATION: (541)..(718)
<220> FEATURE:
<221> NAME/KEY: CDS
<222> LOCATION: (802)..(915)
<220> FEATURE:
<221> NAME/KEY: CDS
<222> LOCATION: (1028)..(1630)

<400> SEQUENCE: 70

```
agcactgttg aagggctgtt tggaagtttc ttattgtgag agggggctcg agtcacggca      60
accaagttcg gcgcctggtc atctctggag ctgaccacgc ctttggccgt cgtcgattcc     120
gcgtctcaga gccgagttgg cgggccccgt gcaggttaaa ttgtctgcag cgcccggcta     180
cctggaactc cgagcgatta ccagtttcgg ctcggagcac gaccttcgcc aaccccagat     240
cggccacttc aagggaccga aaccgttgcc gtggcccg atg ccg tgc aag tcg agc     296
                                          Met Pro Cys Lys Ser Ser
                                          1               5 ctc ctc ctc ctc ctc ctc tcc tcc ttc ttc tcc tcc gag gcc aa            340
Leu Leu Leu Leu Leu Leu Ser Ser Phe Phe Ser Ser Glu Ala Asn
            10                  15                  20 gtccgtgaat acaccaacga cgccgttacg ttgctgatac ttaagtaagg aagggcgcgg     400
cgctcgctgc tgctgatgtg aagacgagga gcagacttga acattggtaa agcagagcac     460
```

-continued

```
tgtttgattg cgctcgtgca ctcgccacca tcatccaatt aacataccta gcccataatt       520
atcggacact ggcgttcgag c acc gcc cac cgc cca cca tgc gtc tct gcg        571
                        Thr Ala His Arg Pro Pro Cys Val Ser Ala
                                 25                  30 atc gct cac caa gat ggc cgc cat ggc cgg cct gcg cgg ggc gcg tca        619
Ile Ala His Gln Asp Gly Arg His Gly Arg Pro Ala Arg Gly Ala Ser
         35                  40                  45 ctg cag cta gtg acc aac ttt ggc gac aat ccg acc ggt ctg cag aag        667
Leu Gln Leu Val Thr Asn Phe Gly Asp Asn Pro Thr Gly Leu Gln Lys
     50                  55                  60 tat gtg tac gtt ccg gac aaa gtt gcg gtc tcg ccc gcc atc atc gtt        715
Tyr Val Tyr Val Pro Asp Lys Val Ala Val Ser Pro Ala Ile Ile Val
 65                  70                  75 gct gtaagtcaac agagcttgat taacattatt atgtgtttga gttggattga             768
Ala
 80 gtggtgatga ccgctaactt tgttgtcgat cag ctg cat ccc tgt gga gga tcg       822
                                 Leu His Pro Cys Gly Gly Ser
                                                      85 gct cag gga tgg tac tcg cag aca cgg ctc ccg tcg tac gcg gac cag        870
Ala Gln Gly Trp Tyr Ser Gln Thr Arg Leu Pro Ser Tyr Ala Asp Gln
         90                  95                 100 ctt ggg ttc atc ctc atc tac gcc ggc acg acc aag atg agc aac            915
Leu Gly Phe Ile Leu Ile Tyr Ala Gly Thr Thr Lys Met Ser Asn
    105                 110                 115 gtacgcatag ttttttttt ttttgctttt tttttgcttg ctgtattaca tagagagtta       975 taccttact aaccataatt attttcttcc tcgatatttt ctttgccaac ag tgc tgg       1033
                                                        Cys Trp
                                                            120 gac gtc cag aac ccg gcc agc ctg aca cac ggc ggg ggc gac gcc ggg        1081
Asp Val Gln Asn Pro Ala Ser Leu Thr His Gly Gly Gly Asp Ala Gly
                125                 130                 135 ggc atc gtc agc atg gtc aag tac gcg ctg aag cag tac aac ggc gac        1129
Gly Ile Val Ser Met Val Lys Tyr Ala Leu Lys Gln Tyr Asn Gly Asp
        140                 145                 150 gcg tcg agg gtg tac gtc atg ggg ggc tcg tcg ggg gcc atg atg acc        1177
Ala Ser Arg Val Tyr Val Met Gly Gly Ser Ser Gly Ala Met Met Thr
        155                 160                 165 aac gtg ctg gcg ggc tcg tac ccg gac gtg ttc gag gcc ggc gcg gcc        1225
Asn Val Leu Ala Gly Ser Tyr Pro Asp Val Phe Glu Ala Gly Ala Ala
    170                 175                 180 ttc tcc ggg gtg gcg cac gcg tgc ttc ctc ggg gcc gac tcg gcg acg        1273
Phe Ser Gly Val Ala His Ala Cys Phe Leu Gly Ala Asp Ser Ala Thr
185                 190                 195                 200 ccc ttc tcg cct aac cag acg tgc gcg cag ggc cgg atc cag cgg tcg        1321
Pro Phe Ser Pro Asn Gln Thr Cys Ala Gln Gly Arg Ile Gln Arg Ser
            205                 210                 215 gcg cgc gag tgg ggg gac ctg gtg cgc aac tcg ttc ccg gcc tac gac        1369
Ala Arg Glu Trp Gly Asp Leu Val Arg Asn Ser Phe Pro Ala Tyr Asp
            220                 225                 230 ggc cgc cgc ccg cgc atg cag atc ttc cac ggc aac gcc gac ttc ctc        1417
Gly Arg Arg Pro Arg Met Gln Ile Phe His Gly Asn Ala Asp Phe Leu
        235                 240                 245 gtc cat ccc gag tgc gcc cac cag gcc ctc gcc cag tgg gcc gac gtc        1465
Val His Pro Glu Cys Ala His Gln Ala Leu Ala Gln Trp Ala Asp Val
    250                 255                 260 ctc ggc ctc cag ctg acc cag acc aac aag ggc gtg ccc tcg gcc gag        1513
Leu Gly Leu Gln Leu Thr Gln Thr Asn Lys Gly Val Pro Ser Ala Glu
265                 270                 275                 280
```

```
tac acc cag gag gtc tac ggc gac ggc acc cag ctg cag ggc ttc ttt     1561
Tyr Thr Gln Glu Val Tyr Gly Asp Gly Thr Gln Leu Gln Gly Phe Phe
                285                 290                 295
ggc gac ggc gtc ggc cac atc gcc ccg gtc aac gag ccc gtc atg ctc     1609
Gly Asp Gly Val Gly His Ile Ala Pro Val Asn Glu Pro Val Met Leu
            300                 305                 310
cgc ttc ttt ggc ctg atg aac tagctcgtac cggatgtact gtaccgtaaa       1660
Arg Phe Phe Gly Leu Met Asn
        315
tgatccatca tttaatagcg aatagtacat agttacatac cagtatgtaa ctgacatgca   1720
tgtcaagatc ccgacattgt gctccgagtc aaccttggat gggaggtgat gacagcctgg   1780
aggacgaaag ttgatttgac cgtagcatgc tgtctgtgct cttttgaggt ctgaacgcct   1840
cattattacc gcgaacggtg cattgcatta tggggggtcg ataaacttcc aaggggtata   1900
gttatacgcg cgtagaaat                                                 1919

<210> SEQ ID NO 71
<211> LENGTH: 319
<212> TYPE: PRT
<213> ORGANISM: Chrysosporium lucknowense

<400> SEQUENCE: 71

Met Pro Cys Lys Ser Ser Leu Leu Leu Leu Leu Leu Ser Ser Phe Phe
1               5                   10                  15

Ser Ser Glu Ala Asn Thr Ala His Arg Pro Pro Cys Val Ser Ala Ile
            20                  25                  30

Ala His Gln Asp Gly Arg His Gly Arg Pro Ala Arg Gly Ala Ser Leu
        35                  40                  45

Gln Leu Val Thr Asn Phe Gly Asp Asn Pro Thr Gly Leu Gln Lys Tyr
    50                  55                  60

Val Tyr Val Pro Asp Lys Val Ala Val Ser Pro Ala Ile Ile Val Ala
65                  70                  75                  80

Leu His Pro Cys Gly Gly Ser Ala Gln Gly Trp Tyr Ser Gln Thr Arg
                85                  90                  95

Leu Pro Ser Tyr Ala Asp Gln Leu Gly Phe Ile Leu Ile Tyr Ala Gly
            100                 105                 110

Thr Thr Lys Met Ser Asn Cys Trp Asp Val Gln Asn Pro Ala Ser Leu
        115                 120                 125

Thr His Gly Gly Gly Asp Ala Gly Gly Ile Val Ser Met Val Lys Tyr
    130                 135                 140

Ala Leu Lys Gln Tyr Asn Gly Asp Ala Ser Arg Val Tyr Val Met Gly
145                 150                 155                 160

Gly Ser Ser Gly Ala Met Met Thr Asn Val Leu Ala Gly Ser Tyr Pro
                165                 170                 175

Asp Val Phe Glu Ala Gly Ala Ala Phe Ser Gly Val Ala His Ala Cys
            180                 185                 190

Phe Leu Gly Ala Asp Ser Ala Thr Pro Phe Ser Pro Asn Gln Thr Cys
        195                 200                 205

Ala Gln Gly Arg Ile Gln Arg Ser Ala Arg Glu Trp Gly Asp Leu Val
    210                 215                 220

Arg Asn Ser Phe Pro Ala Tyr Asp Gly Arg Arg Pro Arg Met Gln Ile
225                 230                 235                 240

Phe His Gly Asn Ala Asp Phe Leu Val His Pro Glu Cys Ala His Gln
                245                 250                 255

Ala Leu Ala Gln Trp Ala Asp Val Leu Gly Leu Gln Leu Thr Gln Thr
```

```
                  260                 265                 270
Asn Lys Gly Val Pro Ser Ala Glu Tyr Thr Gln Glu Val Tyr Gly Asp
            275                 280                 285

Gly Thr Gln Leu Gln Gly Phe Phe Gly Asp Gly Val Gly His Ile Ala
        290                 295                 300

Pro Val Asn Glu Pro Val Met Leu Arg Phe Phe Gly Leu Met Asn
305                 310                 315

<210> SEQ ID NO 72
<211> LENGTH: 957
<212> TYPE: DNA
<213> ORGANISM: Chrysosporium lucknowense

<400> SEQUENCE: 72
atgccgtgca agtcgagcct cctcctcctc ctcctctcct ccttcttctc ctccgaggcc    60
aacaccgccc accgcccacc atgcgtctct gcgatcgctc accaagatgg ccgccatggc   120
cggcctgcgc ggggcgcgtc actgcagcta gtgaccaact ttggcgacaa tccgaccggt   180
ctgcagaagt atgtgtacgt tccggacaaa gttgcggtct cgcccgccat catcgttgct   240
ctgcatccct gtggaggatc ggctcaggga tggtactcgc agacacggct cccgtcgtac   300
gcggaccagc ttgggttcat cctcatctac gccggcacga ccaagatgag caactgctgg   360
gacgtccaga accggccag cctgacacac ggcgggggcg acgccggggg catcgtcagc   420
atggtcaagt acgcgctgaa gcagtacaac ggcgacgcgt cgagggtgta cgtcatgggg   480
ggctcgtcgg gggccatgat gaccaacgtg ctggcgggc cgtacccgga cgtgttcgag   540
gccggcgcgg ccttctccgg ggtggcgcac gcgtgcttcc tcgggccga ctcggcgacg   600 cccttctcgc ctaaccagac gtgcgcgcag gccggatcc agcggtcggc gcgcgagtgg   660
ggggacctgg tgcgcaactc gttcccggcc tacgacggcc gccgcccgcg catgcagatc   720
ttccacggca acgccgactt cctcgtccat cccgagtgcg cccaccaggc cctcgcccag   780
tgggccgacg tcctcggcct ccagctgacc cagaccaaca agggcgtgcc ctcggccgag   840
tacacccagg aggtctacgg cgacggcacc cagctgcagg gcttctttgg cgacggcgtc   900
ggccacatcg ccccggtcaa cgagcccgtc atgctccgct ctttggcct gatgaac      957

<210> SEQ ID NO 73
<211> LENGTH: 1560
<212> TYPE: DNA
<213> ORGANISM: Chrysosporium lucknowense
<220> FEATURE:
<221> NAME/KEY: CDS
<222> LOCATION: (221)..(1330)

<400> SEQUENCE: 73
gtgagttaca catagttata taaaggataa ccccatcggg ggaaccagtc ctcgctgcat     60
atctgcttcc ggcacggatc ttcagttatt tcgcctcgcg cttggccggc tgctcccct    120 gttcccaccg ccgaagtacg aagtaattaa tagtcattgc gcggacccaa ctgattgtgc   180
ctgctccgtg tgaagcagag aaaaggagga caccgccatc atg cgt ctc acc aag     235
                                                Met Arg Leu Thr Lys
                                                  1               5 acg gac ctc agc gtc gcg ctg ctc gcg tcg gcc cta ccc gca acc cag     283
Thr Asp Leu Ser Val Ala Leu Leu Ala Ser Ala Leu Pro Ala Thr Gln
            10                  15                  20 gcg gcg tgc agc ctc ccc tcg tcc tac cgg tgg acg tcg acg ggc gcg     331
Ala Ala Cys Ser Leu Pro Ser Ser Tyr Arg Trp Thr Ser Thr Gly Ala
    25                  30                  35
```

```
ttg gct cag ccc aaa tcg ggg tgg gct aac ctc aag gac ttc acc cac       379
Leu Ala Gln Pro Lys Ser Gly Trp Ala Asn Leu Lys Asp Phe Thr His
        40                  45                  50 gtg cct tac aac ggc aag cac ctt gtg tac ggg agc tac tac tct aac       427
Val Pro Tyr Asn Gly Lys His Leu Val Tyr Gly Ser Tyr Tyr Ser Asn
55                  60                  65 gcc tac ggc tca atg aac ttc ggc ctc ttc tcg gac tgg agc gag atg       475
Ala Tyr Gly Ser Met Asn Phe Gly Leu Phe Ser Asp Trp Ser Glu Met
70                  75                  80                  85 ggc tcg gcc agc cag aac cag atg agc cag gcc gcg gtc gcg ccc acg       523
Gly Ser Ala Ser Gln Asn Gln Met Ser Gln Ala Ala Val Ala Pro Thr
            90                  95                 100 ctc ttc tac ttc tcc cca aag aac atc tgg gtc ctg gcc tac cag tgg       571
Leu Phe Tyr Phe Ser Pro Lys Asn Ile Trp Val Leu Ala Tyr Gln Trp
                105                 110                 115 ggt gcc acc cct ttc tcc tac cgc acc tcg acc gat ccg acc aac ccc       619
Gly Ala Thr Pro Phe Ser Tyr Arg Thr Ser Thr Asp Pro Thr Asn Pro
        120                 125                 130 aac ggc tgg tcc gct ccc cag ccg ctc ttc tcg ggc tcc atc tcc gac       667
Asn Gly Trp Ser Ala Pro Gln Pro Leu Phe Ser Gly Ser Ile Ser Asp
135                 140                 145 tcg gac acg ggc ccc atc gac cag acc ctg atc ggc gac gac aag aac       715
Ser Asp Thr Gly Pro Ile Asp Gln Thr Leu Ile Gly Asp Asp Lys Asn
150                 155                 160                 165 atg tac ctg ttc ttc gcc ggc gac aac ggc aag atc tac cgc gcc agc       763
Met Tyr Leu Phe Phe Ala Gly Asp Asn Gly Lys Ile Tyr Arg Ala Ser
                170                 175                 180 atg ccg ctc ggc aac ttc ccg ggc aac ttt ggc tcg gcc gcc acc gtc       811
Met Pro Leu Gly Asn Phe Pro Gly Asn Phe Gly Ser Ala Ala Thr Val
        185                 190                 195 gtc ctg agc ggc gcc cgc tac gac ctg ttc gag gcc gtg cag gta tac       859
Val Leu Ser Gly Ala Arg Tyr Asp Leu Phe Glu Ala Val Gln Val Tyr
200                 205                 210 acg gtc gtc ggc cag agc tcg ccg acc tat ctg atg atc gtc gag tcc       907
Thr Val Val Gly Gln Ser Ser Pro Thr Tyr Leu Met Ile Val Glu Ser
215                 220                 225 atc ggc gcg cgc ggg cgc tac ttc cgc tcc tac acg gcc agc cgg ctc       955
Ile Gly Ala Arg Gly Arg Tyr Phe Arg Ser Tyr Thr Ala Ser Arg Leu
230                 235                 240                 245 gac ggc gcc tgg acg gcc cag gcg gcc agc gag agc cag ccg ttc gcc      1003
Asp Gly Ala Trp Thr Ala Gln Ala Ala Ser Glu Ser Gln Pro Phe Ala
            250                 255                 260 ggc gcg gcc aac agc ggc gcc tcc tgg acc agc gac atc agc cac ggc      1051
Gly Ala Ala Asn Ser Gly Ala Ser Trp Thr Ser Asp Ile Ser His Gly
                265                 270                 275 gac ctc atc cgc atc gac gcc aac cac acc atg ccc gtc gac ccc tgc      1099
Asp Leu Ile Arg Ile Asp Ala Asn His Thr Met Pro Val Asp Pro Cys
        280                 285                 290 cgc ctc cag ctg ctc tac cag ggc cgc tcc ggc gac agc gcc gac tac      1147
Arg Leu Gln Leu Leu Tyr Gln Gly Arg Ser Gly Asp Ser Ala Asp Tyr
295                 300                 305 aac tcc ctc ccc tac cgc ccg ggc ctg ctc acc ctg cag ggc gct tct      1195
Asn Ser Leu Pro Tyr Arg Pro Gly Leu Leu Thr Leu Gln Gly Ala Ser
310                 315                 320                 325 tcc ggc ggc ggc gac aac ggc ggc ggc ggc ggc gta acc gtc ccc          1243
Ser Gly Gly Gly Asp Asn Gly Gly Gly Gly Gly Val Thr Val Pro
                330                 335                 340 cgg tac ggc cag tgc ggt ggc cag ggc tac acg ggg ccg aca acg tgc      1291
Arg Tyr Gly Gln Cys Gly Gly Gln Gly Tyr Thr Gly Pro Thr Thr Cys
        345                 350                 355
```

```
gag agc cca tac acg tgc aag tac cag aat gat tgt aag tgatgtctta      1340
Glu Ser Pro Tyr Thr Cys Lys Tyr Gln Asn Asp Cys Lys
        360                 365                 370 tttaactctg gtttttcttt ttcttccctc tcttgtgaat cctgtgggta gtagccagtc   1400
tgaatcaatt tactaattaa caattcttga aagggtactc ccaatgcctc tgacaagcga   1460
cggaataatt aataagtaag taaaagtggg tgagagcggc cttgaagctg cgggttccct   1520
tttttactgc tgagttcaga tgtatgcata cgtaggtata                         1560

<210> SEQ ID NO 74
<211> LENGTH: 370
<212> TYPE: PRT
<213> ORGANISM: Chrysosporium lucknowense

<400> SEQUENCE: 74

Met Arg Leu Thr Lys Thr Asp Leu Ser Val Ala Leu Leu Ala Ser Ala
1               5                   10                  15

Leu Pro Ala Thr Gln Ala Ala Cys Ser Leu Pro Ser Ser Tyr Arg Trp
            20                  25                  30

Thr Ser Thr Gly Ala Leu Ala Gln Pro Lys Ser Gly Trp Ala Asn Leu
        35                  40                  45

Lys Asp Phe Thr His Val Pro Tyr Asn Gly Lys His Leu Val Tyr Gly
    50                  55                  60

Ser Tyr Tyr Ser Asn Ala Tyr Gly Ser Met Asn Phe Gly Leu Phe Ser
65                  70                  75                  80

Asp Trp Ser Glu Met Gly Ser Ala Ser Gln Asn Gln Met Ser Gln Ala
                85                  90                  95

Ala Val Ala Pro Thr Leu Phe Tyr Phe Ser Pro Lys Asn Ile Trp Val
            100                 105                 110

Leu Ala Tyr Gln Trp Gly Ala Thr Pro Phe Ser Tyr Arg Thr Ser Thr
        115                 120                 125

Asp Pro Thr Asn Pro Asn Gly Trp Ser Ala Pro Gln Pro Leu Phe Ser
    130                 135                 140

Gly Ser Ile Ser Asp Ser Asp Thr Gly Pro Ile Asp Gln Thr Leu Ile
145                 150                 155                 160

Gly Asp Asp Lys Asn Met Tyr Leu Phe Phe Ala Gly Asp Asn Gly Lys
                165                 170                 175

Ile Tyr Arg Ala Ser Met Pro Leu Gly Asn Phe Pro Gly Asn Phe Gly
            180                 185                 190

Ser Ala Ala Thr Val Val Leu Ser Gly Ala Arg Tyr Asp Leu Phe Glu
        195                 200                 205

Ala Val Gln Val Tyr Thr Val Val Gly Gln Ser Ser Pro Thr Tyr Leu
    210                 215                 220

Met Ile Val Glu Ser Ile Gly Ala Arg Gly Arg Tyr Phe Arg Ser Tyr
225                 230                 235                 240

Thr Ala Ser Arg Leu Asp Gly Ala Trp Thr Ala Gln Ala Ala Ser Glu
                245                 250                 255

Ser Gln Pro Phe Ala Gly Ala Ala Asn Ser Gly Ala Ser Trp Thr Ser
            260                 265                 270

Asp Ile Ser His Gly Asp Leu Ile Arg Ile Asp Ala Asn His Thr Met
        275                 280                 285

Pro Val Asp Pro Cys Arg Leu Gln Leu Leu Tyr Gln Gly Arg Ser Gly
    290                 295                 300

Asp Ser Ala Asp Tyr Asn Ser Leu Pro Tyr Arg Pro Gly Leu Leu Thr
305                 310                 315                 320
```

```
        Leu Gln Gly Ala Ser Ser Gly Gly Asp Asn Gly Gly Gly Gly
                        325                 330                 335

Gly Val Thr Val Pro Arg Tyr Gly Gln Cys Gly Gln Gly Tyr Thr
                    340                 345                 350

Gly Pro Thr Thr Cys Glu Ser Pro Tyr Thr Cys Lys Tyr Gln Asn Asp
                355                 360                 365

Cys Lys
            370

<210> SEQ ID NO 75
<211> LENGTH: 1110
<212> TYPE: DNA
<213> ORGANISM: Chrysosporium lucknowense

<400> SEQUENCE: 75
atgcgtctca ccaagacgga cctcagcgtc gcgctgctcg cgtcggccct accgcaacc      60 caggcggcgt gcagcctccc ctcgtcctac cggtggacgt cgacgggcgc gttggctcag    120
cccaaatcgg ggtgggctaa cctcaaggac ttcacccacg tgccttacaa cggcaagcac    180
cttgtgtacg ggagctacta ctctaacgcc tacggctcaa tgaacttcgg cctcttctcg    240
gactggagcg agatgggctc ggccagccag aaccagatga gccaggccgc ggtcgcgccc    300
acgctcttct acttctcccc aaagaacatc tgggtcctgg cctaccagtg gggtgccacc    360
cctttctcct accgcacctc gaccgatccg accaaccccca acggctggtc cgctccccag    420
ccgctcttct cgggctccat ctccgactcg gacacgggcc ccatcgacca gaccctgatc    480
ggcgacgaca agaacatgta cctgttcttc gccggcgaca cggcaagat ctaccgcgcc    540 agcatgccgc tcggcaactt cccgggcaac tttggctcgg ccgccaccgt cgtcctgagc    600
ggcgcccgct acgacctgtt cgaggccgtg caggtataca cggtcgtcgg ccagagctcg    660
ccgacctatc tgatgatcgt cgagtccatc ggcgcgcgcg ggcgctactt ccgctcctac    720
acggccagcc ggctcgacgg cgcctggacg gcccaggcgg ccagcgagag ccagccgttc    780
gccggcgcgg ccaacagcgg cgcctcctgg accagcgaca tcagccacgg cgacctcatc    840
cgcatcgacg ccaaccacac catgcccgtc gaccctgcc gcctccagct gctctaccag     900
ggccgctccg cgacagcgc cgactacaac tccctcccct accgcccggg cctgctcacc    960
ctgcagggcg cttcttccgg cggcggcgac aacggcggcg gcggcggcgg cgtaaccgtc   1020
ccccggtacg gccagtgcgg tggccagggc tacacggggc cgacaacgtg cgagagccca   1080
tacacgtgca gtaccagaa tgattgtaag                                      1110

<210> SEQ ID NO 76
<211> LENGTH: 1310
<212> TYPE: DNA
<213> ORGANISM: Chrysosporium lucknowense
<220> FEATURE:
<221> NAME/KEY: CDS
<222> LOCATION: (114)..(1076)

<400> SEQUENCE: 76
gtatatatca gcgcgtagac agcccgcctc tctcccgggc gttcatgtac tcgtcgacaa      60
cgcctctctg atctctctat atcgccacgt ggaacaaaca cccccatccc acc atg       116
                                                            Met
                                                              1 agg cca aca cgc ccc ggt atc gtg ctc ctc gcc acc gcg acc tcg gtt      164
Arg Pro Thr Arg Pro Gly Ile Val Leu Leu Ala Thr Ala Thr Ser Val
            5                  10                  15 gcc gga cag tca tgc gag ctc ccc tcc tcg tac cgc tgg aca tca acc      212
```

```
Ala Gly Gln Ser Cys Glu Leu Pro Ser Ser Tyr Arg Trp Thr Ser Thr
     20              25              30 ggc gcg ctg gca cag ccg aaa agc ccg tgg gtg tcg ctc aag gac ttc     260
Gly Ala Leu Ala Gln Pro Lys Ser Pro Trp Val Ser Leu Lys Asp Phe
 35              40              45 acc gtc gtc ccg tac gac ggc cag cac ctg gtc tac gca acg aca aac     308
Thr Val Val Pro Tyr Asp Gly Gln His Leu Val Tyr Ala Thr Thr Asn
 50              55              60              65 gac ggg acc aac tgg ggc tcc atg ggc ttc agc ctc ttc agc gac tgg     356
Asp Gly Thr Asn Trp Gly Ser Met Gly Phe Ser Leu Phe Ser Asp Trp
             70              75              80 gat gcc atg ggc tcg gcg acg cag acg ggc atg agc tcc agc gcg gtg     404
Asp Ala Met Gly Ser Ala Thr Gln Thr Gly Met Ser Ser Ser Ala Val
         85              90              95 gcg ccc acc ctg ttc tac ttc gag ccc aag aac gtt tgg atc ctc gcc     452
Ala Pro Thr Leu Phe Tyr Phe Glu Pro Lys Asn Val Trp Ile Leu Ala
             100             105             110 cac cag tgg ggc ccg acg gcc ttc tcg tac cgg acg tcc aac gat tcc     500
His Gln Trp Gly Pro Thr Ala Phe Ser Tyr Arg Thr Ser Asn Asp Ser
 115             120             125 acc aac ccc aac agc tgg tcc cag ccc cag ccc ctc ttc acc ggc acc     548
Thr Asn Pro Asn Ser Trp Ser Gln Pro Gln Pro Leu Phe Thr Gly Thr
 130             135             140             145 atc tcg ggc tcg agc acc ggc ccc atc gac cag acc ctc atc ggc gac     596
Ile Ser Gly Ser Ser Thr Gly Pro Ile Asp Gln Thr Leu Ile Gly Asp
             150             155             160 gac cag aat atg tac ctc ttc ttc tgc ggc gac aac ggc aag atc tac     644
Asp Gln Asn Met Tyr Leu Phe Phe Cys Gly Asp Asn Gly Lys Ile Tyr
         165             170             175 cgc gcc agc atg ccc atc ggc aac ttc ccc gga aac ttt ggc agc gag     692
Arg Ala Ser Met Pro Ile Gly Asn Phe Pro Gly Asn Phe Gly Ser Glu
             180             185             190 tcg acc gtc gtc atg agc gac agc acc aac aac ctc ttc gag gcc gtc     740
Ser Thr Val Val Met Ser Asp Ser Thr Asn Asn Leu Phe Glu Ala Val
 195             200             205 cag gtg tac aag gtg aac ggg agg cag cag tac ctc atg ctc gtc gag     788
Gln Val Tyr Lys Val Asn Gly Arg Gln Gln Tyr Leu Met Leu Val Glu
210             215             220             225 gcc atc ggc gcc cag ggc cgc tac ttc cgc tcc ttc acg gcc acg agg     836
Ala Ile Gly Ala Gln Gly Arg Tyr Phe Arg Ser Phe Thr Ala Thr Arg
             230             235             240 ctc gac ggc gag tgg acg ccc aac gcg gtc agc gag gct agt ccc ttc     884
Leu Asp Gly Glu Trp Thr Pro Asn Ala Val Ser Glu Ala Ser Pro Phe
         245             250             255 gcc ggc aag gcc aac tcg ggc gcc agc tgg acc aac gac atc agc cac     932
Ala Gly Lys Ala Asn Ser Gly Ala Ser Trp Thr Asn Asp Ile Ser His
         260             265             270 ggc gag ctc gtc cgc ctc agc gcc gac cag acc ttc ccc atc gac ccc     980
Gly Glu Leu Val Arg Leu Ser Ala Asp Gln Thr Phe Pro Ile Asp Pro
 275             280             285 tgc aac ctg cag ctg ctc tac cag ggc cgc gac ccc agc tcg gga ggc    1028
Cys Asn Leu Gln Leu Leu Tyr Gln Gly Arg Asp Pro Ser Ser Gly Gly
290             295             300             305 gat tac aac cgc ctg ccc tac cgc ccc ggc gtc ctt acc ctg cag cgc    1076
Asp Tyr Asn Arg Leu Pro Tyr Arg Pro Gly Val Leu Thr Leu Gln Arg
             310             315             320 tgatctgata ggctctcttt tcgtactttc atccccaggt gcgtcaaatg gggtagctgg   1136
tcgatggggc gggtcagaga aaccctgggc acgcggggaa gttcaaatcg agatgctttg   1196
ttctatacct cactttttg cggttagcag ccctagtctg tcgagggatg tcagagcaat    1256
```
ttctctaaca atttcgactc actaagggta caacgttcat ctgcaatcgc tgca       1310

<210> SEQ ID NO 77
<211> LENGTH: 321
<212> TYPE: PRT
<213> ORGANISM: Chrysosporium lucknowense

<400> SEQUENCE: 77

| | | | | | | | | | | | | | | |
|---|---|---|---|---|---|---|---|---|---|---|---|---|---|---|
| Met | Arg | Pro | Thr | Arg | Pro | Gly | Ile | Val | Leu | Leu | Ala | Thr | Ala | Thr | Ser |
| 1 | | | | 5 | | | | | 10 | | | | | 15 | |
| Val | Ala | Gly | Gln | Ser | Cys | Glu | Leu | Pro | Ser | Ser | Tyr | Arg | Trp | Thr | Ser |
| | | | 20 | | | | | 25 | | | | | 30 | | |
| Thr | Gly | Ala | Leu | Ala | Gln | Pro | Lys | Ser | Pro | Trp | Val | Ser | Leu | Lys | Asp |
| | | 35 | | | | | 40 | | | | | 45 | | | |
| Phe | Thr | Val | Val | Pro | Tyr | Asp | Gly | Gln | His | Leu | Val | Tyr | Ala | Thr | Thr |
| | 50 | | | | | 55 | | | | | 60 | | | | |
| Asn | Asp | Gly | Thr | Asn | Trp | Gly | Ser | Met | Gly | Phe | Ser | Leu | Phe | Ser | Asp |
| 65 | | | | | 70 | | | | | 75 | | | | | 80 |
| Trp | Asp | Ala | Met | Gly | Ser | Ala | Thr | Gln | Thr | Gly | Met | Ser | Ser | Ser | Ala |
| | | | | 85 | | | | | 90 | | | | | 95 | |
| Val | Ala | Pro | Thr | Leu | Phe | Tyr | Phe | Glu | Pro | Lys | Asn | Val | Trp | Ile | Leu |
| | | | 100 | | | | | 105 | | | | | 110 | | |
| Ala | His | Gln | Trp | Gly | Pro | Thr | Ala | Phe | Ser | Tyr | Arg | Thr | Ser | Asn | Asp |
| | | 115 | | | | | 120 | | | | | 125 | | | |
| Ser | Thr | Asn | Pro | Asn | Ser | Trp | Ser | Gln | Pro | Gln | Pro | Leu | Phe | Thr | Gly |
| | 130 | | | | | 135 | | | | | 140 | | | | |
| Thr | Ile | Ser | Gly | Ser | Ser | Thr | Gly | Pro | Ile | Asp | Gln | Thr | Leu | Ile | Gly |
| 145 | | | | | 150 | | | | | 155 | | | | | 160 |
| Asp | Asp | Gln | Asn | Met | Tyr | Leu | Phe | Phe | Cys | Gly | Asp | Asn | Gly | Lys | Ile |
| | | | | 165 | | | | | 170 | | | | | 175 | |
| Tyr | Arg | Ala | Ser | Met | Pro | Ile | Gly | Asn | Phe | Pro | Gly | Asn | Phe | Gly | Ser |
| | | | 180 | | | | | 185 | | | | | 190 | | |
| Glu | Ser | Thr | Val | Val | Met | Ser | Asp | Ser | Thr | Asn | Asn | Leu | Phe | Glu | Ala |
| | | 195 | | | | | 200 | | | | | 205 | | | |
| Val | Gln | Val | Tyr | Lys | Val | Asn | Gly | Arg | Gln | Gln | Tyr | Leu | Met | Leu | Val |
| | 210 | | | | | 215 | | | | | 220 | | | | |
| Glu | Ala | Ile | Gly | Ala | Gln | Gly | Arg | Tyr | Phe | Arg | Ser | Phe | Thr | Ala | Thr |
| 225 | | | | | 230 | | | | | 235 | | | | | 240 |
| Arg | Leu | Asp | Gly | Glu | Trp | Thr | Pro | Asn | Ala | Val | Ser | Glu | Ala | Ser | Pro |
| | | | | 245 | | | | | 250 | | | | | 255 | |
| Phe | Ala | Gly | Lys | Ala | Asn | Ser | Gly | Ala | Ser | Trp | Thr | Asn | Asp | Ile | Ser |
| | | | 260 | | | | | 265 | | | | | 270 | | |
| His | Gly | Glu | Leu | Val | Arg | Leu | Ser | Ala | Asp | Gln | Thr | Phe | Pro | Ile | Asp |
| | | 275 | | | | | 280 | | | | | 285 | | | |
| Pro | Cys | Asn | Leu | Gln | Leu | Leu | Tyr | Gln | Gly | Arg | Asp | Pro | Ser | Ser | Gly |
| | 290 | | | | | 295 | | | | | 300 | | | | |
| Gly | Asp | Tyr | Asn | Arg | Leu | Pro | Tyr | Arg | Pro | Gly | Val | Leu | Thr | Leu | Gln |
| 305 | | | | | 310 | | | | | 315 | | | | | 320 |
| Arg | | | | | | | | | | | | | | | |

<210> SEQ ID NO 78
<211> LENGTH: 963
<212> TYPE: DNA
<213> ORGANISM: Chrysosporium lucknowense

<400> SEQUENCE: 78

```
atgaggccaa cacgcccgg tatcgtgctc ctcgccaccg cgacctcggt tgccggacag      60
tcatgcgagc tcccctcctc gtaccgctgg acatcaaccg gcgcgctggc acagccgaaa    120
agcccgtggg tgtcgctcaa ggacttcacc gtcgtcccgt acgacggcca gcacctggtc    180
tacgcaacga caaacgacgg gaccaactgg ggctccatgg gcttcagcct cttcagcgac    240
tgggatgcca tgggctcggc gacgcagacg ggcatgagct ccagcgcggt ggcgcccacc    300
ctgttctact tcgagcccaa gaacgtttgg atcctcgccc accagtgggg cccgacggcc    360
ttctcgtacc ggacgtccaa cgattccacc aaccccaaca gctggtccca gcccagccc     420 ctcttcaccg gcaccatctc gggctcgagc accggcccca tcgaccagac cctcatcggc    480
gacgaccaga atatgtacct cttcttctgc ggcgacaacg gcaagatcta ccgcgccagc    540
atgcccatcg gcaacttccc cggaaacttt ggcagcgagt cgaccgtcgt catgagcgac    600
agcaccaaca acctcttcga ggccgtccag gtgtacaagg tgaacgggag gcagcagtac    660
ctcatgctcg tcgaggccat cggcgcccag ggccgctact tccgctcctt cacggccacg    720
aggctcgacg gcgagtggac gcccaacgcg gtcagcgagg ctagtccctt cgccggcaag    780
gccaactcgg gcgccagctg gaccaacgac atcagccacg gcgagctcgt ccgcctcagc    840
gccgaccaga ccttccccat cgaccctgc aacctgcagc tgctctacca gggccgcgac    900
cccagctcgg gaggcgatta caaccgcctg ccctaccgcc ccggcgtcct tacctgcag    960 cgc                                                                   963

<210> SEQ ID NO 79
<211> LENGTH: 1422
<212> TYPE: DNA
<213> ORGANISM: Chrysosporium lucknowense
<220> FEATURE:
<221> NAME/KEY: CDS
<222> LOCATION: (68)..(221)
<220> FEATURE:
<221> NAME/KEY: CDS
<222> LOCATION: (288)..(411)
<220> FEATURE:
<221> NAME/KEY: CDS
<222> LOCATION: (465)..(570)
<220> FEATURE:
<221> NAME/KEY: CDS
<222> LOCATION: (648)..(827)
<220> FEATURE:
<221> NAME/KEY: CDS
<222> LOCATION: (890)..(1234)

<400> SEQUENCE: 79
aaaccttcta tcaccacctc acttcaactt cactctgccg tcgttttaaa ccggcaactc      60 gcccaga atg tgg cct act ccc aag gtt gct tac ctc ttg ctg gca gct     109
        Met Trp Pro Thr Pro Lys Val Ala Tyr Leu Leu Leu Ala Ala
          1               5                  10 cac tcg ctg ctc gtc agc ggg act ccc gtc gac gcc gag gcc gtg gac     157
His Ser Leu Leu Val Ser Gly Thr Pro Val Asp Ala Glu Ala Val Asp
 15                  20                  25                  30 acg gcc atc ctc gcc aag cgc caa tgc ccg cag atc cat atc ttc gga     205
Thr Ala Ile Leu Ala Lys Arg Gln Cys Pro Gln Ile His Ile Phe Gly
                 35                  40                  45 gct cga gaa acg aca g gtttgtcgta ttcttgccag gttactaatg tgcatctgag   261
Ala Arg Glu Thr Thr
             50 gtcgtctagc tgacaatacg ggacag ca  cca ccc gga tat gga act gcc ggt    313
                            Ala Pro Pro Gly Tyr Gly Thr Ala Gly
                                          55                  60
```

```
acc gtc gtc aac ctg att ctc aat gcg ttc cct ggg gcc acg gcc gaa      361
Thr Val Val Asn Leu Ile Leu Asn Ala Phe Pro Gly Ala Thr Ala Glu
             65                  70                  75 gca atc aac tat ccc gcc tgc ggt gga caa gca tct tgt gga gga gtc      409
Ala Ile Asn Tyr Pro Ala Cys Gly Gly Gln Ala Ser Cys Gly Gly Val
             80                  85                  90 ca   gaacgtgatc ccttctattt gcgccatgat atcgtcgact aaccatccta cag g    465
Gln tac ggt gac tcg gca agg cag ggc acc gac gcg gtg gct tcg gcg gtg      513
Tyr Gly Asp Ser Ala Arg Gln Gly Thr Asp Ala Val Ala Ser Ala Val
         95                 100                 105 aac agc ttc aac cag cgg tgt ccc aac act cag atc gtg ctt gtt ggc      561
Asn Ser Phe Asn Gln Arg Cys Pro Asn Thr Gln Ile Val Leu Val Gly
110                 115                 120                 125 tac tcc cag gtgcgtgtcg atgagaatga caagacacat ctgggaaagg              610
Tyr Ser Gln acaaagatga aggaacgg ggttctaaca aacgcag ggc ggt caa atc atc gac       665
                                        Gly Gly Gln Ile Ile Asp
                                                    130 aat gct gtt tgt ggt ggc cct gac acg ggc tct gga atc acg acc acg      713
Asn Ala Val Cys Gly Gly Pro Asp Thr Gly Ser Gly Ile Thr Thr Thr
135                 140                 145                 150 act cct ccc atc tcg gct gcg gcc ctg aac cag atc aag gcc gtc atc      761
Thr Pro Pro Ile Ser Ala Ala Ala Leu Asn Gln Ile Lys Ala Val Ile
                155                 160                 165 gaa atg ggc tct cca cgg ttc gtc gcc ggc ttg tcc tac gac gtc ggt      809
Glu Met Gly Ser Pro Arg Phe Val Ala Gly Leu Ser Tyr Asp Val Gly
                170                 175                 180 acc tgc acg gca caa ggt gtaagtggct tcgtcctctc tcgaatgagg             857
Thr Cys Thr Ala Gln Gly
                185 tattctctag tttctaacac acgcattcct ag ttt gct gcg cgc ccg cgt ggc      910
                                   Phe Ala Ala Arg Pro Arg Gly
                                       190                 195 tac gtc tgc ggc tcc aac tcg gcg tcc aag atc cag agc tac tgc gat      958
Tyr Val Cys Gly Ser Asn Ser Ala Ser Lys Ile Gln Ser Tyr Cys Asp
                200                 205                 210 tcg acc gac ccc tac tgc tgc acc ggc aac gac gcc aac agc cac cag      1006
Ser Thr Asp Pro Tyr Cys Cys Thr Gly Asn Asp Ala Asn Ser His Gln
                215                 220                 225 cag tat ggc aac aag tac gga cag cag gcc ctg gct ttt gtc aag gcc      1054
Gln Tyr Gly Asn Lys Tyr Gly Gln Gln Ala Leu Ala Phe Val Lys Ala
                230                 235                 240 agg ctc agc ggc agc ggc gga act ccg acg tcg tcg gcc ggc ggc tcc      1102
Arg Leu Ser Gly Ser Gly Gly Thr Pro Thr Ser Ser Ala Gly Gly Ser
245                 250                 255 gtt ccg acc ggc ggc aac ggc ggc act tgc agc ccg ctg tac gga cag      1150
Val Pro Thr Gly Gly Asn Gly Gly Thr Cys Ser Pro Leu Tyr Gly Gln
260                 265                 270                 275 tgc ggt ggc cag gga tgg acg ggt ccc acg tgc tgc tct cag gga acc      1198
Cys Gly Gly Gln Gly Trp Thr Gly Pro Thr Cys Cys Ser Gln Gly Thr
                280                 285                 290 tgc agg gca tcc aac cag tgg tac tcc cag tgc ttg taaatccagg           1244
Cys Arg Ala Ser Asn Gln Trp Tyr Ser Gln Cys Leu
                295                 300 gcgtgactcc gtgaggaaca tgggttccaa ggactcgacc tcttcttgta aatatcttga    1304
ttgcggcagt gtgaatacag cccggcacat agcggaattc ctttctgccc cttctgacta    1364
acaccgagag cagcataagt agatatatgc ttaggaacag accgagccag ataaaaaa      1422
```

<210> SEQ ID NO 80
<211> LENGTH: 303
<212> TYPE: PRT
<213> ORGANISM: Chrysosporium lucknowense

<400> SEQUENCE: 80

```
Met Trp Pro Thr Pro Lys Val Ala Tyr Leu Leu Leu Ala Ala His Ser
1               5                   10                  15

Leu Leu Val Ser Gly Thr Pro Val Asp Ala Glu Ala Val Asp Thr Ala
            20                  25                  30

Ile Leu Ala Lys Arg Gln Cys Pro Gln Ile His Ile Phe Gly Ala Arg
        35                  40                  45

Glu Thr Thr Ala Pro Pro Gly Tyr Gly Thr Ala Gly Thr Val Val Asn
    50                  55                  60

Leu Ile Leu Asn Ala Phe Pro Gly Ala Thr Ala Glu Ala Ile Asn Tyr
65                  70                  75                  80

Pro Ala Cys Gly Gly Gln Ala Ser Cys Gly Gly Val Gln Tyr Gly Asp
                85                  90                  95

Ser Ala Arg Gln Gly Thr Asp Ala Val Ala Ser Ala Val Asn Ser Phe
            100                 105                 110

Asn Gln Arg Cys Pro Asn Thr Gln Ile Val Leu Val Gly Tyr Ser Gln
        115                 120                 125

Gly Gly Gln Ile Ile Asp Asn Ala Val Cys Gly Gly Pro Asp Thr Gly
    130                 135                 140

Ser Gly Ile Thr Thr Thr Thr Pro Pro Ile Ser Ala Ala Ala Leu Asn
145                 150                 155                 160

Gln Ile Lys Ala Val Ile Glu Met Gly Ser Pro Arg Phe Val Ala Gly
                165                 170                 175

Leu Ser Tyr Asp Val Gly Thr Cys Thr Ala Gln Gly Phe Ala Ala Arg
            180                 185                 190

Pro Arg Gly Tyr Val Cys Gly Ser Asn Ser Ala Ser Lys Ile Gln Ser
        195                 200                 205

Tyr Cys Asp Ser Thr Asp Pro Tyr Cys Cys Thr Gly Asn Asp Ala Asn
    210                 215                 220

Ser His Gln Gln Tyr Gly Asn Lys Tyr Gly Gln Gln Ala Leu Ala Phe
225                 230                 235                 240

Val Lys Ala Arg Leu Ser Gly Ser Gly Gly Thr Pro Thr Ser Ser Ala
                245                 250                 255

Gly Gly Ser Val Pro Thr Gly Gly Asn Gly Gly Thr Cys Ser Pro Leu
            260                 265                 270

Tyr Gly Gln Cys Gly Gly Gln Gly Trp Thr Gly Pro Thr Cys Cys Ser
        275                 280                 285

Gln Gly Thr Cys Arg Ala Ser Asn Gln Trp Tyr Ser Gln Cys Leu
    290                 295                 300
```

<210> SEQ ID NO 81
<211> LENGTH: 909
<212> TYPE: DNA
<213> ORGANISM: Chrysosporium lucknowense

<400> SEQUENCE: 81

```
atgtggccta ctcccaaggt tgcttacctc ttgctggcag ctcactcgct gctcgtcagc      60
gggactcccg tcgacgccga ggccgtggac acggccatcc tcgccaagcg ccaatgcccg     120
cagatccata tcttcggagc tcgagaaacg acagcaccac ccggatatgg aactgccggt     180
accgtcgtca acctgattct caatgcgttc cctggggcca cggccgaagc aatcaactat     240
```

```
cccgcctgcg gtggacaagc atcttgtgga ggagtccagt acggtgactc ggcaaggcag      300
ggcaccgacg cggtggcttc ggcggtgaac agcttcaacc agcggtgtcc caacactcag      360
atcgtgcttg ttggctactc ccagggcggt caaatcatcg acaatgctgt tgtggtggc       420 cctgacacgg gctctggaat cacgaccacg actcctccca tctcggctgc ggccctgaac      480
cagatcaagg ccgtcatcga atgggctct  ccacggttcg tcgccggctt gtcctacgac      540
gtcggtacct gcacggcaca aggttttgct gcgcgcccgc gtggctacgt ctgcggctcc      600
aactcggcgt ccaagatcca gagctactgc gattcgaccg accccactg  ctgcaccggc      660 aacgacgcca acagccacca gcagtatggc aacaagtacg acagcaggc  cctggctttt      720 gtcaaggcca ggctcagcgg cagcggcgga actccgacgt cgtcggccgg cggctccgtt      780
ccgaccggcg gcaacggcgg cacttgcagc ccgctgtacg acagtgcgg  tggccaggga      840 tggacgggtc ccacgtgctg ctctcaggga acctgcaggg catccaacca gtggtactcc      900
cagtgcttg                                                              909

<210> SEQ ID NO 82
<211> LENGTH: 1440
<212> TYPE: DNA
<213> ORGANISM: Chrysosporium lucknowense
<220> FEATURE:
<221> NAME/KEY: CDS
<222> LOCATION: (282)..(402)
<220> FEATURE:
<221> NAME/KEY: CDS
<222> LOCATION: (470)..(594)
<220> FEATURE:
<221> NAME/KEY: CDS
<222> LOCATION: (672)..(929)
<220> FEATURE:
<221> NAME/KEY: CDS
<222> LOCATION: (987)..(1166)

<400> SEQUENCE: 82
cccaaagaga ttaaagcgac cttccggcgt gccattaggc agccttccgc cgaccctttc       60
tccgtcttcc ctatttcgaa cacccgtccg tccgggctcc ggggtgtaac atagggtctc      120
ggacgagggt catcagacgg tgtcgagtga tgctctggtt tgtaatgtag ttatataata      180
taagaatcca cccgactctt cggtgtactt gtagccgatg tttgatcagg gcacatctca      240
agtccatcta tactcttcaa tcagaataac atatacacgc c atg aag gtc acc gcc      296
                                            Met Lys Val Thr Ala
                                              1               5 gtt gcc gtt ccc gtc ctg gct ggc att gcc agc gcc aac ccc gtc gac      344
Val Ala Val Pro Val Leu Ala Gly Ile Ala Ser Ala Asn Pro Val Asp
              10                  15                  20 gtc gag gcc cgc cag tcg tgc ccc gag gtc cac gta ttc ggc gcc cgg      392
Val Glu Ala Arg Gln Ser Cys Pro Glu Val His Val Phe Gly Ala Arg
         25                  30                  35 gaa act aca g gtaattaagc ttagggttgg ggttgtctca gggtaatta              442
Glu Thr Thr
        40 cggctaccta actaacgtca acatcag ca   ccc cct ggc tat ggc aca tcc caa   495
                                  Ala Pro Pro Gly Tyr Gly Thr Ser Gln
                                                                  45 ggc ctc gtc aac atg gtc gtg cag gcg tac ccc gga gca aca agc gag      543
Gly Leu Val Asn Met Val Val Gln Ala Tyr Pro Gly Ala Thr Ser Glu
 50                  55                  60                  65 gcc ata aac tac ccc gca tgc ggc ggt cag gcg tct tgc ggt gga atc      591
Ala Ile Asn Tyr Pro Ala Cys Gly Gly Gln Ala Ser Cys Gly Gly Ile
              70                  75                  80
```

```
gat gcaagtgacc ccgaaaatgc cgctgactgt aaatcaggtg catccgttgt          644
Asp
tcctaacgag taactcgggg cttttag tac aat acc tct gcg aac cag ggc act    698
                              Tyr Asn Thr Ser Ala Asn Gln Gly Thr
                                      85                  90
cag gcg gtt gtc tcc gct gtg acg agc ttt aac cag cgc tgc cct gac      746
Gln Ala Val Val Ser Ala Val Thr Ser Phe Asn Gln Arg Cys Pro Asp
            95                  100                 105
aca aag atc gtc ttg atc ggc tat tcg cag ggt ggc cag atc atg gac      794
Thr Lys Ile Val Leu Ile Gly Tyr Ser Gln Gly Gly Gln Ile Met Asp
        110                 115                 120
aac gcc tac tgc ggc ggc gcc ggt gcc acc ctc agc ggc agc gcc ctc      842
Asn Ala Tyr Cys Gly Gly Ala Gly Ala Thr Leu Ser Gly Ser Ala Leu
    125                 130                 135
aac gcc gtt aaa gcc acg gtc tgg ttc gga aat ccg cat tat ctg agc      890
Asn Ala Val Lys Ala Thr Val Trp Phe Gly Asn Pro His Tyr Leu Ser
140                 145                 150                 155
caa tta agt tat cga gtt ggg aca tgc cag gcc gga ggg gtaggttcct       939
Gln Leu Ser Tyr Arg Val Gly Thr Cys Gln Ala Gly Gly
                160                 165
ctattgtcga tgtattttcg tgagacacga catgctgacc gagatag ttc gcg gcc      995
                                                    Phe Ala Ala
                                                        170
cgc cct ccc gga ttc caa tgt tcg cct ggt aac cca gat aac atc aag     1043
Arg Pro Pro Gly Phe Gln Cys Ser Pro Gly Asn Pro Asp Asn Ile Lys
            175                 180                 185
tcg tac tgc gat gcc gag gat ccg tac tgc tgc aat gga aac gat gca     1091
Ser Tyr Cys Asp Ala Glu Asp Pro Tyr Cys Cys Asn Gly Asn Asp Ala
        190                 195                 200
aac cac cac caa cag tac gtc acc atc tac ggc cag cag gcg ctc gcc     1139
Asn His His Gln Gln Tyr Val Thr Ile Tyr Gly Gln Gln Ala Leu Ala
    205                 210                 215
ttc atc aag tcg aag ctc gac gct gct taagcgtagg gagatacgct           1186
Phe Ile Lys Ser Lys Leu Asp Ala Ala
220                 225
gcgttggaaa gggggcgatg gagcacatta ccaagtaaat acagtgccac gtccgtttgt   1246
atgtacacag gtagccaaaa aaacagccat gctcggatcc atatgtttgc ccctctctct   1306
tggagtgacc cgactctgtt gaggttgttg gtatcgcggt acgagaaagt ggacgaccaa   1366
ggcaccaatg agctgctgct ctttgcaatg gacatttctg ggcgatattt gccgtgaact   1426
atcacactcg ccat                                                     1440

<210> SEQ ID NO 83
<211> LENGTH: 228
<212> TYPE: PRT
<213> ORGANISM: Chrysosporium lucknowense

<400> SEQUENCE: 83

Met Lys Val Thr Ala Val Ala Val Pro Val Leu Ala Gly Ile Ala Ser
1               5                   10                  15

Ala Asn Pro Val Asp Val Glu Ala Arg Gln Ser Cys Pro Glu Val His
            20                  25                  30

Val Phe Gly Ala Arg Glu Thr Thr Ala Pro Pro Gly Tyr Gly Thr Ser
        35                  40                  45

Gln Gly Leu Val Asn Met Val Val Gln Ala Tyr Pro Gly Ala Thr Ser
    50                  55                  60

Glu Ala Ile Asn Tyr Pro Ala Cys Gly Gly Gln Ala Ser Cys Gly Gly
65                  70                  75                  80
```

```
Ile Asp Tyr Asn Thr Ser Ala Asn Gln Gly Thr Gln Ala Val Val Ser
                85                  90                  95
Ala Val Thr Ser Phe Asn Gln Arg Cys Pro Asp Thr Lys Ile Val Leu
            100                 105                 110
Ile Gly Tyr Ser Gln Gly Gly Gln Ile Met Asp Asn Ala Tyr Cys Gly
        115                 120                 125
Gly Ala Gly Ala Thr Leu Ser Gly Ser Ala Leu Asn Ala Val Lys Ala
    130                 135                 140
Thr Val Trp Phe Gly Asn Pro His Tyr Leu Ser Gln Leu Ser Tyr Arg
145                 150                 155                 160
Val Gly Thr Cys Gln Ala Gly Phe Ala Ala Arg Pro Pro Gly Phe
                165                 170                 175
Gln Cys Ser Pro Gly Asn Pro Asp Asn Ile Lys Ser Tyr Cys Asp Ala
            180                 185                 190
Glu Asp Pro Tyr Cys Cys Asn Gly Asn Asp Ala Asn His His Gln Gln
        195                 200                 205
Tyr Val Thr Ile Tyr Gly Gln Gln Ala Leu Ala Phe Ile Lys Ser Lys
    210                 215                 220
Leu Asp Ala Ala
225

<210> SEQ ID NO 84
<211> LENGTH: 684
<212> TYPE: DNA
<213> ORGANISM: Chrysosporium lucknowense

<400> SEQUENCE: 84
atgaaggtca ccgccgttgc cgttcccgtc ctggctggca ttgccagcgc caaccccgtc     60
gacgtcgagg cccgccagtc gtgccccgag gtccacgtat tcggcgcccg ggaaactaca    120
gcaccccctg ctatggcac atcccaaggc ctcgtcaaca tggtcgtgca ggcgtacccc    180
ggagcaacaa gcgaggccat aaactacccc gcatgcggcg gtcaggcgtc ttgcggtgga    240
atcgattaca atacctctgc gaaccagggc actcaggcgg ttgtctccgc tgtgacgagc    300
tttaaccagc gctgccctga cacaaagatc gtcttgatcg gctattcgca gggtggccag    360
atcatggaca cgcctactg cggcggcgcc ggtgccaccc tcagcggcag cgccctcaac    420
gccgttaaag ccacggtctg gttcggaaat ccgcattatc tgagccaatt aagttatcga    480
gttgggacat gccaggccgg agggttcgcg gcccgcccct ccggattcca atgttcgcct    540
ggtaacccag ataacatcaa gtcgtactgc gatgccgagg atccgtactg ctgcaatgga    600
aacgatgcaa accaccacca acagtacgtc accatctacg ccagcaggc gctcgccttc    660
atcaagtcga agctcgacgc tgct                                           684

<210> SEQ ID NO 85
<211> LENGTH: 1401
<212> TYPE: DNA
<213> ORGANISM: Chrysosporium lucknowense
<220> FEATURE:
<221> NAME/KEY: CDS
<222> LOCATION: (85)..(371)
<220> FEATURE:
<221> NAME/KEY: CDS
<222> LOCATION: (432)..(849)
<220> FEATURE:
<221> NAME/KEY: CDS
<222> LOCATION: (927)..(1075)
<220> FEATURE:
<221> NAME/KEY: CDS
<222> LOCATION: (1143)..(1198)
```

```
<220> FEATURE:
<221> NAME/KEY: CDS
<222> LOCATION: (1263)..(1345)

<400> SEQUENCE: 85
agcttctcag catggacatg ttgaatgcct agcagacgga aatcccatca gtaatatact      60
tagtcttctg gaaacttgct cgtc atg agg cta tcc ctt tgc agg ttg gca       111
                           Met Arg Leu Ser Leu Cys Arg Leu Ala
                            1               5 tcg gcg gtg cta tcc ctg acc ttt gtg ggc gat gct ttg cct ggt gct      159
Ser Ala Val Leu Ser Leu Thr Phe Val Gly Asp Ala Leu Pro Gly Ala
 10              15                  20                  25 tct gcg cag gcc gcg agc cgg acc act ccg ccg agc gga tgt ctg tca      207
Ser Ala Gln Ala Ala Ser Arg Thr Thr Pro Pro Ser Gly Cys Leu Ser
             30                  35                  40 gta gga agc ggc agg cag tac agc acc atc acg gaa gcg ata act gcc      255
Val Gly Ser Gly Arg Gln Tyr Ser Thr Ile Thr Glu Ala Ile Thr Ala
                 45                  50                  55 ttg ggt tct ggc act tca gct gcc tgc att ttc atc tac ccg gga acc      303
Leu Gly Ser Gly Thr Ser Ala Ala Cys Ile Phe Ile Tyr Pro Gly Thr
                     60                  65                  70 tac aac gtt gct gat ggt gtt tcg atc aag tac aag ggc ccg ctg aca      351
Tyr Asn Val Ala Asp Gly Val Ser Ile Lys Tyr Lys Gly Pro Leu Thr
 75                  80                  85 ctg tat ggg tca acc tcg ga gtgagtactt acataataac tgccaaatgc          401
Leu Tyr Gly Ser Thr Ser Asp
 90                  95 cgtattcacc actattaatc accatggcag t acc agc aag cag agc gcc aac       453
                                   Thr Ser Lys Gln Ser Ala Asn
                                                   100 cag gtg acc ttt acc agg aac aag ggt tcg gcc gat gct ggg agc ctg      501
Gln Val Thr Phe Thr Arg Asn Lys Gly Ser Ala Asp Ala Gly Ser Leu
                 105                 110                 115 gac gcg tct gcc acg ttc aac atc gtg agc agc aac ttc cgg gcg tac      549
Asp Ala Ser Ala Thr Phe Asn Ile Val Ser Ser Asn Phe Arg Ala Tyr
120                 125                 130                 135 aac atc aac ttt cgt aac aca tac ggc acg cag ggc cag gcc gtg gcc      597
Asn Ile Asn Phe Arg Asn Thr Tyr Gly Thr Gln Gly Gln Ala Val Ala
                 140                 145                 150 gtg gcc gcc aac ggc gac aag cag gcc tac tat gcg tgc ggt ttc tac      645
Val Ala Ala Asn Gly Asp Lys Gln Ala Tyr Tyr Ala Cys Gly Phe Tyr
             155                 160                 165 ggc tac cag gac acg ctg tac gcc aag agc ggt cgc cag tac tac tcc      693
Gly Tyr Gln Asp Thr Leu Tyr Ala Lys Ser Gly Arg Gln Tyr Tyr Ser
         170                 175                 180 aac tgc tac atc gag ggc gcc gtc gac ttc atc ttt ggc gcc gcg gct      741
Asn Cys Tyr Ile Glu Gly Ala Val Asp Phe Ile Phe Gly Ala Ala Ala
     185                 190                 195 gcc tgg ttt ggc gag tgt acc gtt gcc tcc aac ggc ggg ggg tac atc      789
Ala Trp Phe Gly Glu Cys Thr Val Ala Ser Asn Gly Gly Gly Tyr Ile
200                 205                 210                 215 acc gct aac tct cgc tcc act acg gct gat act acc tgg tat gct ttt      837
Thr Ala Asn Ser Arg Ser Thr Thr Ala Asp Thr Thr Trp Tyr Ala Phe
                 220                 225                 230 gat cac agt act gtaagttcac cgtccaaagc aagtccaacg ctccgtgccc          889
Asp His Ser Thr
             235 acaactatta acgattgtcc cgcttcgcta ttatcag atc cgg gcg gct gcc gga    944
                                         Ile Arg Ala Ala Ala Gly
                                                     240
```

```
att agc ttg gcc ggc aaa gtg ttc ctc ggc cga ccg tgg cgc gta ctt     992
Ile Ser Leu Ala Gly Lys Val Phe Leu Gly Arg Pro Trp Arg Val Leu
        245                 250                 255 gcc cgc gtt atc ttc caa aat tcc gag ttg acc gac gtc gtg cac cct    1040
Ala Arg Val Ile Phe Gln Asn Ser Glu Leu Thr Asp Val Val His Pro
    260                 265                 270 gag ggc tgg acc aga atg gct gca gga gct act cc gtaagtgatt          1085
Glu Gly Trp Thr Arg Met Ala Ala Gly Ala Thr Pro
275                 280 ctctatccgc gacttctggt gacccagatg ctgacaaata tggcgaaact cttgcag c   1143 gag ttc cgg gag ttc caa aac act ggt gca gga tct aac aca tcc cag   1191
Glu Phe Arg Glu Phe Gln Asn Thr Gly Ala Gly Ser Asn Thr Ser Gln
            290                 295                 300 aga aag t gtaagtgaat gtatcttcta ctctagaggg cactgaattg ctaacgctct   1248
Arg Lys tggtgtgtat gcag gg ctc act ttc cca acg act gct ggt gtc act aag    1297
                 Trp Leu Thr Phe Pro Thr Thr Ala Gly Val Thr Lys
                     305                 310                 315 acc cag ctc tgg ggc agt gac tgg aag act tgg ata gat act gca tgg   1345
Thr Gln Leu Trp Gly Ser Asp Trp Lys Thr Trp Ile Asp Thr Ala Trp
                320                 325                 330 tgagaggacg tgtccaaggt tggcaatcag cacctcaaat caacggacat aattaa     1401

<210> SEQ ID NO 86
<211> LENGTH: 331
<212> TYPE: PRT
<213> ORGANISM: Chrysosporium lucknowense

<400> SEQUENCE: 86

Met Arg Leu Ser Leu Cys Arg Leu Ala Ser Ala Val Leu Ser Leu Thr
1               5                   10                  15

Phe Val Gly Asp Ala Leu Pro Gly Ala Ser Ala Gln Ala Ala Ser Arg
                20                  25                  30

Thr Thr Pro Pro Ser Gly Cys Leu Ser Val Gly Ser Gly Arg Gln Tyr
            35                  40                  45

Ser Thr Ile Thr Glu Ala Ile Thr Ala Leu Gly Ser Gly Thr Ser Ala
        50                  55                  60

Ala Cys Ile Phe Ile Tyr Pro Gly Thr Tyr Asn Val Ala Asp Gly Val
65                  70                  75                  80

Ser Ile Lys Tyr Lys Gly Pro Leu Thr Leu Tyr Gly Ser Thr Ser Asp
                85                  90                  95

Thr Ser Lys Gln Ser Ala Asn Gln Val Thr Phe Thr Arg Asn Lys Gly
            100                 105                 110

Ser Ala Asp Ala Gly Ser Leu Asp Ala Ser Ala Thr Phe Asn Ile Val
        115                 120                 125

Ser Ser Asn Phe Arg Ala Tyr Asn Ile Asn Phe Arg Asn Thr Tyr Gly
    130                 135                 140

Thr Gln Gly Gln Ala Val Ala Val Ala Ala Asn Gly Asp Lys Gln Ala
145                 150                 155                 160

Tyr Tyr Ala Cys Gly Phe Tyr Gly Tyr Gln Asp Thr Leu Tyr Ala Lys
                165                 170                 175

Ser Gly Arg Gln Tyr Tyr Ser Asn Cys Tyr Ile Glu Gly Ala Val Asp
            180                 185                 190

Phe Ile Phe Gly Ala Ala Ala Trp Phe Gly Glu Cys Thr Val Ala
        195                 200                 205

Ser Asn Gly Gly Gly Tyr Ile Thr Ala Asn Ser Arg Ser Thr Thr Ala
    210                 215                 220
```

| Asp | Thr | Thr | Trp | Tyr | Ala | Phe | Asp | His | Ser | Thr | Ile | Arg | Ala | Ala |
| --- | --- | --- | --- | --- | --- | --- | --- | --- | --- | --- | --- | --- | --- | --- |
| 225 | | | | 230 | | | | 235 | | | | 240 | | |

| Gly | Ile | Ser | Leu | Ala | Gly | Lys | Val | Phe | Leu | Gly | Arg | Pro | Trp | Arg | Val |
| --- | --- | --- | --- | --- | --- | --- | --- | --- | --- | --- | --- | --- | --- | --- | --- |
| | | | | 245 | | | | | 250 | | | | | 255 | |

| Leu | Ala | Arg | Val | Ile | Phe | Gln | Asn | Ser | Glu | Leu | Thr | Asp | Val | Val | His |
| --- | --- | --- | --- | --- | --- | --- | --- | --- | --- | --- | --- | --- | --- | --- | --- |
| | | | 260 | | | | | 265 | | | | | 270 | | |

| Pro | Glu | Gly | Trp | Thr | Arg | Met | Ala | Ala | Gly | Ala | Thr | Pro | Glu | Phe | Arg |
| --- | --- | --- | --- | --- | --- | --- | --- | --- | --- | --- | --- | --- | --- | --- | --- |
| | | 275 | | | | | 280 | | | | | 285 | | | |

| Glu | Phe | Gln | Asn | Thr | Gly | Ala | Gly | Ser | Asn | Thr | Ser | Gln | Arg | Lys | Trp |
| --- | --- | --- | --- | --- | --- | --- | --- | --- | --- | --- | --- | --- | --- | --- | --- |
| | 290 | | | | | 295 | | | | | 300 | | | | |

| Leu | Thr | Phe | Pro | Thr | Thr | Ala | Gly | Val | Thr | Lys | Thr | Gln | Leu | Trp | Gly |
| --- | --- | --- | --- | --- | --- | --- | --- | --- | --- | --- | --- | --- | --- | --- | --- |
| 305 | | | | | 310 | | | | | 315 | | | | | 320 |

| Ser | Asp | Trp | Lys | Thr | Trp | Ile | Asp | Thr | Ala | Trp |
| --- | --- | --- | --- | --- | --- | --- | --- | --- | --- | --- |
| | | | 325 | | | | | 330 | | |

<210> SEQ ID NO 87
<211> LENGTH: 993
<212> TYPE: DNA
<213> ORGANISM: Chrysosporium lucknowense

<400> SEQUENCE: 87

```
atgaggctat ccctttgcag gttggcatcg gcggtgctat ccctgacctt tgtgggcgat      60
gctttgcctg gtgcttctgc gcaggccgcg agccggacca ctccgccgag cggatgtctg     120
tcagtaggaa gcggcaggca gtacagcacc atcacggaag cgataactgc cttgggttct     180
ggcacttcag ctgcctgcat tttcatctac ccgggaacct acaacgttgc tgatggtgtt     240
tcgatcaagt acaagggccc gctgacactg tatgggtcaa cctcggatac cagcaagcag     300
agcgccaacc aggtgacctt taccaggaac aagggttcgg ccgatgctgg gagcctggac     360
gcgtctgcca cgttcaacat cgtgagcagc aacttccggg cgtacaacat caactttcgt     420
aacacatacg gcacgcaggg ccaggccgtg gccgtggccg ccaacggcga caagcaggcc     480
tactatgcgt gcggtttcta cggctaccag gacacgctgt acgccaagag cggtcgccag     540
tactactcca actgctacat cgagggcgcc gtcgacttca tctttggcgc cgcggctgcc     600
tggtttggcg agtgtaccgt tgcctccaac ggcggcgggt acatcaccgc taactctcgc     660
tccactacgg ctgatactac ctggtatgct tttgatcaca gtactatccg gcggctgcc      720
ggaattagct tggccggcaa agtgttcctc ggccgaccgt ggcgcgtact tgcccgcgtt     780
atcttccaaa attccgagtt gaccgacgtc gtgcaccctg agggctggac cagaatggct     840
gcaggagcta ctcccgagtt ccgggagttc caaaacactg gtgcaggatc taacacatcc     900
cagagaaagt ggctcacttt cccaacgact gctggtgtca ctaagaccca gctctggggc     960
agtgactgga agacttggat agatactgca tgg                                  993
```

<210> SEQ ID NO 88
<211> LENGTH: 1504
<212> TYPE: DNA
<213> ORGANISM: Chrysosporium lucknowense
<220> FEATURE:
<221> NAME/KEY: CDS
<222> LOCATION: (296)..(565)
<220> FEATURE:
<221> NAME/KEY: CDS
<222> LOCATION: (650)..(1240)
<220> FEATURE:
<221> NAME/KEY: CDS
<222> LOCATION: (1351)..(1452)

<400> SEQUENCE: 88

-continued

```
acaccctcac gacaagtcgc aacctcgatt tcccgtgtgc ccggagcttg caacgcgtc      60 acgacccata gttagtagta tcgtcaaggg ccgtctcgct aaaagtagcg tggtttcaga    120
aaccgtttat ttagcgacct taaataatta ttattgatta tctcccgaca acctccgggc    180
ctcgtcggcg ggtttctgtc taactgctgc tgcaaacttc aggcggctgt ccgtcgtgtt    240
cggtcattct caccttgcca gctttggcta attaccttac cttgctctac caacg atg    298
                                                               Met
                                                                1
```

```
aag aga tcc ggc ctt ctg ggg acg gtg gct ctt ctg ttc ccg gcc ctc      346
Lys Arg Ser Gly Leu Leu Gly Thr Val Ala Leu Leu Phe Pro Ala Leu
          5                  10                  15 gtt tct gcc tat gcg ctc ccg ggc gaa tgt act gga gtc tgc aac aac      394
Val Ser Ala Tyr Ala Leu Pro Gly Glu Cys Thr Gly Val Cys Asn Asn
     20                  25                  30 tcc cac gac ccg tca atc atc cgc cgc gca gat ggg acg tac ttc cgc      442
Ser His Asp Pro Ser Ile Ile Arg Arg Ala Asp Gly Thr Tyr Phe Arg
 35                  40                  45 ttc tcg act ggt ggc aag atc gcc att cac acg gcg ccg agc ctg acc      490
Phe Ser Thr Gly Gly Lys Ile Ala Ile His Thr Ala Pro Ser Leu Thr
50                  55                  60                  65 ggc ccg tgg acc tat agg ggc gcc gcc ttg ccg gcc ggg tcc tcc atc      538
Gly Pro Trp Thr Tyr Arg Gly Ala Ala Leu Pro Ala Gly Ser Ser Ile
                 70                  75                  80 aac ttg gac ggg aac cag gac ctc tgg gtaagaagaa caaggcgttc            585
Asn Leu Asp Gly Asn Gln Asp Leu Trp
                 85                  90
```

```
acggcccgca gcctggatgt aatttattta tgggtgatga tgatgttgac gacgagctcg    645 ccag gcc ccc gat gtt gca cag gtc gga gac cag tac tac ctg tac tac    694
     Ala Pro Asp Val Ala Gln Val Gly Asp Gln Tyr Tyr Leu Tyr Tyr
                 95                  100                 105 tcc gtc agc acc ttc ggc gtc cag aac tcg gcc atc ggc ata gcc cgc      742
Ser Val Ser Thr Phe Gly Val Gln Asn Ser Ala Ile Gly Ile Ala Arg
                 110                 115                 120 tca tcg agc ctg gac gcc ggc acc tgg acc gac ctc ggg tct acc ggt      790
Ser Ser Ser Leu Asp Ala Gly Thr Trp Thr Asp Leu Gly Ser Thr Gly
             125                 130                 135 gtc acc tcc agc acg ggc tcg gcg tac aac gcc atc gac ggc aac ctg      838
Val Thr Ser Ser Thr Gly Ser Ala Tyr Asn Ala Ile Asp Gly Asn Leu
         140                 145                 150 atc aac gag ccg ggg acc agc aac tac ttc ctc acg ttt ggc agc ttc      886
Ile Asn Glu Pro Gly Thr Ser Asn Tyr Phe Leu Thr Phe Gly Ser Phe
     155                 160                 165 tgg aac ggc atc cat cgc gtc cgc atg acg ccc acc aag acg aac ggc      934
Trp Asn Gly Ile His Arg Val Arg Met Thr Pro Thr Lys Thr Asn Gly
170                 175                 180                 185 aac gtg tac cag gtc gcc ttt gat ccc aac gac ccg gcc atg gaa ggc      982
Asn Val Tyr Gln Val Ala Phe Asp Pro Asn Asp Pro Ala Met Glu Gly
                 190                 195                 200 ccg acc gtc ttc aag tac ggc gac tac tac ctt ttc ttc tcc aag         1030
Pro Thr Val Phe Lys Tyr Gly Asp Tyr Tyr Leu Phe Phe Ser Lys
             205                 210                 215 ggc acg tgc tgc ggc tac gac cag aac agg ccg ccc gcc gga cag gag     1078
Gly Thr Cys Cys Gly Tyr Asp Gln Asn Arg Pro Pro Ala Gly Gln Glu
         220                 225                 230 tac agg atc atg gtg tgc agg tcg acc tcg ccc acc ggc ccc ttc gag     1126
Tyr Arg Ile Met Val Cys Arg Ser Thr Ser Pro Thr Gly Pro Phe Glu
     235                 240                 245 gac agg gac ggc aag tcg tgc cgc tcg ggc ggt gga act ctg gtg ctc     1174
Asp Arg Asp Gly Lys Ser Cys Arg Ser Gly Gly Gly Thr Leu Val Leu
```

-continued

```
Asp Arg Asp Gly Lys Ser Cys Arg Ser Gly Gly Thr Leu Val Leu
250                 255                 260                 265 ccg tct cac gac tgg gtg tac ggc ccc ggc ggc caa ggt gtc tac cag      1222
Pro Ser His Asp Trp Val Tyr Gly Pro Gly Gly Gln Gly Val Tyr Gln
                270                 275                 280 gac ccc gaa cac gga ccg gttagttccc cgtcctttct cccgtacggg             1270
Asp Pro Glu His Gly Pro
                285 cctagcattc agcatcgggg atcgagcatc aagcatcacc ctgcttgaac ccatctcttg    1330 ctaacgctct tccttcccag gtc ttg tac tac cat tat gtt gat act cgc att   1383
                      Val Leu Tyr Tyr His Tyr Val Asp Thr Arg Ile
                                  290                 295 ggc tat gcg gac ggc cag aag aag ttt ggt tgg aat cgc atc gac ttt      1431
Gly Tyr Ala Asp Gly Gln Lys Lys Phe Gly Trp Asn Arg Ile Asp Phe
300                 305                 310 tca agc ggt tgg ccg gtt gtc tgagaaaccc gagacgcttg acttgtttat         1482
Ser Ser Gly Trp Pro Val Val
315                 320 ttacaggtat taccggtatt aa                                             1504
```

<210> SEQ ID NO 89
<211> LENGTH: 321
<212> TYPE: PRT
<213> ORGANISM: Chrysosporium lucknowense

<400> S

```
Ser Thr Ser Pro Thr Gly Pro Phe Glu Asp Arg Asp Gly Lys Ser Cys
            245                 250                 255

Arg Ser Gly Gly Gly Thr Leu Val Leu Pro Ser His Asp Trp Val Tyr
            260                 265                 270

Gly Pro Gly Gly Gln Gly Val Tyr Gln Asp Pro Glu His Gly Pro Val
            275                 280                 285

Leu Tyr Tyr His Tyr Val Asp Thr Arg Ile Gly Tyr Ala Asp Gly Gln
            290                 295                 300

Lys Lys Phe Gly Trp Asn Arg Ile Asp Phe Ser Ser Gly Trp Pro Val
305                 310                 315                 320

Val

<210> SEQ ID NO 90
<211> LENGTH: 963
<212> TYPE: DNA
<213> ORGANISM: Chrysosporium lucknowense

<400> SEQUENCE: 90
atgaagagat ccggccttct ggggacggtg gctcttctgt tcccggccct cgtttctgcc      60
tatgcgctcc cgggcgaatg tactggagtc tgcaacaact cccacgaccc gtcaatcatc     120
cgccgcgcag atgggacgta cttccgcttc tcgactggtg gcaagatcgc cattcacacg     180
gcgccgagcc tgaccggccc gtggacctat agggcgccg ccttgccggc cgggtcctcc      240
atcaacttgg acgggaacca ggacctctgg gccccgatg ttgcacaggt cggagaccag      300
tactacctgt actactccgt cagcaccttc ggcgtccaga ctcggccat cggcatagcc      360
cgctcatcga gcctggacgc cggcacctgg accgacctcg gtctaccgg tgtcacctcc      420
agcacgggct cggcgtacaa cgccatcgac ggcaacctga tcaacgagcc ggggaccagc     480
aactacttcc tcacgtttgg cagcttctgg aacggcatcc atcgcgtccg catgacgccc     540
accaagacga acggcaacgt gtaccaggtc gcctttgatc ccaacgaccc ggccatggaa     600
ggcccgaccg tcttcaagta cggcgactac tactaccttt tcttctccaa gggcacgtgc     660
tgcggctacg accagaacag gccgccgcc ggacaggagt acaggatcat ggtgtgcagg      720
tcgacctcgc ccaccggccc cttcgaggac agggacggca agtcgtgccg ctcgggcggt     780
ggaactctgg tgctcccgtc tcacgactgg gtgtacggcc ccggcggcca aggtgtctac     840
caggacccg aacacggacc ggtcttgtac taccattatg ttgatactcg cattggctat      900
gcggacggcc agaagaagtt tggttggaat cgcatcgact tttcaagcgg ttggccggtt     960
gtc                                                                  963

<210> SEQ ID NO 91
<211> LENGTH: 2451
<212> TYPE: DNA
<213> ORGANISM: Chrysosporium lucknowense
<220> FEATURE:
<221> NAME/KEY: CDS
<222> LOCATION: (57)..(1851)
<220> FEATURE:
<221> NAME/KEY: CDS
<222> LOCATION: (1954)..(2357)

<400> SEQUENCE: 91
aggaccgtca aacgtaaggg cagctctagc tcaccagata cgagacgtcg cccatc atg     59
                                                                Met
                                                                  1 acc ctt caa gcc ttt gcg ctg ctg gcg gcg gcg gcc ctt gta cgg ggc      107
Thr Leu Gln Ala Phe Ala Leu Leu Ala Ala Ala Ala Leu Val Arg Gly
         5                  10                  15
```

```
gag acc ccg acc aag gtc cct cgc gac gct ccg aga gga gct gct gct      155
Glu Thr Pro Thr Lys Val Pro Arg Asp Ala Pro Arg Gly Ala Ala Ala
            20                  25                  30 tgg gaa gct gcc cac tcc tca gca gcc gct gcc ttg gga aag ctg tcc      203
Trp Glu Ala Ala His Ser Ser Ala Ala Ala Leu Gly Lys Leu Ser
35                  40                  45 cag cag gac aag atc aac atc gtg acg ggc gtc ggc tgg aac aag ggg      251
Gln Gln Asp Lys Ile Asn Ile Val Thr Gly Val Gly Trp Asn Lys Gly
50                  55                  60                  65 ccc tgc gtg ggc aat act ccc gct atc agc tcc atc aac tac ccg cag      299
Pro Cys Val Gly Asn Thr Pro Ala Ile Ser Ser Ile Asn Tyr Pro Gln
                70                  75                  80 ctc tgc ctc caa gac gga ccc ctg ggc gtc cgc ttc ggt tcc agc atc      347
Leu Cys Leu Gln Asp Gly Pro Leu Gly Val Arg Phe Gly Ser Ser Ile
                85                  90                  95 acc gct ttc act cca ggc att cag gcc gcg tcg acg tgg gat gtg gac      395
Thr Ala Phe Thr Pro Gly Ile Gln Ala Ala Ser Thr Trp Asp Val Asp
            100                 105                 110 ctg atc cga caa cga ggc gag tac atg ggc gcc gag ttc aag ggg tgt      443
Leu Ile Arg Gln Arg Gly Glu Tyr Met Gly Ala Glu Phe Lys Gly Cys
115                 120                 125 ggc atc cac gtc cag cta ggc ccc gtg gcc ggg ccc ttg ggt aag gtt      491
Gly Ile His Val Gln Leu Gly Pro Val Ala Gly Pro Leu Gly Lys Val
130                 135                 140                 145 ccg caa ggc ggc cgc aac tgg gag ggc ttt ggc gtg gat ccc tac ctc      539
Pro Gln Gly Gly Arg Asn Trp Glu Gly Phe Gly Val Asp Pro Tyr Leu
                150                 155                 160 acc ggc att gcc atg gcc gag acc atc gag ggg ata cag tca gcg ggc      587
Thr Gly Ile Ala Met Ala Glu Thr Ile Glu Gly Ile Gln Ser Ala Gly
                165                 170                 175 gtg caa gcc acc gcc aag cat tac atc ctc aac gag cag gag ctc aac      635
Val Gln Ala Thr Ala Lys His Tyr Ile Leu Asn Glu Gln Glu Leu Asn
            180                 185                 190 cgc gag acc atg agc agc aat gtc gac gac cgc acc ttg cac gag ctg      683
Arg Glu Thr Met Ser Ser Asn Val Asp Asp Arg Thr Leu His Glu Leu
195                 200                 205 tac ctc tgg cct ttt gca gac gct gtt cac tct aac gtg gcc agc gtc      731
Tyr Leu Trp Pro Phe Ala Asp Ala Val His Ser Asn Val Ala Ser Val
210                 215                 220                 225 atg tgc agt tac aac aag atc aac ggc acg tgg gcg tgc gag aac gac      779
Met Cys Ser Tyr Asn Lys Ile Asn Gly Thr Trp Ala Cys Glu Asn Asp
                230                 235                 240 cgg gtg ctg aac gtc att ctg aag cag gag ctt ggg ttt ccg ggc tat      827
Arg Val Leu Asn Val Ile Leu Lys Gln Glu Leu Gly Phe Pro Gly Tyr
                245                 250                 255 gtg atg agc gac tgg aac gcg cag cac tcg acc gac gac gcg gcc aac      875
Val Met Ser Asp Trp Asn Ala Gln His Ser Thr Asp Asp Ala Ala Asn
            260                 265                 270 cac ggc atg gac atg acg atg ccc ggc agc gac ttc aac gga ggg acg      923
His Gly Met Asp Met Thr Met Pro Gly Ser Asp Phe Asn Gly Gly Thr
275                 280                 285 atc ctc tgg ggc ccg cag ctc gac agc gcc gtc aac agc ggc cgg gtg      971
Ile Leu Trp Gly Pro Gln Leu Asp Ser Ala Val Asn Ser Gly Arg Val
290                 295                 300                 305 ccc aag tcc cgc ctc gac gac atg gtc gag cgc atc ctc gcg gcg tgg     1019
Pro Lys Ser Arg Leu Asp Asp Met Val Glu Arg Ile Leu Ala Ala Trp
                310                 315                 320 tac ctt ctc ggt cag gac agc aat tac ccg gct atc aac atc ggc gcc     1067
Tyr Leu Leu Gly Gln Asp Ser Asn Tyr Pro Ala Ile Asn Ile Gly Ala
            325                 330                 335
```

```
aac gta cag ggc aac cac aag gag aac gtg cgg gcg gtc gcg cgc gat    1115
Asn Val Gln Gly Asn His Lys Glu Asn Val Arg Ala Val Ala Arg Asp
            340                 345                 350 ggc atc gtg ctc ctc aag aac gac gac ggc atc ctc ccg ctc aag aag    1163
Gly Ile Val Leu Leu Lys Asn Asp Asp Gly Ile Leu Pro Leu Lys Lys
355                 360                 365 ccc gcc aag ctc gcc ctc atc ggt tcg gcc gcc gtc gtc aac ccg cag    1211
Pro Ala Lys Leu Ala Leu Ile Gly Ser Ala Ala Val Val Asn Pro Gln
370                 375                 380                 385 gga ctg aac tcc tgc cag gat cag ggc tgc aac aaa ggc gcg ctg ggc    1259
Gly Leu Asn Ser Cys Gln Asp Gln Gly Cys Asn Lys Gly Ala Leu Gly
            390                 395                 400 atg gga tgg ggg tcc ggg gcg gtc aac tac ccg tac ttt gtc gcg ccg    1307
Met Gly Trp Gly Ser Gly Ala Val Asn Tyr Pro Tyr Phe Val Ala Pro
            405                 410                 415 tac gac gcg ctc aag gcc cgc gcc caa gag gac ggg acg acg gtc agc    1355
Tyr Asp Ala Leu Lys Ala Arg Ala Gln Glu Asp Gly Thr Thr Val Ser
            420                 425                 430 ctg cac aac tcg gac agc acg agc ggg gtg gcg aac gtg gcc tcg gac    1403
Leu His Asn Ser Asp Ser Thr Ser Gly Val Ala Asn Val Ala Ser Asp
435                 440                 445 gcg gac gcg gcc atc gtg gtc atc acg gcc gac tcg ggc gag ggt tac    1451
Ala Asp Ala Ala Ile Val Val Ile Thr Ala Asp Ser Gly Glu Gly Tyr
450                 455                 460                 465 atc aca gtc gaa ggc gcc ggg gac cgg ctg aac ctc gac ccg tgg         1499
Ile Thr Val Glu Gly Ala Ala Gly Asp Arg Leu Asn Leu Asp Pro Trp
                470                 475                 480 cac aac ggc aac gag ctg gta aag gcg gtg gcg gcg gcc aac aag aac    1547
His Asn Gly Asn Glu Leu Val Lys Ala Val Ala Ala Ala Asn Lys Asn
            485                 490                 495 acc atc gtc gtc gtg cac agc gtc ggg ccc atc atc ctc gag acc atc    1595
Thr Ile Val Val Val His Ser Val Gly Pro Ile Ile Leu Glu Thr Ile
500                 505                 510 ctg gca acc gaa ggg gtc aag gcg att gtg tgg gcc ggc ctg cca agc    1643
Leu Ala Thr Glu Gly Val Lys Ala Ile Val Trp Ala Gly Leu Pro Ser
515                 520                 525 cag gag aat ggt aac gcg ctg gtg gac atc ctg tac ggt ctg gcc tcg    1691
Gln Glu Asn Gly Asn Ala Leu Val Asp Ile Leu Tyr Gly Leu Ala Ser
530                 535                 540                 545 ccg tcg ggc aag ctg gtc tac acc atc gcc aag cga gaa cag gac tac    1739
Pro Ser Gly Lys Leu Val Tyr Thr Ile Ala Lys Arg Glu Gln Asp Tyr
            550                 555                 560 ggc act gcg gtc gtt cgc gga gac gac aca ttt ccg gag ggc ctg ttt    1787
Gly Thr Ala Val Val Arg Gly Asp Asp Thr Phe Pro Glu Gly Leu Phe
            565                 570                 575 gtc gac tac cgg cac ttt gac aag gag aac atc gag ccg cgg tac gag    1835
Val Asp Tyr Arg His Phe Asp Lys Glu Asn Ile Glu Pro Arg Tyr Glu
            580                 585                 590 ttt ggg ttt ggg ctg t gtaagttgtt ctctgtcata aagagtgtcc ccgtccactc  1891
Phe Gly Phe Gly Leu
595 cgccatcttt ttttttttt cagttttacc tcgtcctaac agcaagtgaa acaaactggc   1951 ag ca  tac acc aac ttc acg tac gcc gac ctc gaa ctc acc tcg acc    1997
   Ser Tyr Thr Asn Phe Thr Tyr Ala Asp Leu Glu Leu Thr Ser Thr
                600                 605                 610 gcc acg gcc ggc cca gcg acg ggc gag acc atc ccc ggc ggc gcg gcc   2045
Ala Thr Ala Gly Pro Ala Thr Gly Glu Thr Ile Pro Gly Gly Ala Ala
615                 620                 625 gac ctc tgg gag gag gtg gcc acg gtc acg gcg acc atc acc aac agc   2093
Asp Leu Trp Glu Glu Val Ala Thr Val Thr Ala Thr Ile Thr Asn Ser
```

-continued

```
Asp Leu Trp Glu Glu Val Ala Thr Val Thr Ala Thr Ile Thr Asn Ser
630                 635                 640                 645 ggc ggc gtg gac ggc gcc gag gtg gcc cag ctg tac ctg acg ttg ccg      2141
Gly Gly Val Asp Gly Ala Glu Val Ala Gln Leu Tyr Leu Thr Leu Pro
                650                 655                 660 tcg tcg gcg ccg gcg acc ccg ccc aag cag ctc cgc ggc ttc gcc aag      2189
Ser Ser Ala Pro Ala Thr Pro Pro Lys Gln Leu Arg Gly Phe Ala Lys
            665                 670                 675 ctc aag ctg gcg gcc ggc gcc agc ggg acc gcg acg ttt agt ctg cgc      2237
Leu Lys Leu Ala Ala Gly Ala Ser Gly Thr Ala Thr Phe Ser Leu Arg
        680                 685                 690 agg cgc gac ctc agc tac tgg gac acc ggc cgc ggg cag tgg gtg gtg      2285
Arg Arg Asp Leu Ser Tyr Trp Asp Thr Gly Arg Gly Gln Trp Val Val
    695                 700                 705 ccg gag ggc gag ttt ggc gtc tcg gtc ggg gcg agc tcg cgc gat atc      2333
Pro Glu Gly Glu Phe Gly Val Ser Val Gly Ala Ser Ser Arg Asp Ile
710                 715                 720                 725 cgg ctg acg ggg agc ttc cga gta tgaaaggaaa tatcctgggg cggatagttt     2387
Arg Leu Thr Gly Ser Phe Arg Val
                730 ctgcttcttc gatggagtga actatatata ggtgcgcccg gacgccagag atatggacaa    2447 taac                                                                 2451

<210> SEQ ID NO 92
<211> LENGTH: 733
<212> TYPE: PRT
<213> ORGANISM: Chrysosporium lucknowense

<400> SEQUENCE: 92

Met Thr Leu Gln Ala Phe Ala Leu Leu Ala Ala Ala Leu Val Arg
1               5                   10                  15

Gly Glu Thr Pro Thr Lys Val Pro Arg Asp Ala Pro Arg Gly Ala Ala
                20                  25                  30

Ala Trp Glu Ala Ala His Ser Ser Ala Ala Ala Ala Leu Gly Lys Leu
            35                  40                  45

Ser Gln Gln Asp Lys Ile Asn Ile Val Thr Gly Val Gly Trp Asn Lys
        50                  55                  60

Gly Pro Cys Val Gly Asn Thr Pro Ala Ile Ser Ser Ile Asn Tyr Pro
65                  70                  75                  80

Gln Leu Cys Leu Gln Asp Gly Pro Leu Gly Val Arg Phe Gly Ser Ser
                85                  90                  95

Ile Thr Ala Phe Thr Pro Gly Ile Gln Ala Ala Ser Thr Trp Asp Val
            100                 105                 110

Asp Leu Ile Arg Gln Arg Gly Glu Tyr Met Gly Ala Glu Phe Lys Gly
        115                 120                 125

Cys Gly Ile His Val Gln Leu Gly Pro Val Ala Gly Pro Leu Gly Lys
    130                 135                 140

Val Pro Gln Gly Gly Arg Asn Trp Glu Gly Phe Gly Val Asp Pro Tyr
145                 150                 155                 160

Leu Thr Gly Ile Ala Met Ala Glu Thr Ile Glu Gly Ile Gln Ser Ala
                165                 170                 175

Gly Val Gln Ala Thr Ala Lys His Tyr Ile Leu Asn Glu Gln Glu Leu
            180                 185                 190

Asn Arg Glu Thr Met Ser Ser Asn Val Asp Asp Arg Thr Leu His Glu
        195                 200                 205

Leu Tyr Leu Trp Pro Phe Ala Asp Ala Val His Ser Asn Val Ala Ser
    210                 215                 220
```

-continued

```
Val Met Cys Ser Tyr Asn Lys Ile Asn Gly Thr Trp Ala Cys Glu Asn
225                 230                 235                 240

Asp Arg Val Leu Asn Val Ile Leu Lys Gln Glu Leu Gly Phe Pro Gly
                245                 250                 255

Tyr Val Met Ser Asp Trp Asn Ala Gln His Ser Thr Asp Asp Ala Ala
            260                 265                 270

Asn His Gly Met Asp Met Thr Met Pro Gly Ser Asp Phe Asn Gly Gly
        275                 280                 285

Thr Ile Leu Trp Gly Pro Gln Leu Asp Ser Ala Val Asn Ser Gly Arg
290                 295                 300

Val Pro Lys Ser Arg Leu Asp Asp Met Val Glu Arg Ile Leu Ala Ala
305                 310                 315                 320

Trp Tyr Leu Leu Gly Gln Asp Ser Asn Tyr Pro Ala Ile Asn Ile Gly
                325                 330                 335

Ala Asn Val Gln Gly Asn His Lys Glu Asn Val Arg Ala Val Ala Arg
                340                 345                 350

Asp Gly Ile Val Leu Leu Lys Asn Asp Asp Gly Ile Leu Pro Leu Lys
            355                 360                 365

Lys Pro Ala Lys Leu Ala Leu Ile Gly Ser Ala Ala Val Val Asn Pro
        370                 375                 380

Gln Gly Leu Asn Ser Cys Gln Asp Gln Gly Cys Asn Lys Gly Ala Leu
385                 390                 395                 400

Gly Met Gly Trp Gly Ser Gly Ala Val Asn Tyr Pro Tyr Phe Val Ala
                405                 410                 415

Pro Tyr Asp Ala Leu Lys Ala Arg Ala Gln Glu Asp Gly Thr Thr Val
                420                 425                 430

Ser Leu His Asn Ser Asp Ser Thr Ser Gly Val Ala Asn Val Ala Ser
            435                 440                 445

Asp Ala Asp Ala Ala Ile Val Val Ile Thr Ala Asp Ser Gly Glu Gly
450                 455                 460

Tyr Ile Thr Val Glu Gly Ala Ala Gly Asp Arg Leu Asn Leu Asp Pro
465                 470                 475                 480

Trp His Asn Gly Asn Glu Leu Val Lys Ala Val Ala Ala Ala Asn Lys
                485                 490                 495

Asn Thr Ile Val Val His Ser Val Gly Pro Ile Ile Leu Glu Thr
            500                 505                 510

Ile Leu Ala Thr Glu Gly Val Lys Ala Ile Val Trp Ala Gly Leu Pro
        515                 520                 525

Ser Gln Glu Asn Gly Asn Ala Leu Val Asp Ile Leu Tyr Gly Leu Ala
530                 535                 540

Ser Pro Ser Gly Lys Leu Val Tyr Thr Ile Ala Lys Arg Glu Gln Asp
545                 550                 555                 560

Tyr Gly Thr Ala Val Arg Gly Asp Asp Thr Phe Pro Glu Gly Leu
                565                 570                 575

Phe Val Asp Tyr Arg His Phe Asp Lys Glu Asn Ile Glu Pro Arg Tyr
                580                 585                 590

Glu Phe Gly Phe Gly Leu Ser Tyr Thr Asn Phe Thr Tyr Ala Asp Leu
        595                 600                 605

Glu Leu Thr Ser Thr Ala Thr Ala Gly Pro Ala Thr Gly Glu Thr Ile
        610                 615                 620

Pro Gly Gly Ala Ala Asp Leu Trp Glu Val Ala Thr Val Thr Ala
625                 630                 635                 640

Thr Ile Thr Asn Ser Gly Gly Val Asp Gly Ala Glu Val Ala Gln Leu
```

```
                   645                 650                 655
Tyr Leu Thr Leu Pro Ser Ser Ala Pro Ala Thr Pro Pro Lys Gln Leu
            660                 665                 670

Arg Gly Phe Ala Lys Leu Lys Leu Ala Ala Gly Ala Ser Gly Thr Ala
            675                 680                 685

Thr Phe Ser Leu Arg Arg Arg Asp Leu Ser Tyr Trp Asp Thr Gly Arg
            690                 695                 700

Gly Gln Trp Val Val Pro Glu Gly Glu Phe Gly Val Ser Val Gly Ala
705                 710                 715                 720

Ser Ser Arg Asp Ile Arg Leu Thr Gly Ser Phe Arg Val
            725                 730

<210> SEQ ID NO 93
<211> LENGTH: 2199
<212> TYPE: DNA
<213> ORGANISM: Chrysosporium lucknowense

<400> SEQUENCE: 93
atgacccttc aagcctttgc gctgctggcg gcggcggccc ttgtacgggg cgagaccccg      60
accaaggtcc ctcgcgacgc tccgagagga gctgctgctt gggaagctgc ccactcctca     120
gcagccgctg ccttgggaaa gctgtcccag caggacaaga tcaacatcgt gacgggcgtc     180
ggctggaaca aggggccctg cgtgggcaat actcccgcta tcagctccat caactacccg     240
cagctctgcc tccaagacgg accctgggc gtccgcttcg gttccagcat caccgctttc     300
actccaggca ttcaggccgc gtcgacgtgg gatgtggacc tgatccgaca acgaggcgag     360
tacatgggcg ccgagttcaa ggggtgtggc atccacgtcc agctaggccc cgtggccggg     420
cccttgggta aggttccgca aggcggccgc aactgggagg ctttggcgt ggatccctac      480 ctcaccggca ttgccatggc cgagaccatc gagggatac agtcagcggg cgtgcaagcc      540
accgccaagc attacatcct caacgagcag gagctcaacc gcgagaccat gagcagcaat     600
gtcgacgacc gcaccttgca cgagctgtac ctctggcctt ttgcagacgc tgttcactct     660
aacgtggcca cgtcatgtg cagttacaac aagatcaacg gcacgtgggc gtgcgagaac      720
gaccgggtgc tgaacgtcat tctgaagcag gagcttgggt ttccgggcta tgtgatgagc     780
gactggaacg cgcagcactc gaccgacgac gcggccaacc acggcatgga catgacgatg     840
cccggcagcg acttcaacgg agggacgatc ctctggggcc cgcagctcga cagcgccgtc     900
aacagcggcc gggtgcccaa gtcccgcctc gacgacatgg tcgagcgcat cctcgcggcg     960
tggtaccttc tcggtcagga cagcaattac ccggctatca acatcggcgc caacgtacag    1020
ggcaaccaca aggagaacgt gcgggcggtc gcgcgcgatg gcatcgtgct cctcaagaac    1080
gacgacggca tcctcccgct caagaagccc gccaagctcg ccctcatcgg ttcggccgcc    1140
gtcgtcaacc gcagggact gaactcctgc caggatcagg ctgcaacaa aggcgcgctg      1200 ggcatgggat gggggtccgg ggcggtcaac tacccgtact tgtcgcgcc gtacgacgcg     1260 ctcaaggccc gcgccaaga ggacgggacg acggtcagcc tgcacaactc ggacagcacg     1320
agcggggtgg cgaacgtggc ctcggacgcg gacgcggcca tcgtggtcat cacggccgac    1380
tcgggcgagg gttacatcac agtcgaaggc gccgccgggg accggctgaa cctcgacccg    1440
tggcacaacg gcaacgagct ggtaaaggcg gtggcggcgg ccaacaagaa caccatcgtc    1500
gtcgtgcaca cgtcgggcc catcatcctc gagaccatcc tggcaaccga aggggtcaag    1560
gcgattgtgt gggccggcct gccaagccag gagaatggta acgcgctggt ggacatcctg    1620
tacggtctgg cctcgccgtc gggcaagctg gtctacacca tcgccaagcg agaacaggac    1680
```

```
tacggcactg cggtcgttcg cggagacgac acatttccgg agggcctgtt tgtcgactac    1740
cggcactttg acaaggagaa catcgagccg cggtacgagt ttgggtttgg gctgtcatac    1800
accaacttca cgtacgccga cctcgaactc acctcgaccg ccacggccgg cccagcgacg    1860
ggcgagacca tccccggcgg cgcggccgac ctctgggagg aggtggccac ggtcacggcg    1920
accatcacca cagcggcgg cgtggacggc gccgaggtgg cccagctgta cctgacgttg    1980
ccgtcgtcgg cgccggcgac cccgcccaag cagctccgcg gcttcgccaa gctcaagctg    2040
gcggccggcg ccagcgggac cgcgacgttt agtctgcgca ggcgcgacct cagctactgg    2100
gacaccggcc gcgggcagtg ggtggtgccg gagggcgagt ttggcgtctc ggtcggggcg    2160
agctcgcgcg atatccggct gacggggagc ttccgagta                           2199
```

<210> SEQ ID NO 94
<211> LENGTH: 389
<212> TYPE: PRT
<213> ORGANISM: Chrysosporium lucknowense

<400> SEQUENCE: 94

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285
```

-continued

```
Ser Gly Thr His Ala Glu Cys Val Ser Ser Asn Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Glu Val Trp Leu Gly
                340                 345                 350

Ala Leu Trp Trp Ala Ala Gly Pro Trp Trp Gly Asp Tyr Met Tyr Ser
            355                 360                 365

Phe Glu Pro Pro Ser Gly Thr Gly Tyr Val Asn Tyr Asn Ser Ile Leu
    370                 375                 380

Lys Lys Tyr Leu Pro
385
```

US 7,923,236 B2

FUNGAL ENZYMES

REFERENCE TO SEQUENCE LISTING

This application contains a Sequence Listing submitted as an electronic text file named "5671-5_ST25.txt", having a size in bytes of 366 kb, and created on 2 Aug. 2007. the information contained in this electronic file is hereby incorporated by reference in its entirety pursuant to 37 CFR §1.52 (e)(5).

FIELD OF THE INVENTION

This invention relates to novel enzymes and novel methods for producing the same. More specifically this invention relates to enzymes produced by fungi. The invention also relates to a method to convert lignocellulosic biomass to fermentable sugars with enzymes that degrade the lignocellulosic material and novel combinations of enzymes, including those that provide a synergistic release of sugars from plant biomass. The invention also relates to methods to use the novel enzymes and compositions of such enzymes in a variety of other processes, including washing of clothing, detergent processes, deinking and biobleaching of paper and pulp, and treatment of waste streams.

BACKGROUND OF THE INVENTION

Large amounts of carbohydrates in plant biomass provide a plentiful source of potential energy in the form of sugars (both five carbon and six carbon sugars) that can be utilized for numerous industrial and agricultural processes. However, the enormous energy potential of these carbohydrates is currently under-utilized because the sugars are locked in complex polymers, and hence are not readily accessible for fermentation. These complex polymers are often referred to collectively as lignocellulose. Sugars generated from degradation of plant biomass potentially represent plentiful, economically competitive feedstocks for fermentation into chemicals, plastics, and fuels, including ethanol as a substitute for petroleum.

For example, distillers' dried grains (DDG) are lignocellulosic byproducts of the corn dry milling process. Milled whole corn kernels are treated with amylases to liquefy the starch within the kernels and hydrolyze it to glucose. The glucose so produced is then fermented in a second step to ethanol. The residual solids after the ethanol fermentation and distillation are centrifuged and dried, and the resulting product is DDG, which is used as an animal feed stock. Although DDG composition can vary, a typical composition for DDG is: 32% hemicellulose, 22% cellulose, 30% protein, 10% lipids, 4% residual starch, and 4% inorganics. In theory, the cellulose and hemicellulose fractions, comprising about 54% of the weight of the DDG, can be efficiently hydrolyzed to fermentable sugars by enzymes; however, it has been found that the carbohydrates comprising lignocellulosic materials in DDG are more difficult to digest. To date, the efficiency of hydrolysis of these (hemi) cellulosic polymers by enzymes is much lower than the hydrolytic efficiency of starch, due to the more complex and recalcitrant nature of these substrates. Accordingly, the cost of producing the requisite enzymes is higher than the cost of producing amylases for starch hydrolysis.

Major polysaccharides comprising lignocellulosic materials include cellulose and hemicelluloses. The enzymatic hydrolysis of these polysaccharides to soluble sugars (and finally to monomers such as glucose, xylose and other hexoses and pentoses) is catalyzed by several enzymes acting in concert. For example, endo-1,4-β-glucanases (EGs) and exo-cellobiohydrolases (CBHs) catalyze the hydrolysis of insoluble cellulose to cellooligosachharides (with cellobiose the main product), while β-glucosidaes (BGLs) convert the oligosaccharides to glucose. Similarly, xylanases, together with other enzymes such as α-L-arabinofuranosidases, feruloyl and acetylxylan esterases and β-xylosidases, catalyze the hydrolysis of hemicelluloses.

Regardless of the type of cellulosic feedstock, the cost and hydrolytic efficiency of enzymes are major factors that restrict the widespread use of biomass bioconversion processes. The hydrolytic efficiency of a multi-enzyme complex in the process of lignocellulosic saccharification depends both on properties of the individual enzymes and the ratio of each enzyme within the complex.

Enzymes useful for the hydrolysis of complex polysaccharides are also highly useful in a variety of industrial textile applications, as well as industrial paper and pulp applications, and in the treatment of waste streams. For example, as an alternative to the use of pumice in the stone washing process, methods for treating cellulose-containing fabrics for clothing with hydrolytic enzymes, such as cellulases, are known to improve the softness or feel of such fabrics. Cellulases are also used in detergent compositions, either for the purpose of enhancing the cleaning ability of the composition or as a softening agent. Cellulases are also used in combination with polymeric agents in processes for providing a localized variation in the color density of fibers. Such enzymes can also be used for the saccharification of lignocellulosic biomass in waste streams, such as municipal solid waste, for biobleaching of wood pulp, and for deinking of recycled print paper. As with the hydrolysis of these polysaccharides in lignocellulosic materials for use as feedstocks described above, the cost and hydrolytic efficiency of the enzymes are major factors that control the use of enzymes in these processes.

Filamentous fungi are a source of cellulases and hemicellulases, as well as other enzymes useful in the enzymatic hydrolysis of major polysaccharides. In particular, strains of *Trichoderma* sp., such as *T. viride, T. reesei* and *T. longibrachiatum*, and *Penicillium* sp., and enzymes derived from these strains, have previously been used to hydrolyze crystalline cellulose. However, the costs associated with producing enzymes from these fungi, as well as the presence of additional, undesirable enzymes, remains a drawback. It is therefore desirable to produce inexpensive enzymes and enzyme mixtures that efficiently degrade cellulose and hemicellulose for use in a variety of agricultural and industrial applications.

SUMMARY OF THE INVENTION

The present invention provides isolated nucleic acid molecules comprising a nucleic acid sequence selected from the group consisting of:
  a) a nucleic acid sequence encoding a protein comprising an amino acid sequence selected from the group consisting of: SEQ ID NO:11, SEQ ID NO:23, SEQ ID NO:29, SEQ ID NO:32, SEQ ID NO:35, SEQ ID NO:38, SEQ ID NO:41, SEQ ID NO:44, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, and SEQ ID NO:94.
  b) a nucleic acid sequence encoding a fragment of the protein of (a), wherein the fragment has a biological activity of the protein of (a); and c) a nucleic acid sequence encoding an amino acid sequence that is at least 70% identical to an amino acid sequence of (a) and has a biological activity of the protein comprising the amino acid sequence.

In some embodiments, the nucleic acid sequence encodes an amino acid sequence that is at least 90%, at least 95%, at least 97%, or at least 99% identical to the amino acid sequence of (a) and has a biological activity of the protein comprising the amino acid sequence.

In some embodiments, the nucleic acid sequence encodes a protein comprising an amino acid sequence selected from the group consisting of: SEQ ID NO:1, SEQ ID NO:23, SEQ ID NO:29, SEQ ID NO:32, SEQ ID NO:35, SEQ ID NO:38, SEQ ID NO:41, SEQ ID NO:44, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, and SEQ ID NO:94.

In some embodiments, the nucleic acid sequence consists of a nucleic acid sequence selected from the group consisting of: SEQ ID NO:1, SEQ ID NO:3, SEQ ID NO:4, SEQ ID NO:6, SEQ ID NO:10, SEQ ID NO:12, SEQ ID NO:22, SEQ ID NO:24, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:41, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:70, SEQ ID NO:72, SEQ ID NO:73, SEQ ID NO:75, SEQ ID NO:76, SEQ ID NO:78, SEQ ID NO:79, SEQ ID NO:90, SEQ ID NO:91 and SEQ ID NO:93.

In some embodiments, the nucleic acid sequence encodes a protein comprising the amino acid sequence of SEQ ID NO:11, wherein the protein has cellobiohydrolase activity.

In some embodiments, the nucleic acid sequence encodes a protein comprising an amino acid sequence selected from the group consisting of: SEQ ID NO:94 and SEQ ID NO:23, wherein the protein has endoglucanase activity.

In some embodiments, the nucleic acid sequence encodes a protein comprising an amino acid sequence selected from the group consisting of: SEQ ID NO:29, SEQ ID NO:32, SEQ ID NO:35, SEQ ID NO:38 and SEQ ID NO:41, wherein the protein has xylanase activity.

In some embodiments, the nucleic acid sequence encodes a protein comprising an amino acid sequence of SEQ ID NO:44, wherein the protein has β-glucosidase activity.

In some embodiments, the nucleic acid sequence encodes a protein comprising an amino acid sequence selected from the group consisting of: SEQ ID NO:50, SEQ ID NO:53, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, and SEQ ID NO:92, wherein the protein has hemicellulase activity.

In some embodiments, the nucleic acid sequence encodes a protein comprising the amino acid sequence of SEQ ID NO:50, wherein the protein has glucoamylase activity.

In some embodiments, the nucleic acid sequence encodes a protein comprising the amino acid sequence of SEQ ID NO:53, wherein the protein has pectate lyase activity.

In some embodiments, the nucleic acid sequence encodes a protein comprising an amino acid sequence selected from the group consisting of: SEQ ID NO:56 and SEQ ID NO:59, wherein the protein has chitinase activity.

In some embodiments, the nucleic acid sequence encodes a protein comprising an amino acid sequence selected from the group consisting of: SEQ ID NO:62, SEQ ID NO:80, and SEQ ID NO:83, wherein the protein has acetylxylan esterase activity.

In some embodiments, the nucleic acid sequence encodes a protein comprising an amino acid sequence selected from the group consisting of: SEQ ID NO:65, SEQ ID NO:68, and SEQ ID NO:71, wherein the protein has ferulic acid esterase activity.

In some embodiments, the nucleic acid sequence encodes a protein comprising an amino acid sequence selected from the group consisting of: SEQ ID NO:74 and SEQ ID NO:77, wherein the protein has arabinofuranosidase activity.

In some embodiments, the nucleic acid sequence encodes a protein comprising the amino acid sequence of SEQ ID NO:86, wherein the protein has pectin methyl esterase activity.

In some embodiments, the nucleic acid sequence of (a) encodes a protein comprising the amino acid sequence of SEQ ID NO:89, wherein the protein has endo-arabinase activity.

In some embodiments, the nucleic acid sequence encodes a protein comprising the amino acid sequence of SEQ ID NO:92, wherein the protein has β-xylosidase or β-glucosidase activity.

In some embodiments, the nucleic acid sequence encoding a protein comprising an amino acid sequence selected from the group consisting of: SEQ ID NO:2 and SEQ ID NO:5.

In some embodiments, the nucleic acid sequence is fully complementary to any of the nucleic acid sequences described above.

The invention also provides a protein comprising an amino acid sequence encoded by the nucleic acid molecules of the present invention.

In some embodiments, the protein comprises an amino acid sequence selected from the group consisting of: SEQ ID NO:11, SEQ ID NO:23, SEQ ID NO:29, SEQ ID NO:32, SEQ ID NO:35, SEQ ID NO:38, SEQ ID NO:41, SEQ ID NO:44, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, and SEQ ID NO:94.

In some embodiments, the protein comprises an amino acid sequence selected from SEQ ID NO:56 and SEQ ID NO:59, wherein the protein has chitinase activity.

The invention also provides an isolated fusion protein comprising an isolated protein of the present invention fused to a protein comprising an amino acid sequence that is heterologous to the isolated protein of the present invention.

The invention also provides an isolated antibody or antigen binding fragment thereof that selectively binds to a protein of the present invention.

The invention also provides a kit for degrading a lignocellulosic material to fermentable sugars comprising at least one isolated protein of the present invention.

The invention also provides a detergent comprising at least one isolated protein of the present invention The invention also provides a composition for the degradation of a lignocellulosic material comprising at least one isolated protein of the present invention.

The invention also provides a recombinant nucleic acid molecule comprising an isolated nucleic acid molecule of the present invention, operatively linked to at least one expression control sequence.

In some embodiments, the recombinant nucleic acid molecule comprises an expression vector. In some embodiments, the recombinant nucleic acid molecule comprises a targeting vector.

The invention also provides an isolated host cell transfected with a nucleic acid molecule of the present invention.

In some embodiments, the host cell is a fungus. In some embodiments, the host cell is a filamentous fungus. In some embodiments, the filamentous fungus is from a genus selected from the group consisting of: *Chrysosporium, Thielavia, Neurospora, Aureobasidium, Filibasidium, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola*, and *Trichoderma*, and anamorphs and teleomorphs thereof. In some embodiments, the host cell is a bacterium.

The invention also provides an oligonucleotide consisting essentially of at least 12 consecutive nucleotides of a nucleic acid sequence selected from the group consisting of: SEQ ID NO:1, SEQ ID NO:3, SEQ ID NO:4, SEQ ID NO:6, SEQ ID NO:10, SEQ ID NO:12, SEQ ID NO:22, SEQ ID NO:24, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:41, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:70, SEQ ID NO:72, SEQ ID NO:73, SEQ ID NO:75, SEQ ID NO:76, SEQ ID NO:78, SEQ ID NO:79, SEQ ID NO:90, SEQ ID NO:91, and SEQ ID NO:93, or the complement thereof.

The invention also provides a kit comprising at least one oligonucleotide of the present invention.

The invention also provides a method for producing a protein of the present invention, comprising culturing a cell that has been transfected with a nucleic acid molecule comprising a nucleic acid sequence encoding the protein, and expressing the protein with the transfected cell.

In some embodiments, the method further comprises recovering the protein from the cell or from a culture comprising the cell.

The invention also provides a genetically modified organism comprising components suitable for degrading a lignocellulosic material to fermentable sugars, wherein the organism has been genetically modified to express at least one protein of the present invention.

In some embodiments, the genetically modified organism is a microorganism. In some embodiments, the microorganism is a filamentous fungus.

In some embodiments, the filamentous fungus is from a genus selected from the group consisting of: *Chrysosporium, Thielavia, Neurospora, Aureobasidium, Filibasidium, Piromyces, Corynascus, Cryptococcus, Acremonium, Tolypocladium, Scytalidium, Schizophyllum, Sporotrichum, Penicillium, Talaromyces, Gibberella, Myceliophthora, Mucor, Aspergillus, Fusarium, Humicola*, and *Trichoderma*.

In some embodiments, the filamentous fungus is selected from the group consisting of: *Trichoderma reesei, Chrysosporium lucknowense, Aspergillus japonicus, Penicillium canescens, Penicillium solitum, Penicillium funiculosum*, and *Talaromyces flavus*.

In some embodiments, the organism has been genetically modified to express at least one additional enzyme.

In some embodiments, the additional enzyme is an accessory enzyme selected from the group consisting of: cellulase, xylanase, ligninase, glucuronidase, arabinofuranosidase, arabinogalactanase, ferulic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase.

In some embodiments, the genetically modified organism is a plant.

The invention also provides a recombinant enzyme isolated from a genetically modified microorganism of the present invention.

In some embodiments, the enzyme has been subjected to a purification step.

The invention also provides a crude fermentation product produced by culturing the comprising a genetically modified microorganism of the present invention, wherein the crude fermentation product contains at least one protein of the present invention.

The invention also provides a multi-enzyme composition comprising enzymes produced by a genetically modified organism of the present invention and recovered therefrom.

The invention also provides a multi-enzyme composition comprising at least one protein of the present invention and at least one additional protein for degrading a lignocellulosic material or a fragment thereof that has biological activity.

In some embodiments, the at least one additional protein for degrading a lignocellulosic material to fermentable sugars is selected from the group consisting of: SEQ ID NO:8, SEQ ID NO:14, SEQ ID NO:17, SEQ ID NO:20, SEQ ID NO:26 and SEQ ID NO:47, or a fragment thereof that has biological activity.

In some embodiments, the multi-enzyme composition comprises at least one cellobiohydrolase, at least one xylanase, at least one endoglucanase, at least one β-glucosidase, at least one β-xylosidase, and at least one accessory enzyme.

In some embodiments, between about 50% and about 70% of the enzymes in the composition are cellobiohydrolases.

In some embodiments, between about 10% and about 30% of the enzymes in the composition are xylanases.

In some embodiments, between about 5% and about 15% of the enzymes in the composition are endoglucanases.

In some embodiments, between about 1% and about 5% of the enzymes in the composition are β-glucosidases.

In some embodiments, between about 1% and about 3% of the enzymes in the composition are β-xylosidases.

In some embodiments, the composition comprises about 60% cellobiohydrolases, about 20% xylanases, about 10% endoglucanases, about 3% β-glucosidases, about 2% β-xylosidases, and about 5% accessory enzymes.

In some embodiments, the xylanases are selected from the group consisting of: endoxylanases, exoxylanases, and β-xylosidases.

In some embodiments, the accessory enzymes include an enzyme selected from the group consisting of: ligninase, glucuronidase, arabinofuranosidase, arabinogalactanase, furilic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase.

In some embodiments, the composition comprises at least one protein comprising the amino acid sequence of SEQ ID NO:11, wherein the protein has cellobiohydrolase activity, at least one protein comprising an amino acid sequence selected from the group consisting of: SEQ ID NO:94 and SEQ ID NO:23, wherein the protein has endoglucanase activity, at least one protein comprising an amino acid sequence selected from the group consisting of: SEQ ID NO:29, SEQ ID NO:32, SEQ ID NO:35, SEQ ID NO:38 and SEQ ID NO:41, wherein the protein has xylanase activity, at least one protein comprising an amino acid sequence of SEQ ID NO:44, wherein the protein has β-glucosidase activity, and at least one protein comprising an amino acid sequence selected from the group consisting of: SEQ ID NO:50, SEQ ID NO:53, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, and SEQ ID NO:92, wherein the protein has hemicellulase activity.

In some embodiments, the composition comprises at least one first protein comprising an amino acid sequence that is at least 95% identical to an amino acid sequence selected from the group consisting of: SEQ ID NO:2, SEQ ID NO:5, SEQ ID NO:8 and SEQ ID NO:11 and has cellobiohydrolase activity, or a fragment thereof that has cellobiohydrolase activity; at least one second protein comprising an amino acid sequence that is at least 95% identical to an amino acid sequence selected from the group consisting of: SEQ ID NO:14, SEQ ID NO:94, SEQ ID NO:17, SEQ ID NO:20 and SEQ ID NO:23 and has endoglucanase activity, or a fragment thereof that has endoglucanase activity; and at least one third protein comprising an amino acid sequence that is at least 95% identical to an amino acid sequence selected from the group consisting of: SEQ ID NO:26, SEQ ID NO:29, SEQ ID NO:32, SEQ ID NO:35, SEQ ID NO:38 and SEQ ID NO:41 and has xylanase activity, or a fragment thereof that has xylanase activity.

In some embodiments, the composition further comprises a fourth protein comprising an amino acid sequence that is at least 95% identical to SEQ ID NO:44 and has β-glucosidase activity, or a fragment thereof that has β-glucosidase activity.

In some embodiments, the composition further comprises at least one fifth protein comprising an amino acid sequence that is at least 95% identical to an amino acid sequence selected from the group consisting of: SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, and SEQ ID NO:92, and has hemicellulase or chitinase activity, or a fragment thereof that has hemicellulase or chitinase activity The invention also provides a multi-enzyme composition comprising a first protein comprising an amino acid sequence that is at least 95% identical to SEQ ID NO:2 and has cellobiohydrolase activity, or a fragment thereof that has cellobiohydrolase activity; a second protein comprising an amino acid sequence that is at least 95% identical to SEQ ID NO:8 and has cellobiohydrolase activity, or a fragment thereof that has cellobiohydrolase activity; a third protein comprising an amino acid sequence that is at least 95% identical to SEQ ID NO:94 and has endoglucanase activity, or a fragment thereof that has endoglucanase activity; a fourth protein comprising an amino acid sequence that is at least 95% identical to SEQ ID NO:29 and has xylanase activity, or a fragment thereof that has xylanase activity; and a fifth protein comprising an amino acid sequence that is at least 95% identical to SEQ ID NO:44 and has β-glucosidase activity, or a fragment thereof that has β-glucosidase activity.

In some embodiments, the multi-enzyme composition further comprises a sixth protein that has β-xylosidase activity, or a fragment thereof that has β-xylosidase activity.

In some embodiments, the multi-enzyme composition further comprises one or more proteins selected from the group consisting of:

a) a protein comprising an amino acid sequence that is at least 95% identical to SEQ ID NO:5 and has cellobiohydrolase activity, or a fragment thereof that has cellobiohydrolase activity;

b) a protein comprising an amino acid sequence that is at least 95% identical to SEQ ID NO:20 and has endoglucanase activity, or a fragment thereof that has endoglucanase activity;

c) a protein comprising an amino acid sequence that is at least 95% identical to SEQ ID NO:26 and has xylanase activity, or a fragment thereof that has xylanase activity; and d) a protein comprising an amino acid sequence that is at least 95% identical to SEQ ID NO:47 and has arabinogalactanase activity, or a fragment thereof that has arabinogalactanase activity.

In some embodiments, the multi-enzyme composition comprises at least one hemicellulase.

In some embodiments, the hemicellulase is selected from the group consisting of a xylanase, an arabinofuranosidase, an acetyl xylan esterase, a glucuronidase, and endo-galactanase, a mannanase, an endo arabinase, an exo arabinase, an exo-galactanase, a ferulic acid esterase, a galactomannanase, a xylogluconase, and mixtures thereof.

In some embodiments, the xylanase is selected from the group consisting of endoxylanases, exoxylanase, and β-xylosidase.

In some embodiments, the multi-enzyme composition comprises at least one cellulase.

In some embodiments, the composition is a crude fermentation product.

In some embodiments, the composition is a crude fermentation product that has been subjected to a purification step.

In some embodiments, the multi-enzyme composition further comprises one or more accessory enzymes.

In some embodiments, the accessory enzyme includes at least one enzyme selected from the group consisting of: cellulase, xylanase, ligninase, glucuronidase, arabinofuranosidase, arabinogalactanase, furilic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase.

In some embodiments, the accessory enzyme is selected from the group consisting of a glucoamylase, a pectinase, and a ligninase.

In some embodiments, the accessory enzyme is a glucoamylase.

In some embodiments, the accessory enzyme is added as a crude or a semi-purified enzyme mixture.

In some embodiments, the accessory enzyme is produced by culturing at least one organism on a substrate to produce the enzyme.

The invention also provides a method for degrading a lignocellulosic material to fermentable sugars, comprising contacting the lignocellulosic material with at least one isolated protein of the present invention.

In some embodiments, the isolated protein is part of a multi-enzyme composition.

The invention also provides a method for degrading a lignocellulosic material to fermentable sugars, comprising contacting the lignocellulosic material with at least one multi-enzyme composition of the present invention.

The invention also provides a method for producing an organic substance, comprising:

a) saccharifying a lignocellulosic material with a multi-enzyme composition of the present invention;

b) fermenting the saccharified lignocellulosic material obtained with one or more fermentating microoganisms; and c) recovering the organic substance from the fermentation.

In some embodiments, the steps of saccharifying and fermenting are performed simultaneously.

In some embodiments, the organic substance is an alcohol, organic acid, ketone, amino acid, or gas.

In some embodiments, the organic substance is an alcohol. In some embodiments, the alcohol is ethanol.

In some embodiments, the lignocellulosic material is selected from the group consisting of consisting of herbaceous material, agricultural residue, forestry residue, municipal solid waste, waste paper, and pulp and paper mill residue.

In some embodiments, the lignocellulosic material is distiller's dried grains or distiller's dried grains with solubles.

In some embodiments, the distiller's dried grains or distiller's dried grains with solubles is derived from corn.

The invention also provides a method for degrading a lignocellulosic material consisting of distiller's dried grains or distiller's dried grains with solubles to sugars, the method comprising contacting the distiller's dried grains or distiller's dried grains with solubles with a multi-enzyme composition, whereby at least 10% of the fermentable sugars are liberated, wherein the multi-enzyme composition is the multi-enzyme composition of the present invention.

In some embodiments, at least 15% of the sugars are liberated. In some embodiments, at least 20% of the sugars are liberated. In some embodiments, at least 23% of the sugars are liberated.

In some embodiments, the distiller's dried grains or distiller's dried grains with solubles is derived from corn.

In some embodiments, the method further comprises a pretreatment process for pretreating the lignocellulosic material.

In some embodiments, the pretreatment process is selected from the group consisting of physical treatment, metal ion, ultraviolet light, ozone, organosolv treatment, steam explosion treatment, lime impregnation with steam explosion treatment, hydrogen peroxide treatment, hydrogen peroxide/ozone (peroxone) treatment, acid treatment, dilute acid treatment, and base treatment.

In some embodiments, the pretreatment process is selected from the group consisting of organosolv, steam explosion, heat treatment and AFEX.

In some embodiments, the heat treatment comprises heating the lignocellulosic material to 121° C. for 15 minutes.

In some embodiments, the method further comprises detoxifying the lignocellulosic material.

In some embodiments, the method further comprises recovering the fermentable sugar.

In some embodiments, the sugar is selected from the group consisting of glucose, xylose, arabinose, galactose, mannose, rhamnose, sucrose and fructose.

In some embodiments, the method further comprises recovering the contacted lignocellulosic material after the fermentable sugars are degraded.

The invention also provides a feed additive comprising a recovered lignocellulosic material.

In some embodiments, the protein content of the recovered lignocellulosic material is higher than that of the starting lignocellulosic material.

The invention also provides a method of improving the performance of an animal which comprises administering to the animal a feed additive of the present invention.

The invention also provides a method for improving the nutritional quality of an animal feed comprising adding a feed additive of the present invention to an animal feed.

The invention also provides a method for stonewashing a fabric, comprising contacting the fabric with at least one isolated protein of the present invention.

The invention also provides a method for stonewashing a fabric, comprising contacting the fabric with at least one multi-enzyme composition of the present invention.

In some embodiments, the fabric is denim.

The invention also provides a method for enhanching the softness or feel of a fabric or depilling a fabric, comprising contacting the fabric with at least one isolated protein of the present invention or a fragment thereof comprising a cellulose binding domain (CBD) of the protein.

The invention also provides a method for enhanching the softness or feel of a fabric or depilling a fabric, comprising contacting the fabric with at least one multi-enzyme composition of the present invention.

The invention also provides a method for restoring color to or brightening a fabric, comprising contacting the fabric with at least one isolated protein of the present invention.

The invention also provides a method for restoring color to or brightening a fabric, comprising contacting the fabric with at least one multi-enzyme composition of the present invention.

The invention also provides a method of biopolishing, defibrillating, bleaching, dyeing or desizing a fabric, comprising contacting the fabric with at least one isolated protein of the present invention.

The invention also provides a method of biopolishing, defibrillating, bleaching, dyeing or desizing a fabric, comprising contacting the fabric with at least one multi-enzyme composition of the present invention.

The invention also provides a method of deinking or biobleaching paper or pulp, comprising contacting the paper or pulp with at least one isolated protein of the present invention.

The invention also provides a method of deinking or biobleaching paper or pulp, comprising contacting the paper or pulp with at least one multi-enzyme composition of the present invention.

The invention also provides a method for enhancing the cleaning ability of a detergent composition, comprising adding at least one isolated protein of the present invention to the detergent composition.

The invention also provides a method for enhancing the cleaning ability of a detergent composition, comprising adding at least one multi-enzyme composition of the present invention to the detergent composition.

The invention also provides a detergent composition, comprising at least one isolated protein of the present invention and at least one surfactant.

The invention also provides a detergent composition, comprising at least one multi-enzyme composition of the present invention and at least one surfactant.

The invention also provides a method for inhibiting or reducing fungal growth, comprising contacting a fungus or an area susceptible to fungal growth with at least one isolated protein comprising an amino acid sequence selected from the group consisting of: SEQ ID NO:56 and SEQ ID NO:59, wherein the protein has chitinase activity.

The invention also provides a method for reducing or preventing insect infestation on a plant, comprising contacting the plant with at least one isolated protein comprising an amino acid sequence selected from the group consisting of: SEQ ID NO:56 and SEQ ID NO:59, wherein the protein has chitinase activity.

The invention also provides a method for reducing or preventing allergic inflammation or asthma, comprising administering at least one isolated protein comprising an amino acid sequence selected from the group consisting of: SEQ ID NO:56 and SEQ ID NO:59, wherein the protein has chitinase activity.

The invention also provides a lysing enzyme for the generation of protoplasts from fungi, comprising at least one isolated protein comprising an amino acid sequence selected from the group consisting of: SEQ ID NO:56 and SEQ ID NO:59, wherein the protein has chitinase activity.

The invention also provides an insecticide composition, comprising at least one isolated protein comprising an amino acid sequence selected from the group consisting of: SEQ ID NO:56 and SEQ ID NO:59, wherein the protein has chitinase activity.

BRIEF DESCRIPTION OF THE FIGURES

In FIG. 22A, the following numbers represent the indicated structure: 1: glass vessel, 2: plastic tube, 3: denim swatch, 4: rubber ring, 5: buckshot balls, and 6: teflon disk. In FIG. 22B, the following numbers represent the indicated structure: 1: lid with a thread inside, 2: rubber ring, 3: cell body (stainless steel), 4: cylindrical cartridge, 5: stainless steel cylinders, 6: circular denim swatch.

DETAILED DESCRIPTION OF THE INVENTION

Figure 1:
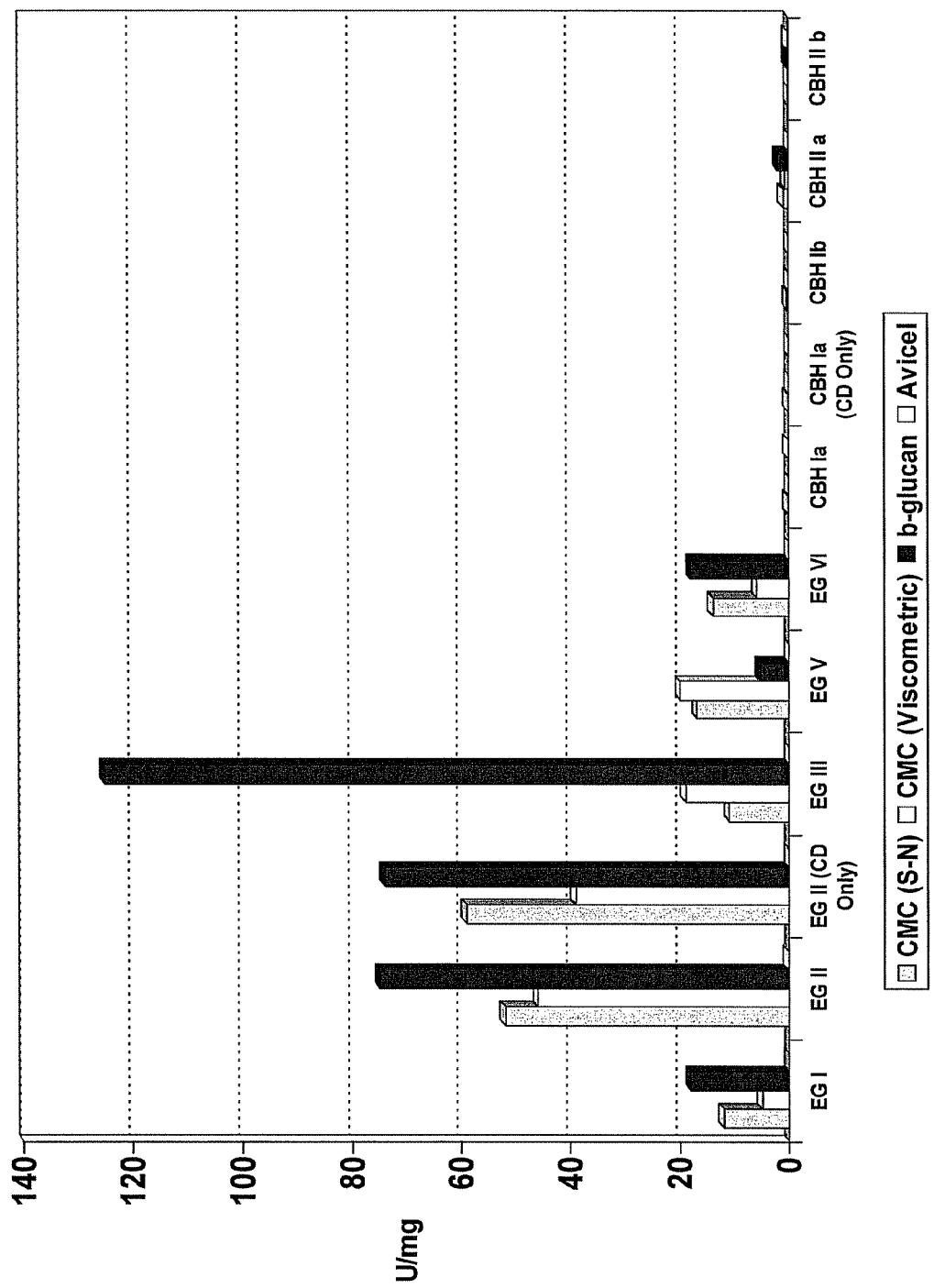
FIG. 1 shows the specific activity of cellobiohydrolases and endoglucanases of the present invention toward the indicated substrates. Specific activites (Units/mg) were determined at pH 5.0 and 50° C.

The present invention relates generally to proteins that play a role in the degradation of cellulose and hemicellulose and nucleic acids encoding the same. In particular, the present invention relates to enzymes isolated from a filamentous fungal strain denoted herein as C1 (Accession No. VKM F-3500-D), nucleic acids encoding the enzymes, and methods of producing and using the enzymes. The invention also provides compositions that include at least one of the enzymes described herein for uses including, but not limited to, the hydrolysis of lignocellulose. The invention stems, in part, from the discovery of a variety of novel cellulases and hemicellulases produced by the C1 fungus that exhibit high activity toward cellulose and other components of biomass.

The present invention also provides methods and compositions for the conversion of plant biomass to fermentable sugars that can be converted to useful products. The methods include methods for degrading lignocellulosic material using enzyme mixtures to liberate sugars. The compositions of the invention include enzyme combinations that break down lignocellulose. As used herein the terms "biomass" or "lignocellulosic material" includes materials containing cellulose and/or hemicellulose. Generally, these materials also contain xylan, lignin, protein, and carbohydrates, such as starch and sugar. Lignocellulose is generally found, for example, in the stems, leaves, hulls, husks, and cobs of plants or leaves, branches, and wood of trees. The process of converting a complex carbohydrate (such as starch or cellulose) into fermentable sugars is also referred to herein as "saccharification." Fermentable sugars, as used herein, refers to simple sugars, such as glucose, xylose, arabinose, galactose, mannose, rhamnose, sucrose and fructose.

Biomass can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn kernel including fiber from kernels, products and by-products from milling of grains such as corn, wheat and barley (including wet milling and dry milling) as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof.

Biomass high in starch, sugar, or protein such as corn, grains, fruits and vegetables are usually consumed as food. Conversely, biomass high in cellulose, hemicellulose and lignin are not readily digestible and are primarily utilized for wood and paper products, animal feed, fuel, or are typically disposed. Generally, the substrate is of high lignocellulose content, including distillers' dried grains corn stover, corn cobs, rice straw, hay, sugarcane bagasse, and other agricultural biomass, switchgrass, forestry wastes, poplar wood chips, pine wood chips, sawdust, yard waste, and the like, including any combination of substrate.

In one embodiment, the lignocellulosic material is distillers' dried grains (DDG). DDG (also known as dried distiller's grain, or distiller's spent grain) is spent, dried grains recovered after alcohol fermentation. The lignocellulosic material can also be distiller's dried grain with soluble material recycled back (DDGS). While reference will be made herein to DDG for convenience and simplicity, it should be understood that both DDG and DDGS are contemplated as desired lignocellulosic materials. These are largely considered to be waste products and can be obtained after the fermentation of the starch derived from any of a number of grains, including corn, wheat, barley, oats, rice and rye. In one embodiment the DDG is derived from corn.

It should be noted that the distiller's grains do not necessarily have to be dried. Although the grains normally, currently dried, water and enzymes are added to the DDG substrate in the present invention. If the saccharification were done on site, the drying step could be eliminated and enzymes could be added to the distiller's grains without drying.

Due in part to the many components that comprise biomass and lignocellulosic materials, enzymes or a mixture of enzymes capable of degrading xylan, lignin, protein, and carbohydrates are needed to achieve saccharification. The present invention includes enzymes or compositions thereof with, for example, cellobiohydrolase, endoglucanase, xylanase, β-glucosidase, hemicellulase and chitinase activities.

The enzymes of the present invention may also be used for stone washing cellulosic fabrics such as cotton (e.g., denim), linen, hemp, ramie, cupro, lyocell, newcell, rayon and the like. See, for example, U.S. Pat. No. 6,015,707. The enzymes and compositions of the present invention are suitable for industrial textile applications in addition to the stone washing process. For example, cellulases are used in detergent compositions, either for the purpose of enhancing the cleaning ability of the composition or as a softening agent. When so used, the cellulase will degrade a portion of the cellulosic material, e.g., cotton fabric, in the wash, which facilitates the cleaning and/or softening of the fabric. The endoglucanase components of fungal cellulases have also been used for the purposes of enhancing the cleaning ability of detergent compositions, for use as a softening agent, and for use in improving the feel of cotton fabrics, and the like. Enzymes and compositions of the present invention may also be used in the treatment of paper pulp (e.g., for improving the drainage or for de-inking of recycled paper) or for the treatment of wastewater streams (e.g., to hydrolyze waste material containing cellulose, hemicellulose and pectins to soluble lower molecular weight polymers).

In one aspect, the present invention includes proteins isolated from, or derived from the knowledge of enzymes from, a fungus such as C. lucknowense or a mutant or other derivative thereof, and more particularly, from the fungal strain denoted herein as C1 (Accession No. VKM F-3500-D). Preferably, the proteins of the invention possess enzymatic activity. As described in U.S. Pat. Nos. 6,015,707 or 6,573,086, each of which is incorporated herein by reference for all purposes, a strain called C1 (Accession No. VKM F-3500-D), was isolated from samples of forest alkaline soil from Sola Lake, Far East of the Russian Federation. This strain was deposited at the All-Russian Collection of Microorganisms of Russian Academy of Sciences (VKM), Bakhurhina St. 8, Moscow, Russia, 113184, under the terms of the Budapest Treaty on the International Regulation of the Deposit of Microorganisms for the Purposes of Patent Procedure on Aug. 29, 1996, as *Chrysosporium lucknowense* Garg 27K, VKM-F 3500 D. Various mutant strains of *C. lucknowense* C1 have been produced and these strains have also been deposited at the All-Russian Collection of Microorganisms of Russian Academy of Sciences (VKM), Bakhurhina St. 8, Moscow, Russia, 113184, under the terms of the Budapest Treaty on the International Regulation of the Deposit of Microorganisms for the Purposes of Patent Procedure on Sep. 2, 1998. For example, Strain C1 was mutagenised by subjecting it to ultraviolet light to generate strain UV13-6 (Accession No. VKM F-3632 D). This strain was subsequently further mutated with N-methyl-N'-nitro-N-nitrosoguanidine to generate strain NG7C-19 (Accession No. VKM F-3633 D). This latter strain in turn was subjected to mutation by ultraviolet light, resulting in strain UV18-25 (VKM F-3631 D). Strain C1 was classified as a *Chrysosporium lucknowense* based on morphological and growth characteristics of the microorganism, as discussed in detail in U.S. Pat. Nos. 6,015,707 and 6,573,086.

In certain embodiments of the present invention, a protein of the invention comprises, consists essentially of, or consists of an amino acid sequence selected from: SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, or SEQ ID NO:94. The present invention also includes homologues of any of the above sequences, including fragments and sequences having a given identity to any of the above sequences, wherein the homologue or fragment has at least one biological activity of the wild-type protein, as described herein.

In general, the proteins disclosed herein possess carbohydrase enzymatic activity, or the ability to degrade carbohydrate-containing materials. More specifically, the proteins may possess cellulase activity such as endoglucanase activity (e.g., 1,4-β-D-glucan-4-glucanohydrolases), exoglucanase activity (e.g., 1,4-β-D-glucan cellobiohydrolases), and β-glucosidase activity. The proteins may possess hemicellulase activity such as endoxylanase activity, exoxylanase activity, or β-xylosidase activity. The proteins may possess laminarinase, xyloglucanase, galactanase, glucoamylase, pectate lyase, chitinase, exo-β-D-glucosaminidase, cellobiose dehydrogenase, acetylxylan esterase, ligninase, amylase, glucuronidase, ferulic acid esterase, arabinofuranosidase, pectin methyl esterase, arabinase, lipase, glucosidase or glucomannanase activities. Physical properties, biochemical characteristics and substrate specificities of proteins of the present invention are illustrated below.

As used herein, "carbohydrase" refers to any protein that catalyzes the hydrolysis of carbohydrates, "Glycoside hydrolase" or "glycosidase" refers to a protein that catalyzes the hydrolysis of the glycosidic bonds between carbohydrates or between a carbohydrate and a non-carbohydrate residue. Endoglucanases, cellobiohydrolases, β-glucosidases, α-glucosidases, xylanases, β-xylosidases, galactanases, α-galactosidases, β-galactosidases, α-amylases, glucoamylases, endo-arabinases, arabinofuranosidases, mannanases, β-mannosidases, pectinases, acetyl xylan esterases, acetyl mannan esterases, ferulic acid esterases, coumaric acid esterases, pectin methyl esterases, and chitinases are examples of glycosidases.

"Cellulase" refers to a protein that catalyzes the hydrolysis of 1,4-β-D-glycosidic linkages in cellulose (such as bacterial cellulose, cotton, filter paper, phosphoric acid swollen cellulose, Avicel); cellulose derivatives (such as carboxymethylcellulose and hydroxyethylcellulose); plant lignocellulosic materials, beta-D-glucans or xyloglucans. Cellulose is a linear beta-(1-4) glucan consisting of anhydrocellobiose units. Endoglucanases, cellobiohydrolases, and β-glucosidases are examples of cellulases. "Endoglucanase" refers to a protein that catalyzes the hydrolysis of cellulose to oligosaccharide chains at random locations by means of an endoglucanase activity. "Cellobiohydrolase" refers to a protein that catalyzes the hydrolysis of cellulose to cellobiose via an exoglucanase activity, sequentially releasing molecules of cellobiose from the reducing or non-reducing ends of cellulose or cellooligosaccharides. "β-glucosidase" refers to an enzyme that catalyzes the conversion of cellobiose and oligosaccharides to glucose.

"Hemicellulase" refers to a protein that catalyzes the hydrolysis of hemicellulose, such as that found in lignocellulosic materials. Hemicellulose is a complex polymer, and its composition often varies widely from organism to organism, and from one tissue type to another. Hemicelluloses include a variety of compounds, such as xylans, arabinoxylans, xyloglucans, mannans, glucomannans, and galactomannans. Hemicellulose can also contain glucan, which is a general term for beta-linked glucose residues. In general, a main component of hemicellulose is beta-1,4-linked xylose, a five carbon sugar. However, this xylose is often branched as beta-1,3 linkages or beta-1,2 linkages, and can be substituted with linkages to arabinose, galactose, mannose, glucuronic acid, or by esterification to acetic acid. The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-beta-linked glucose chains with 1,6-alpha-linked xylosyl side chains. In monocots, including most grain crops, the principal components of hemicellulose are heteroxylans. These are primarily comprised of 1,4-beta-linked xylose backbone polymers with 1,2- or 1,3-beta linkages to arabinose, galactose and mannose as well as xylose modified by ester-linked acetic acids. Also present are branched beta glucans comprised of 1,3- and 1,4-beta-linked glucosyl chains. In monocots, cellulose, heteroxylans and beta glucans are present in roughly equal amounts, each comprising about 15-25% of the dry matter of cell walls. Hemicellulolytic enzymes, i.e. hemicellulases, include both endo-acting and exo-acting enzymes, such as xylanases, β-xylosidases. galactanases, α-galactosidases, β-galactosidases, endo-arabinases, arabinofuranosidases, mannanases, β-mannosidases. Hemicellulases also include the accessory enzymes, such as acetylesterases, ferulic acid esterases, and coumaric acid esterases. Among these, xylanases and acetyl xylan esterases cleave the xylan and acetyl side chains of xylan and the remaining xylo-oligomers are unsubstituted and can thus be hydrolysed with β-xylosidase only. In addition, several less known side activities have been found in enzyme preparations which hydrolyze hemicellulose. Accordingly, xylanases, acetylesterases and β-xylosidases are examples of hemicellulases.

"Xylanase" specifically refers to an enzyme that hydrolyzes the β-1,4 bond in the xylan backbone, producing short xylooligosaccharides.

β-Mannanases hydrolyze mannan-based hemicelluloses (mannan, glucomannan, galactomannan) and produce short β-1,4-mannooligosaccharides.

"Galactanase" or "arabinogalactan endo-1,4-β-galactosidase" refers to a protein that catalyzes the hydrolysis of endo-1,4-β-D-galactosidic linkages in arabinogalactans.

"Glucoamylase" refers to a protein that catalyzes the hydrolysis of terminal 1,4-linked β-D-glucose residues successively from non-reducing ends of the chains with the release of β-D-glucose.

"Chitinase" or "exo-β-D-chitinase" refers to a protein that catalyzes the hydrolysis of N-acetyl-β-D-glucosaminide 1,4-β-linkages in chitin and chitodextrins.

"α-L-arabinofuranosidase" or "arabinofuranosidase" refers to a protein that hydrolyzes arabinofuranosyl-containing hemicelluloses. Some of these enzymes remove arabinofuranoside residues from O-2 and/or O-3 single substituted xylose residues, as well as from O-2 and O-3 doubly substituted xylose residues "Endo-arabinase" refers to a protein that catalyzes the hydrolysis of 1,5-α-arabinofuranosidic linkages in 1,5-arabinans.

"β-xylosidase" refers to a protein that hydrolyzes short 1,4-β-D-xylooligomers into xylose.

"Acetyl xylan esterase" refers to a protein that catalyzes the removal of the acetyl groups from xylose residues. "Acetyl mannan esterase" refers to a protein that catalyzes the removal of the acetyl groups from mannose residues. "Feruloyl esterase" or "ferulic acid esterase" refers to a protein that hydrolyzes the ester bond between the arabinose substituent group and ferulic acid. "Coumaric acid esterase" refers to a protein that hydrolyzes the ester bond between the arabinose substituent group and coumaric acid. Acetyl xylan esterases, ferulic acid esterases and pectin methyl esterases are examples of carbohydrate esterases.

"Pectate lyase" refers to a protein that catalyzes the cleavage of 1,4-α-D-galacturonan in oligosaccharide substrates.

Glycosidases (glycoside hydrolases; GH), a large family of enzymes that includes cellulases and hemicellulases, catalyze the hydrolysis of glycosidic linkages, predominantly in carbohydrates. Glycosidases such as the proteins of the present invention may be assigned to families on the basis of sequence similarities, and there are now over 100 different such families defined (see the CAZy (Carbohydrate Active EnZymes database) website, maintained by the Architecture of Fonction de Macromolecules Biologiques of the Centre National de la Recherche Scientifique, which describes the families of structurally-related catalytic and carbohydrate-binding modules (or functional domains) of enzymes that degrade, modify, or create glycosidic bonds; Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12). Because there is a direct relationship between the amino acid sequence of a protein and its folding similarities, such a classification reflects the structural features of these enzymes and their substrate specificity. Such a classification system can help to reveal the evolutionary relationships between these enzymes and provide a convenient tool to determine information such as a enzyme's activity and function. Thus, enzymes assigned to a particular family based on sequence homology with other members of the family are expected to have similar enzymatic activities and related substrate specifities. CAZy family classifications also exist for glycosyltransferases (GT), polysaccharide lyases (PL), and carbohydrate esterases (CE). Likewise, sequence homology may be used to identify particular domains within proteins, such as cellulose binding modules (CBMs; also known as cellulose binding domains (CBDs)). The CAZy homologies of proteins of the present invention are disclosed below.

Proteins of the present invention may also include homologues and fragments of the proteins disclosed herein. The protein fragments include, but are not limited to, fragments comprising a catalytic domain (CD) and/or a cellulose-binding domain (also known as a cellulose binding module (CBM); both are referred to herein as CBD). The identity and location of domains within proteins of the present invention are disclosed in detail below. The present invention encompasses all combinations of the disclosed domains. For example, a protein fragment may comprise a CD of a protein but not a CBD of the protein or a CBD of a protein but not a CD. Similarly, domains from different proteins may be combined. Protein fragments comprising a CD, CBD or combinations thereof for each protein disclosed herein can be readily produced using standard techniques known in the art. In some embodiments, a protein fragment comprises a domain of a protein that has at least one biological activity of the full-length protein. Homologues of proteins of the invention that have at least one biological activity of the full-length protein are described in detail below. As used herein, the phrase "biological activity" of a protein refers to any function (s) exhibited or performed by the protein that is ascribed to the naturally occurring form of the protein as measured or observed in vitro or in vivo. In certain embodiments, a protein fragment comprises a domain of a protein that has the catalytic activity of the full-length enzyme. Specific biological activities of the proteins of the invention, and structures within the proteins that are responsible for the activities, are described below.

Cellobiohydrolases

Certain proteins of the present invention possess cellobiohydrolase enzymatic activity. For example, the polypeptides denoted herein as CBH Ia (SEQ ID NO:2), CBH Ib (SEQ ID NO:5), CBH IIa (SEQ ID NO:8), and CBH IIb (SEQ ID NO:11) possess cellobiohydrolase activity. These enzymes participate in the hydrolytic conversion of insoluble cellulose to cellooligosaccharides, with cellobiose being a primary product of the enzymatic catalysis.

The enzyme denoted CBH Ia is encoded by the genomic nucleic acid sequence represented herein as SEQ ID NO:1 and the cDNA sequence represented herein as SEQ ID NO:3. The CBH Ia nucleic acid sequence encodes a 526 amino acid sequence, represented herein as SEQ ID NO:2. The signal peptide for CBH Ia is located from positions 1 to about position 17 of SEQ ID NO:2, with the mature protein spanning from about position 18 to position 526 of SEQ ID NO:2. Within CBH Ia are two domains: a catalytic domain (CD) and a cellulose-binding domain (CBD). The amino acid sequence containing the CD of CBH Ia spans from a starting point of about position 19 of SEQ ID NO:2 to an ending point of about position 453 of SEQ ID NO:2. The amino acid sequence containing the CBD of CBH Ia spans from a starting point of about position 490 of SEQ ID NO:2 to an ending point of about position 519 of SEQ ID NO:2. Based on homology, CBH Ia can be assigned to CAZy Families GH 7 and CBM 1. As evidenced below, CBH Ia exhibits cellobiohydrolase activity.

The enzyme denoted CBH Ib is encoded by the nucleic acid sequence represented herein as SEQ ID NO:4 and the cDNA sequence represented herein as SEQ ID NO:6. The CBH Ib nucleic acid sequence encodes a 450 amino acid sequence, represented herein as SEQ ID NO:5. The signal peptide for CBH Ia is located from positions 1 to about position 20 of SEQ ID NO:5, with the mature protein spanning from about position 21 to position 450 of SEQ ID NO:5. Within CBH Ia is a catalytic domain (CD). The amino acid sequence containing the CD of CBH Ib spans from a starting point of about position 22 of SEQ ID NO:5 to an ending point of about position 450 of SEQ ID NO:5. Based on homology, CBH Ib can be assigned to CAZy Family GH 7. As evidenced below, CBH Ib exhibits cellobiohydrolase activity.

The enzyme denoted CBH IIa is encoded by the nucleic acid sequence represented herein as SEQ ID NO:7 and the cDNA sequence represented herein as SEQ ID NO:9. The CBH IIa nucleic acid sequences encodes a 395 amino acid sequence, represented herein as SEQ ID NO:8. The signal peptide for CBH IIa is located from positions 1 to about position 17 of SEQ ID NO:8, with the mature protein spanning from about position 18 to position 395 of SEQ ID NO:8. Within CBH IIa is a catalytic domain (CD). The amino acid sequence containing the CD of CBH IIa spans from a starting point of about position 40 of SEQ ID NO:8 to an ending point of about position 395 of SEQ ID NO:8. Based on homology, CBH IIa can be assigned to CAZy Family GH 6. As evidenced below, CBH IIa exhibits cellobiohydrolase activity.

The enzyme denoted CBH IIb is encoded by the nucleic acid sequence represented herein as SEQ ID NO:10 and the cDNA sequence represented herein as SEQ ID NO:12. The CBH IIb nucleic acid sequence encodes a 482 amino acid sequence, represented herein as SEQ ID NO:11. The signal peptide for CBH IIb is located from positions 1 to about position 17 of SEQ ID NO:11, with the mature protein spanning from about position 18 to position 482 of SEQ ID NO:11. Within CBH IIb are two domains: a catalytic domain (CD) and a cellulose-binding domain (CBD). The amino acid sequence containing the CBD of CBH IIb spans from a starting point of about position 27 of SEQ ID NO:11 to an ending point of about position 62 of SEQ ID NO:11. The amino acid sequence containing the CD of CBH IIb spans from a starting point of about position 125 of SEQ ID NO:11 to an ending point of about position 482 of SEQ ID NO:11. Based on homology, CBH IIb can be assigned to CAZy Families GH 6 and CBM 1. As evidenced below, CBH IIb exhibits cellobiohydrolase activity.

Physical properties, biochemical characteristics and substrate specificities of cellobiohydrolases of the present invention are illustrated in Tables 1 and 2 below. Physical and biochemical characteristics include molecular weight, isoelectric point, pH and temperature optima of enzymatic activity, and the stability of the enzymes after heating to 50° C. for five hours at pH 5.0 or 7.0. Substrate specificities demonstrating enzyme activity for the indicated substrates were determined using standard assays known in the art, such as those disclosed in the Examples below. FIG. 1 illustrates the specific activity of cellobiohydrolases of the present invention toward substrates selected from Table 2.

TABLE 1

Physical and Biochemical Properties of C1 Cellobiohydrolases

| Enzyme | SEQ ID NO | MW (kDa) | pI | pH (50%) | T ° C. (50%) | Stability pH 5.0 | Stability pH 7.0 |
|---|---|---|---|---|---|---|---|
| CBH Ia | 2 | 65 | 4.5 | 5.0 (3.5-6.5) | 60 (45->80) | 99% | 96% |
| CBH Ia (CD) | 2 (CD Only) | 52 | 4.5 | 5.0 (3.5-6.5) | 60 (45->80) | 97% | 95% |
| CBH Ib | 5 | 60 | 3.8 | 4.7 (3.3-6.3) | 65 (50->80) | 80% | 80% |
| CBH IIa | 8 | 43 | 4.2 | 5.0 (3.5-6.5) | 60 (50-72) | 98% | 70% |
| CBH IIb | 11 | 70 | 5.6 | 5.0 (<3.0-6.5) | 60 (50-75) | 100% | 80% |

MW = Molecular Weight, kiloDaltons (kDa)
pI = isoelectric point
pH (50%) = pH optimum of enzyme activity (range of at least 50% activity)
T ° C. (50%) = Temperature optimum of enzyme activity (range of at least 50% activity)
Stability pH 5.0 = residual enzyme activity after 5 hour incubation at 50° C., pH 5.0
Stability pH 7.0 = residual enzyme activity after 5 hour incubation at 50° C., pH 7.0

TABLE 2

Substrate Specificities of C1 Cellobiohydrolases
(Activity Towards Specific Substrates (units/mg))

Figure 2:
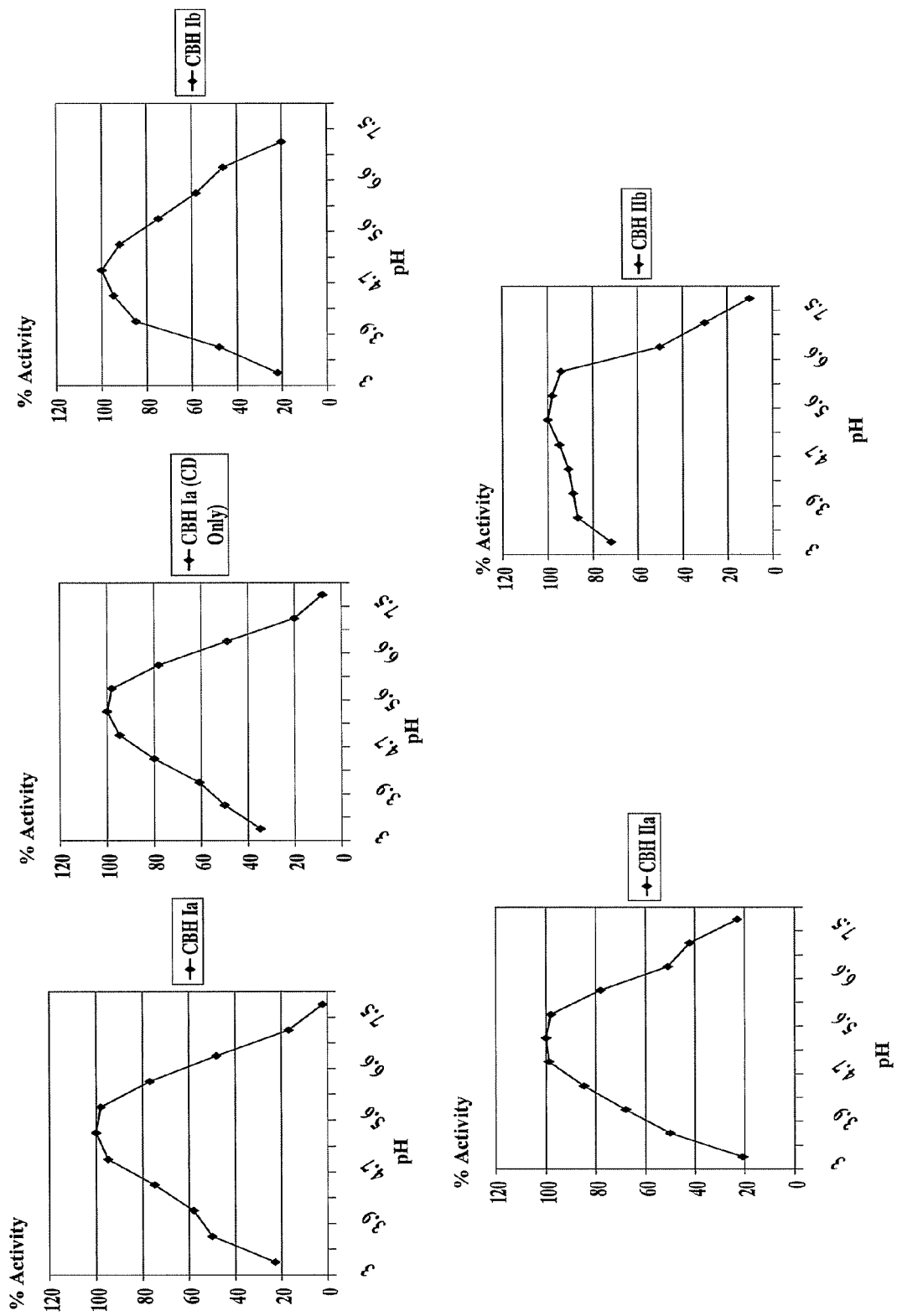
FIG. 2 illustrates the enzymatic activity (percentage of maximum) of cellobiohydrolases of the present invention at varying pH levels. The activities were determined using an Avicel substrate at 40° C.
Figure 3:
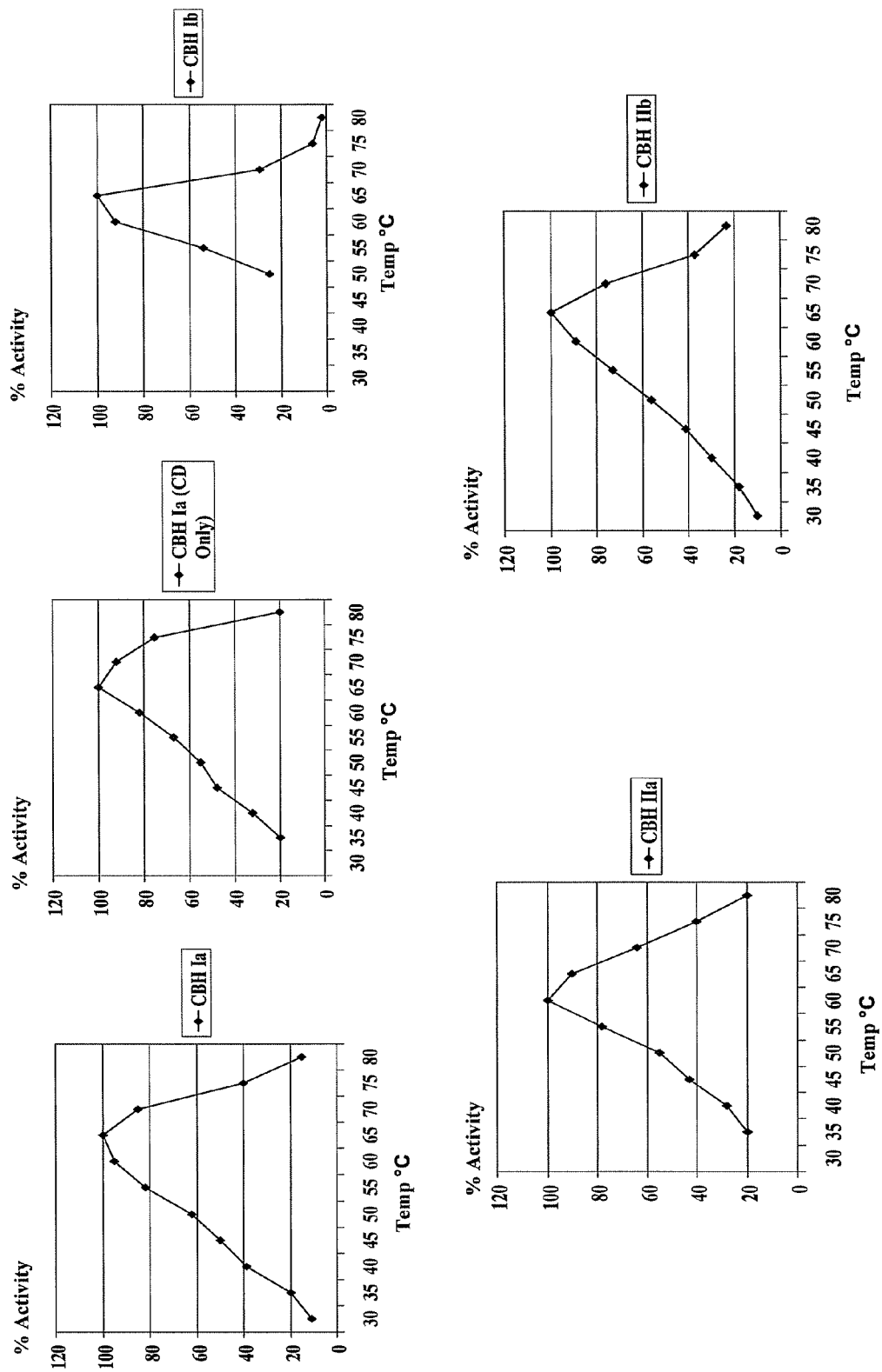
FIG. 3 illustrates the enzymatic activity (percentage of maximum) of cellobiohydrolases of the present invention at varying temperature levels. The activities were determined using an Avicel substrate at pH 5.0.

| Substrate | CBH Ia | CBH Ia (CD) | CBH Ib | CBH IIa | CBH IIb |
|---|---|---|---|---|---|
| CMC (S—N Assay) | 0.2 | 0.2 | 0.3 | 1.1 | 0.1 |
| CMC (Viscometric) | 0.01 | 0.02 | 0.02 | 0.6 | 0.01 |
| β-glucan | <0.1 | <0.1 | <0.1 | 2.0 | 0.2 |
| Avicel | 0.21 | 0.10 | 0.12 | 0.08 | 0.22 |
| Birchwood Xylan | 0 | 0 | 0 | 1.4 | 0.03 |
| Xyloglucan | 0 | 0 | 0 | 0 | 0 |
| Laminarin | 0 | 0 | 0 | 0 | 0 |
| Arabinan | 0 | 0 | 0 | 0.1 | 0 |
| Galactan | 0 | 0 | 0 | 0 | 0 |
| Galactomannan | 0 | 0 | 0 | 0 | 0 |
| p-NPh-β-D-cellobioside | 0.021 | 0.025 | 0.02 | 0 | 0 |
| p-NPh-β-D-lactoside | 0.12 | 0.11 | 0.09 | 0 | 0 | pH and temperature dependencies of cellobiohydrolases of the present invention are illustrated in Tables 3 and 4 below. pH and temperature dependencies were determined using the Avicel cellulase assay described in Example 5 below. pH dependencies were assayed by varying the pH at 40° C. for one hour, while temperature dependencies were assayed by varying the temperature at pH 5.0 for one hour. The temperature/pH that exhibited the highest enzyme activity was set at 100% in the tables below, with the remaining values expressed a percentage of this standard. The pH and temperature dependencies of the cellobiohydrolases are also illustrated graphically in FIGS. 2 and 3, respectively.

TABLE 3 pH Dependency of C1 Cellobiohydrolases (% Activity)

| pH | CBH Ia | CBH Ia (CD) | CBH Ib | CBH IIa | CBH IIb |
|---|---|---|---|---|---|
| 3 | 23 | 35 | 22 | 21 | 72 |
| 3.55 | 50 | 50 | 48 | 50.0 | 87 |
| 3.9 | 58 | 61 | 85 | 68 | 89 |
| 4.3 | 75 | 80 | 95 | 85 | 91 |
| 4.7 | 95 | 95 | 100 | 99 | 95 |
| 5.08 | 100 | 100 | 92 | 100 | 100 |
| 5.6 | 98 | 98 | 75 | 98 | 98 |
| 6 | 77 | 78 | 58 | 78 | 94 |
| 6.6 | 48 | 49 | 46 | 51.6 | 50 |
| 7.1 | 17.4 | 20 | 20 | 42 | 30 |
| 7.5 | 2 | 8 | | 23 | 10 |

TABLE 4

Temperature Dependency of C1 Cellobiohydrolases (% Activity)

| Temp ° C. | CBH Ia | CBH Ia (CD) | CBH Ib | CBH IIa | CBH IIb |
|---|---|---|---|---|---|
| 30 | 11.0 | | | | 10 |
| 35 | 20 | 20 | | 20.0 | 18 |
| 40 | 39 | 32 | | 28 | 30 |
| 45 | 50 | 48 | | 43 | 41 |
| 50 | 62 | 55 | 25 | 55 | 55.6 |
| 55 | 82 | 67 | 54 | 78 | 73 |
| 60 | 95 | 82 | 92 | 100 | 89 |
| 65 | 100 | 100 | 100 | 90 | 100 |
| 70 | 85 | 92 | 29 | 64 | 76 |
| 75 | 40 | 75 | 6 | 40 | 36.5 |
| 80 | 15 | 20 | 2 | 20 | 23 |

Endoglucanases

Some proteins of the present invention possess endo-1,4-β-glucanase enzymatic activity. For example, the polypeptides EG I (SEQ ID NO:14), EG II (SEQ ID NO:94), EG III (SEQ ID NO:17), EG V (SEQ ID NO:20), and EG VI (SEQ ID NO:23) possess endo-1,4-β-glucanase activity. As with the cellobiohydrolases described above, these endoglucanases also participate in the hydrolytic conversion of insoluble cellulose to cellooligosaccharides, with cellobiose being a primary product of the enzymatic catalysis.

The enzyme denoted EG I is encoded by the nucleic acid sequence represented herein as SEQ ID NO:13 and the cDNA sequence represented herein as SEQ ID NO:15. The EG I nucleic acid sequence encodes a 456 amino acid sequence, represented herein as SEQ ID NO:14. The signal peptide for EG I is located from positions 1 to about position 20 of SEQ ID NO:14, with the mature protein spanning from about position 21 to position 456 of SEQ ID NO:14. Within EG I is a catalytic domain (CD). The amino acid sequence containing the CD of EG I spans from a starting point of about position 22 of SEQ ID NO:14 to an ending point of about position 420 of SEQ ID NO:14. Based on homology, EG I can be assigned to CAZy Family GH 7. As evidenced below, EG I exhibits endoglucanase activity.

The enzyme denoted EG II is a 389 amino acid sequence, represented herein as SEQ ID NO:94. The signal peptide for EG II is located from positions 1 to about position 16 of SEQ ID NO:94, with the mature protein spanning from about position 17 to position 389 of SEQ ID NO:94. Within EG II are two domains: a catalytic domain (CD) and a cellulose-binding domain (CBD). The amino acid sequence containing the CBD of EG II spans from a starting point of about position 17 of SEQ ID NO:94 to an ending point of about position 52 of SEQ ID NO:94. The amino acid sequence containing the CD of EG II spans from a starting point of about position 84 of SEQ ID NO:94 to an ending point of about position 388 of SEQ ID NO:94. As evidenced below, EG II exhibits endoglucanase activity.

The enzyme denoted EG III is encoded by the nucleic acid sequence represented herein as SEQ ID NO:16 and the cDNA sequence represented herein as SEQ ID NO:18. The EG III nucleic acid sequence encodes a 247 amino acid sequence, represented herein as SEQ ID NO:17. The signal peptide for EG III is located from positions 1 to about position 15 of SEQ ID NO:17, with the mature protein spanning from about position 16 to position 247 of SEQ ID NO:17. Within EG III is a catalytic domain (CD). The amino acid sequence containing the CD of EG III spans from a starting point of about position 91 of SEQ ID NO:17 to an ending point of about position 247 of SEQ ID NO:17. Based on homology, EG III can be assigned to CAZy Family GH 12. As evidenced below, EG III exhibits endoglucanase activity.

The enzyme denoted EG V is encoded by the nucleic acid sequence represented herein as SEQ ID NO:19 and the cDNA sequence represented herein as SEQ ID NO:21. The EG V nucleic acid sequence encodes a 225 amino acid sequence, represented herein as SEQ ID NO:20. The signal peptide for EG V is located from positions 1 to about position 18 of SEQ ID NO:20, with the mature protein spanning from about position 19 to position 225 of SEQ ID NO:20. Within EG V is a catalytic domain (CD). The amino acid sequence containing the CD of EG V spans from a starting point of about position 23 of SEQ ID NO:20 to an ending point of about position 224 of SEQ ID NO:20. Based on homology, EG V can be assigned to CAZy Family GH 45. As evidenced below, EG V exhibits endoglucanase activity.

The enzyme denoted EG VI is encoded by the nucleic acid sequence represented herein as SEQ ID NO:22 and the cDNA sequence represented herein as SEQ ID NO:24. The EG VI nucleic acid sequence encodes a 381 amino acid sequence, represented herein as SEQ ID NO:23. The signal peptide for EG VI is located from positions 1 to about position 18 of SEQ ID NO:23, with the mature protein spanning from about position 19 to position 381 of SEQ ID NO:23. Within EG VI is a catalytic domain (CD). The amino acid sequence containing the CD of EG VI spans from a starting point of about position 33 of SEQ ID NO:23 to an ending point of about position 378 of SEQ ID NO:23. Based on homology, EG VI can be assigned to CAZy Family GH 6. As evidenced below, EG VI exhibits endoglucanase activity.

Physical properties, biochemical characteristics and substrate specificities of endoglucanases of the present invention are illustrated in Tables 5 and 6 below. Physical and biochemical characteristics include molecular weight, isoelectric point, pH and temperature optima of enzymatic activity, and the stability of the enzymes after heating to 50° C. for five hours at pH 5.0 or 7.0. Substrate specificities demonstrating enzyme activity for the indicated substrates were determined using standard assays known in the art, such as those disclosed in the Examples below. FIG. 1 illustrates the specific activity of endoglucanases of the present invention toward substrates selected from Table 6.

TABLE 5

Physical and Biochemical Properties of C1 Endoglucanases

| Enzyme | SEQ ID NO | MW (kDa) | pI | pH (50%) | T ° C. (50%) | Stability pH 5.0 | Stability pH 7.0 |
|---|---|---|---|---|---|---|---|
| EG I | 14 | 60 | 3.7 | 4.8 (3.5-7.5) | 60 (43-76) | 80% | 80% |
| EG II | 97 | 51 | 4.8 | 4.7 (3.5-7.5) | 70 (53-77) | 93% | 93% |
| EG II (CD) | 97 (CD Only) | 44 | 6.0 | 5.2 (3.5-7.5) | 70 (53-77) | 90% | 90% |
| EG III | 17 | 28 | 5.7 | 5.3 (3.8-7.0) | 60 (30-75) | 92% | 74% |
| EG V | 20 | 25 | 4.0 | 5.5 (3.5-8.5) | 65 (50-75) | 95% | 92% |
| EG VI | 23 | 47 | 5.7 | 6.0 (4.5->8.5) | 70 (40-82) | 60% | 75% |

MW = Molecular Weight, kiloDaltons (kDa)
pI = isoelectric point
pH (50%) = pH optimum of enzyme activity (range of at least 50% activity)
T ° C. (50%) = Temperature optimum of enzyme activity (range of at least 50% activity)
Stability pH 5.0 = residual enzyme activity after 5 hour incubation at 50° C., pH 5.0
Stability pH 7.0 = residual enzyme activity after 5 hour incubation at 50° C., pH 7.0

TABLE 6

Substrate Specificities of C1 Endoglucanases
(Activity Towards Specific Substrates (units/mg))

| Substrate | EG I | EG II | EG II (CD) | EG III | EG V | EG VI |
|---|---|---|---|---|---|---|
| CMC (S—N Assay) | 12 | 52 | 59 | 11 | 17 | 14 |
| CMC (Viscometric) | 5 | 46 | 39 | 19 | 20 | 6 |
| β-glucan | 18 | 75 | 74 | 125 | 5.3 | 18 |
| Avicel | 0.08 | 0.19 | 0.06 | 0.02 | 0.06 | 0.07 |
| Birchwood Xylan | 0 | 0.18 | 0.07 | 0.2 | 0 | 0.08 |
| Xyloglucan | 0 | 0 | 0 | 15.6 | 1.9 | 0 |
| Laminarin | 0 | 0.1 | 0.1 | 0 | 0 | 0 |
| Arabinan | 0 | 0 | 0.3 | 0 | 0 | 0 |
| Galactan | 0 | 0 | 0.6 | 0 | 0 | 0.1 |
| Galactomannan | 0 | 1.1 | 1 | 0 | 0.1 | 0 |

TABLE 6-continued

Substrate Specificities of C1 Endoglucanases
(Activity Towards Specific Substrates (units/mg))

Figure 4:
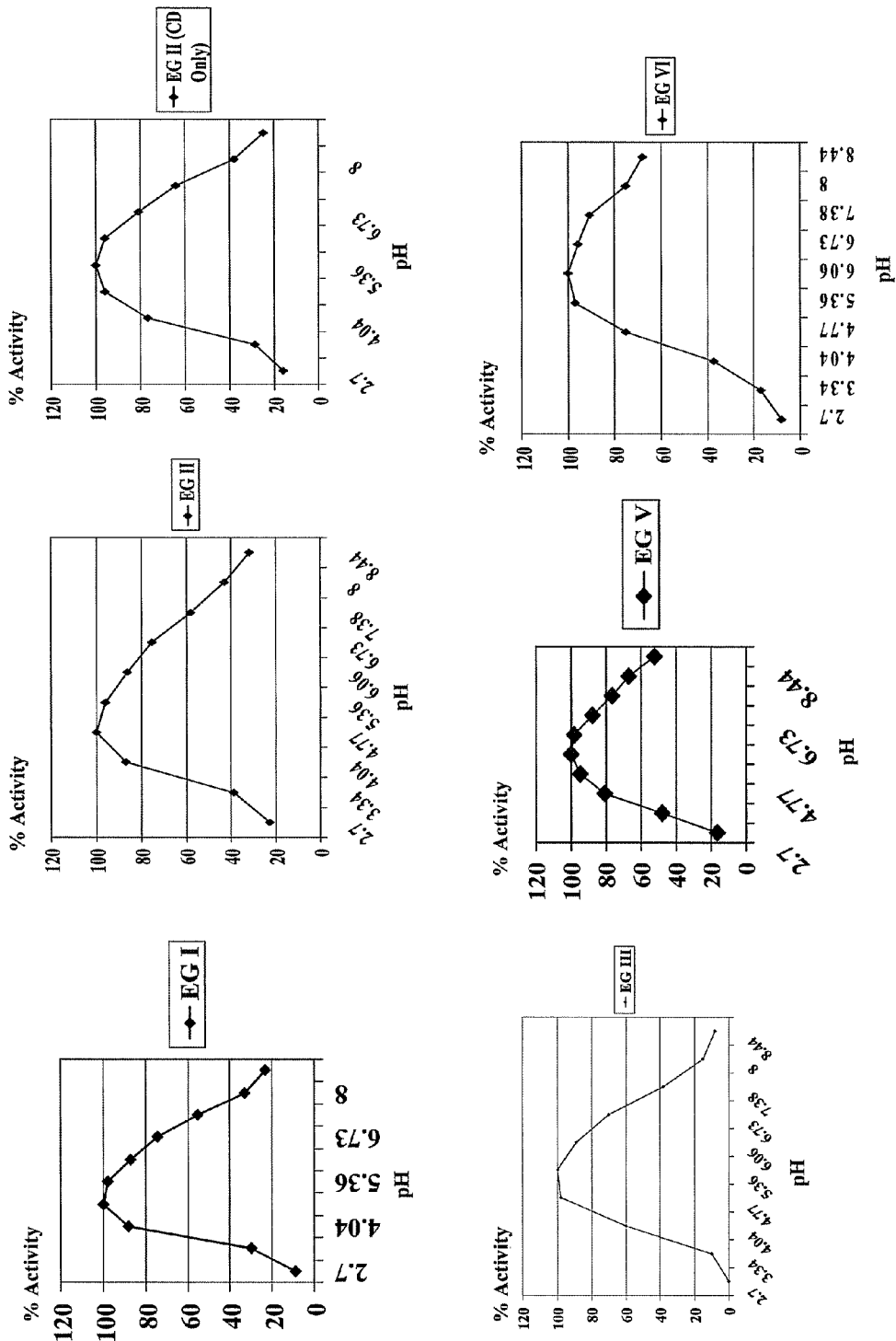
FIG. 4 illustrates the enzymatic activity (percentage of maximum) of endoglucanases of the present invention at varying pH levels. The activities were determined using an CMC substrate at 50° C.
Figure 5:
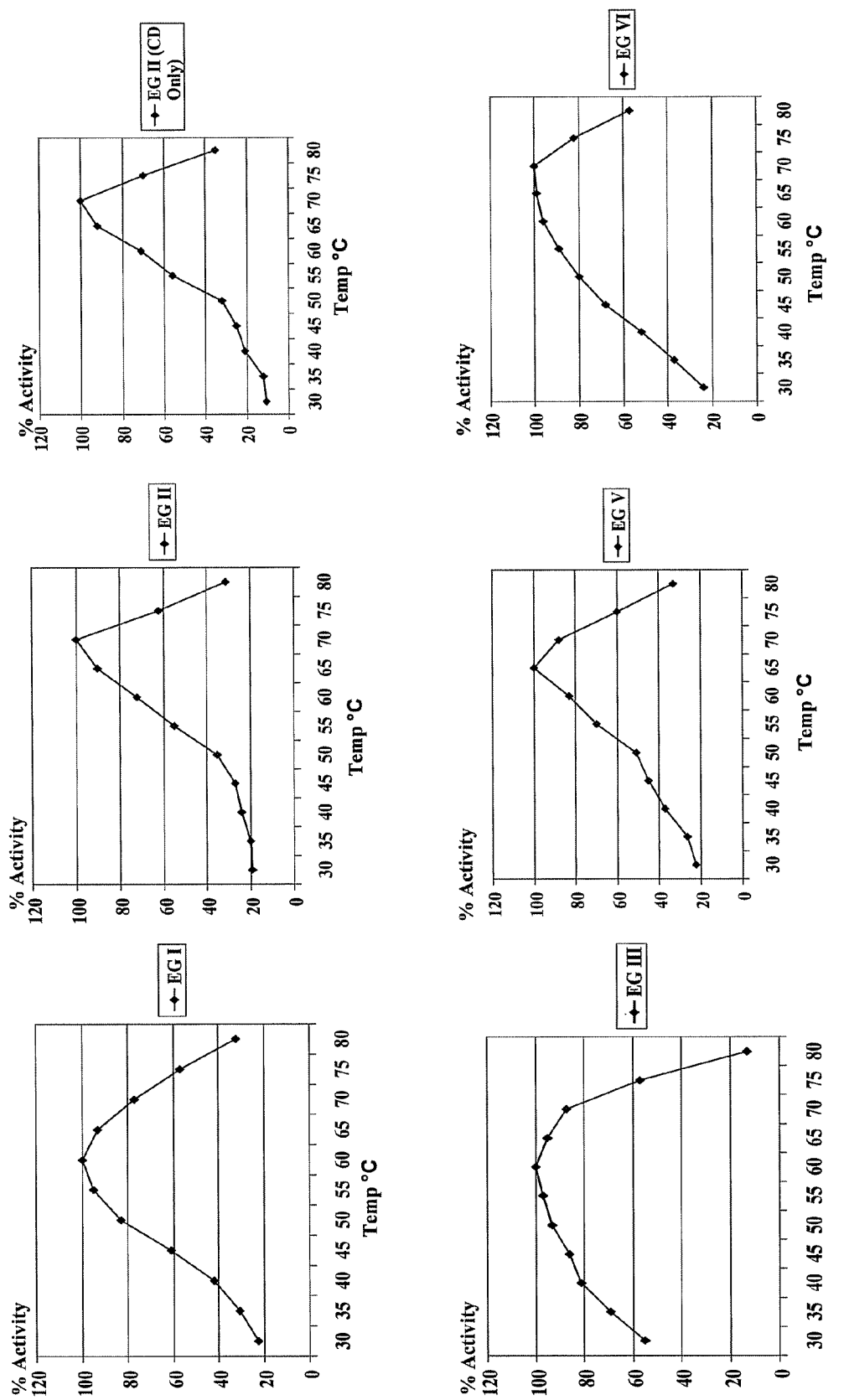
FIG. 5 illustrates the enzymatic activity (percentage of maximum) of endoglucanases of the present invention at varying temperature levels. The activities were determined using a CMC substrate at pH 5.0.

| Substrate | EG I | EG II | EG II (CD) | EG III | EG V | EG VI |
|---|---|---|---|---|---|---|
| p-NPh-β-D-cellobioside | 0.12 | 0 | 0 | 0 | 0 | 0 |
| p-NPh-β-D-lactoside | 0.27 | 0 | 0 | 0 | 0 | 0 | pH and temperature dependencies of endoglucanases of the present invention are illustrated in Tables 7 and 8 below. pH and temperature dependencies were determined using the CMC cellulase assay described in Example 3 below. pH dependencies were assayed by varying the pH at 50° C. for five minutes, while temperature dependencies were assayed by varying the temperature at pH 5.0 for five minutes. The temperature/pH that exhibited the highest enzyme activity was set at 100% in the tables below, with the remaining values expressed a percentage of this standard. The pH and temperature dependencies of the endoglucanases are also illustrated graphically in FIGS. 4 and 5, respectively.

TABLE 7 pH Dependency of C1 Endoglucanases (% Activity)

| pH | EG I | EG II | EG II (CD) | EG III | EG V | EG VI |
|---|---|---|---|---|---|---|
| 2.7 | 9 | 23 | 16 | 0 | 16.5 | 8 |
| 3.34 | 30 | 39 | 29 | 10 | 48 | 17 |
| 4.04 | 88 | 87 | 77 | 60 | 81 | 37 |
| 4.777 | 100 | 100 | 95 | 98 | 94.5 | 75 |
| 5.36 | 98 | 96 | 100 | 100 | 100 | 97 |
| 6.06 | 87 | 86 | 96 | 89 | 98 | 100 |
| 6.73 | 74 | 75 | 81 | 70 | 88 | 96 |
| 7.38 | 55 | 58 | 64 | 38 | 76.5 | 91 |
| 8 | 33 | 43 | 38 | 15 | 67 | 75 |
| 8.44 | 23 | 32 | 25 | 8 | 52 | 68 |

TABLE 8

Temperature Dependency of C1 Endoglucanases (% Activity)

| Temp ° C. | EG I | EG II | EG II (CD) | EG III | EG V | EG VI |
|---|---|---|---|---|---|---|
| 30 | 22.5 | 19 | 10.5 | 55.2 | 22 | 24.7 |
| 35 | 30.5 | 20 | 12 | 69.1 | 26 | 37.0 |
| 40 | 42.3 | 24 | 20.7 | 80.6 | 37 | 52 |
| 45 | 61.1 | 27 | 25 | 86.3 | 45 | 68.5 |
| 50 | 83.3 | 35.4 | 32 | 93.2 | 51 | 79.8 |
| 55 | 95.5 | 55 | 56 | 97.5 | 70 | 89.0 |
| 60 | 100 | 72 | 71 | 100 | 83.3 | 96.1 |
| 65 | 93.5 | 90 | 92 | 95.9 | 100 | 99 |
| 70 | 77.6 | 100 | 100 | 87.9 | 88 | 100 |
| 75 | 57.3 | 62 | 70 | 57.5 | 60 | 82.2 |
| 80 | 32.4 | 31 | 35 | 13.4 | 33 | 57.5 |

Xylanases

Certain proteins of the present invention possess xylanase enzymatic activity. For example, the polypeptides Xyl 1 (SEQ ID NO:26), Xyl 2 (SEQ ID NO:29), Xyl 3 (SEQ ID NO:32), Xyl 4 (SEQ ID NO:35), Xyl 5 (SEQ ID NO:38), and Xyl 6 (SEQ ID NO:41) possess xylanase activity. These xylanases participate in the hydrolytic conversion of hemicellulose into xylose.

The enzyme denoted Xyl 1 is encoded by the nucleic acid sequence represented herein as SEQ ID NO:25 and the cDNA sequence represented herein as SEQ ID NO:27. The Xyl 1 nucleic acid sequence encodes a 384 amino acid sequence, represented herein as SEQ ID NO:26. The signal peptide for Xyl 1 is located from positions 1 to about position 17 of SEQ ID NO:26, with the mature protein spanning from about position 18 to position 384 of SEQ ID NO:26. Within Xyl 1 are two domains: a catalytic domain (CD) and a cellulose-binding domain (CBD). The amino acid sequence containing the CBD of Xyl 1 spans from a starting point of about position 18 of SEQ ID NO:26 to an ending point of about position 53 of SEQ ID NO:26. The amino acid sequence containing the CD of Xyl 1 spans from a starting point of about position 83 of SEQ ID NO:26 to an ending point of about position 384 of SEQ ID NO:26. Based on homology, Xyl 1 can be assigned to CAZy Families GH 10 and CBM 1. As evidenced below, Xyl 1 exhibits xylanase activity.

The enzyme denoted Xyl 2 is encoded by the nucleic acid sequence represented herein as SEQ ID NO:28 and the cDNA sequence represented herein as SEQ ID NO:30. The Xyl 2 nucleic acid sequence encodes a 221 amino acid sequence, represented herein as SEQ ID NO:29. The signal peptide for Xyl 2 is located from positions 1 to about position 18 of SEQ ID NO:29, with the mature protein spanning from about position 19 to position 221 of SEQ ID NO:29. Within Xyl 2 is a catalytic domain (CD). The amino acid sequence containing the CD of Xyl 2 spans from a starting point of about position 25 of SEQ ID NO:29 to an ending point of about position 219 of SEQ ID NO:29. Based on homology, Xyl 2 can be assigned to CAZy Family GH 11. As evidenced below, Xyl 2 exhibits xylanase activity.

The enzyme denoted Xyl 3 is encoded by the nucleic acid sequence represented herein as SEQ ID NO:31 and the cDNA sequence represented herein as SEQ ID NO:33. The Xyl 3 nucleic acid sequence encodes a 413 amino acid sequence, represented herein as SEQ ID NO:32. The signal peptide for Xyl 3 is located from positions 1 to about position 17 of SEQ ID NO:32, with the mature protein spanning from about position 18 to position 413 of SEQ ID NO:32. Within Xyl 3 are two domains: a catalytic domain (CD) and a cellulose-binding domain (CBD). The amino acid sequence containing the CD of Xyl 3 spans from a starting point of about position 18 of SEQ ID NO:32 to an ending point of about position 336 of SEQ ID NO:32. The amino acid sequence containing the CBD of Xyl 3 spans from a starting point of about position 377 of SEQ ID NO:32 to an ending point of about position 413 of SEQ ID NO:32. Based on homology, Xyl 3 can be assigned to CAZy Family GH 10. As evidenced below, Xyl 3 exhibits xylanase activity.

The enzyme denoted Xyl 4 is encoded by the nucleic acid sequence represented herein as SEQ ID NO:34 and the cDNA sequence represented herein as SEQ ID NO:36. The Xyl 4 nucleic acid sequence encodes a 375 amino acid sequence, represented herein as SEQ ID NO:35. The signal peptide for Xyl 4 is located from positions 1 to about position 19 of SEQ ID NO:35, with the mature protein spanning from about position 20 to position 375 of SEQ ID NO:35. Within Xyl 4 is a catalytic domain (CD). The amino acid sequence containing the CD of Xyl 4 spans from a starting point of about position 31 of SEQ ID NO:35 to an ending point of about position 354 of SEQ ID NO:35. Based on homology, Xyl 4 can be assigned to CAZy Family GH 10. As evidenced below, Xyl 4 exhibits xylanase activity.

The enzyme denoted Xyl 5 is encoded by the nucleic acid sequence represented herein as SEQ ID NO:37 and the cDNA sequence represented herein as SEQ ID NO:39. The Xyl 5 nucleic acid sequence encodes a 226 amino acid sequence, represented herein as SEQ ID NO:38. The signal peptide for Xyl 5 is located from positions 1 to about position 21 of SEQ ID NO:38, with the mature protein spanning from about position 22 to position 226 of SEQ ID NO:38. Within Xyl 5 is a catalytic domain (CD). The amino acid sequence containing the CD of Xyl 5 spans from a starting point of about position 42 of SEQ ID NO:38 to an ending point of about position 223 of SEQ ID NO:38. Based on homology, Xyl 5 can be assigned to CAZy Families GH 11 and CE 4. As evidenced below, Xyl 5 exhibits xylanase activity.

The enzyme denoted Xyl 6 is encoded by the nucleic acid sequence represented herein as SEQ ID NO:40 and the cDNA sequence represented herein as SEQ ID NO:42. The Xyl 6 nucleic acid sequence encodes a 228 amino acid sequence, represented herein as SEQ ID NO:41. The signal peptide for Xyl 6 is located from positions 1 to about position 20 of SEQ ID NO:41, with the mature protein spanning from about position 21 to position 228 of SEQ ID NO:41. Within Xyl 6 is a catalytic domain (CD). The amino acid sequence containing the CD of Xyl 6 spans from a starting point of about position 37 of SEQ ID NO:41 to an ending point of about position 226 of SEQ ID NO:41. Based on homology, Xyl 6 can be assigned to CAZy Family GH 11. As evidenced below, Xyl 6 exhibits xylanase activity.

Figure 6:
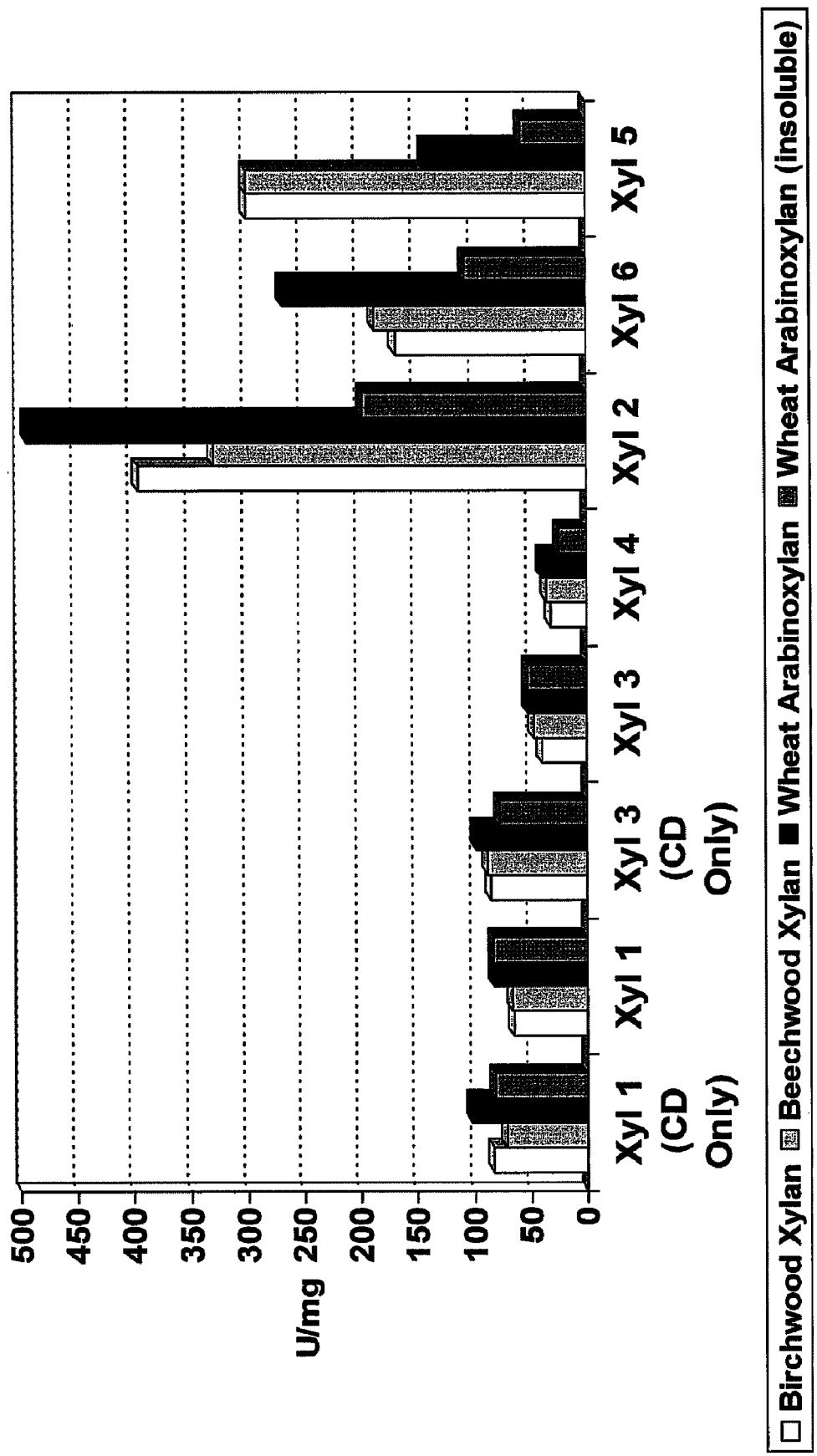
FIG. 6 shows the specific activity of xylanases of the present invention toward the indicated substrates. Specific activites (Units/mg) were determined at pH 5.0 and 50° C.

Physical properties, biochemical characteristics and substrate specificities of xylanases of the present invention are illustrated in Tables 9, 10, 11 and 12 below. Physical and biochemical characteristics include molecular weight, isoelectric point, pH and temperature optima of enzymatic activity, and the stability of the enzymes after heating to 50° C. for five hours at pH 5.0 or 7.0, or after heating to 80° C. for twenty seconds. Substrate specificities demonstrating enzyme activity for the indicated substrates (specific and non-specific) were determined using standard assays known in the art, such as those disclosed in the Examples below. The degree of xylan exhaustive hydrolysis of specific substrates is also indicated. FIG. 6 illustrates the specific activity of xylanases of the present invention toward substrates selected from Table 10.

TABLE 10

Substrate Specificities of C1 Xylanases
(Activity Towards Specific Substrates (units/mg))

| Substrate | Xyl 1 | Xyl 1 (CD) | Xyl 2 | Xyl 3 | Xyl 3 (CD) | Xyl 4 | Xyl 5 | Xyl 6 |
|---|---|---|---|---|---|---|---|---|
| Birchwood Xylan | 65 | 83 | 395 | 39 | 85 | 32 | 300 | 169 |
| Beechwood Xylan | 66 | 71 | 329 | 47 | 88 | 36 | 300 | 188 |
| Wheat Arabinoxylan | 83 | 102 | 494 | 52 | 98 | 40 | 143 | 268 |
| Wheat Arabinoxylan (Insoluble) | 83 | 82 | 198 | 52 | 78 | 24 | 57 | 107 |
| Arabinoxylan from Oat Spelts | 96 | 100 | 485 | 63 | 107 | 42 | 320 | 329 |
| Viscometric Activity, Wheat Arabinoxylan | 1311 | 1382 | 2158 | 807 | 1210 | 234 | 2700 | 2452 |

TABLE 11

Degree of Xylan Exhaustive Hydrolysis
of Specific Substrates by C1 Xylanases (%)

| Substrate | Xyl 1 | Xyl 1 (CD) | Xyl 2 | Xyl 3 | Xyl 3 (CD) | Xyl 4 | Xyl 5 | Xyl 6 |
|---|---|---|---|---|---|---|---|---|
| Birchwood Xylan | 26 | 24 | 19 | 24 | 23 | 25 | 22 | 21 |
| Beechwood Xylan | 24 | 22 | 15 | 22 | 20 | 23 | 18 | 17 |
| Wheat Arabinoxylan | 26 | 28 | 15 | 30 | 29 | 24 | 18 | 17 |

TABLE 9

Physical and Biochemical Properties of C1 Xylanases

| Enzyme | SEQ ID NO | MW (kDa) | pI | pH | T ° C. | Stability pH 5.0 | Stability pH 7.0 | Stability 80° C. |
|---|---|---|---|---|---|---|---|---|
| Xyl 1 | 26 | 42 | 7.8 | 5.5–7.0 | 65–70 | 100% (81%) | 100% (85%) | 12% |
| Xyl 1 (CD) | 26 (CD Only) | 31 | 8.9 | 5.5–7.0 | 65–70 | 100% (76%) | 100% (88%) | 19% |
| Xyl 2 | 29 | 24 | 7.9 | 5.7–7.5 | 70 | 84% (35%) | 71% (25%) | 23% |
| Xyl 3 | 32 | 57 | 4.4 | 5.5–6.5 | 80–85 | 100% (90%) | 100% (92%) | 75% |
| Xyl 3 (CD) | 32 (CD Only) | 46 | 4.3 | 5.5–6.5 | 80–85 | 100% (95%) | 100% (97%) | 98% |
| Xyl 4 | 35 | 38 | 4.8 | 5.0 | 80 | 100% (82%) | 100% (70%) | 82% |
| Xyl 5 | 38 | 22 | 6.7 | 4.5 | 65 | 45% (35%) | Unstable at pH ≥ 7.0 | 68% |
| Xyl 6 | 41 | 23 | 8.4 | 6.0 | 65–70 | 90% (12%) | 95% (20%) | 60% |

MW = Molecular Weight, kiloDaltons (kDa)
pI = isoelectric point
pH = pH optimum of enzyme activity
T ° C. = Temperature optimum of enzyme activity
Stability pH 5.0 = residual enzyme activity after 1 hour incubation at 50° C. (60° C.), pH 5.0
Stability pH 7.0 = residual enzyme activity after 1 hour incubation at 50° C. (60° C.), pH 7.0
Stability 80° C. = residual enzyme activity after 20 seconds at 80° C.

TABLE 11-continued

Degree of Xylan Exhaustive Hydrolysis
of Specific Substrates by C1 Xylanases (%)

| Substrate | Xyl 1 | Xyl 1 (CD) | Xyl 2 | Xyl 3 | Xyl 3 (CD) | Xyl 4 | Xyl 5 | Xyl 6 |
|---|---|---|---|---|---|---|---|---|
| Wheat Arabinoxylan (Insoluble) | 12 | 13 | 7 | 14 | 11 | 12 | 9 | 8 |
| Arabinoxylan from Oat Spelts | 28 | 27 | 19 | 29 | 25 | 26 | 20 | 19 |

TABLE 12

Substrate Specificities of C1 Xylanases
(Activity Towards Non-Specific Substrates (units/mg))

Figure 7:
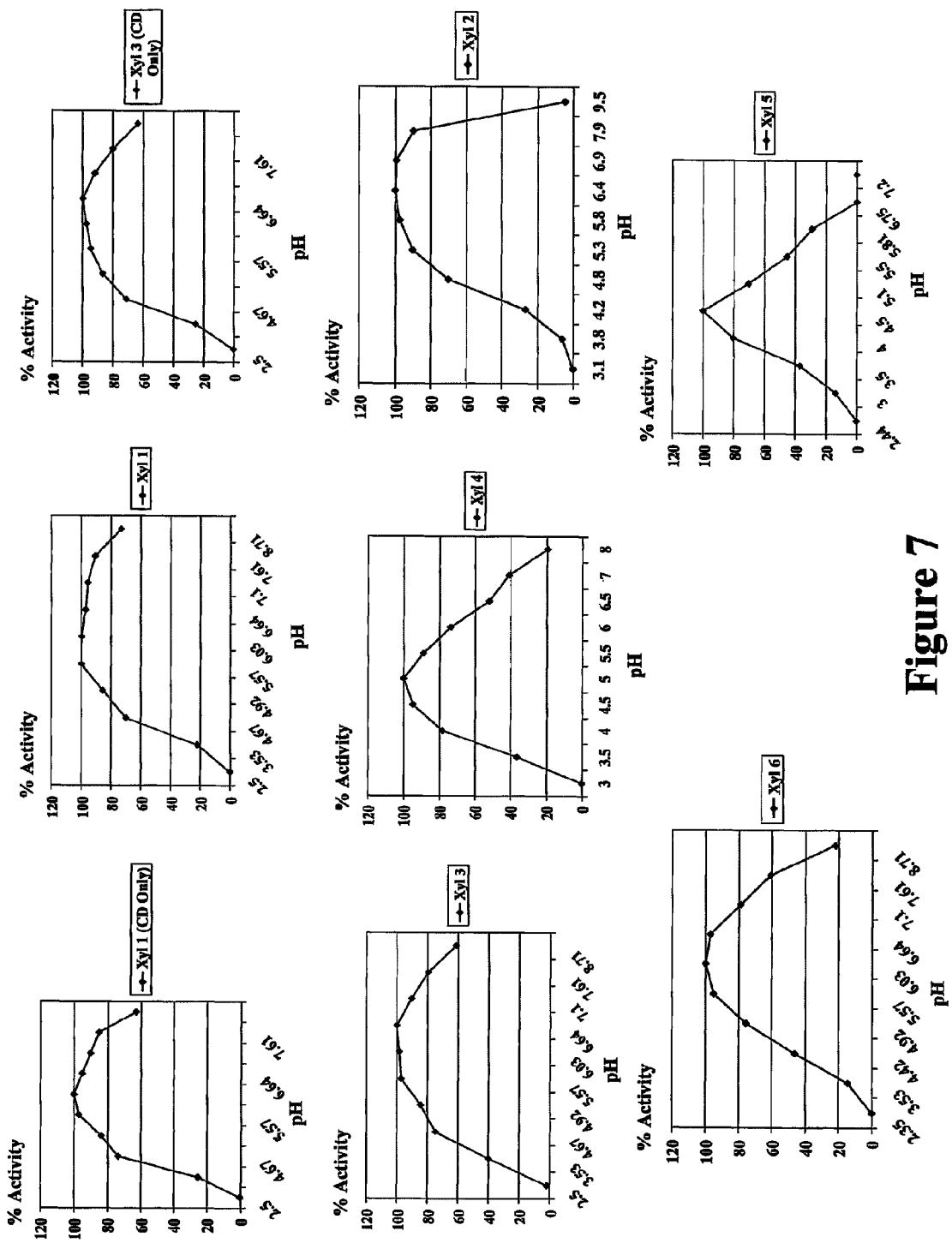
FIG. 7 illustrates the enzymatic activity (percentage of maximum) of xylanases of the present invention at varying pH levels. The activities were determined using a soluble xylan substrate at 40° C.
Figure 8:
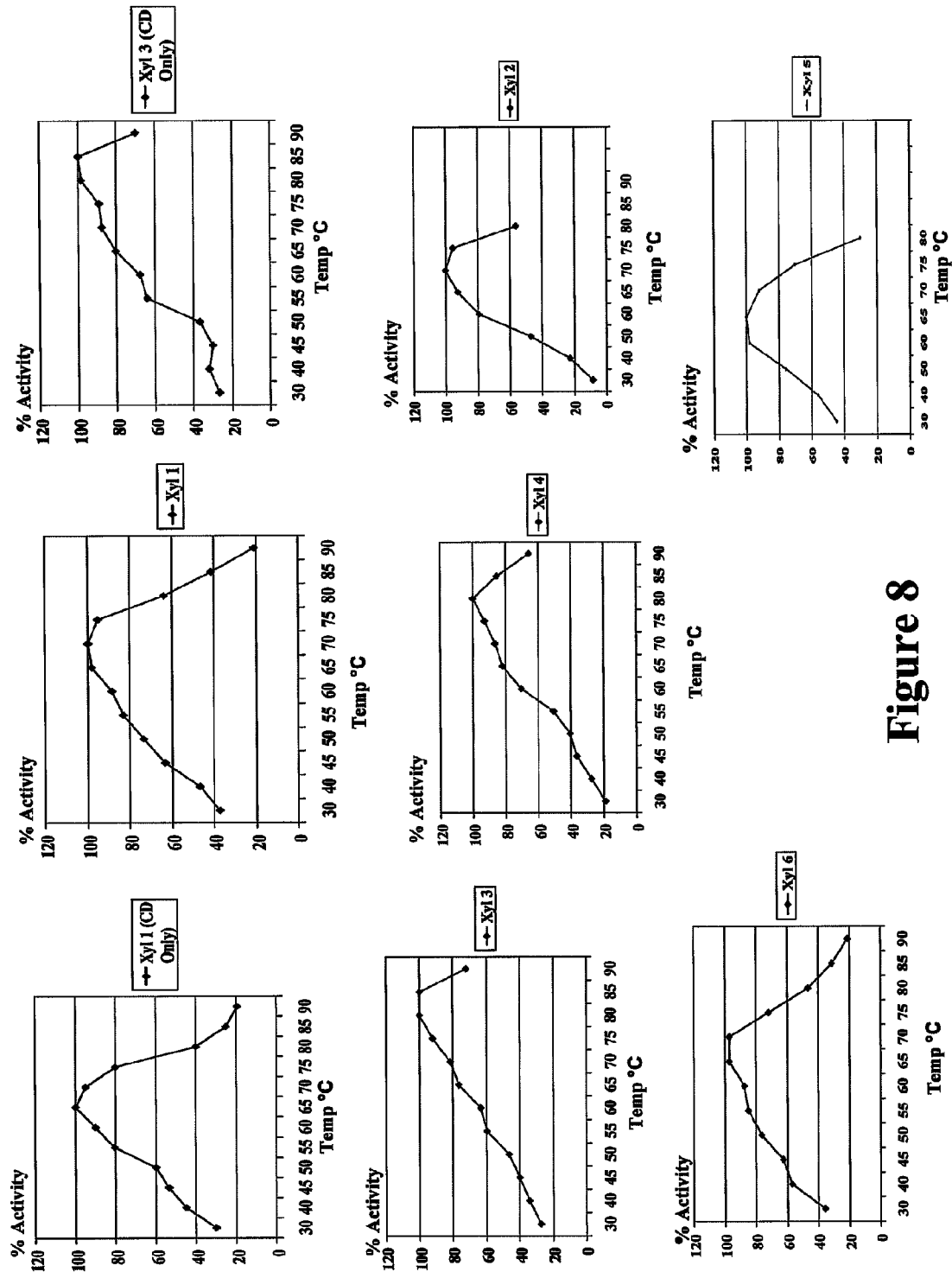
FIG. 8 illustrates the enzymatic activity (percentage of maximum) of xylanases of the present invention at varying temperature levels. The activities were determined using a soluble xylan substrate at pH 5.0.

| Substrate | Xyl 1 | Xyl 1 (CD) | Xyl 2 | Xyl 3 | Xyl 3 (CD) | Xyl 4 | Xyl 5 | Xyl 6 |
|---|---|---|---|---|---|---|---|---|
| CMC | 0.65 | 1 | 0 | 0.12 | 0.2 | 0 | 0 | 0 |
| Avicel | 0 | 0 | 0 | 0 | 0 | 0 | 0 | 0 |
| p-NPh-β-D-xylopyranoside | 0 | 0 | 0 | 0.3 | 0.6 | 0.3 | 0 | 0 |
| p-NPh-β-D-cellobioside | 0.36 | 0.42 | 0 | 0.84 | 1.6 | 4.0 | 0 | 0 | pH and temperature dependencies of xylanases of the present invention are illustrated in Tables 13 and 14 below. pH and temperature dependencies were determined using the xylanase assay (on soluble xylan) described in Example 7 below. pH dependencies were assayed by varying the pH at 40° C. for 10 minutes, while temperature dependencies were assayed by varying the temperature at pH 5.0 for 10 minutes. The temperature/pH that exhibited the highest enzyme activity was set at 100% in the table below, with the remaining values expressed a percentage of this standard. The pH and temperature dependencies of the xylanases are also illustrated graphically in FIGS. 7 and 8, respectively.

TABLE 13 pH Dependency of C1 Xylanases (% Activity)

| pH | Xyl 1 | Xyl 1 (CD) | Xyl 3 | Xyl 3 (CD) | pH | Xyl 4 | pH | Xyl 2 | pH | Xyl 6 | pH | Xyl 5 |
|---|---|---|---|---|---|---|---|---|---|---|---|---|
| 2.5 | 0.00 | 0.46 | 1.83 | 0.42 | 3.0 | 0.37 | 3.1 | 0 | 2.35 | 0.00 | 2.44 | 0.00 |
| 3.53 | 22.00 | 25.48 | 39.99 | 25.32 | 3.5 | 36.33 | 3.8 | 5.89 | 3.53 | 14.25 | 3 | 13.65 |
| 4.67 | 70.23 | 73.56 | 74.68 | 71.26 | 4.0 | 78.51 | 4.2 | 26.66 | 4.42 | 45.85 | 3.5 | 36.97 |
| 4.92 | 85.63 | 83.69 | 84.23 | 86.62 | 4.5 | 94.89 | 4.8 | 70.06 | 4.92 | 75.55 | 4 | 80.39 |
| 5.57 | 100 | 97.00 | 97.22 | 95.00 | 5.0 | 100 | 5.3 | 90.00 | 5.57 | 94.76 | 4.5 | 100 |
| 6.03 | 99.59 | 100 | 98.33 | 97.53 | 5.5 | 89.22 | 5.8 | 97.26 | 6.03 | 100 | 5.1 | 70.32 |
| 6.64 | 97.33 | 95.34 | 100 | 100 | 6.0 | 73.65 | 6.4 | 100 | 6.64 | 96.92 | 5.5 | 45.14 |
| 7.1 | 95.46 | 90.08 | 90.43 | 91.99 | 6.5 | 52.16 | 6.9 | 99.05 | 7.1 | 78.61 | 5.81 | 29.11 |
| 7.61 | 90.76 | 85.16 | 79.49 | 79.90 | 7.0 | 40.83 | 7.9 | 89.62 | 7.61 | 60.77 | 6.75 | 0.00 |
| 8.71 | 72.12 | 62.86 | 61.10 | 63.44 | 8.0 | 19.64 | 9.5 | 4.40 | 8.71 | 21.99 | 7.2 | 0.00 |

TABLE 14

Temperature Dependency of C1 Xylanases (% Activity)

| Temp ° C. | Xyl 1 | Xyl 1 (CD) | Xyl 2 | Xyl 3 | Xyl 3 (CD) | Xyl 4 | Xyl 5 | Xyl 6 |
|---|---|---|---|---|---|---|---|---|
| 30 | 37.5 | 37.5 | 8.3 | 27.3 | 26.5 | 18.6 | 44.8 | 35.4 |
| 40 | 46.8 | 46.8 | 22.7 | 34.1 | 31.7 | 27.4 | 56.3 | 57.0 |
| 45 | 63.1 | 63.1 | | 40.0 | 30.0 | 36.4 | | 62.6 |
| 50 | 73.1 | 73.1 | 47.2 | 46.4 | 36.5 | 40.3 | 75.9 | 76.1 |
| 55 | 82.9 | 82.9 | | 59.5 | 63.8 | 50.5 | | 85.0 |
| 60 | 88.1 | 88.1 | 79.0 | 63.3 | 67.5 | 70.3 | 98.3 | 87.5 |
| 65 | 98.0 | 98.0 | 92.5 | 76.1 | 80.4 | 81.8 | 100.0 | 97.2 |
| 70 | 100.0 | 100.0 | 100.0 | 81.5 | 87.5 | 86.4 | 92.2 | 97.3 |
| 75 | 95.0 | 95.0 | 95.2 | 92.0 | 88.8 | 92.6 | 70.1 | 71.6 |
| 80 | 63.7 | 63.7 | 56.4 | 100.0 | 98.3 | 100.0 | 30.2 | 46.2 |
| 85 | 41.0 | 41.0 | | 100.0 | 100.0 | 85.3 | | 31.1 |
| 90 | 21.1 | 21.1 | | 71.9 | 69.8 | 65.6 | | 20.8 |

Additional Glycosidases

Certain proteins of the present invention possess glycosidase enzymatic activity, including β-glucosidase, galactanase, glucoamylase, endo-arabinase, and β-xylosidase activities. The polypeptides denoted herein as Bgl3A (SEQ ID NO:44), Gal53A (SEQ ID NO:47), Gla15A (SEQ ID NO:50), Abn1 (SEQ ID NO:89) and bxl2 (SEQ ID NO:92) possess glycosidase activity, as indicated below.

The enzyme Bgl3A is encoded by the nucleic acid sequence represented herein as SEQ ID NO:43 and the cDNA sequence represented herein as SEQ ID NO:45. The Bgl3A nucleic acid sequence encodes a 871 amino acid sequence, represented herein as SEQ ID NO:44. The signal peptide for Bgl3A is located from positions 1 to about position 19 of SEQ ID NO:44, with the mature protein spanning from about position 20 to position 871 of SEQ ID NO:44. Within Bgl3A is a catalytic domain (CD). The amino acid sequence containing the CD of Bgl3A spans from a starting point of about position 87 of SEQ ID NO:44 to an ending point of about position 643 of SEQ ID NO:44. Based on homology, Bgl3A can be assigned to CAZy Family GH 3.

The enzyme Gal53A is encoded by the nucleic acid sequence represented herein as SEQ ID NO:46 and the cDNA sequence represented herein as SEQ ID NO:48. The Gal53A nucleic acid sequence encodes a 350 amino acid sequence, represented herein as SEQ ID NO:47. The signal peptide for Gal53A is located from positions 1 to about position 18 of SEQ ID NO:47, with the mature protein spanning from about position 19 to position 350 of SEQ ID NO:47. Within Gal53A is a catalytic domain (CD). The amino acid sequence containing the CD of Gal53A spans from a starting point of about position 19 of SEQ ID NO:47 to an ending point of about position 334 of SEQ ID NO:47. Based on homology, Gal53A can be assigned to CAZy Family GH 53. As evidenced below, Gal53A exhibits galactanase (arabinogalactan endo-1,4-β-galactosidase) activity.

The enzyme Gla15A is encoded by the nucleic acid sequence represented herein as SEQ ID NO:49 and the cDNA sequence represented herein as SEQ ID NO:51. The Gla15A nucleic acid sequence encodes a 628 amino acid sequence, represented herein as SEQ ID NO:50. The signal peptide for Gla15A is located from positions 1 to about position 20 of SEQ ID NO:50, with the mature protein spanning from about position 21 to position 628 of SEQ ID NO:50. Within Gla15A are two domains: a catalytic domain (CD) and a starch-binding domain (CBM 20). The amino acid sequence containing the CD of Gla15A spans from a starting point of about position 28 of SEQ ID NO:50 to an ending point of about position 461 of SEQ ID NO:50. The amino acid sequence containing the starch-binding domain of Gla15A spans from a starting point of about position 518 of SEQ ID NO:50 to an ending point of about position 628 of SEQ ID NO:50. Based on homology, Gla15A can be assigned to CAZy Families GH 15 and CBM 20. As evidenced below, Gla15A exhibits glucoamylase activity.

The enzyme Abn1 is encoded by the nucleic acid sequence represented herein as SEQ ID NO:88 and the cDNA sequence represented herein as SEQ ID NO:90. The Abn1 nucleic acid sequence encodes a 321 amino acid sequence, represented herein as SEQ ID NO:89. The signal peptide for Abn1 is located from positions 1 to about position 20 of SEQ ID NO:89, with the mature protein spanning from about position 21 to position 321 of SEQ ID NO:89. Within Abn1 is a catalytic domain (CD). The amino acid sequence containing the CD of Abn1 spans from a starting point of about position 27 of SEQ ID NO:89 to an ending point of about position 321 of SEQ ID NO:89. Based on homology, Abn1 can be assigned to CAZy Family GH 43. As illustrated below in Example 23, Abn1 exhibits endo-arabinase activity as measured by the ability to hydrolyze AZCL-arabinan (debranched). Abn1 also possesses significant homology (about 61% from amino acids 13 to 321 of Abn1) with a endo-arabinase from *Aspergillus niger* (Genbank Accession No. AAA32682; see also Flipphi et al., *Appl. Microbiol. Biotechnol.* 40:318 (1993)). Based on this degree of homology, Abn1 is expected to exhibit similar endo-arabinase enzymatic activity.

The enzyme Bxl2 is encoded by the nucleic acid sequence represented herein as SEQ ID NO:91 and the cDNA sequence represented herein as SEQ ID NO:93. The Bxl2 nucleic acid sequence encodes a 733 amino acid sequence, represented herein as SEQ ID NO:92. The signal peptide for Bxl2 is located from positions 1 to about position 17 of SEQ ID NO:92, with the mature protein spanning from about position 18 to position 733 of SEQ ID NO:92. Within Bxl2 is a catalytic domain (CD). The amino acid sequence containing the CD of Bxl2 spans from a starting point of about position 26 of SEQ ID NO:92 to an ending point of about position 602 of SEQ ID NO:92. Based on homology, Bxl2 can be assigned to CAZy Family GH 3. As illustrated below in Example 24, Bxl2 exhibits β-xylosidase activity. Bxl2 also possesses significant homology (about 70% from amino acids 28 to 733 of Bxl2) with a β-glucosidase from *Hypocrea jecorina* (Genbank Accession No. 1713235A; see also Barnett et al., *Biotechnol.* 9:562 (1991)). Based on this degree of homology, Bxl2 is also expected to exhibit similar β-glucosidase enzymatic activity.

Pectate Lyases

Certain proteins of the present invention possess pectate lyase enzymatic activity. The polypeptide denoted herein as Pel1 (SEQ ID NO:53) possesses pectate lyase activity.

The enzyme Pel1 is encoded by the nucleic acid sequence represented herein as SEQ ID NO:52 and the cDNA sequence represented herein as SEQ ID NO:54. The Pel1 nucleic acid sequence encodes a 375 amino acid sequence, represented herein as SEQ ID NO:53. The signal peptide for Pel1 is located from positions 1 to about position 20 of SEQ ID NO:53, with the mature protein spanning from about position 21 to position 375 of SEQ ID NO:53. Within Pel1 is a catalytic domain (CD). The amino acid sequence containing the CD of Pel1 spans from a starting point of about position 21 of SEQ ID NO:53 to an ending point of about position 375 of SEQ ID NO:53. As evidenced below, Pel1 exhibits pectate lyase activity.

Chitinases

Certain proteins of the present invention possess chitinase enzymatic activity. The polypeptides denoted herein as Chi18A (SEQ ID NO:56) and Gls2A (SEQ ID NO:59) possess chitinase activity.

The enzyme Chi18A is encoded by the nucleic acid sequence represented herein as SEQ ID NO:55 and the cDNA sequence represented herein as SEQ ID NO:57. The Chi18A nucleic acid sequence encodes a 426 amino acid sequence, represented herein as SEQ ID NO:56. The signal peptide for Chi18A is located from positions 1 to about position 23 of SEQ ID NO:56, with the mature protein spanning from about position 24 to position 426 of SEQ ID NO:56. Within Chi18A is a catalytic domain (CD). The amino acid sequence containing the CD of Chi18A spans from a starting point of about position 42 of SEQ ID NO:56 to an ending point of about position 386 of SEQ ID NO:56. Based on homology, Chi18A can be assigned to CAZy Family GH 18. As evidenced below, Chi18A exhibits chitinase activity.

The enzyme Gls2A is encoded by the nucleic acid sequence represented herein as SEQ ID NO:58 and the cDNA sequence represented herein as SEQ ID NO:60. The Gls2A nucleic acid sequence encodes a 907 amino acid sequence, represented herein as SEQ ID NO:59. The signal peptide for Gls2A is located from positions 1 to about position 20 of SEQ ID NO:59, with the mature protein spanning from about position 21 to position 907 of SEQ ID NO:59. Within Gls2A is a catalytic domain (CD). The amino acid sequence containing the CD of Gls2A spans from a starting point of about position 210 of SEQ ID NO:59 to an ending point of about position 764 of SEQ ID NO:59. Based on homology, Gls2A can be assigned to CAZy Family GH 2. As evidenced below, Gls2A exhibits chitinase (exo-β-D-chitinase) activity.

Carbohydrate Esterases

Certain proteins of the present invention possess carbohydrate esterase enzymatic activity, such as acetyl xylan esterase, ferulic acid esterase and pectin methyl esterase activity The polypeptides denoted herein as Axe3 (SEQ ID NO:62), FaeA1 (SEQ ID NO:65), FaeA2 (SEQ ID NO:68), FaeB2 (SEQ ID NO:71), Axe1 (SEQ ID NO:80), Axe2 (SEQ ID NO:83) and Pme1 (SEQ ID NO:86) possess carbohydrate esterase activity.

The enzyme Axe3 is encoded by the nucleic acid sequence represented herein as SEQ ID NO:61 and the cDNA sequence represented herein as SEQ ID NO:63. The Axe3 nucleic acid sequence encodes a 313 amino acid sequence, represented herein as SEQ ID NO:62. The signal peptide for Axe3 is located from positions 1 to about position 21 of SEQ ID NO:62, with the mature protein spanning from about position 22 to position 313 of SEQ ID NO:62. Within Axe3 is a catalytic domain (CD). The amino acid sequence containing the CD of Axe3 spans from a starting point of about position 22 of SEQ ID NO:62 to an ending point of about position 255 of SEQ ID NO:62. Based on homology, Axe3 can be assigned to CAZy Family CE 1. As illustrated below in Example 19, Axe3 exhibits acetyl esterase enzymatic activity. Axe3 also possesses significant homology (about 69% from amino acids 41 to 312 of Axe3) with an acetyl xylan esterase from *Penicillium purpurogenum* (Genbank Accession No. AAM93261.1; see also Gordillo et al., *Mycol. Res.* 110:1129 (2006)). Based on this degree of homology, Axe3 is expected to exhibit similar acetyl xylan esterase enzymatic activity.

The enzyme FaeA1 is encoded by the nucleic acid sequence represented herein as SEQ ID NO:64 and the cDNA sequence represented herein as SEQ ID NO:66. The FaeA1 nucleic acid sequence encodes a 279 amino acid sequence, represented herein as SEQ ID NO:65. The signal peptide for FaeA1 is located from positions 1 to about position 20 of SEQ ID NO:65, with the mature protein spanning from about position 21 to position 279 of SEQ ID NO:65. Within FaeA1 is a catalytic domain (CD). The amino acid sequence containing the CD of FaeA1 spans from a starting point of about position 33 of SEQ ID NO:65 to an ending point of about position 216 of SEQ ID NO:65. Based on homology, FaeA1 can be assigned to CAZy Family CE 1. As illustrated below in Example 20, FaeA1 exhibits ferulic acid esterase enzymatic activity. FaeA1 also possesses significant homology (about 51% from amino acids 22 to 264 of FaeA1) with a ferulic acid esterase from *Aspergillus clavatus* (Genbank Accession No. CAC85738). Based on this degree of homology, FaeA1 is expected to exhibit similar ferulic acid esterase enzymatic activity.

The enzyme FaeA2 is encoded by the nucleic acid sequence represented herein as SEQ ID NO:67 and the cDNA sequence represented herein as SEQ ID NO:69. The FaeA2 nucleic acid sequence encodes a 302 amino acid sequence, represented herein as SEQ ID NO:68. The signal peptide for FaeA2 is located from positions 1 to about position 26 of SEQ ID NO:68, with the mature protein spanning from about position 27 to position 302 of SEQ ID NO:68. As illustrated below in Example 20, FaeA2 exhibits ferulic acid esterase enzymatic activity. FaeA2 also possesses significant homology (about 45% from amino acids 32 to 301 of FaeA2) with a ferulic acid esterase from *Aspergillus clavatus* (Genbank Accession No. CAC85738). Based on this degree of homology, FaeA2 is expected to exhibit similar ferulic acid esterase enzymatic activity.

The enzyme FaeB2 is encoded by the nucleic acid sequence represented herein as SEQ ID NO:70 and the cDNA sequence represented herein as SEQ ID NO:72. The FaeB2 nucleic acid sequence encodes a 319 amino acid sequence, represented herein as SEQ ID NO:71. The signal peptide for FaeB2 is located from positions 1 to about position 22 of SEQ ID NO:71, with the mature protein spanning from about position 23 to position 319 of SEQ ID NO:71. Within FaeB2 is a catalytic domain (CD). The amino acid sequence containing the CD of FaeB2 spans from a starting point of about position 63 of SEQ ID NO:71 to an ending point of about position 278 of SEQ ID NO:71. As illustrated below in Example 20, FaeB2 exhibits ferulic acid esterase enzymatic activity. FaeB2 also possesses significant homology (about 68% from amino acids 46 to 319 of FaeB2) with a type B ferulic acid esterase from *Neurospora crassa* (Genbank Accession No. CAC05587). Based on this degree of homology, FaeB2 is expected to exhibit similar ferulic acid esterase enzymatic activity.

The enzyme Axe1 is encoded by the nucleic acid sequence represented herein as SEQ ID NO:79 and the cDNA sequence represented herein as SEQ ID NO:81. The Axe1 nucleic acid sequence encodes a 303 amino acid sequence, represented herein as SEQ ID NO:80. The signal peptide for Axe1 is located from positions 1 to about position 21 of SEQ ID NO:80, with the mature protein spanning from about position 22 to position 303 of SEQ ID NO:80. Within Axe1 are two domains: a catalytic domain (CD) and a cellulose-binding domain (CBD). The amino acid sequence containing the CD of Axe1 spans from a starting point of about position 37 of SEQ ID NO:80 to an ending point of about position 246 of SEQ ID NO:80. The amino acid sequence containing the CBD of Axe1 spans from a starting point of about position 271 of SEQ ID NO:80 to an ending point of about position 303 of SEQ ID NO:80. Based on homology, Axe1 can be assigned to CAZy Families CE 5 and CBM 1. As illustrated below in Example 19, Axe1 exhibits acetyl esterase enzymatic activity. Axe1 also possesses significant homology (about 57% from amino acids 3 to 303 of Axe1) with a acetyl xylan esterase from *Hypocrea jecorina* (Genbank Accession No. CAA93247; see also Margolles-Clark et al., *Eur. J. Biochem.* 237:553 (1996)). Based on this degree of homology, Axe1 is expected to exhibit similar acetyl xylan esterase enzymatic activity.

The enzyme Axe2 is encoded by the nucleic acid sequence represented herein as SEQ ID NO:82 and the cDNA sequence represented herein as SEQ ID NO:84. The Axe2 nucleic acid sequence encodes a 228 amino acid sequence, represented herein as SEQ ID NO:83. The signal peptide for Axe2 is located from positions 1 to about position 17 of SEQ ID NO:83, with the mature protein spanning from about position 18 to position 228 of SEQ ID NO:83. Within Axe2 is a catalytic domain (CD). The amino acid sequence containing the CD of Axe2 spans from a starting point of about position 26 of SEQ ID NO:83 to an ending point of about position 242 of SEQ ID NO:83. Based on homology, Axe2 can be assigned to CAZy Family CE 5. As illustrated below in Example 19, Axe2 exhibits acetyl esterase enzymatic activity. Axe2 also possesses significant homology (about 58% from amino acids 7 to 225 of Axe2) with a acetyl xylan esterase from *Penicillium purpurogenum* (Genbank Accession No. O59893; see also Egana et al., *Biotechnol. Appl. Biochem.* 24(1):33 (1996)). Based on this degree of homology, Axe2 is expected to exhibit similar acetyl xylan esterase enzymatic activity.

The enzyme Pme1 is encoded by the nucleic acid sequence represented herein as SEQ ID NO:85 and the cDNA sequence represented herein as SEQ ID NO:87. The Pme1 nucleic acid sequence encodes a 331 amino acid sequence, represented herein as SEQ ID NO:86. The signal peptide for Pme1 is located from positions 1 to about position 27 of SEQ ID NO:86, with the mature protein spanning from about position 28 to position 331 of SEQ ID NO:86. Within Pme1 is a catalytic domain (CD). The amino acid sequence containing the CD of Pme1 spans from a starting point of about position 43 of SEQ ID NO:86 to an ending point of about position 327 of SEQ ID NO:86. Based on homology, Pme1 can be assigned to CAZy Family CE 8. As illustrated below in Example 22, Pme1 exhibits pectin methyl esterase enzymatic activity on substrates such as methylated pectin (e.g., the ability to hydrolyze citrus pectin with a degree of methylation of 65 leading to the formation of unsubstituted galacturonic acid). Pectin methyl esterases catalyze the hydrolysis of methylester groups of pectins such as those found in the cell walls of plants. Pme1 also possesses significant homology (about 55% from amino acids 7 to 331 of Pme1) with a pectin methyl esterase from *Emericella nidulans* (Genbank Accession No. ABF50865.1; see also Bauer et al., *Proc. Natl. Acad. Sci. U.S.A.* 103:11417 (2006)). Based on this degree of homology, Pme1 is expected to exhibit similar pectin methyl esterase enzymatic activity.

Arabinofuranosidases

Certain proteins of the present invention possess arabinofuranosidase enzymatic activity. The polypeptides denoted herein as Abf1 (SEQ ID NO:74) and Abf2 (SEQ ID NO:77) possess arabinofuranosidase activity.

The enzyme Abf1 is encoded by the nucleic acid sequence represented herein as SEQ ID NO:73 and the cDNA sequence represented herein as SEQ ID NO:75. The Abf1 nucleic acid sequence encodes a 370 amino acid sequence, represented herein as SEQ ID NO:74. The signal peptide for Abf1 is located from positions 1 to about position 22 of SEQ ID NO:74, with the mature protein spanning from about position 23 to position 370 of SEQ ID NO:74. Within Abf1 are two domains: a catalytic domain (CD) and a cellulose-binding domain (CBD). The amino acid sequence containing the CD of Abf1 spans from a starting point of about position 24 of SEQ ID NO:74 to an ending point of about position 294 of SEQ ID NO:74. The amino acid sequence containing the CBD of Abf1 spans from a starting point of about position 339 of SEQ ID NO:74 to an ending point of about position 370 of SEQ ID NO:74. Based on homology, Abf1 can be assigned to CAZy Families CBM 1, CBM 13 and GH 62. As illustrated below in Example 21, Abf1 exhibits α-arabinofuranosidase enzymatic activity. Abf1 also possesses significant homology (about 70% from amino acids 19 to 322 of Abf1) with a arabinofuranosidase from *Streptomyces thermoviolaceus* (Genbank Accession No. JC7820; see also Tsujibo et al., *Biosci. Biotechnol. Biochem.* 66:434 (2002)). Based on this degree of homology, Abf1 is expected to exhibit similar arabinofuranosidase enzymatic activity.

The enzyme Abf2 is encoded by the nucleic acid sequence represented herein as SEQ ID NO:76 and the cDNA sequence represented herein as SEQ ID NO:78. The Abf2 nucleic acid sequence encodes a 321 amino acid sequence, represented herein as SEQ ID NO:77. The signal peptide for Abf2 is located from positions 1 to about position 19 of SEQ ID NO:77, with the mature protein spanning from about position 20 to position 321 of SEQ ID NO:77. Within Abf2 is a catalytic domain (CD). The amino acid sequence containing the CD of Abf2 spans from a starting point of about position 22 of SEQ ID NO:77 to an ending point of about position 291 of SEQ ID NO:77. Based on homology, Abf2 can be assigned to CAZy Family GH 62. As illustrated below in Example 21, Abf2 exhibits α-arabinofuranosidase enzymatic activity. Abf2 also possesses significant homology (about 75% from amino acids 21 to 315 of Abf2) with a arabinofuranosidase from *Streptomyces thermoviolaceus* (Genbank Accession No. JC7820; see also Tsujibo et al., *Biosci. Biotechnol. Biochem.* 66:434 (2002)). Based on this degree of homology, Abf2 is expected to exhibit similar arabinofuranosidase enzymatic activity.

Physical properties, biochemical characteristics and substrate specificities of the glycosidases, pectate lyases, chitinases, carbohydrate esterases, and arabinofuranosidases of the present invention are illustrated in Tables 15, 16, 17 and 18 below. Physical and biochemical characteristics include molecular weight, isoelectric point, pH and temperature optima of enzymatic activity, and the stability of the enzymes after heating to 50° C. for five hours at pH 5.0. Substrate specificities demonstrating enzyme activity for the indicated substrates (specific and non-specific) were determined using standard assays known in the art, such as those disclosed in the Examples below.

TABLE 15

Physical and Biochemical Properties of C1 Enzymes

| Enzyme | SEQ ID NO | MW (kDa) | pI | pH (50%) | T ° C. (50%) | Stability pH 5.0 |
|---|---|---|---|---|---|---|
| Bgl3A | 44 | 106 | 4.8 | 4.0 (2.5-7.0) | 60 (45-70) | 64% |
| Gal53A | 47 | 30 | 8.2 | 4.5 (2.7-6.0) | 55-60 (30-70) | 100% |
| Gla15A | 50 | 68 | 4.3 | 5.5 (3.5-7.0) | 70 | 50% |
| Pel1 | 53 | 33 | 5.3 | 8.5 (7.8-8.8) | 60-65 (30-70) | 100%** |
| Chi18A | 56 | 43 | 4.0 | 7.5 (5.7-8.7) | 70 (60-75) | 76% |
| Gls2A | 59 | 80 | 6.6 | 5.9 (5.0-7.0) | 70 (55-75) | 100% |
| Axe3 | 62 | 35 | 6.5-6.8 | | | |
| FaeA1 | 65 | 25-40 | 3.5-4.0 | | | |
| FaeA2 | 68 | 29.1* | 4.87* | | | |
| FaeB2 | 71 | 29.3* | 4.28* | | | |
| Abf1 | 74 | 35 | 7.3 and 8.5-9.0 | | | |
| Abf2 | 77 | 33 | 4.5-5.0 | | | |
| Axe1 | 80 | 28* | 7.2* | | | |
| Axe2 | 83 | 27 | 6 | | | |
| Pme1 | 86 | 32.6* | 8.79* | | | |
| Abn1 | 89 | 32.8* | 5.57* | | | |
| bxl2 | 95 | 75.9* | 4.8* | | | |

MW = Molecular Weight, kiloDaltons (kDa) (*= Predicted)
pI = isoelectric point (*= Predicted)
pH (50%) = pH optimum of enzyme activity (range of at least 50% activity)
T ° C. (50%) = Temperature optimum of enzyme activity (range of at least 50% activity)
Stability pH 5.0 = residual enzyme activity after 3 hour incubation at 50° C., pH 5.0
**pH 8.5, 1 mM CaCl$_2$

TABLE 16

Substrate Specificities of C1 Enzymes
(Activity Towards Substrates (units/mg))

| Substrate | Bgl3A | Gal53A | Pel1 |
|---|---|---|---|
| CMC (S—N Assay) | 1.5 | 0 | 0 |
| β-glucan from Barley | 18 | 0 | 0 |
| Birchwood GlucuronoXylan | 0 | 0 | 0 |
| Wheat ArabinoXylan | 0 | 0 | 0 |
| Xyloglucan from Tamarind | 0 | 0 | 0 |
| Laminarin (β-1,3; β-1,6) | 109 | 0 | 0 |
| Polygalacturonic acid (RS) | 0 | 0 | 70 |
| Citrus Pectin (Viscosimetry, A235) | 0 | 0 | 525* |
| Citrus Pectin (Etherefication 89%, A235) | 0 | 0 | 82* |
| Citrus Pectin (Etherefication 65%, A235) | 0 | 0 | 126* |
| Citrus Pectin (Etherefication 26%, A235) | 0 | 0 | 133* |
| Galactan | 0 | 620 | 0 |
| Arabinan Debranched | 0 | 97 | 0 |
| Arabinan Branched | 0 | 90 | 0 |
| Arabinogalactan | 0 | 0 | 0 |
| Galactomannan | 0 | 0 | 0 |
| p-NPh-β-D-cellobioside | 0.03 | 0 | 0 |
| p-NPh-β-D-lactoside | 0 | 0 | 0 |
| p-NPh-β-L-arabinofuranoside | 0 | 0 | 0 |
| p-NPh-β-L- | 0 | 0 | 0 |

TABLE 16-continued

Substrate Specificities of C1 Enzymes
(Activity Towards Substrates (units/mg))

| Substrate | Bgl3A | Gal53A | Pel1 |
|---|---|---|---|
| arabinopyranoside | | | |
| o-NPh-β-D-xylopyranoside | 0 | 0 | 0 |
| p-NPh-β-D-glucopyranoside | 39 | 0 | 0 |
| p-NPh-β-L-galactopyranoside | 0 | 0 | 0 |
| Cellobiose (β-1,4) | 52 | 0 | 0 |
| Laminaribiose (β-1,3) | 86 | 0 | 0 |
| α-Sophorose (β-1,2) | 50 | 0 | 0 |
| Gentibiose (β-1,6) | 107 | 0 | 0 |
| Maltose | 0 | 0 | 0 |

*C1 pectate lyase is a $Ca^{+2}$-dependent enzyme, so activities were measured in 1 mM of $CaCl_2$.

TABLE 17

Substrate Specificities of C1 Gla15A
(Activity Towards Substrates (units/mg))

| Substrate | Glucoamylase Activity |
|---|---|
| Starch soluble (potato) NS* | 150 |
| Amylose soluble (potato), NS | 87 |
| Amylopectin soluble (potato), NS | 104 |
| Pullulan (Aureobasidium pullulans) | 11 |
| Starch insoluble (potato) NS | 35 |
| Amylose insoluble (potato), NS | 59 |
| Amylopectin insoluble (potato), NS | 43 |

TABLE 17-continued

Substrate Specificities of C1 Gla15A
(Activity Towards Substrates (units/mg))

| Substrate | Glucoamylase Activity |
|---|---|
| Maltose** | 18 |
| Isomaltose** | 1.2 |
| Maltotriose** | 48 |
| Maltohexaose** | 61 |
| pNph-α-D-glucopiranoside | 0 |

TABLE 18

Substrate Specificities of C1 Enzymes
(Activity Towards Substrates (units/mg))

| Substrate | Chi18A | Gls2A |
|---|---|---|
| Chitosan soluble, 140 kDa | 35 | 28 |
| Chitin Colloid | 8 | 0 |
| CMC | 0 | 0 |
| β-glucan | 0 | 0 |
| Birchwood GlucuronoXylan | 0 | 0 |
| p-NPh-β-D-N-acetylglucosamine | 0.1 | 0 |
| Chitosan, 140 kDa viscometry | 210 | 0 | pH and temperature dependencies of certain enzymes of the present invention are illustrated in Tables 19 and 20 below. pH and temperature dependencies were determined using the standard assays with the substrate and conditions listed below:

| Enzyme | pH | Temperature |
|---|---|---|
| Bgl3A | p-NPh-β-D-glucopyranoside | Cellobiose |
| Gla15A | Potato Starch, 50° C., 10 minutes | Potato Starch, pH 5.0, 10 minutes |
| Chi18A | Colloidal chitin, 50° C., 10 minutes | Chitosan (140 kD), pH 5.0, 10 minutes |
| Gls2A | Chitosan (140 kD), 50° C., 10 minutes | Chitosan (140 kD), pH 5.0, 10 minutes |
| Gal53A[1] | Arabinan branched, 50° C., 10 minutes | Arabinan branched, pH 5.0, 10 minutes |
| Gal53A[2] | Galactan, 50° C., 10 minutes | Not Applicable |
| Pel1 | A235, PGA + 1 mM $CaCl_2$ | A235, PGA + 1 mM $CaCl_2$ |

Figure 9:
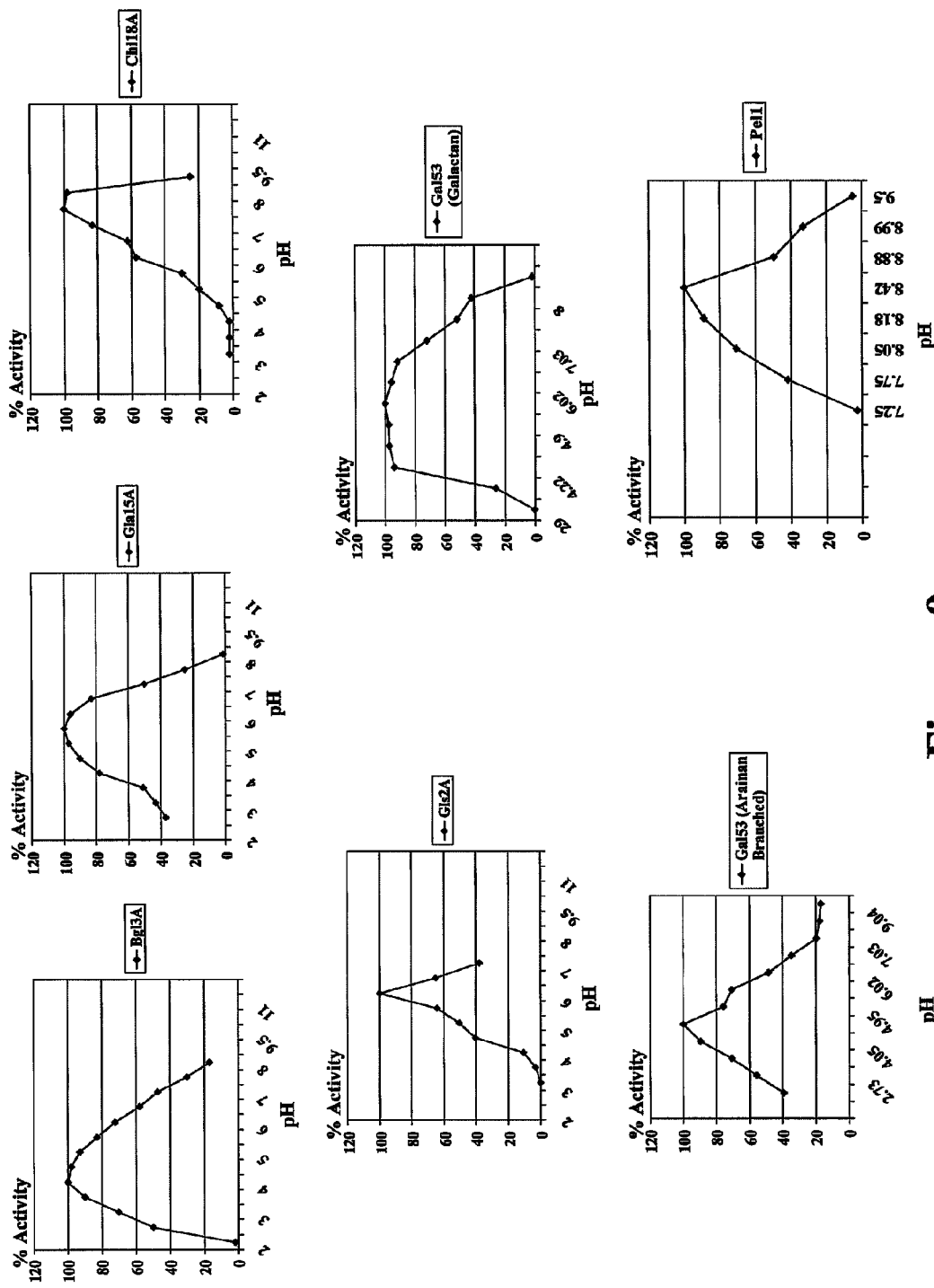
FIG. 9 illustrates the enzymatic activity (percentage of maximum) of enzymes of the present invention at varying pH levels.
Figure 10:
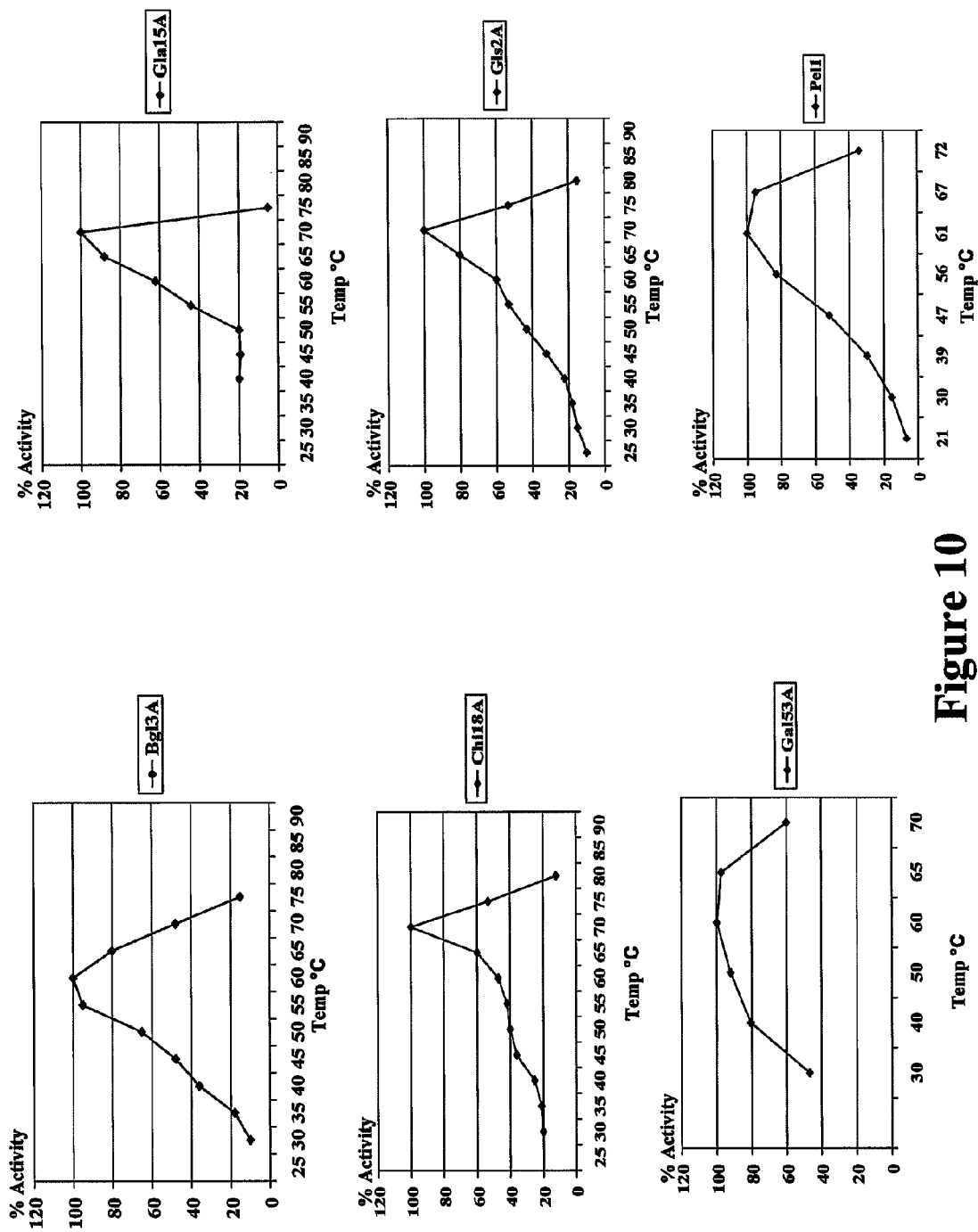
FIG. 10 illustrates the enzymatic activity (percentage of maximum) of enzymes of the present invention at varying temperature levels.

The temperature/pH that exhibited the highest enzyme activity was set at 100% in the tables below, with the remaining values expressed a percentage of this standard. The pH and temperature dependencies of certain enzymes are also illustrated graphically in FIGS. 9 and 10, respectively.

TABLE 19 pH Dependency of C1 Enzymes (% Activity)

| pH | BgI3A | Gla15A | Chi18A | Gls2a | pH | Gal 53A[1] | pH | Gal 53A[2] | pH | Pel1 |
|---|---|---|---|---|---|---|---|---|---|---|
| 2.0 | 2 | | | | | | | | | |
| 2.6 | 50 | 37 | | | 2.45 | 39.5 | 2.9 | 0.3 | | |
| 3.0 | 70 | 43 | 2 | 0 | 2.73 | 55.6 | 3.51 | 26.5 | | |
| 3.53 | 90 | 51 | 2 | 3 | 3.5 | 70.4 | 4.22 | 93.9 | 7.25 | 2.8 |
| 4.0 | 100 | 78 | 2 | 10.3 | 4.05 | 89.3 | 4.62 | 97.4 | 7.75 | 41.9 |
| 4.57 | 98 | 90 | 8 | 40 | 4.5 | 100.0 | 4.90 | 97.7 | 8.05 | 70.5 |
| 5.0 | 93 | 97 | 20 | 50 | 4.95 | 75.6 | 5.45 | 100 | 8.18 | 88.8 |
| 5.5 | 83 | 100 | 30 | 64 | 5.5 | 70.6 | 6.02 | 95.8 | 8.42 | 100 |
| 6.0 | 72 | 96 | 57 | 100 | 6.02 | 48.2 | 6.51 | 91.6 | 8.88 | 49.6 |
| 6.5 | 58 | 83 | 62 | 65 | 6.47 | 34.5 | 7.03 | 71.9 | 8.99 | 33 |
| 7.0 | 47 | 50 | 83 | 37.8 | 7.03 | 19.8 | 7.50 | 51.7 | 9.5 | 5 |
| 7.5 | 30 | 25 | 100 | | 7.5 | 17.8 | 8.00 | 42.2 | | |
| 8 | 17 | 1 | 98 | | 9.04 | 17.1 | 9.11 | 1.7 | | |
| 9 | | | 25 | | | | | | | |

TABLE 20

Temperature Dependency of C1 Enzymes (% Activity)

| Temp °C. | BgI3A | Gla15A | Chi18A | Gls2a | Gal 53A[1] | Temp °C. | PeI1 |
|---|---|---|---|---|---|---|---|
| 25 |  |  |  | 10 |  | 21 | 6.9 |
| 30 | 10 |  | 20 | 15 | 46.6 | 30 | 15.2 |
| 35 | 18 |  | 21 | 18 |  |  |  |
| 40 | 36 | 20 | 25 | 22 | 80.3 | 39 | 29.6 |
| 45 | 48 | 19 | 36 | 32 |  | 47 | 51.5 |
| 50 | 65 | 20 | 40 | 43 | 92.1 |  |  |
| 55 | 95 | 44 | 42 | 53 |  | 56 | 82.5 |
| 60 | 100 | 62 | 47 | 60 | 100 | 61 | 100 |
| 65 | 80 | 88 | 60 | 80 | 97.1 | 67 | 94.8 |
| 70 | 48 | 100 | 100 | 100 | 59.8 | 72 | 33.9 |
| 75 | 15 | 5 | 53 | 53 |  |  |  |
| 80 |  |  | 12 | 15 |  |  |  |
| 85 |  |  |  |  |  |  |  |
| 90 |  |  |  |  |  |  |  |

As used herein, reference to an isolated protein or polypeptide in the present invention, including any of the enzymes disclosed herein, includes full-length proteins, fusion proteins, or any fragment or homologue of such a protein. More specifically, an isolated protein, such as an enzyme according to the present invention, is a protein (including a polypeptide or peptide) that has been removed from its natural milieu (i.e., that has been subject to human manipulation) and can include purified proteins, partially purified proteins, recombinantly produced proteins, synthetically produced proteins, proteins complexed with lipids, soluble proteins, and isolated proteins associated with other proteins, for example. As such, "isolated" does not reflect the extent to which the protein has been purified. Preferably, an isolated protein of the present invention is produced recombinantly. In addition, and by way of example, a "C. lucknowens protein" or "C. lucknowens enzyme" refers to a protein (generally including a homologue of a naturally occurring protein) from Chrysosporium lucknowense or to a protein that has been otherwise produced from the knowledge of the structure (e.g., sequence) and perhaps the function of a naturally occurring protein from Chrysosporium lucknowense. In other words, a C. lucknowens protein includes any protein that has substantially similar structure and function of a naturally occurring C. lucknowens protein or that is a biologically active (i.e., has biological activity) homologue of a naturally occurring protein from C. lucknowens as described in detail herein. As such, a C. lucknowens protein can include purified, partially purified, recombinant, mutated/modified and synthetic proteins. According to the present invention, the terms "modification" and "mutation" can be used interchangeably, particularly with regard to the modifications/mutations to the amino acid sequence of a C. lucknowens protein (or nucleic acid sequences) described herein. An isolated protein according to the present invention can be isolated from its natural source, produced recombinantly or produced synthetically.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with another compound. Such modifications can be considered to be mutations, for example, if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in protein homologues, as compared to the wild-type protein, either agonize, antagonize, or do not substantially change, the basic biological activity of the homologue as compared to the naturally occurring protein. Modifications of a protein, such as in a homologue, may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to the present invention, an isolated protein, including a biologically active homologue or fragment thereof, has at least one characteristic of biological activity of a wild-type, or naturally occurring, protein. As discussed above, in general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). The biological activity of a protein of the present invention can include an enzyme activity (catalytic activity and/or substrate binding activity), such as cellulase activity, hemicellulase activity, β-glucanase activity, β-glucosidase activity, α-galactosidase activity, β-galactosidase activity, xylanase activity or any other activity disclosed herein. Specific biological activities of the proteins disclosed herein are described in detail above and in the Examples. Methods of detecting and measuring the biological activity of a protein of the invention include, but are not limited to, the assays described in the Examples section below. Such assays include, but are not limited to, measurement of enzyme activity (e.g., catalytic activity), measurement of substrate binding, and the like. It is noted that an isolated protein of the present invention (including homologues) is not required to have a biological activity such as catalytic activity. A protein can be a truncated, mutated or inactive protein, or lack at least one activity of the wild-type enzyme, for example. Inactive proteins may be useful in some screening assays, for example, or for other purposes such as antibody production.

Methods to measure protein expression levels of a protein according to the invention include, but are not limited to: western blotting, immunocytochemistry, flow cytometry or other immunologic-based assays; assays based on a property of the protein including but not limited to, ligand binding or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

Many of the enzymes and proteins of the present invention may be desirable targets for modification and use in the processes described herein. These proteins have been described in terms of function and amino acid sequence (and nucleic acid sequence encoding the same) of representative wild-type proteins. In one embodiment of the invention, homologues of a given protein (which can include related proteins from other organisms or modified forms of the given protein) are encompassed for use in the invention. Homologues of a protein encompassed by the present invention can comprise, consist essentially of, or consist of, in one embodiment, an amino acid sequence that is at least about 35% identical, and more preferably at least about 40% identical, and more preferably at least about 45% identical, and more preferably at least about 50% identical, and more preferably at least about 55% identical, and more preferably at least about 60% identical, and more preferably at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical, or any percent identity between 35% and 99%, in whole integers (i.e., 36%, 37%, etc.), to an amino acid sequence disclosed herein that represents the amino acid sequence of an enzyme or protein according to the invention (including a biologically active domain of a full-length protein). Preferably, the amino acid sequence of the homologue has a biological activity of the wild-type or reference protein or of a biologically active domain thereof (e.g., a catalytic domain).

In one embodiment, a protein of the present invention comprises, consists essentially of, or consists of an amino acid sequence that is less than 100% identical to an amino acid sequence selected from: SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, or SEQ ID NO:94 (i.e., a homologue). In another aspect of the invention, a homologue according to the present invention has an amino acid sequence that is less than about 99% identical to any of such amino acid sequences, and in another embodiment, is less than about 98% identical to any of such amino acid sequences, and in another embodiment, is less than about 97% identical to any of such amino acid sequences, and in another embodiment, is less than about 96% identical to any of such amino acid sequences, and in another embodiment, is less than about 95% identical to any of such amino acid sequences, and in another embodiment, is less than about 94% identical to any of such amino acid sequences, and in another embodiment, is less than about 93% identical to any of such amino acid sequences, and in another embodiment, is less than about 92% identical to any of such amino acid sequences, and in another embodiment, is less than about 91% identical to any of such amino acid sequences, and in another embodiment, is less than about 90% identical to any of such amino acid sequences, and so on, in increments of whole integers.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) PSI-BLAST with the standard default parameters (Position-Specific Iterated BLAST; and/or (4) CAZy homology determined using standard default parameters from the Carbohydrate Active EnZymes database (Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12).

It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
 Reward for match=1
 Penalty for mismatch=−2
 Open gap (5) and extension gap (2) penalties
 gap x_dropoff (50) expect (10) word size (11) filter (on)
For blastp, using 0 BLOSUM62 matrix:
 Open gap (11) and extension gap (1) penalties
 gap x_dropoff (50) expect (10) word size (3) filter (on).

A protein of the present invention can also include proteins having an amino acid sequence comprising at least 10 contiguous amino acid residues of any of the sequences described herein (i.e., 10 contiguous amino acid residues having 100% identity with 10 contiguous amino acids of SEQ ID NO:2). In other embodiments, a homologue of a protein amino acid sequence includes amino acid sequences comprising at least 20, or at least 30, or at least 40, or at least 50, or at least 75, or at least 100, or at least 125, or at least 150, or at least 175, or at least 150, or at least 200, or at least 250, or at least 300, or at least 350 contiguous amino acid residues of any of the amino acid sequence represented disclosed herein. Even small fragments of proteins without biological activity are useful in the present invention, for example, in the preparation of antibodies against the full-length protein or in a screening assay (e.g., a binding assay). Fragments can also be used to construct fusion proteins, for example, where the fusion protein comprises functional domains from two or more different proteins (e.g., a CBD from one protein linked to a CD from another protein). In one embodiment, a homologue has a measurable or detectable biological activity associated with the wild-type protein (e.g., enzymatic activity).

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a protein of the present invention, including a homologue, includes a protein having an amino acid sequence that is sufficiently similar to a natural amino acid sequence that a nucleic acid sequence encoding the homologue is capable of hybridizing under moderate, high or very high stringency conditions (described below) to (i.e., with) a nucleic acid molecule encoding the natural protein (i.e., to the complement of the nucleic acid strand encoding the natural amino acid sequence). Preferably, a homologue of a protein of the present invention is encoded by a nucleic acid molecule comprising a nucleic acid sequence that hybridizes under low, moderate, or high stringency conditions to the complement of a nucleic acid sequence that encodes a protein comprising, consisting essentially of, or consisting of, an amino acid sequence represented by any of: SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, or SEQ ID NO:94. Such hybridization conditions are described in detail below.

A nucleic acid sequence complement of nucleic acid sequence encoding a protein of the present invention refers to the nucleic acid sequence of the nucleic acid strand that is complementary to the strand which encodes the protein. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence such as SEQ ID NO:2, and/or with the complement of the nucleic acid sequence that encodes an amino acid sequence such as SEQ ID NO:2. Methods to deduce a complementary sequence are known to those skilled in the art. It should be noted that since nucleic acid sequencing technologies are not entirely error-free, the sequences presented herein, at best, represent apparent sequences of the proteins of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×–0.5×SSC, followed by at least one wash at about 68° C. in about 0.1×–0.5×SSC).

The minimum size of a protein and/or homologue of the present invention is a size sufficient to have biological activity or, when the protein is not required to have such activity, sufficient to be useful for another purpose associated with a protein of the present invention, such as for the production of antibodies that bind to a naturally occurring protein. In one embodiment, the protein of the present invention is at least 20 amino acids in length, or at least about 25 amino acids in length, or at least about 30 amino acids in length, or at least about 40 amino acids in length, or at least about 50 amino acids in length, or at least about 60 amino acids in length, or at least about 70 amino acids in length, or at least about 80 amino acids in length, or at least about 90 amino acids in length, or at least about 100 amino acids in length, or at least about 125 amino acids in length, or at least about 150 amino acids in length, or at least about 175 amino acids in length, or at least about 200 amino acids in length, or at least about 250 amino acids in length, and so on up to a full length of each protein, and including any size in between in increments of one whole integer (one amino acid). There is no limit, other than a practical limit, on the maximum size of such a protein in that the protein can include a portion of a protein or a full-length protein, plus additional sequence (e.g., a fusion protein sequence), if desired.

The present invention also includes a fusion protein that includes a domain of a protein of the present invention (including a homologue) attached to one or more fusion segments, which are typically heterologous in sequence to the protein sequence (i.e., different than protein sequence). Suitable fusion segments for use with the present invention include, but are not limited to, segments that can: enhance a protein's stability; provide other desirable biological activity; and/or assist with the purification of the protein (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the domain of a protein of the present invention and can be susceptible to cleavage in order to enable straight-forward recovery of the protein. Fusion proteins are preferably produced by culturing a recombinant cell transfected with a fusion nucleic acid molecule that encodes a protein including the fusion segment attached to either the carboxyl and/or amino terminal end of a domain of a protein of the present invention. Accordingly, proteins of the present invention also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of a membrane protein, or genes having signal sequences removed which are poorly tolerated in a particular recombinant host).

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived.

The present invention also provides enzyme combinations that break down lignocellulose material. Such enzyme combinations or mixtures can include a multi-enzyme composition that contains at least one protein of the present invention in combination with one or more additional proteins of the present invention or one or more enzymes or other proteins from other microorganisms, plants, or similar organisms. Synergistic enzyme combinations and related methods are contemplated. The invention includes methods to identify the optimum ratios and compositions of enzymes with which to degrade each lignocellulosic material. These methods entail tests to identify the optimum enzyme composition and ratios for efficient conversion of any lignocellulosic substrate to its constituent sugars. The Examples below include assays that may be used to identify optimum ratios and compositions of enzymes with which to degrade lignocellulosic materials.

Any combination of the proteins disclosed herein is suitable for use in the multi-enzyme compositions of the present invention. Due to the complex nature of most biomass sources, which can contain xylan, lignin, protein, and carbohydrates, among other components, preferred enzyme combinations may contain enzymes with a range of substrate specificities that work together to degrade biomass into fermentable sugars in the most efficient manner. One example of a multi-enzyme complex for lignocellulose saccharification is a mixture of cellobiohydrolase(s), xylanase(s), endoglucanase(s), β-glucosidase(s), β-xylosidase(s), and accessory enzymes. However, it is to be understood that any of the enzymes described specifically herein can be combined with any one or more of the enzymes described herein or with any other available and suitable enzymes, to produce a multi-enzyme composition. The invention is not restricted or limited to the specific exemplary combinations listed below.

In one embodiment, the cellobiohydrolase(s) comprise between about 30% and about 90% or between about 50% and about 70% of the enzymes in the composition, and more preferably, between about 55% and 65%, and more preferably, about 60% of the enzymes in the composition (including any percentage between 50% and 70% in 0.5% increments (e.g., 50%, 50.5%, 51%, etc.).

In one embodiment, the xylanase(s) comprise between about 10% and about 30% of the enzymes in the composition, and more preferably, between about 15% and about 25%, and more preferably, about 20% of the enzymes in the composition (including any percentage between 10% and 30% in 0.5% increments).

In one embodiment, the endoglucanase(s) comprise between about 5% and about 15% of the enzymes in the composition, and more preferably, between about 7% and about 13%, and more preferably, about 10% of the enzymes in the composition (including any percentage between 5% and 15% in 0.5% increments).

In one embodiment, the β-glucosidase(s) comprise between about 1% and about 5% of the enzymes in the composition, and preferably between about 2% and 4%, and more preferably, about 3% of the enzymes in the composition (including any percentage between 1% and 5% in 0.5% increments).

In one embodiment, the β-xylosidase(s) comprise between about 1% and about 3% of the enzymes in the composition, and preferably, between about 1.5% and about 2.5%, and more preferably, about 2% of the enzymes in the composition (including any percentage between 1% and 3% in 0.5% increments.

In one embodiment, the accessory enzymes comprise between about 2% and about 8% of the enzymes in the composition, and preferably, between about 3% and about 7%, and more preferably, about 5% of the enzymes in the composition (including any percentage between 2% and 8% in 0.5% increments.

One particularly preferred example of a multi-enzyme complex for lignocellulose saccharification is a mixture of about 60% cellobiohydrolase(s), about 20% xylanase(s), about 10% endoglucanase(s), about 3% β-glucosidase(s), about 2% β-xylosidase(s) and about 5% accessory enzyme (s).

The multi-enzyme composition may comprise at least one cellobiohydrolase. In some embodiments, the cellobiohydrolase may have an amino acid sequence selected from SEQ ID NO:2, SEQ ID NO:5, SEQ ID NO:8 SEQ ID NO:11 or a homologue, fusion protein, or fragment thereof that has cellobiohydrolase activity. Compositions comprising at least 2, 3, 4, 5, 6, 7, 8, 9 or 10 or more cellobiohydrolases are contemplated by the invention.

The multi-enzyme composition may comprise at least one endoglucanase. In certain embodiments, the endoglucanase may have an amino acid sequence selected from SEQ ID NO:14, SEQ ID NO:94, SEQ ID NO:17, SEQ ID NO:20 or SEQ ID NO:23 or a homologue, fusion protein, or fragment thereof that has endoglucanase activity. Compositions comprising at least 2, 3, 4, 5, 6, 7, 8, 9 or 10 or more endoglucanases are contemplated by the invention.

The multi-enzyme composition may comprise at least one xylanase. In some embodiments, the xylanase may have an amino acid sequence selected from SEQ ID NO:26, SEQ ID NO:29, SEQ ID NO:32, SEQ ID NO:35, SEQ ID NO:38 or SEQ ID NO:41 or a homologue, fusion protein, or fragment thereof that has xylanase activity. Compositions comprising at least 2, 3, 4, 5, 6, 7, 8, 9 or 10 or more xylanases are contemplated by the invention.

The multi-enzyme composition may further comprise a β-glucosidase. In one embodiment, the β-glucosidase may have an amino acid sequence of SEQ ID NO:44 or a homologue, fusion protein, or fragment thereof that has β-glucosidase activity. Compositions comprising at least 2, 3, 4, 5, 6, 7, 8, 9 or 10 or more β-glucosidases are contemplated by the invention.

The multi-enzyme composition of may further comprise a hemicellulase. In certain embodiments, the hemicellulase may have an amino acid sequence selected from SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, or a homologue, fusion protein, or fragment thereof that has a hemicellulase activity. Compositions comprising at least 2, 3, 4, 5, 6, 7, 8, 9 or 10 or more hemicellulases are contemplated by the invention.

One or more components of a multi-enzyme composition (other than proteins of the present invention) can be obtained from or derived from a microbial, plant, or other source or combination thereof, and will contain enzymes capable of degrading lignocellulosic material. Examples of enzymes included in the multi-enzyme compositions of the invention include cellulases, hemicellulases (such as xylanases, including endoxylanases, exoxylanase, and β-xylosidase), ligninases, amylases, glucuronidases, proteases, esterases (including ferulic acid esterase), lipases, glucosidases (such as β-glucosidase), glucomannanases, and xylogluconases.

While the multi-enzyme composition may contain many types of enzymes, mixtures comprising enzymes that increase or enhance sugar release from biomass are preferred, including hemicellulases. In one embodiment, the hemicellulase is selected from a xylanase, an arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xylogluconase, or mixtures of any of these. In particular, the enzymes can include glucoamylase, β-xylosidase and/or β-glucosidase. The enzymes of the multi-enzyme composition can be provided by a variety of sources. In one embodiment, the enzymes can be produced by a growing microorganisms or plants which produce the enzymes naturally or by virtue of being genetically modified to express the enzyme or enzymes. In another embodiment, at least one enzyme of the multi-enzyme composition is a commercially available enzyme.

In some embodiments, the multi-enzyme compositions comprise an accessory enzyme. An accessory enzyme is any additional enzyme capable of hydrolyzing lignocellulose or enhancing or promoting the hydrolysis of lignocellulose, wherein the accessory enzyme is typically provided in addition to a core enzyme or core set of enzymes. An accessory enzyme can have the same or similar function or a different function as an enzyme or enzymes in the core set of enzymes. These enzymes have been described elsewhere herein, and can generally include cellulases, xylanases, ligninases, amylases, lipidases, or glucuronidases, for example. Accessory enzymes can include enzymes that when contacted with biomass in a reaction, allow for an increase in the activity of enzymes (e.g., hemicellulases) in the multi-enzyme composition. An accessory enzyme or enzyme mix may be composed of enzymes from (1) commercial suppliers; (2) cloned genes expressing enzymes; (3) complex broth (such as that resulting from growth of a microbial strain in media, wherein the strains secrete proteins and enzymes into the media); (4) cell lysates of strains grown as in (3); and, (5) plant material expressing enzymes capable of degrading lignocellulose. In some embodiments, the accessory enzyme is a glucoamylase, a pectinase, or a ligninase.

As used herein, a ligninase is an enzyme that can hydrolyze or break down the structure of lignin polymers, including lignin peroxidases, manganese peroxidases, laccases, and other enzymes described in the art known to depolymerize or otherwise break lignin polymers. Also included are enzymes capable of hydrolyzing bonds formed between hemicellulosic sugars (notably arabinose) and lignin.

In one embodiment, the multi-enzyme composition comprises the enzyme CBH Ia (SEQ ID NO:2), a biologically active (e.g., has enzyme activity) homologue thereof, or a fragment comprising, consisting essentially of, or consisting of the CD thereof. In another embodiment, the multi-enzyme composition comprises the enzyme CBH IIb (SEQ ID NO:11), a biologically active homologue thereof, or a fragment comprising, consisting essentially of, or consisting of the CD thereof. In another embodiment, the multi-enzyme composition comprises the enzyme EG II (SEQ ID NO:94), a biologically active homologue thereof, or a fragment comprising, consisting essentially of, or consisting of the CD thereof. In a further embodiment, the multi-enzyme composition comprises the enzyme Xyl 2 (SEQ ID NO:29), a biologically active homologue thereof, or a fragment comprising, consisting essentially of, or consisting of the CD thereof. In yet another embodiment, the multi-enzyme composition comprises the enzyme β-glucosidase (SEQ ID NO:44), a biologically active homologue thereof, or a fragment comprising, consisting essentially of, or consisting of the CD thereof. In certain embodiments, the multi-enzyme composition comprises any combination of the enzymes listed above. In other embodiments, the multi-enzyme composition comprises at least one of the enzymes listed above in combination with a xylosidase enzyme.

In one embodiment, the multi-enzyme composition comprises CBH Ia (SEQ ID NO:2), CBH IIb (SEQ ID NO:11), EG II (SEQ ID NO:94), the CD of Xyl 2 (SEQ ID NO:29) and the CD of β-glucosidase (SEQ ID NO:44). This preferred enzyme combination may further comprise a β-xylosidase enzyme. One of skill in the art will appreciate, however, that any enzyme in the combinations described above may be replaced with an enzyme exhibiting a similar substrate specificity. Further, the optimal enzyme combination for a particular use (e.g., for degradation of a biomass derived from a specific source) can be determined by one of skill in the art using routine experimentation and assays known in the art, such as those disclosed herein.

In one embodiment, the multi-enzyme composition comprises the enzyme CBH Ib (SEQ ID NO:5), a biologically active homologue thereof, or a fragment comprising, consisting essentially of, or consisting of the CD thereof. In an additional embodiment, the multi-enzyme composition comprises the enzyme EG V (SEQ ID NO:20), a biologically active homologue thereof, or a fragment comprising, consisting essentially of, or consisting of the CD thereof. In still another embodiment, the multi-enzyme composition comprises the enzyme Xyl 1 (SEQ ID NO:26), a biologically active homologue thereof, or a fragment comprising, consisting essentially of, or consisting of the CD thereof. In further embodiments, the multi-enzyme composition comprises the enzyme arabinogalactanase (SEQ ID NO:47), a biologically active homologue thereof, or a fragment comprising, consisting essentially of, or consisting of the CD thereof. In certain embodiments, the multi-enzyme composition comprises any combination of the enzymes listed above. In other embodiments, the multi-enzyme composition comprises at least one of the enzymes listed above in combination with at least one accessory enzyme such as, for example, α-L-arabinofuranosidase.

In a preferred embodiment, the multi-enzyme composition comprises the CD of CBH Ib (SEQ ID NO:5), the CD of EG V (SEQ ID NO:20), the CD of Xyl 1 (SEQ ID NO:26) and the CD of arabinogalactanase (SEQ ID NO:47). This preferred enzyme combination may further comprise at least one accessory enzyme. One of skill in the art will appreciate, however, that any enzyme in the combinations described above may be replaced with an enzyme exhibiting a similar substrate specificity. Further, the optimal enzyme combination for a particular use (e.g., for degradation of a biomass derived from a specific source) can be determined by one of skill in the art using routine experimentation and assays known in the art, such as those disclosed herein.

The multi-enzyme compositions, in some embodiments, comprise a biomass comprising microorganisms or a crude fermentation product of microorganisms. A crude fermentation product refers to the fermentation broth which has been separated from the microorganism biomass (by filtration, for example). In general, the microorganisms are grown in fermentors, optionally centrifuged or filtered to remove biomass, and optionally concentrated, formulated, and dried to produce an enzyme(s) or a multi-enzyme composition that is a crude fermentation product. In other embodiments, enzyme(s) or multi-enzyme compositions produced by the microorganism (including a genetically modified microorganism as described below) are subjected to one or more purification steps, such as ammonium sulfate precipitation, chromatography, and/or ultrafiltration, which result in a partially purified or purified enzyme(s). If the microorganism has been genetically modified to express the enzyme(s), the enzyme(s) will include recombinant enzymes. If the genetically modified microorganism also naturally expresses the enzyme(s) or other enzymes useful for lignocellulosic saccharification, the enzyme(s) may include both naturally occurring and recombinant enzymes.

Another embodiment of the present invention relates to a composition comprising at least about 500 ng, and preferably at least about 1 µg, and more preferably at least about 5 µg, and more preferably at least about 10 µg, and more preferably at least about 25 µg, and more preferably at least about 50 µg, and more preferably at least about 75 µg, and more preferably at least about 100 µg, and more preferably at least about 250 µg, and more preferably at least about 500 µg, and more preferably at least about 750 µg, and more preferably at least about 1 mg, and more preferably at least about 5 mg, of an isolated protein comprising any of the proteins or homologues or fragments thereof discussed herein. Such a composition of the present invention may include any carrier with which the protein is associated by virtue of the protein preparation method, a protein purification method, or a preparation of the protein for use in any method according to the present invention. For example, such a carrier can include any suitable buffer, extract, or medium that is suitable for combining with the protein of the present invention so that the protein can be used in any method described herein according to the present invention.

In one embodiment of the invention, one or more enzymes of the invention is bound to a solid support, i.e., an immobilized enzyme. As used herein, an immobilized enzyme includes immobilized isolated enzymes, immobilized microbial cells which contain one or more enzymes of the invention, other stabilized intact cells that produce one or more enzymes of the invention, and stabilized cell/membrane homogenates. Stabilized intact cells and stabilized cell/membrane homogenates include cells and homogenates from naturally occurring microorganisms expressing the enzymes of the invention and preferably, from genetically modified microorganisms as disclosed elsewhere herein. Thus, although methods for immobilizing enzymes are discussed below, it will be appreciated that such methods are equally applicable to immobilizing microbial cells and in such an embodiment, the cells can be lysed, if desired.

A variety of methods for immobilizing an enzyme are disclosed in Industrial Enzymology 2nd Ed., Godfrey, T. and West, S. Eds., Stockton Press, New York, N.Y., 1996, pp. 267-272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, Calif., 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic, biopolymer or inorganic supports that can form a bond with an enzyme without significantly effecting the activity of the enzyme. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. In one embodiment, the solid support is selected from the group consisting of stabilized intact cells and/or crude cell homogenates (e.g., produced from the microbial host cells expressing recombinant enzymes, alone or in combination with natural enzymes). Preparation of such supports requires a minimum of handling and cost. Additionally, such supports provide excellent stability of the enzyme.

Stabilized intact cells and/or cell/membrane homogenates can be produced, for example, by using bifunctional crosslinkers (e.g., glutaraldehyde) to stabilize cells and cell homogenates. In both the intact cells and the cell membranes, the cell wall and membranes act as immobilizing supports. In such a system, integral membrane proteins are in the "best" lipid membrane environment. Whether starting with intact cells or homogenates, in this system the cells are either no longer "alive" or "metabolizing", or alternatively, are "resting" (i.e., the cells maintain metabolic potential and active enzyme, but under the culture conditions are not growing); in either case, the immobilized cells or membranes serve as biocatalysts.

An enzyme of the invention can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports in a bead form are particularly well-suited. The particle size of an adsorption solid support can be selected such that the immobilized enzyme is retained in the reactor by a mesh filter while the substrate is allowed to flow through the reactor at a desired rate. With porous particulate supports it is possible to control the adsorption process to allow enzymes or cells to be embedded within the cavity of the particle, thus providing protection without an unacceptable loss of activity.

Cross-linking of an enzyme to a solid support involves forming a chemical bond between a solid support and the enzyme. It will be appreciated that although cross-linking generally involves linking the enzyme to a solid support using an intermediary compound, it is also possible to achieve a covalent bonding between the enzyme and the solid support directly without the use of an intermediary compound. Cross-linking commonly uses a bifunctional or multifunctional reagent to activate and attach a carboxyl group, amino group, sulfur group, hydroxy group or other functional group of the enzyme to the solid support. The term "activate" refers to a chemical transformation of a functional group which allows a formation of a bond at the functional group. Exemplary amino group activating reagents include water-soluble carbodiimides, glutaraldehyde, cyanogen bromide, N-hydroxysuccinimide esters, triazines, cyanuric chloride, and carbonyl diimidazole. Exemplary carboxyl group activating reagents include water-soluble carbodiimides, and N-ethyl-5-phenyl-isoxazolium-3-sulfonate. Exemplary tyrosyl group activating reagents include diazonium compounds. And exemplary sulfhydryl group activating reagents include dithiobis-5,5'-(2-nitrobenzoic acid), and glutathione-2-pyridyl disulfide. Systems for covalently linking an enzyme directly to a solid support include Eupergit®, a polymethacrylate bead support available from Rohm Pharma (Darmstadt, Germany), kieselguhl (Macrosorbs), available from Sterling Organics, kaolinite available from English China Clay as "Biofix" supports, silica gels which can be activated by silanization, available from W. R. Grace, and high-density alumina, available from UOP (Des Plains, Ill.).

Entrapment can also be used to immobilize an enzyme. Entrapment of an enzyme involves formation of, inter alia, gels (using organic or biological polymers), vesicles (including microencapsulation), semipermeable membranes or other matrices. Exemplary materials used for entrapment of an enzyme include collagen, gelatin, agar, cellulose triacetate, alginate, polyacrylamide, polystyrene, polyurethane, epoxy resins, carrageenan, and egg albumin. Some of the polymers, in particular cellulose triacetate, can be used to entrap the enzyme as they are spun into a fiber. Other materials such as polyacrylamide gels can be polymerized in solution to entrap the enzyme. Still other materials such as polyglycol oligomers that are functionalized with polymerizable vinyl end groups can entrap enzymes by forming a cross-linked polymer with UV light illumination in the presence of a photo sensitizer.

Further embodiments of the present invention include nucleic acid molecules that encode a protein of the present invention, as well as homologues or fragments of such nucleic acid molecules. A nucleic acid molecule of the present invention includes a nucleic acid molecule comprising, consisting essentially of, or consisting of, a nucleic acid sequence encoding any of the isolated proteins disclosed herein, including a fragment or a homologue of such proteins, described above. Nucleic acid molecules can include a nucleic acid sequence that encodes a fragment of a protein that does not have biological activity, and can also include portions of a gene or polynucleotide encoding the protein that are not part of the coding region for the protein (e.g., introns or regulatory regions of a gene encoding the protein). Nucleic acid molecules can include a nucleic acid sequence that is useful as a probe or primer (oligonucleotide sequences).

In one embodiment, a nucleic molecule of the present invention includes a nucleic acid molecule comprising, consisting essentially of, or consisting of, a nucleic acid sequence represented by SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:41, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:70, SEQ ID NO:72, SEQ ID NO:73, SEQ ID NO:75, SEQ ID NO:76, SEQ ID NO:78, SEQ ID NO:79, SEQ ID NO:90, SEQ ID NO:91, SEQ ID NO:93, or fragments or homologues thereof. Preferably, the nucleic acid sequence encodes a protein (including fragments and homologues thereof) useful in the invention, or encompasses useful oligonucleotides or complementary nucleic acid sequences.

In one embodiment, a nucleic molecule of the present invention includes a nucleic acid molecule comprising, consisting essentially of, or consisting of, a nucleic acid sequence encoding an amino acid sequence represented by SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:94 or fragments or homologues thereof. Preferably, the nucleic acid sequence encodes a protein (including fragments and homologues thereof) useful in the invention, or encompasses useful oligonucleotides or complementary nucleic acid sequences.

In one embodiment, such nucleic acid molecules include isolated nucleic acid molecules that hybridize under moderate stringency conditions, and more preferably under high stringency conditions, and even more preferably under very high stringency conditions, as described above, with the complement of a nucleic acid sequence encoding a protein of the present invention (i.e., including naturally occurring allelic variants encoding a protein of the present invention). Preferably, an isolated nucleic acid molecule encoding a protein of the present invention comprises a nucleic acid sequence that hybridizes under moderate, high, or very high stringency conditions to the complement of a nucleic acid sequence that encodes a protein comprising an amino acid sequence represented by SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, or SEQ ID NO:94.

In accordance with the present invention, an isolated nucleic acid molecule is a nucleic acid molecule (polynucleotide) that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule, and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. An isolated nucleic acid molecule of the present invention can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a protein of the present invention or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein of the present invention can vary due to degeneracies. It is noted that a nucleic acid molecule of the present invention is not required to encode a protein having protein activity. A nucleic acid molecule can encode a truncated, mutated or inactive protein, for example. In addition, nucleic acid molecules of the invention are useful as probes and primers for the identification, isolation and/or purification of other nucleic acid molecules. If the nucleic acid molecule is an oligonucleotide, such as a probe or primer, the oligonucleotide preferably ranges from about 5 to about 50 or about 500 nucleotides, more preferably from about 10 to about 40 nucleotides, and most preferably from about 15 to about 40 nucleotides in length.

According to the present invention, reference to a gene includes all nucleic acid sequences related to a natural (i.e. wild-type) gene, such as regulatory regions that control production of the protein encoded by that gene (such as, but not limited to, transcription, translation or post-translation control regions) as well as the coding region itself. In another embodiment, a gene can be a naturally occurring allelic variant that includes a similar but not identical sequence to the nucleic acid sequence encoding a given protein. Allelic variants have been previously described above. The phrases "nucleic acid molecule" and "gene" can be used interchangeably when the nucleic acid molecule comprises a gene as described above.

Preferably, an isolated nucleic acid molecule of the present invention is produced using recombinant DNA technology (e.g., polymerase chain reaction (PCR) amplification, cloning, etc.) or chemical synthesis. Isolated nucleic acid molecules include any nucleic acid molecules and homologues thereof that are part of a gene described herein and/or that encode a protein described herein, including, but not limited to, natural allelic variants and modified nucleic acid molecules (homologues) in which nucleotides have been inserted, deleted, substituted, and/or inverted in such a manner that such modifications provide the desired effect on protein biological activity or on the activity of the nucleic acid molecule. Allelic variants and protein homologues (e.g., proteins encoded by nucleic acid homologues) have been discussed in detail above.

A nucleic acid molecule homologue (i.e., encoding a homologue of a protein of the present invention) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a protein is gene shuffling (i.e., molecular breeding) (See, for example, U.S. Pat. No. 5,605,793 to Stemmer; Minshull and Stemmer; 1999, *Curr. Opin. Chem. Biol.* 3:284-290; Stemmer, 1994, *P.N.A.S. USA* 91:10747-10751, all of which are incorporated herein by reference in their entirety). This technique can be used to efficiently introduce multiple simultaneous changes in the protein. Nucleic acid molecule homologues can be selected by hybridization with a gene or polynucleotide, or by screening for the function of a protein encoded by a nucleic acid molecule (i.e., biological activity).

The minimum size of a nucleic acid molecule of the present invention is a size sufficient to encode a protein (including a fragment or homologue of a full-length protein) having biological activity, sufficient to encode a protein comprising at least one epitope which binds to an antibody, or sufficient to form a probe or oligonucleotide primer that is capable of forming a stable hybrid with the complementary sequence of a nucleic acid molecule encoding a natural protein (e.g., under moderate, high, or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein encoding sequence, a nucleic acid sequence encoding a full-length protein (including a gene), including any length fragment between about 20 nucleotides and the number of nucleotides that make up the full length cDNA encoding a protein, in whole integers (e.g., 20, 21, 22, 23, 24, 25 . . . nucleotides), or multiple genes, or portions thereof.

The phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

In one embodiment, the polynucleotide probes or primers of the invention are conjugated to detectable markers. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Preferably, the polynucleotide probes are immobilized on a substrate such as: artificial membranes, organic supports, biopolymer supports and inorganic supports.

One embodiment of the present invention relates to a recombinant nucleic acid molecule which comprises the isolated nucleic acid molecule described above which is operatively linked to at least one expression control sequence. More particularly, according to the present invention, a recombinant nucleic acid molecule typically comprises a recombinant vector and any one or more of the isolated nucleic acid molecules as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remain separate from the genome for most applications of the invention. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest, such as an enzyme of the present invention). In this embodiment, a nucleic acid sequence encoding the product to be produced (e.g., the protein or homologue thereof) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

Typically, a recombinant nucleic acid molecule includes at least one nucleic acid molecule of the present invention operatively linked to one or more expression control sequences (e.g., transcription control sequences or translation control sequences). As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is generally used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants and describes an inherited change due to the acquisition of exogenous nucleic acids by the microorganism that is essentially synonymous with the term "transfection." Transfection techniques include, but are not limited to, transformation, particle bombardment, electroporation, microinjection, lipofection, adsorption, infection and protoplast fusion.

One or more recombinant molecules of the present invention can be used to produce an encoded product (e.g., a protein) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., filamentous fungi or yeast), plant, insect, or animal cell that can be transfected. Host cells can be either untransfected cells or cells that are already transfected with at least one other recombinant nucleic acid molecule.

Suitable cells (e.g., a host cell or production organism) include any microorganism (e.g., a bacterium, a protist, an alga, a fungus, or other microbe), and is preferably a bacterium, a yeast or a filamentous fungus. Suitable bacterial genera include, but are not limited to, *Escherichia, Bacillus, Lactobacillus, Pseudomonas* and *Streptomyces*. Suitable bacterial species include, but are not limited to, *Escherichia coli, Bacillus subtilis, Bacillus licheniformis, Lactobacillus brevis, Pseudomonas aeruginosa* and *Streptomyces lividans*. Suitable genera of yeast include, but are not limited to, *Saccharomyces, Schizosaccharomyces, Candida, Hansenula, Pichia, Kluyveromyces*, and *Phaffia*. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus* and *Phaffia rhodozyma*.

Suitable fungal genera include, but are not limited to, *Chrysosporium, Thielavia, Neurospora, Aureobasidium, Filibasidium, Piromyces, Corynascus, Cryplococcus, Acremonium, Tolypocladium, Scytalidium, Schizophyllum, Sporotrichum, Penicillium, Gibberella, Myceliophthora, Mucor, Aspergillus, Fusarium, Humicola*, and *Trichoderma*, and anamorphs and teleomorphs thereof. Suitable fungal species include, but are not limited to, *Aspergillus niger, Aspergillus nidulans, Aspergillus japonicus, Absidia coerulea, Rhizopus oryzae, Chrysosporium lucknowense, Neurospora crassa, Neurospora intermedia, Trichoderma reesei, Penicillium canescens, Penicillium solitum, Penicillium funiculosum,* and *Talaromyces flavus*. In one embodiment, the host cell is a fungal cell of the species *Chrysosporium lucknowense*. In one embodiment, the host cell is a fungal cell of Strain C1 (VKM F-3500-D) or a mutant strain derived therefrom (e.g., UV13-6 (Accession No. VKM F-3632 D); NG7C-19 (Accession No. VKM F-3633 D); or UV18-25 (VKM F-3631D)). Host cells can be either untransfected cells or cells that are already transfected with at least one other recombinant nucleic acid molecule. Additional embodiments of the present invention include any of the genetically modified cells described herein.

In one embodiment, one or more protein(s) expressed by an isolated nucleic acid molecule of the present invention are produced by culturing a cell that expresses the protein (i.e., a recombinant cell or recombinant host cell) under conditions effective to produce the protein. In some instances, the protein may be recovered, and in others, the cell may be harvested in whole, either of which can be used in a composition.

Microorganisms used in the present invention (including recombinant host cells or genetically modified microorganisms) are cultured in an appropriate fermentation medium. An appropriate, or effective, fermentation medium refers to any medium in which a cell of the present invention, including a genetically modified microorganism (described below), when cultured, is capable of expressing enzymes useful in the present invention and/or of catalyzing the production of sugars from lignocellulosic biomass. Such a medium is typically an aqueous medium comprising assimilable carbon, nitrogen and phosphate sources. Such a medium can also include appropriate salts, minerals, metals and other nutrients. Microorganisms and other cells of the present invention can be cultured in conventional fermentation bioreactors. The microorganisms can be cultured by any fermentation process which includes, but is not limited to, batch, fed-batch, cell recycle, and continuous fermentation. The fermentation of microorganisms such as fungi may be carried out in any appropriate reactor, using methods known to those skilled in the art. For example, the fermentation may be carried out for a period of 1 to 14 days, or more preferably between about 3 and 10 days. The temperature of the medium is typically maintained between about 25 and 50° C., and more preferably between 28 and 40° C. The pH of the fermentation medium is regulated to a pH suitable for growth and protein production of the particular organism. The fermentor can be aerated in order to supply the oxygen necessary for fermentation and to avoid the excessive accumulation of carbon dioxide produced by fermentation. In addition, the aeration helps to control the temperature and the moisture of the culture medium. In general the fungal strains are grown in fermentors, optionally centrifuged or filtered to remove biomass, and optionally concentrated, formulated, and dried to produce an enzyme(s) or a multi-enzyme composition that is a crude fermentation product. Particularly suitable conditions for culturing filamentous fungi are described, for example, in U.S. Pat. Nos. 6,015,707 and 6,573,086, supra.

Depending on the vector and host system used for production, resultant proteins of the present invention may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced according to the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins of the present invention are preferably retrieved, obtained, and/or used in "substantially pure" form. As used herein, "substantially pure" refers to a purity that allows for the effective use of the protein in any method according to the present invention. For a protein to be useful in any of the methods described herein or in any method utilizing enzymes of the types described herein according to the present invention, it is substantially free of contaminants, other proteins and/or chemicals that might interfere or that would interfere with its use in a method disclosed by the present invention (e.g., that might interfere with enzyme activity), or that at least would be undesirable for inclusion with a protein of the present invention (including homologues) when it is used in a method disclosed by the present invention (described in detail below). Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the protein of interest is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

Another aspect of the present invention relates to a genetically modified microorganism that has been transfected with one or more nucleic acid molecules of the present invention. As used herein, a genetically modified microorganism can include a genetically modified bacterium, yeast, filamentous fungus, or other microbe. Such a genetically modified microorganism has a genome which is modified (i.e., mutated or changed) from its normal (i.e., wild-type or naturally occurring) form such that the desired result is achieved (i.e., increased or modified activity and/or production of at least one an enzyme or a multi-enzyme composition for the conversion of lignocellulosic material to fermentable sugars). Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press or *Molecular Cloning: A Laboratory Manual*, third edition (Sambrook and Russel, 2001), jointly referred to herein as "Sambrook"). The references of Sambrook, ibid., are incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

In one embodiment, a genetically modified microorganism can endogenously contain and express an enzyme or a multi-enzyme composition for the conversion of lignocellulosic material to fermentable sugars, and the genetic modification can be a genetic modification of one or more of such endogenous enzymes, whereby the modification has some effect on the ability of the microorganism to convert lignocellulosic material to fermentable sugars (e.g., increased expression of the protein by introduction of promoters or other expression control sequences, or modification of the coding region by homologous recombination to increase the activity of the encoded protein).

In another embodiment, a genetically modified microorganism can endogenously contain and express an enzyme for the conversion of lignocellulosic material to fermentable sugars, and the genetic modification can be an introduction of at least one exogenous nucleic acid sequence (e.g., a recombinant nucleic acid molecule), wherein the exogenous nucleic acid sequence encodes at least one additional enzyme useful for the conversion of lignocellulosic material to fermentable sugars and/or a protein that improves the efficiency of the enzyme for the conversion of lignocellulosic material to fermentable sugars. In this aspect of the invention, the microorganism can also have at least one modification to a gene or genes comprising its endogenous enzyme(s) for the conversion of lignocellulosic material to fermentable sugars.

In yet another embodiment, the genetically modified microorganism does not necessarily endogenously (naturally) contain an enzyme for the conversion of lignocellulosic material to fermentable sugars, but is genetically modified to introduce at least one recombinant nucleic acid molecule encoding at least one enzyme or a multiplicity of enzymes for the conversion of lignocellulosic material to fermentable sugars. Such a microorganism can be used in a method of the invention, or as a production microorganism for crude fermentation products, partially purified recombinant enzymes, and/or purified recombinant enzymes, any of which can then be used in a method of the present invention.

Once the proteins (enzymes) are expressed in a host cell, a cell extract that contains the activity to test can be generated. For example, a lysate from the host cell is produced, and the supernatant containing the activity is harvested and/or the activity can be isolated from the lysate. In the case of cells that secrete enzymes into the culture medium, the culture medium containing them can be harvested, and/or the activity can be purified from the culture medium. The extracts/activities prepared in this way can be tested using assays known in the art. Accordingly, methods to identify multi-enzyme compositions capable of degrading lignocellulosic biomass are provided.

Artificial substrates, or complex mixtures of polymeric carbohydrates and lignin, or actual lignocellulose can be used in such tests. One assay that may be used to measure the release of sugars and oligosaccharides from these complex substrates is the dinitrosalicylic acid assay (DNS). In this assay, the lignocellulosic material such as DDG is incubated with enzymes(s) for various times and reducing sugars are measured.

The invention also contemplates genetically modified plants transformed with one or more nucleic acid molecules of the invention. The plants may be used for production of the enzymes, and/or as the lignocellulosic material used as a substrate in the methods of the invention. Methods to generate recombinant plants are known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

Another generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

Another embodiment of the present invention relates to an isolated binding agent capable of selectively binding to a protein of the present invention. Suitable binding agents may be selected from an antibody, an antigen binding fragment, or a binding partner. The binding agent selectively binds to an amino acid sequence selected from SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, or SEQ ID NO:94, including to any fragment of any of the above sequences comprising at least one antibody binding epitope.

According to the present invention, the phrase "selectively binds to" refers to the ability of an antibody, antigen binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

Antibodies are characterized in that they comprise immunoglobulin domains and as such, they are members of the immunoglobulin superfamily of proteins. An antibody of the invention includes polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or $F(ab)_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention. Methods for the generation and production of antibodies are well known in the art.

Monoclonal antibodies may be produced according to the methodology of Kohler and Milstein (*Nature* 256:495-497, 1975). Non-antibody polypeptides, sometimes referred to as binding partners, are designed to bind specifically to a protein of the invention. Examples of the design of such polypeptides, which possess a prescribed ligand specificity are given in Beste et al. (*Proc. Natl. Acad. Sci.* 96:1898-1903, 1999), incorporated herein by reference in its entirety. In one embodiment, a binding agent of the invention is immobilized on a substrate such as: artificial membranes, organic supports, biopolymer supports and inorganic supports such as for use in a screening assay.

Proteins of the present invention, at least one protein of the present invention, compositions comprising such protein(s) of the present invention, and multi-enzyme compositions (examples of which are described above) may be used in any method where it is desirable to hydrolyze glycosidic linkages in lignocellulosic material, or any other method wherein enzymes of the same or similar function are useful.

In one embodiment, the present invention includes the use of at least one protein of the present invention, compositions comprising at least one protein of the present invention, or multi-enzyme compositions in methods for hydrolyzing lignocellulose and the generation of fermentable sugars therefrom. In one embodiment, the method comprises contacting the lignocellulosic material with an effective amount of one or more proteins of the present invention, composition comprising at least one protein of the present invention, or a multi-enzyme composition, whereby at least one fermentable sugar is produced (liberated). The lignocellulosic material may be partially or completely degraded to fermentable sugars. Economical levels of degradation at commercially viable costs are contemplated.

Typically, the amount of enzyme or enzyme composition contacted with the lignocellulose will depend upon the amount of glucan present in the lignocellulose. In some embodiments, the amount of enzyme or enzyme composition contacted with the lignocellulose may be from about 0.1 to about 200 mg enzyme or enzyme composition per gram of glucan; in other embodiments, from about 3 to about 20 mg enzyme or enzyme composition per gram of glucan. The invention encompasses the use of any suitable or sufficient amount of enzyme or enzyme composition between about 0.1 mg and about 200 mg enzyme per gram glucan, in increments of 0.05 mg (i.e., 0.1 mg, 0.15 mg, 0.2 mg . . . 199.9 mg, 199.95 mg, 200 mg).

In a further embodiment, the invention provides a method for degrading DDG, preferably, but not limited to, DDG derived from corn, to sugars. The method comprises contacting the DDG with a protein of the present invention, a composition comprising at least one protein of the present invention, or a multi-enzyme composition. In certain embodiments, at least 10% of fermentable sugars are liberated. In other embodiment, the at least 15% of the sugars are liberated, or at least 20% of the sugars are liberated, or at least 23% of the sugars are liberated, or at least 24% of the sugars are liberated, or at least 25% of the sugars are liberated, or at least 26% of the sugars are liberated, or at least 27% of the sugars are liberated, or at least 28% of the sugars are liberated.

In another embodiment, the invention provides a method for producing fermentable sugars comprising cultivating a genetically modified microorganism of the present invention in a nutrient medium comprising a lignocellulosic material, whereby fermentable sugars are produced.

Also provided are methods that comprise further contacting the lignocellulosic material with at least one accessory enzyme. Accessory enzymes have been described elsewhere herein. The accessory enzyme or enzymes may be added at the same time, prior to, or following the addition of a protein of the present invention, a composition comprising at least one protein of the present invention, or a multi-enzyme composition, or can be expressed (endogenously or overexpressed) in a genetically modified microorganism used in a method of the invention. When added simultaneously, the protein of the present invention, a composition comprising at least one protein of the present invention, or a multi-enzyme composition will be compatible with the accessory enzymes selected. When the enzymes are added following the treatment with the protein of the present invention, a composition comprising at least one protein of the present invention, or a multi-enzyme composition, the conditions (such as temperature and pH) may be altered to those optimal for the accessory enzyme before, during, or after addition of the accessory enzyme. Multiple rounds enzyme addition are also encompassed. The accessory enzyme may also be present in the lignocellulosic material itself as a result of genetically modifying the plant. The nutrient medium used in a fermentation can also comprise one or more accessory enzymes.

In some embodiments, the method comprises a pretreatment process. In general, a pretreatment process will result in components of the lignoncellulose being more accessible for downstream applications or so that it is more digestible by enzymes following treatment in the absence of hydrolysis. The pretreatment can be a chemical, physical or biological pretreatment. The lignocellulose may have been previously treated to release some or all of the sugars, as in the case of DDG. Physical treatments, such as grinding, boiling, freezing, milling, vacuum infiltration, and the like may also be used with the methods of the invention. In one embodiment, the heat treatment comprises heating the lignocellulosic material to 121° C. for 15 minutes. A physical treatment such as milling can allow a higher concentration of lignocellulose to be used in the methods of the invention. A higher concentration refers to about 20%, up to about 25%, up to about 30%, up to about 35%, up to about 40%, up to about 45%, or up to about 50% lignocellulose. The lignocellulose may also be contacted with a metal ion, ultraviolet light, ozone, and the like. Additional pretreatment processes are known to those skilled in the art, and can include, for example, organosolv treatment, steam explosion treatment, lime impregnation with steam explosion treatment, hydrogen peroxide treatment, hydrogen peroxide/ozone (peroxone) treatment, acid treatment, dilute acid treatment, and base treatment, including ammonia fiber explosion (AFEX) technology. Details on pretreatment technologies and processes can be found in Wyman et al., *Bioresource Tech.* 96:1959 (2005); Wyman et al., *Bioresource Tech.* 96:2026 (2005); Hsu, "Pretreatment of biomass" In Handbook on Bioethanol: Production and Utilization, Wyman, Taylor and Francis Eds., p. 179-212 (1996); and Mosier et al., *Bioresource Tech.* 96:673 (2005).

In an additional embodiment, the method comprises detoxifying the lignocellulosic material. Detoxification may be desirable in the event that inhibitors are present in the lignocellulosic material. Such inhibitors can be generated by a pretreatment process, deriving from sugar degradation or are direct released from the lignocellulose polymer. Detoxifying can include the reduction of their formation by adjusting sugar extraction conditions; the use of inhibitor-tolerant or inhibitor-degrading strains of microorganisms. Detoxifying can also be accomplished by the addition of ion exchange resins, active charcoal, enzymatic detoxification using, e.g., laccase, and the like. In some embodiments, the proteins, compositions or products of the present invention further comprises detoxifying agents.

In some embodiments, the methods may be performed one or more times in whole or in part. That is, one may perform one or more pretreatments, followed by one or more reactions with a protein of the present invention, composition or product of the present invention and/or accessory enzyme. The enzymes may be added in a single dose, or may be added in a series of small doses. Further, the entire process may be repeated one or more times as necessary. Therefore, one or more additional treatments with heat and enzymes are contemplated.

The methods described above result in the production of fermentable sugars. During, or subsequent to the methods described, the fermentable sugars may be recovered. In the case of a cultivation of microorganisms, the sugars can be recovered through a continuous, batch or fed-batch method. The sugars recovered can be concentrated or purified. Recovery may occur by any method known in the art, including, but not limited to, washing, gravity flow, pressure, chromatography, extraction, crystallization (e.g., evaporative crystallization), membrane separation, reverse osmosis, distillation, and filtration. The sugars can be subjected further processing; e.g., they can also be sterilized, for example, by filtration.

In a related embodiment, the invention provides means for improving quality of lignocellulosic material, including DDG for animal nutrition. In one embodiment, the treated lignocellulosic material (e.g., a lignocellulosic material which has been saccharified) is recovered (e.g., has the soluble sugars removed). The recovered material can be used as an animal feed additive. It is believed that the recovered material will have beneficial properties for animal nutrition, possibly due to a higher protein content. In some embodiments, the amount of enzyme or enzyme composition contacted with the lignocellulosic material may be from about 0.0001% to about 1.0% of the weight of the lignocellulosic material; in other embodiments, from about 0.005% to about 0.1% of the weight of the lignocellulosic material. The invention includes the use of any amount of enzyme or enzyme composition between about 0.0001% and about 1.0%, in increments of 0.0001 (i.e., 0.0001, 0.0002, 0.0003 . . . etc.).

In an additional embodiment, the invention provides a method for producing an organic substance, comprising saccharifying a lignocellulosic material with an effective amount of a protein of the present invention or a composition comprising at least one protein of the present invention, fermenting the saccharified lignocellulosic material obtained with one or more fermentating microorganisms, and recovering the organic substance from the fermentation. Sugars released from biomass can be converted to useful fermentation products including but not limited to amino acids, vitamins, pharmaceuticals, animal feed supplements, specialty chemicals, chemical feedstocks, plastics, solvents, fuels, or other organic polymers, lactic acid, and ethanol, including fuel ethanol. Specific products that may be produced by the methods of the invention include, but not limited to, biofuels (including ethanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; industrial enzymes, such as proteases, cellulases, amylases, glucanases, lactases, lipases, lyases, oxidoreductases, and transferases; and chemical feedstocks. The methods of the invention are also useful to generate feedstocks for fermentation by fermenting microorganisms. In one embodiment, the method further comprises the addition of at least one fermenting organism. As used herein, "fermenting organism" refers to an organism capable of fermentation, such as bacteria and fungi, including yeast. Such feedstocks have additional nutritive value above the nutritive value provided by the liberated sugars.

Proteins of the present invention and compositions comprising at least one protein of the present invention are also useful in a variety of other applications involving the hydrolysis of glycosidic linkages in lignocellulosic material, such as stone washing, color brightening, depilling and fabric softening, as well as other applications well known in the art. Proteins of the present invention and compositions comprising at least one protein of the present invention are also readily amenable to use as additives in detergent and other media used for such applications. These and other methods of use will readily suggest themselves to those of skill in the art based on the invention described herein.

In one embodiment of this invention, proteins and compositions of the present invention can be used in stone washing procedures for fabrics or other textiles. In some embodiments, the proteins and compositions can be used in stone washing procedures for denim jeans. By way of example, the method for stone washing the fabric comprises contacting the fabric with a protein or composition of the present invention. In an additional embodiment, the protein or composition of the present invention is included in a detergent composition, as described below. A preferred pH range of stone wash applications is between about 5.5 to 7.5, most preferably at about pH 6 to about 7. One of skill in the art will know how to regulate the amount or concentration of the protein or composition produced by this invention based on such factors as the activity of the enzyme and the wash conditions, including but not limited to temperature and pH. Examples of these uses can be found in U.S. Patent Application Publication No. 2003/0157595, the contents of which are hereby incorporated by reference.

In yet another embodiment of this invention, the cellulase compositions of this invention can be used to reduce or eliminate the harshness associated with a fabric or textile by contacting the fabric or textile with a protein or composition of the present invention. In some embodiments, the fabric or textile may be made from cellulose or cotton. By way of example, a preferred range for reducing or eliminating the harshness associated with a fabric or textile is between about pH 8 to about 12, or between about pH 10 to about 11.

The proteins or compositions of the subject invention can be used in detergent compositions. In one embodiment, the detergent composition may comprise at least one protein or composition of the present invention and one or more surfactants. The detergent compositions may also include any additional detergent ingredient known in the art. Detergent ingredients contemplated for use with the detergent compositions of the subject invention include, but are not limited to, detergents, buffers, surfactants, bleaching agents, softeners, solvents, solid forming agents, abrasives, alkalis, inorganic electrolytes, cellulase activators, antioxidants, builders, silicates, preservatives, and stabilizers. The detergent compositions of this invention preferably employ a surface active agent, i.e., surfactant, including anionic, non-ionic, and ampholytic surfactants well known for their use in detergent compositions. In addition to the at least one protein or composition of the present invention and the surface active agent, the detergent compositions of this invention can additionally contain one or more of the following components: the enzymes amylases, cellulases, proteinase, lipases, oxido-reductases, peroxidases and other enzymes; cationic surfactants and long-chain fatty acids; builders; antiredeposition agents; bleaching agents; bluing agents and fluorescent dyes; caking inhibitors; masking agents for factors inhibiting the cellulase activity; cellulase activators; antioxidants; and solubilizers. In addition, perfumes, preservatives, dyes, and the like can be used, if desired, with the detergent compositions of this invention. Examples of detergent compositions employing cellulases are exemplified in U.S. Pat. Nos. 4,435,307; 4,443,355; 4,661,289; 4,479,881; 5,120,463, each of which is incorporated herein by reference in its entirety for all purposes.

When a detergent base used in the present invention is in the form of a powder, it may be one which is prepared by any known preparation method including a spray-drying method and/or a granulation method. The granulation method are the most preferred because of the non-dusting nature of granules compared to spray dry products. The detergent base obtained by the spray-drying method is hollow granules which are obtained by spraying an aqueous slurry of heat-resistant ingredients, such as surface active agents and builders, into a hot space. The granules have a size of from about 50 to about 2000 micrometers. After the spray-drying, perfumes, enzymes, bleaching agents, and/or inorganic alkaline builders may be added. With a highly dense, granular detergent base obtained by such as the spray-drying-granulation method, various ingredients may also be added after the preparation of the base. When the detergent base is a liquid, it may be either a homogenous solution or an inhomogeneous solution.

Other textile applications in which proteins and compositions of the present invention may be used include, but are not limited to, garment dyeing applications such as enzymatic mercerizing of viscose, bio-polishing applications, enzymatic surface polishing; biowash (washing or washing down treatment of textile materials), enzymatic microfibrillation, enzymatic "cottonization" of linen, ramie and hemp; and treatment of Lyocel or Newcell (i.e., "TENCEL" from Courtauld's), Cupro and other cellulosic fibers or garments, dye removal from dyed cellulosic substrates such as dyed cotton (Leisola & Linko—(1976) Analytical Biochemistry, v. 70, p. 592. Determination Of The Solubilizing Activity Of A Cellulase Complex With Dyed Substrates; Blum & Stahl—Enzymic Degradation Of Cellulose Fibers; Reports of the Shizuoka Prefectural Hamamatsu Textile Industrial Research Institute No. 24 (1985)), as a bleaching agent to make new indigo dyed denim look old (Fujikawa—Japanese Patent Application Kokai No. 50-132269), to enhance the bleaching action of bleaching agents (Suzuki—Great Britain Patent No. 2 094 826), and in a process for compositions for enzymatic desizing and bleaching of textiles (Windbichtler et al., U.S. Pat. No. 2,974,001. Another example of enzymatic desizing using cellulases is provided in Bhatawadekar (May 1983) Journal of the Textile Association, pages 83-86.

The amount of enzyme or enzyme composition contacted with a textile may vary with the particular application. Typically, for biofinishing and denim washing applications, from about 0.02 wt. % to about 5 wt. % of an enzyme or enzyme composition may be contacted with the textile. In some embodiments, from about 0.5 wt. % to about 2 wt. % of an enzyme or enzyme composition may be contacted with the textile. For bioscouring, from about 0.1 to about 10, or from about 0.1 to about 1.0 grams of an enzyme or enzyme composition per kilogram of textile may be used, including any amount between about 0.1 grams and about 10 grams, in increments of 0.1 grams.

In other embodiments, the proteins or compositions of the present invention can be used in the saccharification of lignocellulose biomass from agriculture, forest products, municipal solid waste, and other sources, for biobleaching of wood pulp, and for de-inking of recycled print paper all by methods known to one skilled in the art.

The amount of enzyme or enzyme composition used for pulp and paper modification (e.g., biobleaching of wood pulp, de-inking of paper, or biorefining of pulp for paper making) typically varies depending upon the stock that is used, the pH and temperature of the system, and the retention time. In certain embodiments, the amount of enzyme or enzyme composition contacted with the paper or pulp may be from about 0.01 to about 50 U; from about 0.1 to about 15 U; or from about 0.1 to about 5 U of enzyme or enzyme composition per dry gram of fiber, including any amount between about 0.01 and about 50 U, in 0.01 U increments. In other embodiments, the amount of enzyme or enzyme composition contacted with the paper or pulp may be from about 1 to about 2000 grams or from about 100 to about 500 grams enzyme or enzyme composition per dry ton of pulp, including any amount between about 1 and about 2000 grams, in 1 gram increments.

Proteins or compositions of the present invention can added to wastewater to reduce the amount of solids such as sludge or to increase total biochemical oxygen demand (BOD) and chemical oxygen demand (COD) removal. For example, proteins or compositions of the present invention can be used to transform particulate COD to soluble COD in wastewater produced from grain/fruit/cellulose industrial processes or to increase the BOD/COD ratio by increasing waste biodegradability (soluble lower molecular weight polymers in cellulosic/hemicellulosic wastes are typically more readily biodegradable than non-soluble material). In biological wastewater treatment systems, proteins or compositions of the present invention can also be used to increase waste digestion by aerobic and/or anaerobic bacteria.

Chitinases of the present invention (e.g., SEQ ID NOS: 56 and 59) can hydrolyze the $\beta$-1,4-glycosidic linkage present in chitin and thus may be used to degrade chitin-containing materials. Examples of chitin-containing materials include fungal cell walls, insect exoskeletons, the eggs of parasitic worms, and crustacean shells.

Chitinases may be used to inhibit or reduce fungal growth, including the treatment of fungal infections such as those caused by nail fungi. For example, chitinases of the present invention may be applied to any fungus or area susceptible to fungal growth. Chitinases may also be used to coat or treat seeds and flower bulbs to prevent the growth of fungi. Further, chitinases may be added to fungal cultures to lower culture viscosity by increasing cell wall degradation. Chitinases may also by used as lysing enzymes for the generation of protoplasts from fungi (see, e.g., Yano et al., *Biosci Biotechnol Biochem.* 70:1754 (2006).

Chitinases or compositions containing chitinases may be used as a biological control agent such as an insecticide (see, e.g., Kramer et al., *Insect Biochem Mol. Biol.* 27:887 (1997). Chitinases of the present invention have been shown to be effective for controlling white-fly larvae in laboratory tests. Thus, chitinases may be applied to crops, plants and the like to control insect infestations.

Chitin has also been suggested to play a role in inducing allergic inflammation and asthma (see Reese et al., *Nature* 447:92 (2007)). Accordingly, chitinases of the present invention may be administered to a subject to reduce allergic inflammatory responses induced by chitin or to reduce the symptoms of asthma.

Exemplary methods according to the invention are presented below. Examples of the methods described above may also be found in the following references, all of which are incorporated herein in their entirties: *Trichoderma & Gliocladium.* Volume 2. Enzymes, biological control and commercial applications. Editors: Gary E. Harman, Christian P. Kubicek. Taylor & Francis Ltd 1998, 393 (in particular, chapters 14, 15 and 16) Helmut Uhlig. Industrial enzymes and their applications. Translated and updated by Elfriede M. Linsmaier-Bednar. John Wiley & Sons, Inc 1998, p. 454 (in particular, chapters 5.1, 5.2, 5.3, 5.4, 5.5, 5.6, 5.7, 5.9, 5.10, 5.11, and 5.13) For saccharification applications: Hahn-Hägerdal, B., Galbe, M., Gorwa-Grauslund, M. F. Lidén, Zacchi, G. Bio-ethanol—the fuel of tomorrow from the residues of today. *Trends in Biotechnology.* 2006, 24 (12), 549-556; Mielenz, J. R. Ethanol production from biomass: technology and commercialization status. *Current Opinion in Microbiology.* 2001, 4, 324-329; Himmel, M. E., Ruth, M. F., Wyman, C. E. Cellulase for commodity products from cellulosic biomass. *Current Opinion in Biotechnology.* 1999, 10, 358-364; Sheehan, J., Himmel, M. Enzymes, energy, and the environment: a strategic perspective on the U.S. Department of Energy's Research and Development Activities for Bioethanol. *Biotechnology Progress.* 1999, 15, 817-827. For textile processing applications: Galante, Y. M., Formantici, C. Enzyme applications in detergency and in manufacturing industries. *Current Organic Chemistry.* 2003, 7, 1399-1422. For pulp and paper applications: Bajpai, P., Bajpai, P. K Deinking with enzymes: a review. *TAPPI Journal.* 1998. 81(12), 111-117; Viikari, L., Pere, J., Suurnäkki, A., Oksanen, T., Buchert, J. Use of cellulases in pulp and paper applications. In: "*Carbohydrates from Trichoderma reesei and other microorganisms. Structure, Biochemistry, Genetics and Applications*." Editors: Mark Claessens, Wim Nerinckx, and Kathleen Piens. The Royal Society of Chemistry 1998, 245-254. For food and beverage applications: Roller, S., Dea, I. C. M. Biotechnology in the production and modification of biopolymers for foods. *Critical Reviews in Biotechnology.* 1992, 12(3), 261-277.

Each publication or reference cited herein is incorporated herein by reference in its entirety for all purposes.

The following examples are provided for the purpose of illustration and are not intended to limit the scope of the present invention.

EXAMPLES

Example 1

The following example illustrates the Somogyi-Nelson assay used to measure beta-glucanase enzymatic activity.

This assay measures the release of reducing sugars (as glucose equivalents) by the action of β-glucanase on a soluble β-glucan. One β-glucanase unit of activity is the amount of enzyme that liberates 1 micromole of reducing sugars, expressed as glucose equivalents, in one minute at 50° C. and pH 5.0.

Reagents

Acetate buffer (0.05 M, pH 5.0) is prepared as follows. 4.1 g of anhydrous sodium acetate or 6.8 g of sodium acetate*$3H_2O$ is dissolved in distilled water so that the final volume of the solution is 1000 mL (Solution A). In a separate flask, 3.0 g (2.86 mL) of glacial acetic acid is mixed with distilled water to make a total volume of 1000 mL (Solution B). The final 0.05 M acetate buffer, pH 5.0, is prepared by mixing Solution A with Solution B until the pH of the resulting solution is equal to 5.0.

β-glucan from barley (medium viscosity, Megazyme, P-BGBM) is used as the assay substrate. The substrate is milled in a mortar before dissolving. 1% w/v stock solution is prepared as follows. 500 mg of β-glucan is mixed with 50 mL of distilled water and agitated on a magnetic stirrer for 1 hour. After that, the suspension is placed into a Bandelin SONOREX TK52 ultrasonic bath for 10 minutes to destroy undissolved particles and then into a boiling water bath until the solution becomes clear. Finally, the solution is stirred on a magnetic stirrer for 30 minutes. The solution is typically stable for 2 days.

The Somogyi reagent is prepared as follows. 24 g of anhydrous sodium carbonate and 12 g of sodium-potassium tartrate tetrahydrate are dissolved in 250 mL of distilled water. A solution of copper sulfate pentahydrate (4 g in 40 mL of distilled water) is added on stirring, and then 16 g of sodium bicarbonate is dissolved to obtain Solution A. In a separate flask, 180 g of sodium sulfate is dissolved in 500 mL of hot (~80° C.) distilled water and boiled for 5 minutes (Solution B). Solution A is mixed with Solution B and the final volume is adjusted to 1000 mL. The reagent is stable for 2-3 months on storing in a dark glass vessel.

The Nelson reagent is prepared as follows. 50 g of ammonium molybdate is dissolved in 900 mL of hot (~60° C.) distilled water. The solution is cooled to 5-10° C. and 42 g of concentrated sulfuric acid containing 6 g of sodium arsenate are carefully added on stirring. The volume of the mixture is adjusted to 1000 mL. The flask is incubated at 40° C. for 48 hours and then the solution is filtered if necessary. The reagent is stable for 2-3 months.

Using the above reagents, the assay is performed as detailed below.

Reagent Blank 0.5 mL of 0.05 M sodium acetate buffer is mixed in a graduated glass test tube (1.5 cm×15 cm) with 0.5 mL of Somogyi reagent and incubated in a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water.

Enzyme Sample 0.25 mL of 1% w/v β-glucan stock solution is mixed with 0.15 mL of 0.05 M acetate buffer, pH 5.0, in graduated glass test tubes (1.5 cm×15 cm) and preheated at 50° C. for 5 minutes. Enzyme sample is suitably diluted by the 0.05 M sodium acetate buffer (the dilution of the enzyme sample is chosen so that $A_{610}$ should be between 0.05 and 0.4 units of optical density). 0.1 mL of suitably diluted enzyme sample is added to 0.4 mL of the preheated substrate solution, mixed and incubated at 50° C. for 10 minutes. After exactly 10 minutes of incubation, 0.5 mL of Somogyi reagent is added, and test tubes are placed into a boiling water bath for 40 minutes. Then, the test tubes are cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_S$ (enzyme sample).

Enzyme Blank 0.4 mL of 0.05 M sodium acetate buffer is mixed in a graduated glass test tube (1.5 cm×15 cm) with 0.1 mL of enzyme sample having the same dilution as above. 0.5 mL of Somogyi reagent is added and the test tube is incubated in a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_{EB}$ (enzyme blank).

Substrate Blank 0.25 mL of 1% w/v β-glucan stock solution is mixed with 0.25 mL of 0.05 M acetate buffer, pH 5.0, in a graduated glass test tube (1.5 cm×15 cm), 0.5 mL of Somogyi reagent is added, and the test tube is placed into a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_{SB}$ (substrate blank). The value of $A_{SB}$ should not exceed 0.05 units of optical density.

All enzyme samples and enzyme and substrate blanks should be boiled together.

Standard Calibration Plot

Stock glucose solution (1 mg/mL) is prepared by dissolving 100 mg of D-glucose in 100 mL of 0.05 M acetate buffer, pH 5.0. Then, different dilutions of stock glucose solution are prepared as follows:

| Stock solution (mL) | 0.05M acetate buffer (mL) | Glucose concentration (mg/mL) |
|---|---|---|
| 0.05 | 4.95 | 0.01 |
| 0.10 | 4.90 | 0.02 |
| 0.15 | 4.85 | 0.03 |
| 0.20 | 4.80 | 0.04 |
| 0.25 | 4.75 | 0.05 |
| 0.30 | 4.70 | 0.06 |
| 0.35 | 4.65 | 0.07 |
| 0.40 | 4.60 | 0.08 |
| 0.45 | 4.55 | 0.09 |
| 0.50 | 4.50 | 0.10 |

Samples (0.5 mL) of glucose solution with different dilutions are placed to graduated glass test tubes (1.5 cm×15 cm). 0.5 mL of Somogyi reagent is added and test tubes are placed into a boiling water bath for 40 minutes. Then, the test tubes are cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank. The following typical $A_{610}$ data obtained with different glucose dilutions are given below:

| Glucose, mg/mL | 0.01 | 0.02 | 0.03 | 0.04 | 0.05 | 0.06 | 0.07 | 0.08 | 0.09 | 0.10 |
|---|---|---|---|---|---|---|---|---|---|---|
| $A_{610}$ | 0.11 | 0.20 | 0.28 | 0.41 | 0.48 | 0.60 | 0.72 | 0.79 | 0.93 | 1.06 |

Figure 11:
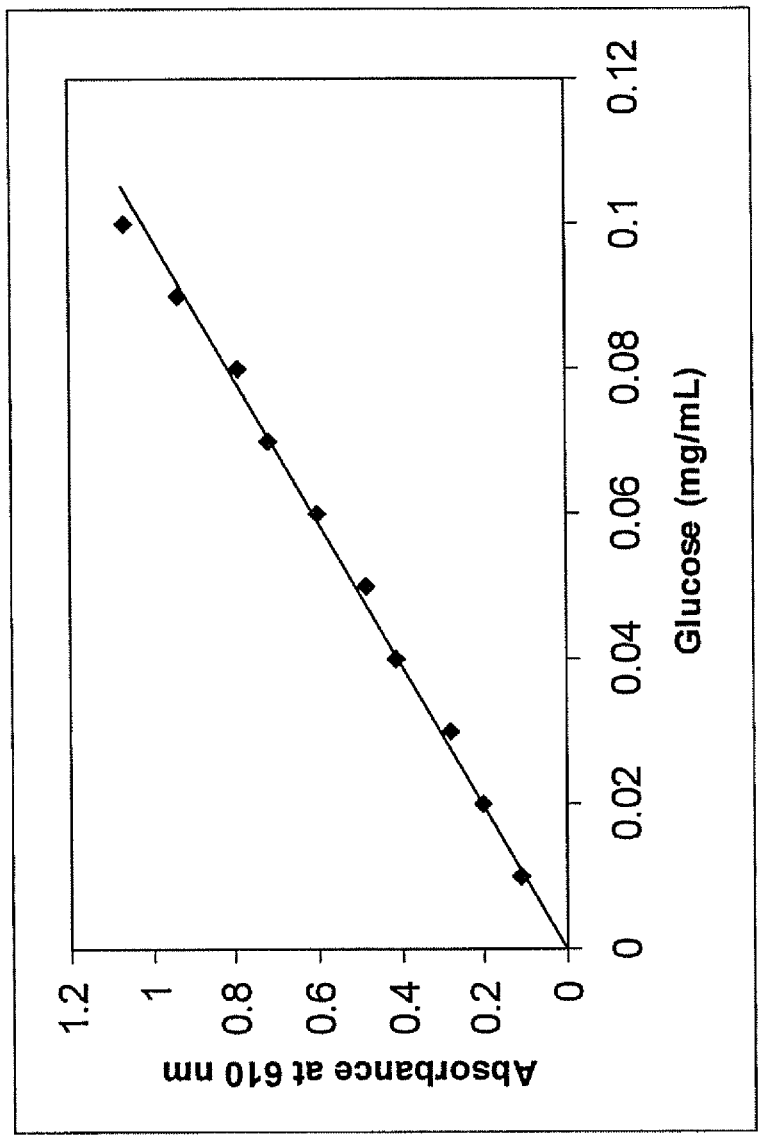
FIG. 11 shows a standard calibration plot for the Somogyi-Nelson assay used for the measurement of reducing sugars in enzymatic hydrolyzates.

Absorbance ($A_{610}$) on the y-axis versus glucose concentration (G, mg/mL) on the x-axis is plotted to generate a standard calibration plot such as that shown in the FIG. 11. From FIG. 11, the inverse of the slop (1/a=0.098) is calculated.

Calculation of Activity

Activity is calculated as follows: activity (IU/mL)=1/a*$\Delta A_{610}$*DF*2.78, where 1/a−inverse of the slope calculated from the standard calibration plot, $\Delta A_{610}=A_S$ (enzyme sample)−$A_B$ (enzyme blank)−$A_{SB}$ (substrate blank), DF is the enzyme dilution factor, and 2.78 is the coefficient that accounts for additional 5-fold enzyme dilution in the reaction mixture (0.1 mL enzyme+0.4 mL substrate), reaction time (10 minutes) and molecular weight of glucose (0.18016 mg/micromole), i.e. 5/(10*0.18016)=2.78

An example calculation is supplied below.

| B4 UF concentrate | |
|---|---|
| DF | $\Delta A_{610}$ |
| 20,000 | 0.545 |
| 40,000 | 0.316 |
| 80,000 | 0.154 |

β-glucanase activity (IU/mL)
=0.098*0.316*40000*2.78=3444

Example 2

The following example illustrates the assays used to measure beta-glucosidase, α-galactosidase and β-galactosidase enzymatic activities.

This assay measures the release of p-nitrophenol by the action of β-glucosidase on p-nitrophenyl β-D-glucopyranoside (PNPG). Modifications to the assay for measuring α-galactosidase and β-galactosidase enzymatic activities are discussed below. One β-glucosidase unit of activity is the amount of enzyme that liberates 1 micromole of p-nitrophenol in one minute at 40° C. and pH 5.0.

Reagents

Acetate buffer (0.1 M, pH 5.0) is prepared as follows. 8.2 g of anhydrous sodium acetate or 13.6 g of sodium acetate*3H$_2$O is dissolved in distilled water so that the final volume of the solution to be 1000 mL (Solution A). In a separate flask, 6.0 g (5.72 mL) of glacial acetic acid is mixed with distilled water to make the total volume of 1000 mL (Solution B). The final 0.1 M acetate buffer, pH 5.0, is prepared by mixing Solution A with Solution B until the pH of the resulting solution is equal to 5.0.

PNPG from Sigma (USA) is used as the assay substrate. 6 mg of PNPG is dissolved in 2 mL of distilled water using magnetic stirrer to obtain 10 mM stock solution. The solution is stable for 2 days on storage at 4° C.

The stop reagent (1 M sodium carbonate solution) is prepared as follows. 10.6 g of anhydrous sodium carbonate is dissolved in 80 mL of distilled water, and the solution volume is adjusted to 100 mL. This reagent is used to terminate the enzymatic reaction.

Using the above reagents, the assay is performed as detailed below.

Enzyme Sample 0.09 mL of 10 mM PNPG stock solution is mixed with 0.81 mL of 0.1 M acetate buffer, pH 5.0, and preheated at 40° C. for 5 minutes. The enzyme sample is suitably diluted with the 0.1 M sodium acetate buffer (the dilution of the enzyme sample is chosen so that $A_{400}$ should be between 0.05 and 0.35 units of optical density). 0.1 mL of suitably diluted enzyme sample is added to 0.9 mL of the preheated substrate solution, mixed and incubated at 40° C. for 10 minutes. After exactly 10 minutes of incubation, 0.5 mL of 1 M sodium carbonate solution is added and then the absorbance at 400 nm ($A_{400}$) is measured as $A_S$ (enzyme sample).

Substrate Blank 0.09 mL of 10 mM PNPG stock solution is mixed with 0.91 mL of 0.1 M acetate buffer, pH 5.0. Then, 0.5 mL of 1 M sodium carbonate solution is added and the absorbance at 400 nm ($A_{400}$) is measured as $A_{SB}$ (substrate blank).

Calculation of Activity

Activity is calculated as follows: activity (IU/mL)= $\Delta A_{400}*DF*0.082$, where $\Delta A_{400}=A_S$ (enzyme sample)$-A_{SB}$ (substrate blank), DF is the enzyme dilution factor, and 0.082 is the coefficient obtained as follows:

$$0.082 = \frac{10^6}{18300*10*(0.1/0.0015)}$$

where $10^6$ is factor used to convert moles/L in the extinction coefficient to micromoles/L, 18300 M$^{-1}$ cm$^{-1}$ is the extinction coefficient of p-nitrophenol released, 10 minutes is the reaction time, and 0.1 mL is the volume of enzyme solution added to 0.0015 L of total assay volume.

An example calculation is supplied below.

| B4 UF concentrate | |
|---|---|
| DF | $\Delta A_{400}$ |
| 5,000 | 0.495 |
| 10,000 | 0.268 |
| 20,000 | 0.144 |

For DF=10,000: β-glucosidase activity (IU/mL)= 0.268*10000*0.082=220

For DF=20,000: β-glucosidase activity (IU/mL)= 0.144*20000*0.082=236

Finally, β-glucosidase activity=228 IU/mL, as a mean value between two measurements.

(α- and β-Galactosidase Assays

The assay procedures for α- and β-galactosidases are the same as the β-glucosidase assay described above, except that p-nitrophenyl α-D-galactopyranoside and p-nitrophenyl β-D-galactopyranoside are used as substrates, respectively, instead of p-nitrophenyl β-D-glucopyranoside.

Example 3

The following example illustrates the Somogyi-Nelson assay used to measure CMCase enzymatic activity.

This assay measures the release of reducing sugars (as glucose equivalents) by the action of cellulase on a soluble cellulosic substrate (CMC). One CMCase unit of activity is the amount of enzyme that liberates 1 micromole of reducing sugars, expressed as glucose equivalents, in one minute at 50° C., pH 5.0, 0.05 M sodium acetate buffer.

Reagents

Acetate buffer (0.05 M, pH 5.0) is prepared as follows. 4.1 g of anhydrous sodium acetate or 6.8 g of sodium acetate*3H$_2$O is dissolved in distilled water so that the final volume of the solution to be 1000 mL (Solution A). In a separate flask, 3.0 g (2.86 mL) of glacial acetic acid is mixed with distilled water to make the total volume of 1000 mL (Solution B). The final 0.05 M acetate buffer, pH 5.0, is prepared by mixing Solution A with Solution B until the pH of the resulting solution is equal to 5.0.

The sodium salt of carboxymethyl cellulose (CMC, medium viscosity, Sigma, C 4888) is used as the substrate. A 1% w/v stock solution is prepared in 0.05 M acetate buffer, pH 5.0, by adding gradually 1.0 g of CMC to 99 mL of the buffer agitated on a magnetic stirrer. The mixture is stirred until the CMC is completely dissolved. The solution is stable for 2 days at 4° C.

The Somogyi reagent is prepared as follows. 24 g of anhydrous sodium carbonate and 12 g of sodium-potassium tartrate tetrahydrate are dissolved in 250 mL of distilled water. The solution of copper sulfate pentahydrate (4 g in 40 mL of distilled water) is added on stirring, and then 16 g of sodium bicarbonate is dissolved to obtain Solution A. In a separate flask, 18.0 g of sodium sulfate is dissolved in 500 mL of hot (~80° C.) distilled water and boiled for 5 min (Solution B). Solution A is mixed with Solution B and the final volume is adjusted to 1000 mL. The reagent is stable for 2-3 months on storing in a dark glass vessel at room temperature.

The Nelson reagent is prepared as follows. 50 g of ammonium molybdate is dissolved in 900 mL of hot (~60° C.) distilled water. The solution is cooled to 5-10° C. and 42 g of concentrated sulfuric acid containing 6 g of sodium arsenate are carefully added on stirring. The volume of the mixture is adjusted to 1000 mL. The flask is incubated at 40° C. for 48 hours and then the solution is filtered if necessary. The reagent is stable for 2-3 months at room temperature.

Using the above reagents, the assay is performed as detailed below.

Reagent Blank 0.5 mL of 0.05 M sodium acetate buffer is mixed in a graduated glass test tube (1.5 cm×15 cm) with 0.5 mL of Somogyi reagent and incubated in a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water.

Enzyme Sample 0.25 mL of 1% w/v CMC stock solution is preheated in graduated glass test tubes (1.5 cm×15 cm) at 50° C. for 5 minutes. Enzyme sample is suitably diluted by the 0.05 M sodium acetate buffer (the dilution of the enzyme sample is chosen so that $A_{610}$ should be between 0.05 and 0.35 units of optical density) and preheated at 50° C. for 5 minutes. 0.25 mL of suitably diluted enzyme sample is added to 0.25 mL of preheated CMC stock solution, mixed and incubated at 50° C. for 5 minutes. After exactly 5 minutes of incubation, 0.5 mL of Somogyi reagent is added, and test tubes are placed into a boiling water bath for 40 minutes. Then, the test tubes are cooled in an ice or cold water bath and 0.5 mL of Nelson reagent is added and mixed by shaking manually. After 10 minutes incubation at room temperature, 1 mL of acetone is added to dissolve CMC precipitated during the boiling procedure and the solution volume is adjusted to 5 mL with distilled water. Then, the absorbance at 610 nm ($A_{610}$) is measured against the reagent blank as $A_S$ (enzyme sample).

Enzyme Blank 0.25 mL of 0.05 M sodium acetate buffer is mixed in a graduated glass test tube (1.5 cm×15 cm) with 0.25 mL of enzyme sample having the same dilution as above. 0.5 mL of Somogyi reagent is added and the test tube is incubated in a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_B$ (enzyme blank).

All enzyme samples and enzyme blanks should be boiled together.

Standard Calibration Plot

A stock glucose solution (1 mg/mL) is prepared by dissolving 100 mg of D-glucose in 100 mL of 0.05 M acetate buffer, pH 5.0. Then, different dilutions of stock glucose solution are prepared as follows:

| Stock solution (mL) | 0.05M acetate buffer (mL) | Glucose concentration (mg/mL) |
|---|---|---|
| 0.05 | 4.95 | 0.01 |
| 0.10 | 4.90 | 0.02 |
| 0.15 | 4.85 | 0.03 |
| 0.20 | 4.80 | 0.04 |
| 0.25 | 4.75 | 0.05 |
| 0.30 | 4.70 | 0.06 |
| 0.35 | 4.65 | 0.07 |
| 0.40 | 4.60 | 0.08 |
| 0.45 | 4.55 | 0.09 |
| 0.50 | 4.50 | 0.10 |

Samples (0.5 mL) of glucose solution with different dilutions are placed to graduated glass test tubes (1.5 cm×15 cm). 0.5 mL of Somogyi reagent is added and test tubes are placed into a boiling water bath for 40 minutes. Then, the test tubes are cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank. The following typical $A_{610}$ data obtained with different glucose dilutions are given below:

| Glucose, mg/mL | 0.01 | 0.02 | 0.03 | 0.04 | 0.05 | 0.06 | 0.07 | 0.08 | 0.09 | 0.10 |
|---|---|---|---|---|---|---|---|---|---|---|
| $A_{610}$ | 0.11 | 0.20 | 0.28 | 0.41 | 0.48 | 0.60 | 0.72 | 0.79 | 0.93 | 1.06 |

Absorbance ($A_{610}$) on the y-axis versus glucose concentration (G, mg/mL) on the x-axis is plotted to generate a standard calibration plot such as that shown in the FIG. 11. From FIG. 11, the inverse of the slop (1/a=0.098) is calculated.

Calculation of Activity

Activity is calculated as follows: CMCase (IU/mL)=1/a*$\Delta A_{610}$*DF*2.22, where 1/a—inverse of the slope calculated from the standard calibration plot, $\Delta A_{610}=A_S$ (enzyme sample)–$A_B$ (enzyme blank), DF—enzyme dilution factor, and 2.22 is the coefficient that accounts for additional 2-fold enzyme dilution in the reaction mixture (0.25 mL enzyme+ 0.25 mL substrate), reaction time (5 minutes) and molecular weight of glucose (0.18016 mg/micromole), i.e. 2/(5*0.18016)=2.22.

An example calculation is supplied below.

| ACE sample | |
|---|---|
| DF | $\Delta A_{610}$ |
| 40,000 | 0.41 |
| 80,000 | 0.25 |

CMCase activity (IU/mL) =0.098*0.25*80000*2.22=4351

Example 4

The following example illustrates the Lowry protein assay.

The Lowry procedure is one of the most known and widely used protein assays, being first described in 1951 (Lowry O H, Rosebrough N J, Farr A L, Randall R J (1951) J. Biol. Chem. 193: 265-275). Under alkaline conditions, copper complexes with protein. When Folin's phenol reagent (phospho-molybdic-phosphotungstic reagent) is added, it binds to the protein. Bound reagent is slowly reduced and changes color from yellow to blue.

Stock Solutions and Reagents

Lowry A stock solution is 2% $Na_2CO_3$ in 0.1 M NaOH. Lowry B stock solution is 1% $CuSO_4$. $5H_2O$ in distilled water. Lowry C stock solution is 2% sodium potassium tartrate ($NaKC_4H_4O_6.4H_2O$) in distilled water. Lowry stock reagent is prepared fresh daily by mixing 49 ml Lowry A, 0.5 ml Lowry B and 0.5 ml Lowry C. Commercial Folin's Reagent: Phenol reagent—2N (Folin—Ciocalteau reagent) is diluted 1:1 in distilled water before use and stored in a refrigerator.

Bovine serum albumin (BSA) is used as the assay standard. When BSA is weighed out before use, the protein preparation used to prepare the standard should be salt-free to avoid inaccurate results. BSA is dissolved at a concentration of 1 mg/ml in a buffer similar to the solution for analysis. A series of standard dilutions is prepared where the protein (BSA) concentration is varied in the range of 0.05-0.5 mg/ml.

Assay Procedure

Using the above reagents, the assay is performed as follows. 100 μl of sample is added to each tube followed by 1.0 ml of Lowry stock reagent and the mixture is incubate 10 minutes at room temperature. 100 μl of Folin's reagent is added to each tube and the tubes are further incubated for 40 minutes at room temperature. A absorbance at 750 nm is read on a spectrophotometer against a blank (control) prepared in the same way as the sample except the buffer is added to the tube instead of the analyzed protein. Protein concentration is the determined by reading the absorbance at 750 nm for each sample and plotting the result on a BSA calibration graph prepared from the standard dilutions discussed above.

The Lowry procedure should be carried out with caution since it is subjected to interference by a wide variety of chemicals. Among the chemicals reported to interfere with the Lowry procedure are barbital, CAPS, cesium chloride, citrate, cysteine, diethanolamine, dithiothreitol, EDTA, EGTA, HEPES, mercaptoethanol, Nonidet P-40, phenol, polyvinyl pyrrolidone, sodium deoxycholate, sodium salicylate, thimerosol, Tricine, TRIS and Triton X-100.

Example 5

The following example illustrates the Somogyi-Nelson assay used to measure avicelase activity.

The assay measures the velocity of release of reducing sugars by the action of cellulases on insoluble Avicel cellulose (micro crystalline cellulose) when reducing sugars are assayed by Somogyi-Nelson method as glucose equivalents. One unit of avicelase activity is equal to the amount of enzyme that liberates 1 micromole of reducing sugars, expressed as glucose equivalents (when reducing sugars assayed by Somogyi-Nelson method) in one minute at 40° C., pH 5.0 (0.05 M sodium acetate buffer).

Reagents

Acetate buffer (0.05 M, pH 5.0) is prepared as follows. 4.1 g of anhydrous sodium acetate or 6.8 g of sodium acetate*3H$_2$O is dissolved in distilled water so that the final volume of the solution to be 1000 mL (Solution A). In a separate flask, 3.0 g (2.86 mL) of glacial acetic acid is mixed with distilled water to make the total volume of 1000 mL (Solution B). The final 0.05 M acetate buffer, pH 5.0, is prepared by mixing Solution A with Solution B until the pH of the resulting solution is equal to 5.0.

Avicel PH 105 (Serva, FRG) (or any other available source of Avicel) is used as the assay substrate. 1% w/v of stock suspension of Avicel is prepared in 0.05 M acetate buffer, pH 5.0, by adding 50 mg of dry Avicel gradually to a vessel with 5 mL of the buffer agitated on a magnetic stirrer. After that the obtained Avicel suspension is mixed on a magnetic stirrer during 1 hour at room temperature (for swelling of Avicel). 1% w/v stock suspension of Avicel can be stored in covered vessel for 5-7 days at 4° C.

The Somogyi reagent is prepared as follows. 24 g of anhydrous sodium carbonate and 12 g of sodium-potassium tartrate*4H$_2$O are dissolved in 250 mL of distilled water. The solution of copper sulfate*5H$_2$O (4 g in 40 mL of distilled water) is added on stirring, and then 16 g of sodium bicarbonate is dissolved (Solution A). In a separate flask, 18.0 g of sodium sulfate is dissolved in 500 mL of hot (~80° C.) distilled water and boiled for 5 minutes (Solution B). Solution A is mixed with Solution B and the final volume is adjusted to 1000 mL by distill water. The reagent is stable for 2-3 months on storing in a dark glass vessel at room temperature.

The Nelson reagent is prepared as follows. 50 g of ammonium molybdate is dissolved in 900 mL of hot (~60° C.) distilled water. The solution is cooled to 5-10° C. and 42 mL of concentrated sulfuric acid containing 6 g of sodium arsenate are carefully added with stirring. The volume of the mixture is adjusted to 1000 mL with distilled water. The flask with this solution is incubated at 40° C. for 48 hours and then the solution is filtered if necessary. The reagent is stable for 2-3 months at room temperature.

Using the above reagents, the assay is performed as detailed below.

Buffer Blank 0.2 mL of 0.05 M sodium acetate buffer (pH 5.0) is mixed in a graduated glass test tube with 0.2 mL of Somogyi reagent, covered, and incubated in a boiling water bath for 40 minutes. Then, the test tube is cooled in a cold-water bath and 0.2 mL of Nelson reagent is added and mixed by shaking manually. After 10 minutes incubation at room temperature, the solution volume is adjusted to 2 mL with distilled water. The obtained solution is used as a buffer blank.

Determination of Avicelase Activity

Avicelase activity is determined by carrying out of the reaction of Avicel hydrolysis at 40° C. and pH 5.0 for 60 minutes while mixing. A 1% w/v stock suspension of Avicel is mixed on magnetic stirrer for 10 minutes, then 0.25 mL of this 1% w/v Avicel stock solution is placed in a graduated glass test tube. 0.15 mL of 0.05 M acetate buffer (pH 5.0) is added to the tube and the mixture is heated to 40° C. for 10 minutes with stirring. 0.1 mL of enzyme sample, suitably diluted and preheated to 40° C. for 10 minutes, is placed into the tube. The reaction mixture is then incubated for 1 hour at 40° C. with stirring. After 1 hour, the reaction mixture is centrifuged 2 min at 12000 rpm, 0.2 mL of supernatant is withdrawn and placed in a graduated glass test tube. 0.2 mL of Somogyi reagent is added and the mixture incubated, covered, in a boiling water bath for 40 minutes. Then, the tube is cooled in a cold water bath and 0.2 mL of Nelson reagent is added and mixed by shaking manually. After 10 minutes incubation at room temperature, the solution volume is adjusted to 2 mL with distilled water. Then, the absorbance at 610 nm ($A_{610}$) is measured against the buffer blank as $A_{ES}$ (enzyme sample). The enzyme sample must be diluted with the 0.05 M sodium acetate buffer so that $A_{610}$ is between 0.5 and 1.5 units of optical density at 610 nm.

Enzyme Blank 0.16 mL of 0.05 M sodium acetate buffer (pH 5.0) is mixed in a graduated glass test tube with 0.04 mL of enzyme sample having the same dilution rate as above. 0.2 mL of Somogyi reagent is added to the test tube, and the tube is incubated, covered, in a boiling water bath for 40 minutes. Then, the test tube is cooled in a cold water bath, 0.2 mL of Nelson reagent is added and the tube is mixed by shaking manually. After 10 minutes incubation at room temperature, the solution volume is adjusted to 2 mL with distilled water. Then, the absorbance at 610 nm ($A_{610}$) is measured against the buffer blank as $A_E$ (enzyme blank).

Substrate Blank

A 1% w/v stock suspension of Avicel is mixed using a magnetic stirrer for 10 minutes, then 0.25 mL of the 1% w/v Avicel stock solution is placed into a graduated glass test tube. 0.25 mL of 0.05 M acetate buffer (pH 5.0) is added to the tube and the mixture is heated to 40° C. for 10 minutes with stirring. 0.1 mL of enzyme sample, suitably diluted and preheated to 40° C. for 10 minutes, is placed into the tube. The reaction mixture is then incubated for 1 hour at 40° C. with stirring. After 1 hour, the reaction mixture is centrifuged 2 min at 12000 rpm, 0.2 mL of supernatant is withdrawn and placed in a graduated glass test tube. 0.2 mL of Somogyi reagent is added and the mixture incubated, covered, in a boiling water bath for 40 minutes. Then, the tube is cooled in a cold water bath and 0.2 mL of Nelson reagent is added and mixed by shaking manually. After 10 minutes incubation at room temperature, the solution volume is adjusted to 2 mL with distilled water. Then, the absorbance at 610 nm ($A_{610}$) is measured against the buffer blank as $A_S$ (substrate blank).

Standard Calibration Plot

Stock glucose solution (0.5 mg/mL) is prepared by dissolving 10 mg of D-glucose in 20 mL of 0.05 M acetate buffer, pH 5.0. Then, different dilutions of stock glucose solution are prepared as follows:

| Stock solution (mL) | 0.05M acetate buffer (mL) | Glucose concentration (mg/mL) |
|---|---|---|
| 0.020 | 0.180 | 0.02 |
| 0.040 | 0.160 | 0.04 |
| 0.060 | 0.140 | 0.06 |
| 0.080 | 0.120 | 0.08 |
| 0.100 | 0.100 | 0.10 |
| 0.120 | 0.080 | 0.12 |
| 0.140 | 0.060 | 0.14 |
| 0.160 | 0.040 | 0.16 |
| 0.180 | 0.020 | 0.18 |
| 0.200 | 0 | 0.20 |

Samples (0.2 mL) of glucose solution with different dilutions are placed to graduated glass test tubes. 0.2 mL of Somogyi reagent is added and the test tubes are placed into a boiling water bath for 40 minutes. Then, the test tubes are cooled in a cold water bath and 0.2 mL of Nelson reagent is added to each tube, and the tubes mixed by shaking manually. After 10 minutes incubation at room temperature, the solution volume in each tube is adjusted to 2 mL with distilled water. Then, the absorbance at 610 nm ($A_{610}$) is measured against the buffer blank. The following typical $A_{610}$ data obtained with different glucose dilutions are given below:

| Glucose, mg/mL | | | | | | | | | |
|---|---|---|---|---|---|---|---|---|---|
| 0.02 | 0.04 | 0.06 | 0.08 | 0.10 | 0.12 | 0.14 | 0.16 | 0.18 | 0.20 |
| $A_{610}$ 0.02 | 0.12 | 0.38 | 0.50 | 0.70 | 0.92 | 1.10 | 1.38 | 1.54 | 1.67 |

Absorbance ($A_{610}$) on the y-axis versus glucose concentration (G, mg/mL) on the x-axis is plotted to generate a standard calibration plot such as that shown in the FIG. 11.

The dependence of $A_{610}$ from G is described by the equation y=ax+b. The concentration of reducing sugars (C) in an assayed sample can be calculated from a calibration plot using the equation C=($\Delta A_{610}$−b)/a, where b=−0.2239 and 1/a=0.204. In other words, C=($\Delta A_{610}$+0.223.9)*0.104 (in mg/mL).

Calculation of Activity

Activity is calculated as follows: Avicelase (U/mL)= ($\Delta A_{610}$−b)*(1/a)*0.463*DR, where $\Delta A_{610}$=$A_{ES}$ (enzyme sample)−$A_E$ (enzyme blank)−$A_S$ (substrate blank), 1/a is 0.204, b is −0.2239, the coefficients from the glucose calibration plot (see above), DR is the enzyme dilution rate (dilution rate of enzyme sample before addition into the reaction mixture), and 0.463 is the coefficient obtained as 5/(0.180*60), where 5 is the additional dilution of enzyme sample in the reaction mixture (0.1 mL of enzyme+0.4 mL of reaction mixture), 0.180 mg/mkmol is the transition coefficient for glucose from mg to mkmol (molecular weight of glucose is 180) and 60 is the reaction time (60 minutes). The enzyme sample must be diluted so that $\Delta A_{610}$ should be between 0.5 and 1.5 units of optical density.

An example calculation is supplied below. The sample the dilution rate of 500, $A_{ES}$ is 1.436, $A_E$ is 0.102, $A_S$ is 0.070, so $\Delta A_{610}$=1.436−0.102−0.070=1.264. The Avicelase activity is: (1.264+0.2239)*0.104*0.463*500=35.8 U/mL.

Example 6

The following example illustrates glucose determination by a glucosooxidase-peroxidase assay.

As a result of β-D-Glucose oxidation by glucose oxidase (GOD), hydrogen peroxide $H_2O_2$ and glucono-lactone are formed. Then, $H_2O_2$ is used by peroxidase (POD) as an oxidizing agent for 4-aminoantipyrine, oxidizing in the presence of phenolic substances. As a result, dyed products accumulate in the reaction mixture and can be detected at 490 nm spectrophotometrically. The amount of dyed products corresponds to glucose concentration as shown in the reaction scheme below:

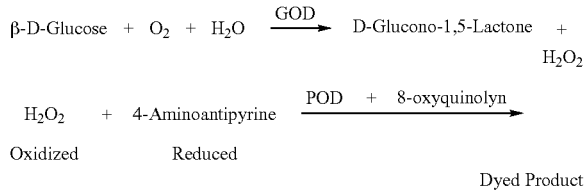

The assay is carried out using a Fotoglucose kit (Impact Ltd., Russia) with the general conditions: 40° C., pH 7.0, duration—15 min, $A_{490}$, light path 1 cm.

Reagents

Reagent 1 (R1) is prepared as follows. Two "Buffer-Substrate" tablets (0.1 mmol/L potassium or ammonium salts of phosphoric acid, 50 mmol/l 4-aminoantipyrine, 0.75 mmom/L 8-oxyquinolyn) are dissolved in 200 mL of distilled water, filtered through a cellulose filter, and the pH adjusted to 7.0 if necessary. The solution can be stored in the dark at 4° C. and should be made fresh weekly.

Reagent 2 (R2) is prepared as follows. One "Enzyme" tablet (2500 units of glucose oxidase and 500 units of peroxidase) is dissolved in 5 mL of distilled water. The solution can be stored in the dark at 4° C. and should be made fresh weekly.

A glucose solution of 10 mmol/L glucose in 0.15% benzoic acid is used as the calibration standard. The solution is diluted with distilled water to obtain glucose solutions of 0 to 5 g/L.

Using the above reagents, the assay is performed as detailed below.

R1 and R2 are mixed at a ratio of 40:1 (this solution may be stored in the dark at 4° C. and should be made fresh weekly) and 1 mL of the mixture is preheated to 40° C. for 5-10 seconds. 0.1 mL of the sample (or glucose standard) is then added and the mixture is incubated at 40° C. for 15 minutes. The mixtures are then placed at room temperature and the $A_{490}$ determined on spectrophotometer. Prolongation of the incubation time to 20 minutes has little or no effect on the results, while decreasing it to less than 15 minutes can result in a lower optical density. Thus, 15-20 min of incubation at 40° C. is preferred for glucose determination.

Calculation of Glucose Concentration

Figure 12:
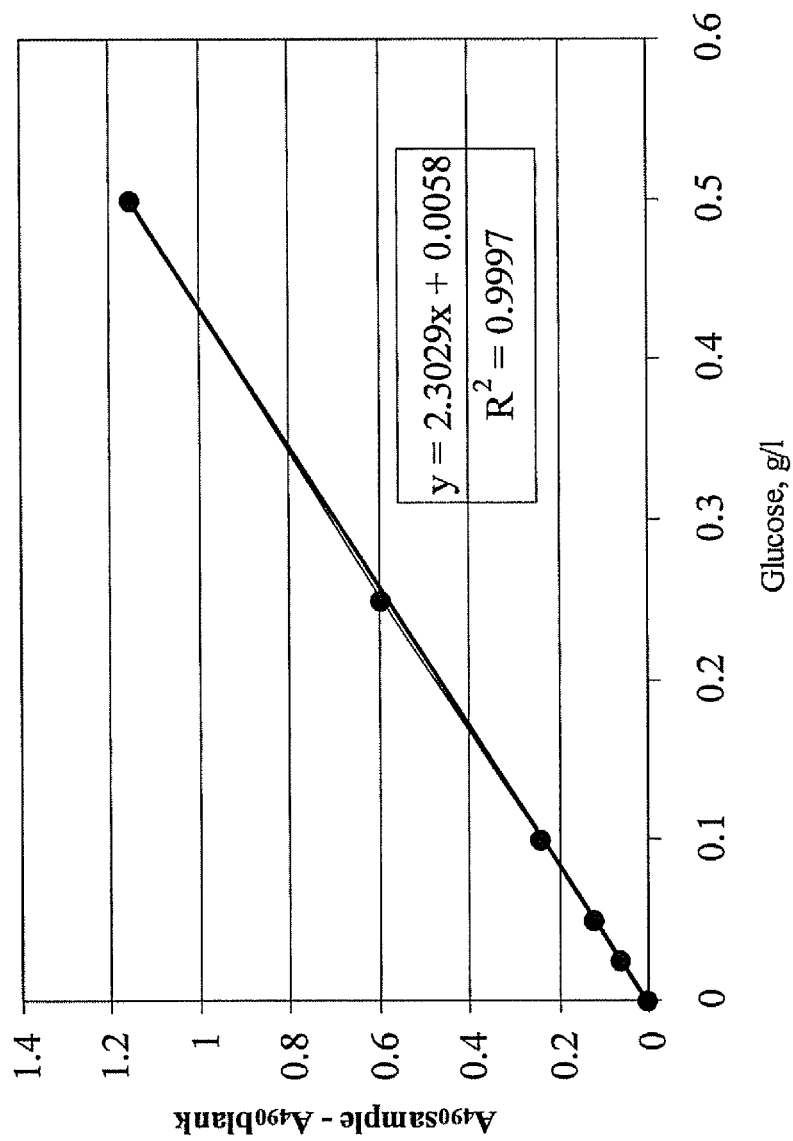
FIG. 12 shows a standard calibration plot with glucose standards from 0.025 g/l to 0.5 g/l for a glucosooxidase-peroxidase assay used to determine glucose levels.

As shown in Table 21, calibration with standards containing varying concentrations of glucose reveals an optical density $A_{490}$ in the range from 0.06 to 1.15 corresponds to glucose concentrations from 0.025 g/L to 0.5 g/L. These data are plotted in FIG. 12, which demonstrates a linear proportion and high reproducibility at these conditions.

Using the calibration results, the following formula is obtained for glucose determination in samples from an $A_{490}$ reading:

GLUCOSE, g/L=$(A_{490}$sample$-A_{490}$blank$)-0.0058)/2.3029$

TABLE 21

Calibration of the reagents using standard glucose solutions (two experiments)

| Glucose, g/L | $A_{490}$ | $A_{490}$ |
|---|---|---|
| 0 | 0.05 | 0.05 |
| 0.0025 | 0.05 | 0.05 |
| 0.005 | 0.06 | 0.06 |
| 0.01 | 0.07 | 0.07 |
| 0.025 | 0.11 | 0.11 |
| 0.05 | 0.17 | 0.17 |
| 0.1 | 0.29 | 0.29 |
| 0.25 | 0.65 | 0.64 |
| 0.5 | 1.20 | 1.20 |
| 1 | 1.71 | 1.72 |
| 2.5 | 1.93 | 1.94 |
| 5 | 2.06 | 2.06 |

Example 7

The following example illustrates the Somogyi-Nelson assay used to measure xylanase activity.

This assay measures the release of reducing sugars (as glucose equivalents) by the action of xylanase on a soluble xylan. One xylanase unit of activity is the amount of enzyme that liberates 1 micromole of reducing sugars, expressed as glucose equivalents, in one minute at 50° C. and pH 5.0.

Reagents

Acetate buffer (0.05 M, pH 5.0) is prepared as follows. 4.1 g of anhydrous sodium acetate or 6.8 g of sodium acetate*3H$_2$O is dissolved in distilled water so that the final volume of the solution is 1000 mL (Solution A). In a separate flask, 3.0 g (2.86 mL) of glacial acetic acid is mixed with distilled water to make a total volume of 1000 mL (Solution B). The final 0.05 M acetate buffer, pH 5.0, is prepared by mixing Solution A with Solution B until the pH of the resulting solution is equal to 5.0.

Xylan from birchwood (Sigma, X 0502) is used as the substrate. A 1% w/v stock solution is prepared by dissolving 500 mg of xylan in 50 mL of distilled water with agitation on a magnetic stirrer for 1 hour. The solution is stable for 2 days at 4° C.

The Somogyi reagent is prepared as follows. 24 g of anhydrous sodium carbonate and 12 g of sodium-potassium tartrate tetrahydrate are dissolved in 250 mL of distilled water. A solution of copper sulfate pentahydrate (4 g in 40 mL of distilled water) is added with stirring, and then 16 g of sodium bicarbonate is dissolved to obtain Solution A. In a separate flask, 180 g of sodium sulfate is dissolved in 500 mL of hot (~80° C.) distilled water and boiled for 5 min (Solution B). Solution A is mixed with Solution B and the final volume is adjusted to 1000 mL. The reagent is stable for 2-3 months on storing in a dark glass vessel.

The Nelson reagent is prepared as follows. 50 g of ammonium molybdate is dissolved in 900 mL of hot (~60° C.) distilled water. The solution is cooled to 5-10° C. and 42 g of concentrated sulfuric acid containing 6 g of sodium arsenate are carefully added with stirring. The volume of the mixture is adjusted to 1000 mL. The flask is incubated at 40° C. for 48 hours and then the solution is filtered if necessary. The reagent is stable for 2-3 months.

Using the above reagents, the assay is performed as detailed below.

Reagent Blank 0.5 mL of 0.05 M sodium acetate buffer is mixed in a graduated glass test tube (1.5 cm×15 cm) with 0.5 mL of Somogyi reagent and incubated in a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water.

Enzyme Sample 0.25 mL of 1% w/v xylan stock solution is mixed with 0.15 mL of 0.05 M acetate buffer, pH 5.0, in graduated glass test tubes (1.5 cm×15 cm) and preheated at 50° C. for 5 minutes. Enzyme sample is suitably diluted by the 0.05 M sodium acetate buffer (the dilution of the enzyme sample is chosen so that $A_{610}$ should be between 0.95 and 1.05 units of optical density). 0.1 mL of suitably diluted enzyme sample is added to 0.4 mL of the preheated substrate solution, mixed and incubated at 50° C. for 10 minutes. After exactly 10 minutes of incubation, 0.5 mL of Somogyi reagent is added, and test tubes are placed into a boiling water bath for 40 minutes. Then, the test tubes are cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_S$ (enzyme sample).

Enzyme Blank 0.4 mL of 0.05 M sodium acetate buffer is mixed in a graduated glass test tube (1.5 cm×15 cm) with 0.1 mL of enzyme sample having the same dilution as above. 0.5 mL of Somogyi reagent is added and the test tube is incubated in a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_{EB}$ (enzyme blank).

Substrate Blank 0.25 mL of 1% w/v xylan stock solution is mixed with 0.25 mL of 0.05 M acetate buffer, pH 5.0, in a graduated glass test tube (1.5 cm×15 cm), 0.5 mL of Somogyi reagent is added, and the test tube is placed into a boiling water bath for 40 minutes. Then, the test tube is cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank as $A_{SB}$ (substrate blank). The value of $A_{SB}$ should not exceed 0.05 units of optical density.

All enzyme samples and enzyme and substrate blanks should be boiled together.

Standard Calibration Plot

Stock glucose solution (1 mg/mL) is prepared by dissolving 100 mg of D-glucose in 100 mL of 0.05 M acetate buffer, pH 5.0. Then, different dilutions of stock glucose solution are prepared as follows:

| Stock solution (mL) | 0.05M acetate buffer (mL) | Glucose concentration (mg/mL) |
|---|---|---|
| 0.05 | 4.95 | 0.01 |
| 0.10 | 4.90 | 0.02 |
| 0.15 | 4.85 | 0.03 |
| 0.20 | 4.80 | 0.04 |
| 0.25 | 4.75 | 0.05 |
| 0.30 | 4.70 | 0.06 |
| 0.35 | 4.65 | 0.07 |
| 0.40 | 4.60 | 0.08 |
| 0.45 | 4.55 | 0.09 |
| 0.50 | 4.50 | 0.10 |

Samples (0.5 mL) of glucose solution with different dilutions are placed in graduated glass test tubes (1.5 cm×15 cm). 0.5 mL of Somogyi reagent is added and test tubes are placed into a boiling water bath for 40 minutes. Then, the test tubes are cooled in an ice or cold water bath and 0.5 mL of Nelson reagent is added and mixed by shaking manually. After 10 minutes incubation at room temperature, the solution volume is adjusted to 5 mL with distilled water. Then, the absorbance at 610 nm ($A_{610}$) is measured against the reagent blank. The following typical $A_{610}$ data obtained with different glucose dilutions are given below:

| | Glucose, mg/mL | | | | | | | | | |
|---|---|---|---|---|---|---|---|---|---|---|
| | 0.01 | 0.02 | 0.03 | 0.04 | 0.05 | 0.06 | 0.07 | 0.08 | 0.09 | 0.10 |
| $A_{610}$ | 0.11 | 0.20 | 0.28 | 0.41 | 0.48 | 0.60 | 0.72 | 0.79 | 0.93 | 1.06 |

Absorbance ($A_{610}$) on the y-axis versus glucose concentration (G, mg/mL) on the x-axis is plotted to demonstrate a standard calibration plot such as that shown in FIG. 11. From FIG. 11, the inverse of the slop (1/a=0.098) is calculated.

Calculation of Activity

Activity is calculated as follows: activity (IU/mL)=1/a*$\Delta A_{610}$*DF*2.78, where 1/a is the inverse of the slope calculated from the standard calibration plot, $\Delta A_{610}$ is $A_S$ (enzyme sample)–$A_{EB}$ (enzyme blank)–$A_{SB}$ (substrate blank), DF is the enzyme dilution factor, and 2.78 is the coefficient that accounts for additional 5-fold enzyme dilution in the reaction mixture (0.1 mL enzyme+0.4 mL substrate), reaction time (10 minutes) and molecular weight of glucose (0.18016 mg/micromole), i.e. 5/(10*0.18016)=2.78

An example calculation is supplied below.

| B4 UF concentrate | |
|---|---|
| DF | $\Delta A_{610}$ |
| 5,000 | 1.61 |
| 10,000 | 1.04 |
| 20,000 | 0.64 |

Xylanase activity (IU/mL)=0.098*1.04*10000*2.78=2833

Example 8

The following example illustrates the assay used to measure the stability of enzymes of the present invention to thermoshock.

The following assay determines the stability of enzymes after short-term treatment at elevated temperature (e.g. temperature of pelletization of animal feed). A solution of enzyme is incubated for approximately two minutes in a glass tube in a thermostat at 80° C. The gradual drop of enzyme activity is recorded over time and the resultant curve is used to determine how long the enzyme is stable (results usually range from 10-60 seconds).

The use of glass tubes that fit tightly in a regular thermostat or eppendorf-type tubes help ensure proper thermal conditions and fast heating of the tube content. The enzyme dilution used is selected so that after additional dilution in reaction mixture the optical density is as high as possible (depends on particular method used for activity determination). For example, when determining xylanase activity by the Somogyi-Nelson assay disclosed in Example 7, the enzyme selected should give an optical density $A_{610}$ 1.0-1.1 after being diluted 5 times in reaction mixture.

Figure 13:
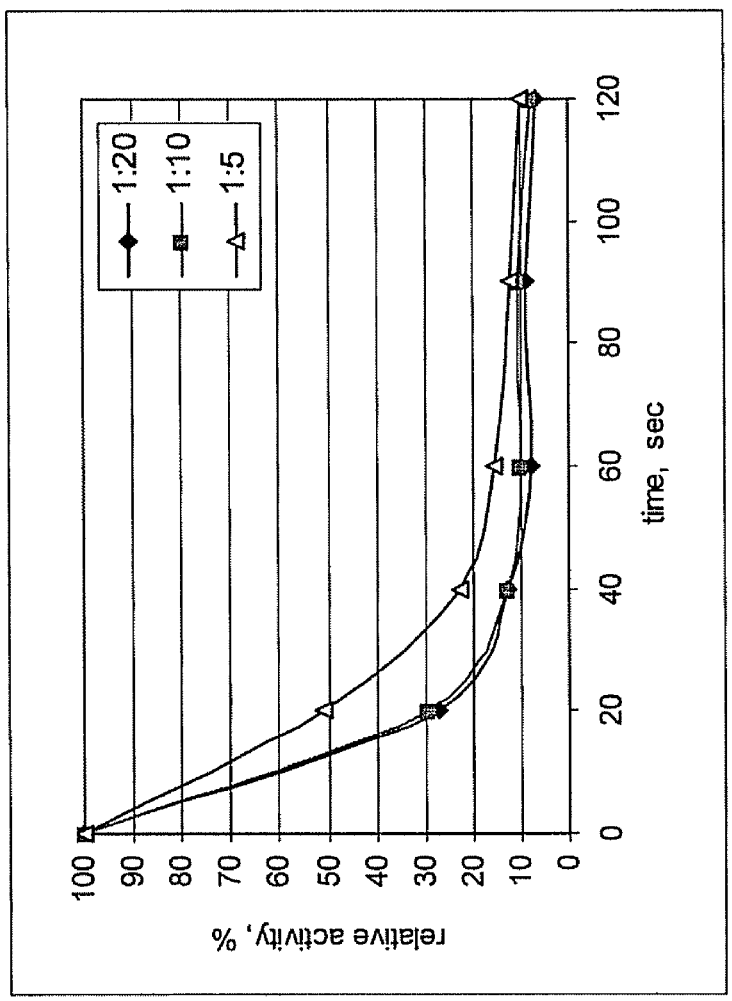
FIG. 13 shows the relative activity over time of xylanase at 20-, 10- and 5-fold dilutions in a thermoshock assay.

For faster equilibration at 80° C., 0.4-0.5 ml water may be placed in the well of thermostat, prior to fitting in a glass tube. The temperature is set at 80.3-80.4° C. to compensate for cooling. 360 •1 of desired buffer is placed in the tube and heated for 2-3 minutes until it reaches 80° C. It is advisable to check the temperature in the tube (using a thermometer) to be sure the temperature has been reached. 40•1 of enzyme solution is then added and the tube is mixed rapidly. After 20, 40, 60, 90 and 120 seconds, aliquots are removed from the tube and immediately transferred in the reaction mixture for determination of activity (assay components are prepared beforehand). To determine zero-point activity (without heating), the same solution (360•1 buffer+40•*1 enzyme) is prepared in the separate tube at room temperature. Determined activities at every time point are then plotted as relative activity (in %) vs. time, with zero time point (without heating) representing 100% activity. FIG. 13 demonstrates these data for stability of xylanase at 20-, 10- and 5-fold dilutions.

In this protocol, a 10-fold dilution of enzyme is used (9:1 preheated buffer solution to cold enzyme solution). In principle one can use higher dilution rates (e.g., 1:20), but typically not lower dilution factors (e.g., 1:5) because mixing of larger volumes of cold enzyme solution can produce inaccurate results. The plot below illustrates this principle. The stability of xylanase was tested using 20-, 10- and 5-fold dilutions, and the results shown in FIG. 13 demonstrate that dilutions of 10- and 20-fold (and likely higher) gave consistent results. In contrast, use of a 5-fold dilution generates overestimated values.

Figure 14:
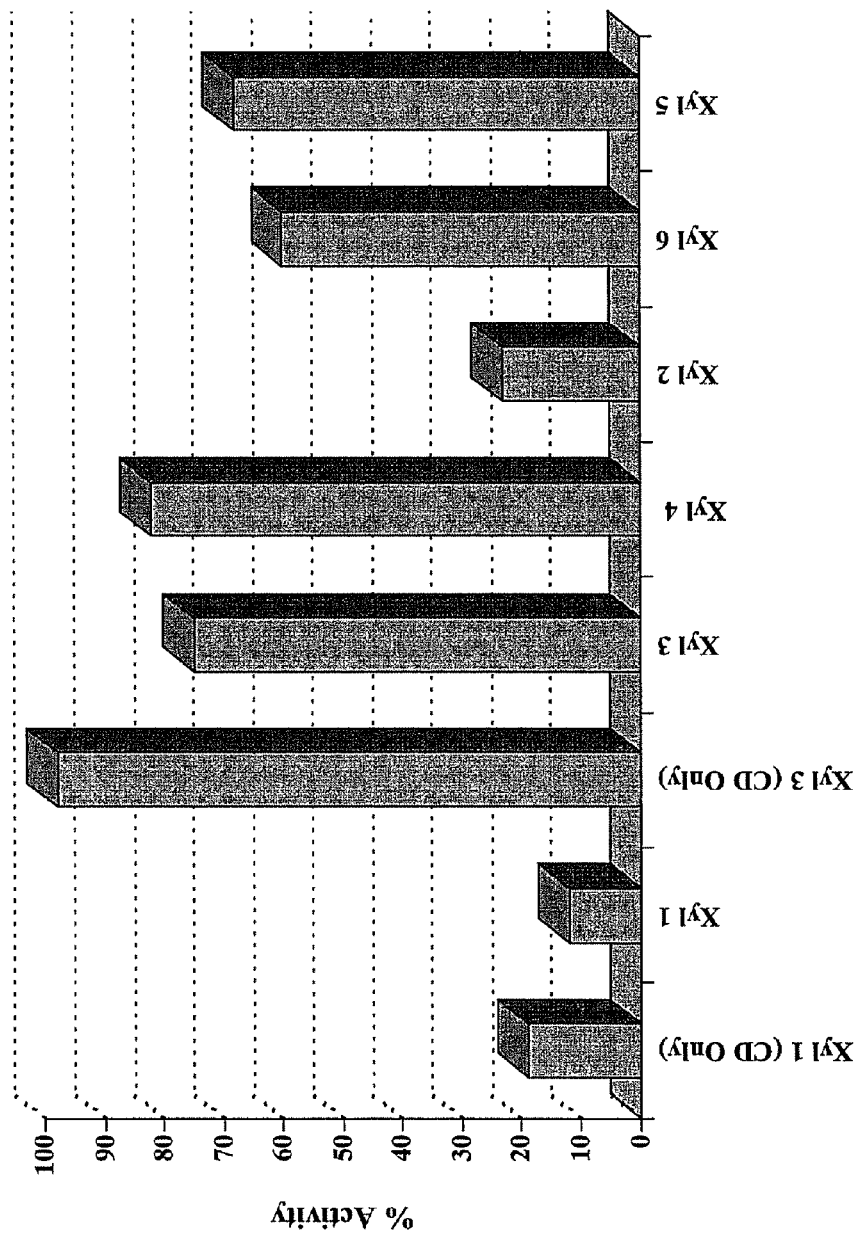
FIG. 14 shows the pelletizing stability of xylanases of the present invention. The percentage of activity after 20 seconds at 80° C. relative to an unheated sample is shown.

The percentages of enzymatic activity of xylanases of the present invention after 20 seconds of incubation at 80° C. (also known as the pelletizing stabilities) are shown below in Table 22 and in the graph depicted in FIG. 14.

TABLE 22

Pelletizing Stability of C1 Xylanses

| Enzyme | % Activity |
|---|---|
| Xyl 1 | 19 |
| Xyl 1 (CD) | 12 |
| Xyl 2 | 98 |
| Xyl 3 | 75 |
| Xyl 3 (CD) | 82 |
| Xyl 4 | 23 |
| Xyl 5 | 60 |
| Xyl 6 | 68 |

Example 9

The following example illustrates the in vitro, semi-quantitative assay used to measure the feed activity of enzymes of the present invention.

The assay was developed to simulate the enzymatic treatment of feed. The assay detects the dynamics of liquid and sludge fraction formation from a uniform slurry of milled rye bran by the action of the enzyme samples in narrow test tubes.

A mixture of enzyme solution and uniform rye bran suspension in acetate buffer (pH 5.0) is placed into a long glass tube (e.g., 2 ml calibrated glass pipettes) and stored at room temperature (or at 40° C.). The action of enzymes on non-starch rye bran generates polysaccharides (e.g. arabinoxyan, β-glucan and others) causing the original uniform rye bran slurry to separate into a liquid phase (containing the polysaccharides) on the top and an insoluble sludge on the bottom of. The volume of liquid phase formed on the top of tubes over the reaction is measured every 10-15 min during 1.5-3 hours (the total assay time depends on enzymatic activity). The data obtained are plotted as "liquid formed" (ml) versus time (minutes) and the slope of the line calculated. The higher the slope of the line on the obtained graph, the higher the in vitro feed activity of the tested enzyme sample.

Substrate

Rye bran is used as a substrate in this example. However, wheat and barley bran, rye, wheat, barley, and soy meal may also be used as assay substrates. Partially de-starched rye bran samples are carefully milled and passed through the fine sieve. The fine fraction is taken as the substrate. Substrate is accurately weighed and placed into a dry 20-ml screw cap vial. The sample of substrate is suspended in acetate buffer to get 30% w/v suspension. The substrate suspension is mixed vigorously with a magnetic stirrer for 30-45 minutes at room temperature. The resulting suspension obtained can be stored at 4° C. in a sealed vial for about 2 days.

Assay Procedure

The reaction mixture contains the following components:
1500 µl of substrate suspension (300 mg/ml)
750 µl of enzyme solution The blank solution contains the same amount of substrate, but the enzyme solution is substituted with the same volume of acetate buffer.

The reaction mixture is subjected to vigorous agitation and placed in appropriate calibrated glass tubes (e.g., 2 ml glass pipettes). Glass tubes or pipettes should be filled with the reaction mixture immediately and placed vertically. The top end of the tube is left open while the bottom end is sealed with a piece of Parafilm or by dipping in melted paraffin.

The concentration of enzyme samples can be measured either in mg/ml of protein or in xylanase units/ml in the reaction mixture (or any other enzyme activities, e.g., β-glucanase, α-galactosidase, protease, etc.). Protein content or xylanase (or other activities) of the enzyme samples are measured separately prior to the experiments. In the experiments, enzyme concentration was equalized to 1 mg/ml of protein in the reaction mixture, or in xylanase activity (2 to 3 U/ml).

Materials and Instruments

Thermostat for 2 ml Eppendorf type test tubes, set at 40° C.
Set of calibrated glass tubes (e.g., 2-ml glass pipettes)
UV-Vis spectrophotometer
Reagents to perform Nelson-Somogyi assay
Analytical electronic balances
Adjustable volume automated pipettes 40-200 µl and 200-1000 µl
Rye bran
0.05 M acetate buffer, pH 5.0

Data Analysis

Data obtained is presented on a graph as liquid formed (ml) versus time (minutes). The higher the slope of the line on the obtained graph, the higher the in vitro feed activity of the tested enzyme sample.

Example 10

The following example illustrates the assay used to measure the ability of enzymes to reduce the viscosity of feed materials.

Enzymatic treatment of barley, rye or wheat can increase the nutritive value by hydrolysis of viscous polysaccharides (beta-glucan, arabino xylan) within cereals. Table 23 below illustrates typical viscous polysaccharide profiles of sample feedstuffs compared with the viscosity of water/meal mixtures.

TABLE 23

Viscous Polysachharide Profiles of Feedstuffs

| | Arabino Xylans g/kg of dry matter | Beta-Glucans, g/kg of dry matter | Relative Viscosity of water/meal mixes, U |
|---|---|---|---|
| RYE | 14.4 | 7.6 | 9.71 |
| BARLEY | 3.3 | 24.3 | 4.21 |
| WHEAT | 3.2 | 5.6 | 2.25 |

As shown in the table, the high viscosity of a water/rye meal mixture is predominantly due to the presence of arabinoxylans. Similarly, the viscosity of a water/barley mixture is predominantly due to the presence of beta-glucans, while the viscosity of water/wheat mixture close to water. However, cereals such as barley, rye and wheat often contain specific inhibitors of the hydrolytic enzymes. Thus, preferred enzymatic preparations that effectively decrease viscosity should be resistant to cereal inhibitors and be enzymatically active at low dosage.

Materials and Instruments 100 ml glass flasks with caps
Ostwald capillary viscometer with thermostat at 40° C.
Shaker for meal incubation at 40° C.
Whole rye, barley, wheat grains or hulls or their mixtures
Rotary mill and 0.5 mm sieve to prepare whole meal
Adjustable volume automated pipettes 40-200 and 200-1000 µl
Distilled water or 0.1M sodium acetate buffer, pH 5.0

Sample Preparation

To prepare the crude barley, wheat or rye meals, whole grains are milled on a rotary mill and passed through a 0.5 mm sieve. 6 g of crude barley or rye meal or 12 g of wheat meal is added to a 100 ml glass flask. 30 ml of distilled water or buffer (blank flask) or 30 ml of the enzyme water solution (experimental flasks) is then added and the flasks are covered. The concentration of 6 g of meal per 30 ml of water is 200 g per liter, while 12 g per 30 ml is 400 g/l.

The flasks are shaken well by hand then placed on a shaker at 40° C., 250 rpm.

After a 1-hour incubation, the mixtures are centrifuged for 5 min at 5000 rpm to separate the insoluble precipitate of the crude meal. The supernatant is then filtered through a cotton pad. 5 ml of the filtered supernatant is placed into an Ostwald viscometer at 40° C. and incubated for at least 3 minutes before the viscosity of the sample is determined. The measurement of the efflux time of the samples from the viscometer bulb should be done later than 80 minutes after starting the incubation.

A dosage of 0.15 kg/t of the meal approximates the dosage used in real practice. For liquid preparations, a dosage of 0.15 kg/t equals 90 µl of the preparation in a 100-fold dilution per flask (30 ml of water/meal mix). For dry preparations, a dosage of 0.15 kg/t equals 90 µl of the 10 g/l solution per flask (30 ml of water/meal mix).

Figure 15:
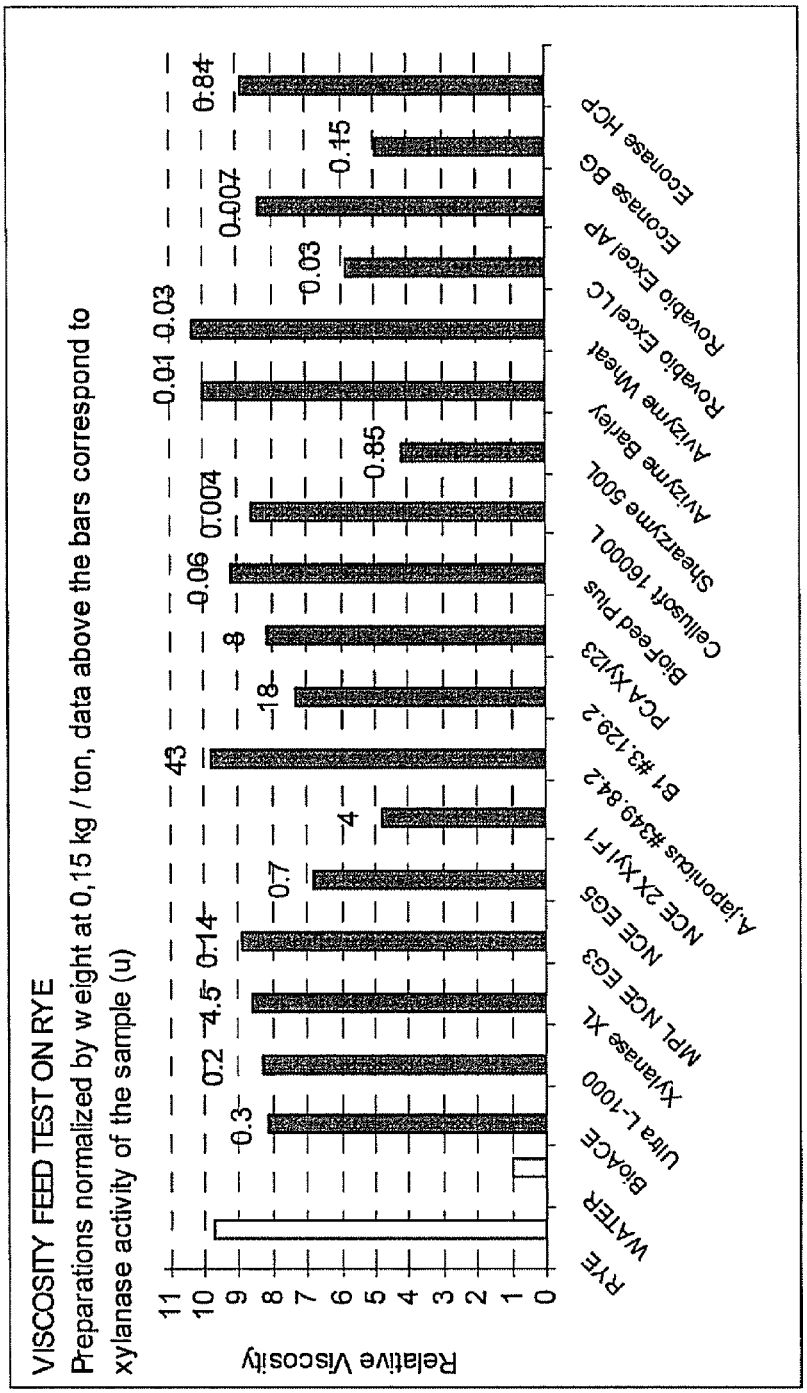
FIG. 15 shows the relative viscosity of water/rye mixes treated with the indicated enzyme(s). To compare the efficiency of the preparations, the xylanase activities of the samples (units per flask) are also indicated.

FIG. 15 shows the relative viscosity of water/rye mixes treated with the indicated enzyme(s). To compare the efficiency of the preparations, the xylanase activities of the samples (units per flask) are also indicated.

Figure 16:
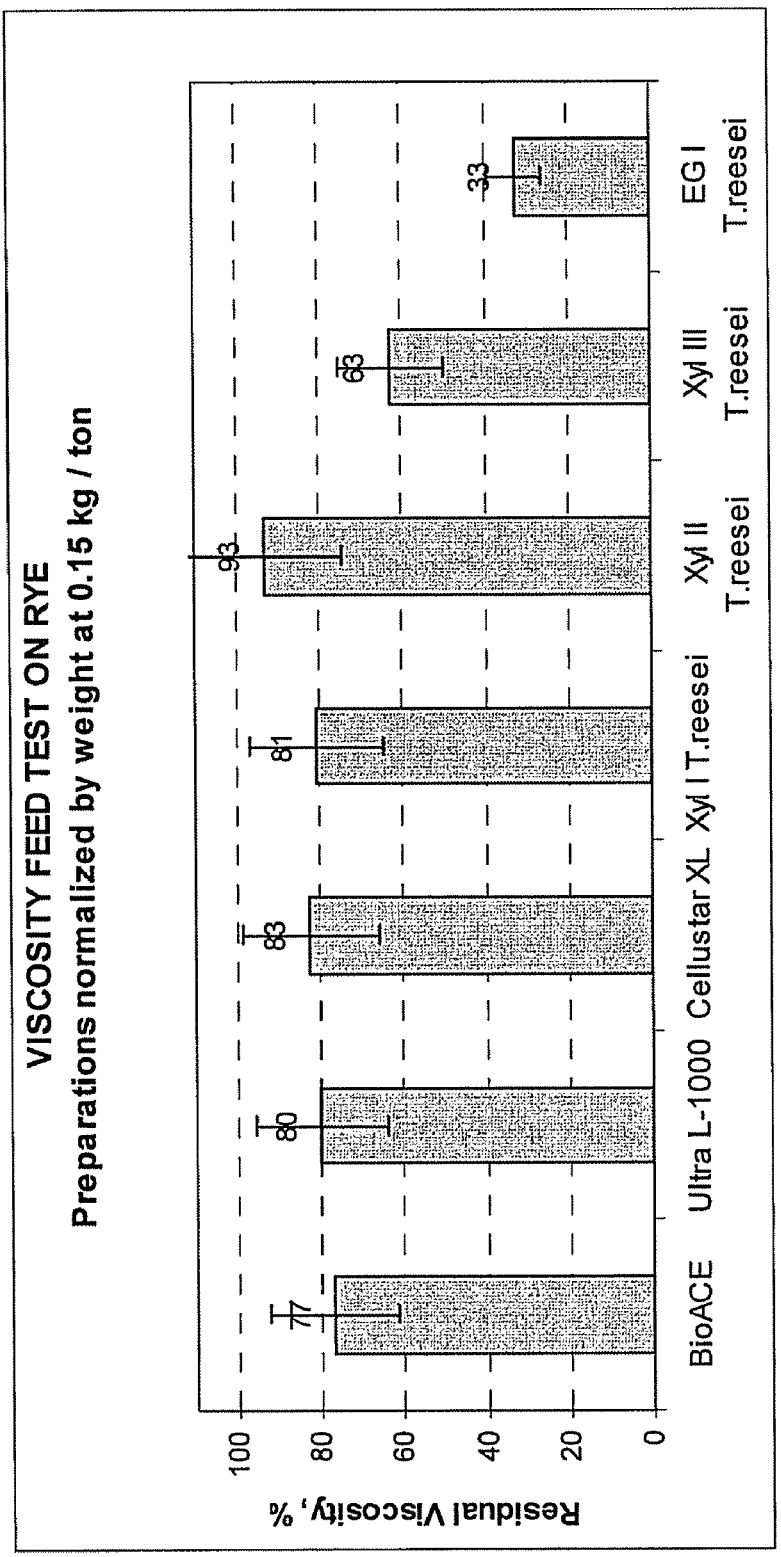
FIG. 16 shows a plot of the residual viscosity (%) of water/rye mixes) after enzymatic treatment.

The efficiency of the preparations may also be compared by plotting the residual viscosity (%) of the water/meal mix after enzymatic treatment, as shown in FIG. 16.

Residual viscosity is calculated as follows:

$$ResV = (Rvi - Rvwater)/(Rvnative - Rvwater) \times 100\%$$

The final formula is:

$$ResV = (Rvi - 1)/(Rvnative - 1) \times 100\%$$

Where ResV is residual viscosity, Rvi is the relative viscosity of the sample with enzyme, Rvnative is the relative viscosity of the native water/meal mix without enzyme, and Rvwater is 1.

Figure 17:
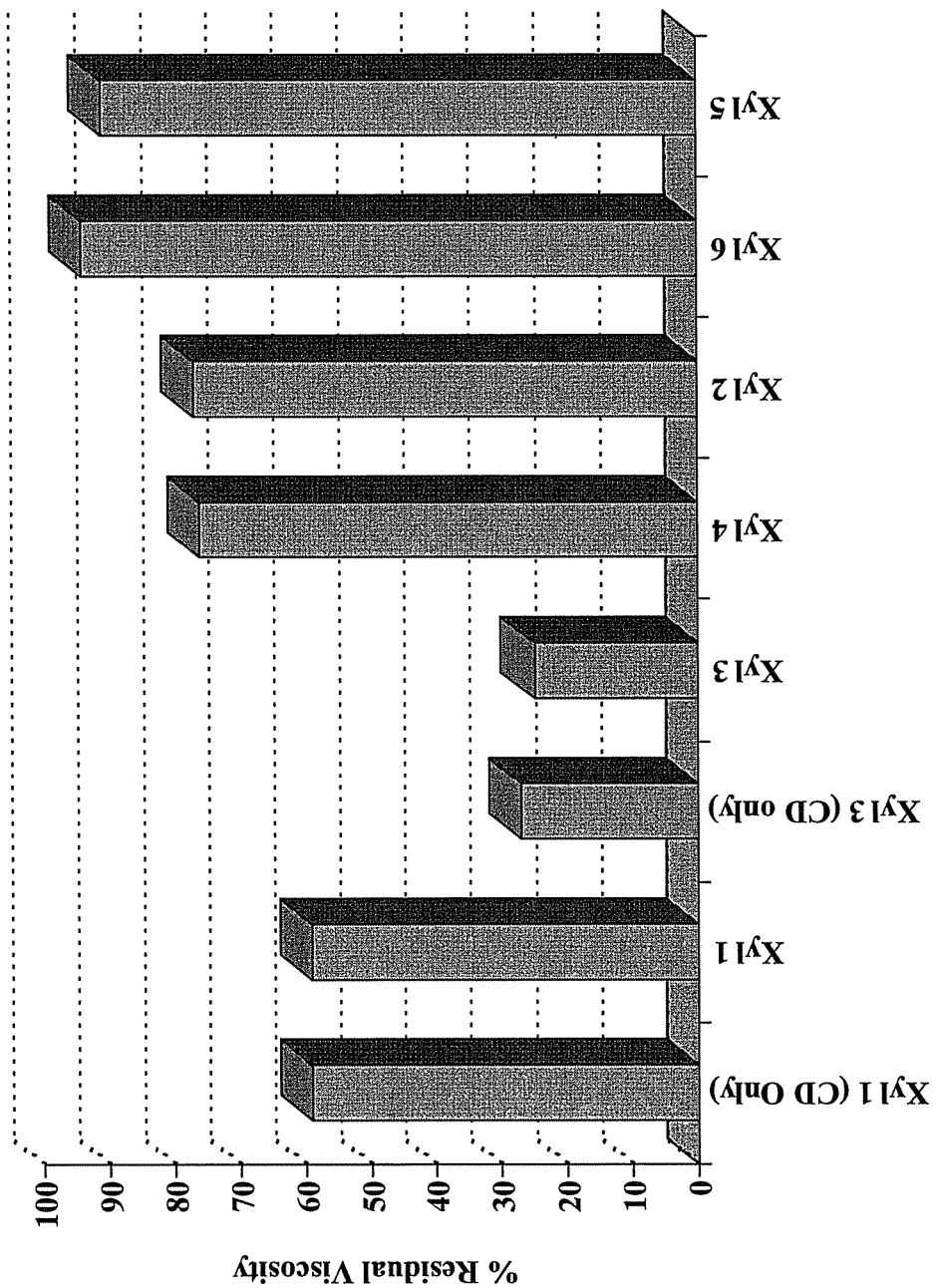
FIG. 17 shows a graph of the residual viscosity (%) of rye meal water extract after a 1-hour incubation with 1 unit of the indicated xylanase (in vitro feed test).

Table 24 shows of the residual viscosity (%) of rye meal water extract after a 1-hour incubation with 1 unit of the xylanases of the present invention. These data are presented graphically in FIG. 17.

TABLE 24

Residual Feed Viscosities of C1 Xylanses

| Enzyme | % Residual Viscosity |
|---|---|
| Xyl 1 | 59 |
| Xyl 1 (CD) | 59 |
| Xyl 2 | 27 |
| Xyl 3 | 25 |
| Xyl 3 (CD) | 76 |
| Xyl 4 | 77 |
| Xyl 5 | 94 |
| Xyl 6 | 91 |

Table 25 shows of the residual viscosity (%) of barley meal after a 1-hour incubation with 1 unit of the endoglucanases of the present invention.

TABLE 25

Residual Feed Viscosities of C1 Endoglucanases

| Enzyme | % Residual Viscosity |
|---|---|
| EG I | 18 |
| EG II | 13 |

TABLE 25-continued

Residual Feed Viscosities of C1 Endoglucanases

| Enzyme | % Residual Viscosity |
|---|---|
| EG II (CD) | 14 |
| EG III | 10 |
| EG V | 18 |
| EG VI | 20 |

Example 11

The following example illustrates an assay used to measure the biobleaching ability of enzymes of the present invention.

Ability of different crude enzyme preparations or purified enzymes to (bio)bleach cellulosic pulp may be evaluated by the assay below. The assay monitors the release of chromogenic phenolic substances from raw cellulosic pulp by the action of enzymes. The phenolic substances are detected by the absorbance at 237 nm ($A_{237}$) or 235 nm ($A_{235}$).

Mini Biobleaching Assay

Raw (wet) eucalyptus cellulosic pulp with natural pH 7.7 (National Paper Fabric, Uruguay) is placed into 5 ml reaction tubes, and the tubes are placed into a water bath shaker, (50° C., 200 rpm). The reaction volume consists 2 ml of enzyme sample appropriately diluted in appropriate buffer solution and 2 ml of cellulosic pulp suspension (0.04 g of cellulosic pulp by dry weight). The concentration of cellulosic pulp is 10 mg/ml. The biobleaching process is started by the addition of 2 ml of enzyme solution to the pulp and the assay is conducted for 2 hours. After that reaction, the mixture is centrifuged and $A_{237}$ of the supernatant is monitored in a spectrophotometer. Since some phenolic compounds are washed out from the raw cellulosic pulp even in the absence of enzymes, the blank experiments with buffer solution only (with no enzymes) are carried out. Some input to $A_{237}$ value could be made by chromogenic substances, existing in the raw enzyme sample, so another blank experiments were carried out to estimate this input. All results take into account both of those blanks as $\Delta A_{237}$. The higher the $\Delta A_{237}$ value, the better was biobleaching performance.

Figure 18:
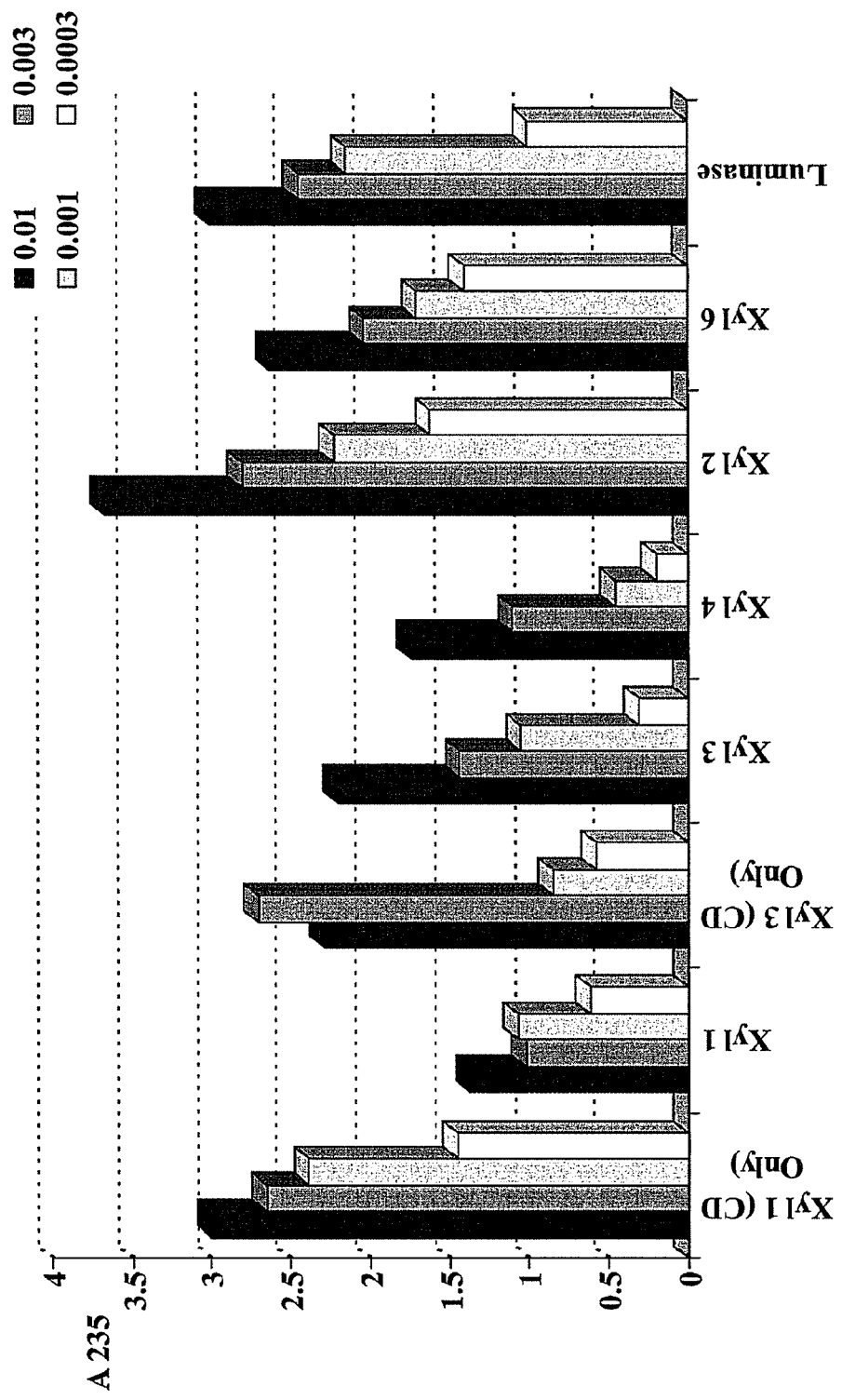
FIG. 18 shows the biobleaching ability ($A_{235}$) of xylanases of the present invention on soft wood pulp at pH 7.5 and 50° C. for 2 hours. For each xylanase, the assay was conducted using 0.01, 0.003, 0.001, 0.0003 mg/ml of enzyme in the reaction mixture, as indicated.
Figure 19:
FIG. 19 shows the biobleaching ability ($A_{235}$) of xylanases of the present invention on hard wood pulp at pH 7.5 and 50° C. for 2 hours. For each xylanase, the assay was conducted using 0.01, 0.003, 0.001, 0.0003 mg/ml of enzyme in the reaction mixture, as indicated.

The assay may also be performed using soft or hard wood pulp at pH 7.5 and 50° C. for 2 hours, with the absorbance determined at 235 nm. Table 26 and FIG. 18 show the biobleaching ability ($A_{235}$) of xylanases of the present invention on soft wood pulp under these conditions, while Table 27 and FIG. 19 show the same biobleaching ability on hard wood pulp. For each xylanase, the assay was conducted using 0.01, 0.003, 0.001, 0.0003 mg/ml of enzyme in the reaction mixture, as indicated. A positive control xylanase preparation (Luminase, Verenium Corp., San Diego, Calif. USA) was also used for comparison.

TABLE 26

Biobleaching Ability of C1 Xylanases on Soft Wood Pulp ($A_{235}$)

| Enzyme (mg/ml) | Xyl 1 (CD) | Xyl 1 | Xyl 3 | Xyl 3 (CD) | Xyl 4 | Xyl 2 | Xyl 6 | Luminase |
|---|---|---|---|---|---|---|---|---|
| 0.01 | 3 | 1.37 | 2.28 | 2.2 | 1.73 | 3.66 | 2.62 | 3 |
| 0.003 | 2.65 | 1.015 | 2.7 | 1.43 | 1.1 | 2.8 | 2.03 | 2.445 |
| 0.001 | 2.385 | 1.07 | 0.85 | 1.05 | 0.455 | 2.22 | 1.7 | 2.14 |
| 0.0003 | 1.45 | 0.615 | 0.575 | 0.31 | 0.2 | 1.615 | 1.4 | 1 |

TABLE 27

Biobleaching Ability of C1 Xylanases on Hard Wood Pulp ($A_{235}$)

| Enzyme (mg/ml) | Xyl 1 (CD) | Xyl 1 | Xyl 3 | Xyl 3 (CD) | Xyl 4 | Xyl 2 | Xyl 6 | Luminase |
|---|---|---|---|---|---|---|---|---|
| 0.01 | 8.5 | 2.355 | 4.2 | 3.715 | 1.9 | 5 | 6.5 | 7.585 |
| 0.003 | 6.25 | 1.82 | 2.24 | 2.27 | 0.82 | 4.45 | 4.5 | 5.6 |
| 0.001 | 5.4 | 1.37 | 1.05 | 1.5 | 0.5 | 2.355 | 3 | 4.8 |
| 0.0003 | 3.5 | 0.4 | 0.61 | 0.675 | 0.3 | 1.5 | 1.26 | 2.785 |

Example 12

The following example illustrates the Saccharification of pretreated lignocellulosic feedstock using crude enzyme preparations.

The assay involves a protocol for enzymatic saccharification of pretreated lignocellulosic biomass with a known moisture content and composition in order to determine the extent of cellulose and hemicellulose digestibility under concrete conditions of saccharification of the feedstock with crude cellulase and hemicellulase enzyme preparations.

Equipment
  INNOVA 40 Thermo Shaker (New Jersey, USA), where agitation of a slurry in plastic vessels is carried out using 250 rpm vibrations (each vessel supplied by one 0.5 cm metal ball to improve mixing of slurry)
  Micro centrifuge
  pH meter
  Vortex mixer
  Analytical balance, sensitive to 0.1 mg
  UV/Vis spectrophotometer
  HPLC with refractive index detector and Silica column with bonded amino phase (4×250 mm) and guard column
  Pipettes with variable sample volume (5-5000 μL)

Reagents and Materials
  Lignocellulosic feedstock with known moisture content and composition (cellulose, hemicellulose, lignin, ash, extractives)
  Sodium acetate buffer (0.1 M, pH 5.0) containing 1 mM of sodium azide to prevent microflora growth
  Enzyme cellulase and hemicellulase preparations from different fungal strains, either in soluble or in dry form
  Reagents for protein determination (either Lowry or Pierce BCA kit)
  Water, distilled and/or deionized
  Ampiox, sodium-salt.
  "Fotoglucose" kit (reagents for glucose determination using glucose oxidase—peroxidase assay) from Impact Ltd., Russia
  Somogyi and Nelson reagents for reducing sugars' assay
  Acetonitrile, HPLC grade
  NaOH, acetic acid for pH adjustments Assay Procedure
  The procedure described below assumes that the hydrolysis is carried out at 5% solids. If the process should be carried out at different substrate concentration, then recalculations should be done for the initial biomass sample weight (on a dry weight basis) using the known moisture content in the sample.
  A biomass sample containing 1 g of solids (on a dry weight basis) is weighed and placed into a 50 ml plastic vessel equipped with a hermetic lid and one metal ball (0.5 cm in diameter) to improve mixing (the moisture content is determined in preliminary experiments by drying the biomass samples at 105° C. until a constant weight is reached). The weight (volume) of water in the sample is noted as $W_s$.

The volume(s) of enzyme(s) necessary to add to the reaction mixture is calculated taking into account the protein concentration (enzyme activity) in a stock solution and the final protein concentration (enzyme activity) in the reaction mixture. Using these data, the volume of buffer ($W_a$) that is necessary for adjusting the total volume of the reaction system to 20 ml is calculated, taking into account water contained in the biomass sample ($W_s$).

The calculated amount ($W_a$) of 0.1 M, pH 5.0 Na-acetate buffer containing 200 mg/l (4 mM) of sodium azide is added to the biomass slurry, and the slurry is thoroughly mix in the 50 ml vessel using a Vortex. The pH is measure and adjusted pH to 5.0 using concentrated acetic acid or NaOH, if necessary. The lid is closed and the vessels incubated in an INNOVA 40 Thermo Shaker for 15 minutes to preheat the sample to 50° C.

The calculated amount(s) of enzyme stock solution(s) is added to the reaction mixture to start the enzymatic reaction. 20 μl of Ampiox solution (100 g/l) is then added to the final reaction mixture, which is allowed to proceed for 72 hours. (50° C. and 250 rpm vibrations).

Aliquots of the reaction slurry (50-100 μL) are typically taken at 6, 24, 48, 72 or 96 hour time points, using a pipette with a cut tip. The aliquots are centrifuged at 15,000 rpm in a micro centrifuge for 3 minutes, and the supernatants are analyzed for glucose by the glucose oxidase—peroxidase assay (see Example 6) and for reducing sugars by the Nelson-Somogyi assay (see, for example, Example 1). Samples (supernatants) are typically analyzed immediately. In some cases, they are subjected to boiling for 5 minutes, then frozen and analyzed later. The final time point (72 hours) is also analyzed for sugars by HPLC.

A substrate blank (control) is prepared in the same way as described above, except that distilled water is added to the vessel instead of the enzyme(s) stock solution(s). The supernatant resulting from the substrate blank is analyzed for glucose by the glucose oxidase—peroxidase assay, reducing sugars by the Nelson-Somogyi assay and also for sugars by HPLC.

Reactions are typically carried out in duplicate. The results of the analysis for sugars are determined as average values together with standard deviations. Typically, the protein content in the reaction system (mg protein/g solids) is used as a measure of enzyme loading. In the experiments with crude enzyme preparations, the enzyme loading is 5, 2.5 and 1 mg protein/g solids. In enzymatic reactions may be carried out in the presence of β-glucosidase preparations (40 Units of p-NPh-β-glucosidase activity per 1 g solids) in order to convert all soluble oligosaccharides to glucose.

Calculations
  To calculate the percent digestibility of cellulose (glucan), the glucose concentration in the final (72 or 96 hour) supernatant of the reaction mixture is determined (data from the glucose oxidase—peroxidase assay and/or HPLC assay), subtract the glucose concentration from the substrate blank (control). The initial cellulose (glucan) content in the reaction system is also calculated. For example, if the cellulose content in the pretreated feedstock is 35% of the total solids (dry matter) and the hydrolysis is carried out at 100 g solids/L, then the initial cellulose concentration would be 35 mg/mL.

The percent digestion of cellulose is calculated as follows:

$$\text{Digestion (\%)} = \frac{\text{Glucose concentration (mg/mL)} \times 100\%}{\text{Initial cellulose concentration (mg/mL)} \times 1.11}$$

The factor 1.11 is a result of hydration of anhydroglucose residues in cellulose (162 Da per one residue) that yields a glucose molecule (180 Da).

To calculate the percent digestibility of hemicellulose (xylan), the total concentration of pentoses (xylose+arabinose) in the final (72 or 96 hour) supernatant of the reaction mixture is determined (data from HPLC assay), subtracting the pentose (xylose+arabinose) concentration from the substrate blank (control). The initial hemicellulose (xylan) content in the reaction system is also calculated. For example, if hemicellulose content in the pretreated feedstock is 30% of the total solids (dry matter) and the hydrolysis is carried out at 100 g solids/l, then the initial hemicellulose concentration would be 30 mg/ml.

The percent digestion of hemicellulose is calculated as follows:

$$\text{Digestion (\%)} = \frac{\text{Total pentose concentration (mg/mL)} \times 100\%}{\text{Initial hemicellulose concentration (mg/mL)} \times 1.136}$$

The factor 1.136 is a result of hydration of anhydropentose (xylose or arabinose) residue in hemicellulose (132 Da per one residue) that yields a pentose molecule (150 Da).

REFERENCES

1. Berezin I V, Rabinovich M L, Sinitsyn A P (1977) Study of applicability of quantitative kinetic spectrophotometric method for glucose determination. Biokhimiya (Moscow) 42:1631-1636.
2. Ghose T K (1987) Measurement of cellulase activities. Pure Appl. Chem. 59:257-268.
3. Gusakov A V, Salanovich T N, Antonov A I, Ustinov B B, Okunev O N, Burlingame R, Emalfarb M, Baez M, Sinitsyn A P (2007) Design of highly efficient cellulase mixtures for enzymatic hydrolysis of cellulose. Biotechnol. Bioeng. 2007 Aug 1:97(5):1028-38.
4. Lowry O H, Rosebrough N J, Farr A L, Randall R J (1951) Protein measurement with the Folin phenol reagent. J. Biol. Chem. 193:265-275.
5. Sinitsyn A P, Chernoglazov V M, Gusakov A V (1990) Methods of investigation and properties of cellulolytic enzymes (in Russian), Biotechnology Series, v.25. Moscow: VINITI Press. 220 p.
6. Somogyi M (1952) Notes on sugar determination. J. Biol. Chem. 195:19-23.

Example 13

The following example illustrates the saccharification of pretreated lignocellulosic feedstock with individual purified enzymes and enzyme mixtures.

The assay involves a protocol for the enzymatic saccharification of pretreated lignocellulosic biomass with known moisture content and composition in order to determine the extent of cellulose and hemicellulose digestibility under concrete conditions of saccharification of the feedstock with individual purified enzymes (monocomponents) and their compositions (mixes of monocomponents).

Equipment
  TS-100 Thermo Shaker (Riga, Latvia), where agitation of a slurry in plastic tubes is carried out using 1200 rpm vibrations
  Micro centrifuge
  pH meter
  Vortex mixer
  Analytical balance, sensitive to 0.1 mg
  UV/Vis spectrophotometer
  HPLC with refractive index detector and Silica column with bonded amino phase (4×250 mm) and guard column
  Pipettes with variable sample volume (5-1000 µL)

Reagents and Materials
  Lignocellulosic feedstock with known moisture content and composition (cellulose, hemicellulose, lignin, ash, extractives)
  Sodium acetate buffer (0.1 M, pH 5.0) containing 1 mM of sodium azide to prevent microflora growth
  Enzyme monocomponents (cellulases, hemicellulases, glycosidases) isolated from different fungal strains, either in solution or freeze-dried
  Reagents for protein determination (either Lowry or Pierce BCA kit)
  Water, distilled and/or deionized
  "Fotoglucose" kit (reagents for glucose determination using glucose oxidase—peroxidase assay) from Impact Ltd., Russia
  Somogyi and Nelson reagents for reducing sugars' assay
  Acetonitrile, HPLC grade
  NaOH, acetic acid for pH adjustments.

Assay Procedure

The procedure described below assumes that the hydrolysis is carried out at 10% solids. If the process should be carried out at different substrate concentration, then recalculations should be done for the initial biomass sample weight (on a dry weight basis) using the known moisture content in the sample.

A biomass sample containing 200 mg of solids (on a dry weight basis) is weighed and placed into a 2 ml plastic tube equipped with a hermetic lid (the moisture content is determined in preliminary experiments by drying the biomass samples at 105° C. until a constant weight is reached). The weight (volume) of water in the sample is noted as $W_s$.

1 ml of Na-acetate buffer (0.1 M, pH 5.0) containing 1 mM of sodium azide is added, and the slurry is thoroughly mixed using a vortex. The pH is measured and adjusted to 5.0 using concentrated acetic acid or NaOH, if necessary.

The volume(s) of enzyme(s) that is necessary to add to the 2 ml tube is calculated, taking into account the protein concentration (enzyme activity) in a stock solution and the final protein concentration (enzyme activity) in the reaction mixture. Using these data, the volume of water (buffer), that is necessary for adjusting the total volume of the reaction system to 2 mL ($W_a$) is calculated, taking into account water contained in the biomass sample ($W_s$) and the previously added 1 ml of buffer.

The calculated amount of the acetate buffer ($W_a$) is added to the biomass slurry, the lid closed and the tube incubated in a TS-100 Thermo Shaker for 5 minutes to preheat the sample to 50° C. The calculated amount(s) of enzyme stock solution (s) is added to the tube to start the enzymatic reaction. The reaction is allowed to proceed at 50° C. and 1200 rpm vibrations in a TS-100 Thermo Shaker for 96 hours.

Aliquots of the reaction slurry (50-100 μL) are typically taken at 3 or 6, 24, 48, 72, and 96 hours, using a pipette with a cut tip. The aliquots are centrifuged at 15,000 rpm in a micro centrifuge for 3 minutes, and the supernatants are analyzed for glucose by the glucose oxidase—peroxidase assay (see Example 6) and for reducing sugars by the Nelson-Somogyi assay (see, for example, Example 1). Samples (supernatants) are typically analyzed immediately. In some cases, they are boiled for 5 minutes, frozen and analyzed later. The final time point (96 hours) is also analyzed for sugars by HPLC.

A substrate blank (control) is prepared in the same way as above, except that distilled water is added to the tube instead of the enzyme(s) stock solution(s). The supernatant resulting from the substrate blank is analyzed for glucose by the glucose oxidase—peroxidase assay, reducing sugars by the Nelson-Somogyi assay and also for sugars by HPLC. Typically, there is no need to prepare enzyme blanks since purified enzymes (monocomponents) usually don't contain sugars.

All reactions are carried out in duplicate, and the results of the analysis for sugars are given as average values together with standard deviations. Typically, protein content in the reaction system (mg protein/g solids) is used as a measure of enzyme loading. In the case of purified enzymes where the amino acid sequences are known, the protein concentration is calculated from the UV absorption at 280 nm using enzyme extinction coefficients predicted by the ProtParam tool (www.expasy.ch/tools/protparam.html). Otherwise, the protein concentration is determined using the Lowry (Pierce BCA) assay.

In the experiments with individual purified enzymes (monocomponents), the enzyme loading is 2 mg protein/g solids. In the case of monocomponent cellulases (endoglucanases and cellobiohydrolases), the enzymatic reactions are carried out in the presence of purified β-glucosidase (0.5 U/ml cellobiase activity) in order to convert all soluble oligosaccharides to glucose.

In the experiments with mixes of monocomponents, the enzyme loading is typically 2 mg of total protein per 1 g of solids, when preliminary screening of mixes is carried out. With selected mixes of monocomponents, the enzyme (protein) loading may be varied (up to 5-10 mg protein/g solids).

Calculations

To calculate the percent digestibility of cellulose (glucan), the glucose concentration in the final (96 hour) supernatant of the reaction mixture is calculated (data from the glucose oxidase—peroxidase assay and/or HPLC assay), subtract the glucose concentration from the substrate blank (control). The initial cellulose (glucan) content in the reaction system is also calculated. For example, if the cellulose content in the pretreated feedstock was 35% of the total solids (dry matter) and the hydrolysis was carried out at 100 g solids/l, then the initial cellulose concentration would be 35 mg/ml.

The percent digestion of cellulose is calculated as follows:

$$\text{Digestion (\%)} = \frac{\text{Glucose concentration (mg/mL)} \times 100\%}{\text{Initial cellulose concentration (mg/mL)} \times 1.11}$$

The factor 1.11 is a result of hydration of anhydroglucose residue in cellulose (162 Da per one residue) that yields a glucose molecule (180 Da).

To calculate the percent digestibility of hemicellulose (xylan), the total concentration of pentoses (xylose+arabinose) in the final (96 hour) supernatant of the reaction mixture is determined (data from HPLC assay), subtract the pentose (xylose+arabinose) concentration from the substrate blank (control). The initial hemicellulose (xylan) content in the reaction system is also calculated. For example, if the hemicellulose content in the pretreated feedstock is 30% of the total solids (dry matter) and the hydrolysis is carried out at 100 g solids/l, then the initial hemicellulose concentration would be 30 mg/ml.

The percent digestion of hemicellulose is calculated as follows:

$$\text{Digestion (\%)} = \frac{\text{Total pentose concentration (mg/mL)} \times 100\%}{\text{Initial hemicellulose concentration (mg/mL)} \times 1.136}$$

The factor 1.136 is a result of hydration of anhydropentose (xylose or arabinose) residue in hemicellulose (132 Da per one residue) that yields in pentose molecule (150 Da).

REFERENCES

1. Berezin I V, Rabinovich M L, Sinitsyn A P (1977) Study of applicability of quantitative kinetic spectrophotometric method for glucose determination. Biokhimiya (Moscow) 42:1631-1636.
2. Ghose T K (1987) Measurement of cellulase activities. Pure Appl. Chem. 59:257-268.
3. Gusakov A V, Salanovich T N, Antonov A I, Ustinov B B, Okunev O N, Burlingame R, Emalfarb M, Baez M, Sinitsyn A P (2007) Design of highly efficient cellulase mixtures for enzymatic hydrolysis of cellulose. Biotechnol. Bioeng. 2007 Aug 1;97(5):1028-38.
4. Lowry O H, Rosebrough N J, Farr A L, Randall R J (1951) Protein measurement with the Folin phenol reagent. J. Biol. Chem. 193:265-275.
5. Sinitsyn A P, Chernoglazov V M, Gusakov A V (1990) Methods of investigation and properties of cellulolytic enzymes (in Russian), Biotechnology Series, v.25. Moscow: VINITI Press. 220 p.
6. Somogyi M (1952) Notes on sugar determination. J. Biol. Chem. 195:19-23.

Example 14

The following example illustrates an assay used to measure the thermal stability of enzymes of the present invention.

This assay allows the determination of the long-term thermal stability of an enzyme at 40, 50 and 70° C. and at different pH values (the preferred values may vary with the area of use of the enzyme and its pH-profile, which is typically from pH 5.0 or 7.0). A solution of enzyme is incubated from 3-24 hours in a thermostat. The gradual drop of enzyme activity is recorded. The resulting data are used to determine enzyme half-life or enzyme activity after 3 hours of incubation under specified conditions (temperature and pH).

An enzyme dilution that gives a high enough optical density to be determined when the enzyme is diluted (e.g., in the range 0.8-1.2 using the Somogyi-Nelson assay described above) should be selected. 500-800 μl of this dilution (prepared using preheated buffer and 10- to 20-fold dilution factors (e.g., 450 μl preheated buffer+50 μl of enzyme)0 is placed into a 1.5-2.0 ml eppendorf tube (capped) in a thermostat set at 40, 50 or 60° C. Aliquots are removed at 15, 30, 45, 60, 90, 120, 180 minutes and activity determined simultaneously using any of the enzyme activity assays disclosed in this application or known in the art. A zero-point activity is determined by preparing the same enzyme dilution at room temperature. Relative activity (in %) is plotted versus time, with the activity of the enzyme at the zero-time point (without heating) set to 100%.

Example 15

The following example illustrates methods of bioscouring textiles using enzymes of the present invention.

The methods below are primarily intended for testing small amount of enzymes (mini-testing in the range of 0.5-5 mg of enzyme sample).

Bioscouring Assays

Scouring removes hydrophobic waxes and pectic substance from the surface of raw cotton fabric. The following methods, which allow the evaluation of the scouring efficiency of pure enzymes and crude enzyme preparations, are listed below:
1) Scouring and evaluating procedure for strips of 2.5×16 cm textile strips,
2) Micromethod of scouring and evaluating procedure for circular pieces of textile, diameter 1.4 cm,
3) Method for determination (staining) of remaining pectic substances in scoured textile (qualitative),
4) Method for determination of remaining waxes in scoured textile.

Method A. Scouring and Evaluation Procedure for the Strips of 2.5×16 cm Textile Strips Sample preparation: For all testing, raw weave 100% cotton fabric is used (density of 142 g/m$^2$). Cotton fabric is desized by α-amylase overnight with surfactant added at room temperature, then rinsed and dried at room temperature. For 1-2 m$^2$ fabric, about 5 liters of solution containing 5 g/l textile α-amylase preparation and 1 g/l nonionic surfactant for scouring is needed. The fabric is rinsed thoroughly with tap water and dried at room temperature overnight. The fabric should not be ironed. The fabric is then cut into strips (2.5×16 cm).

Scouring procedure: The strips are treated in 100 mL plastic vessels on an Elpan water bath shaker at 50° C. at 250 rpm for one hour. Two 16×2.5 cm strips of fabric (1.1-1.2 g total) are loaded in one vessel. The liquor ratio is 20:1, using 0.1M acetate buffer, pH 5.0.

In detail, the strips, usually 20 strips (in 10 vessels), are marked with a textile marker, then dipped into the water to completely wet each strip. An enzyme solution (20 ml) is poured in the vessels. Then, two wet strips are rapidly placed into each vessel using tweezers. The vessels are capped and placed into a preheated water bath shaker (set at 50° C., 250 rpm, amplitude 4) for one hour.

After the treatment, the strips are rinsed with cold tap water for 2-4 minutes, usually in one bath, and then dried at room temperature overnight. More intense rinses have been tested (hot water, sequestrates e.g. EDTA, surfactants) but are not recommended since they provide less reproducible results.

Heating: Dry strips are heated for 1 hour at 105° C., allowed to remain overnight at room temperature, and then assayed for wicking height.

Analysis of wettability: Wettability (wicking height) is measured according to the Russian textile standard. One end of the vertical strip of dry fabric is immersed in a water bath. Wicking height (cm) is measured after 30 minutes. The higher the value of wicking height—the better the scouring result. A value of 8 cm or higher (for heated samples) indicates good scouring. All experiments are conducted in duplicate or triplicate.

Enzyme dosages for commercial preparations are usually within the range 5-60 g preparation per kg textile. Preferably, the preparations should be normalized by protein. The dose of 0.6 mg protein per 1 ml solution (12 g protein per kg textile) proves to be suitable when comparing *T. reesei* preparations and pure enzymes using this method and micromethod B below.

When comparing preparations in one dose, 4 repetitions for each preparation (two vessels with two strips in each) are carried out. It is often more convenient to run a series of 10-16 vessels, with 1 blank (buffer treatment without enzyme) and 1-2 vessels with some standard preparation in each series Preferably, an alkaline scoured strip should also be added in the heating and evaluation procedure. For alkaline scouring, the strips are treated with a solution of 40 g/l NaOH in a boiling water bath for 2 hours at a liquor ratio of 5-20. Adding surfactant is typically not needed for these samples, but low doses of 1 g/l of EM-3 surfactant or similar products may be beneficial.

The strips can be analyzed without heating after drying overnight. However, heating of the strips provides more reproducible result and leads to a greater difference between well and poorly scoured strips. Drying and conditioning of the strips overnight or longer after heating is an important step and should not be shortened. Results may also be improved by using a special conditioning chamber with constant humidity, rather than leaving the samples at room conditions.

Method B. Micromethod of Scouring and Evaluation Procedure for the Circular Pieces of Textile, Diameter 1.4 cm Treatment procedure: In this method, circular pieces (diameter 1.4 cm), of the same desized fabric from method A are used. The fabric should be completely wetted in distilled water before the analysis, with excess water removed using filter paper.

A circular piece of textile is placed in a small cylindrical vial ("penicillin vial", 2.2 cm diameter and 5 cm height) containing 2.0 ml of enzyme solution in 0.1 M Na-acetate buffer (pH 5.0). The vials are placed into a preheated water bath (50° C.) on a shaker (250 rpm) and incubated for 1 hour. The fabric swatch is removed with tweezers, washed 2-3 minutes with cold tap water, and then dried at room temperature conditions overnight. For each enzyme sample and control sample (treatment with no enzyme in buffer), the assay procedure is typically carried out in 2 repetitions (2 pieces).

Heating: Overnight-dried textile swatches are heated for 1 hour at 105° C., then room conditioned overnight prior to being assayed for wettability. Heating generally provides better results, but may be omitted.

Analysis of wettability: Wettability is measured using a drop test. A drop of distilled water, 5 ul, is placed on the surface of fabric and time it takes the drop to adsorb into the material is measured. For each circular piece, 5 measurements are taken, placing each new drop in a dry area within the fabric swatch. The average value for each sample is then calculated.

Enzyme preparations and pure enzymes are tested at 0.6 mg protein per ml solution, but the assays are typically reproducible at doses between 0.6-2.4 mg protein per ml solution This method usually gives greater deviations than method A, but 10-fold less enzyme is needed. Thus, method B is usually recommended where enzyme amounts are limiting.

Testing at one dose with heat treatment reveals preparations of 8-10 cm (e.g. classical ACE, BioACE, IndiAGE 44L, Ecostone L 350, Celloviridin) provide comparative results.

Figure 20:
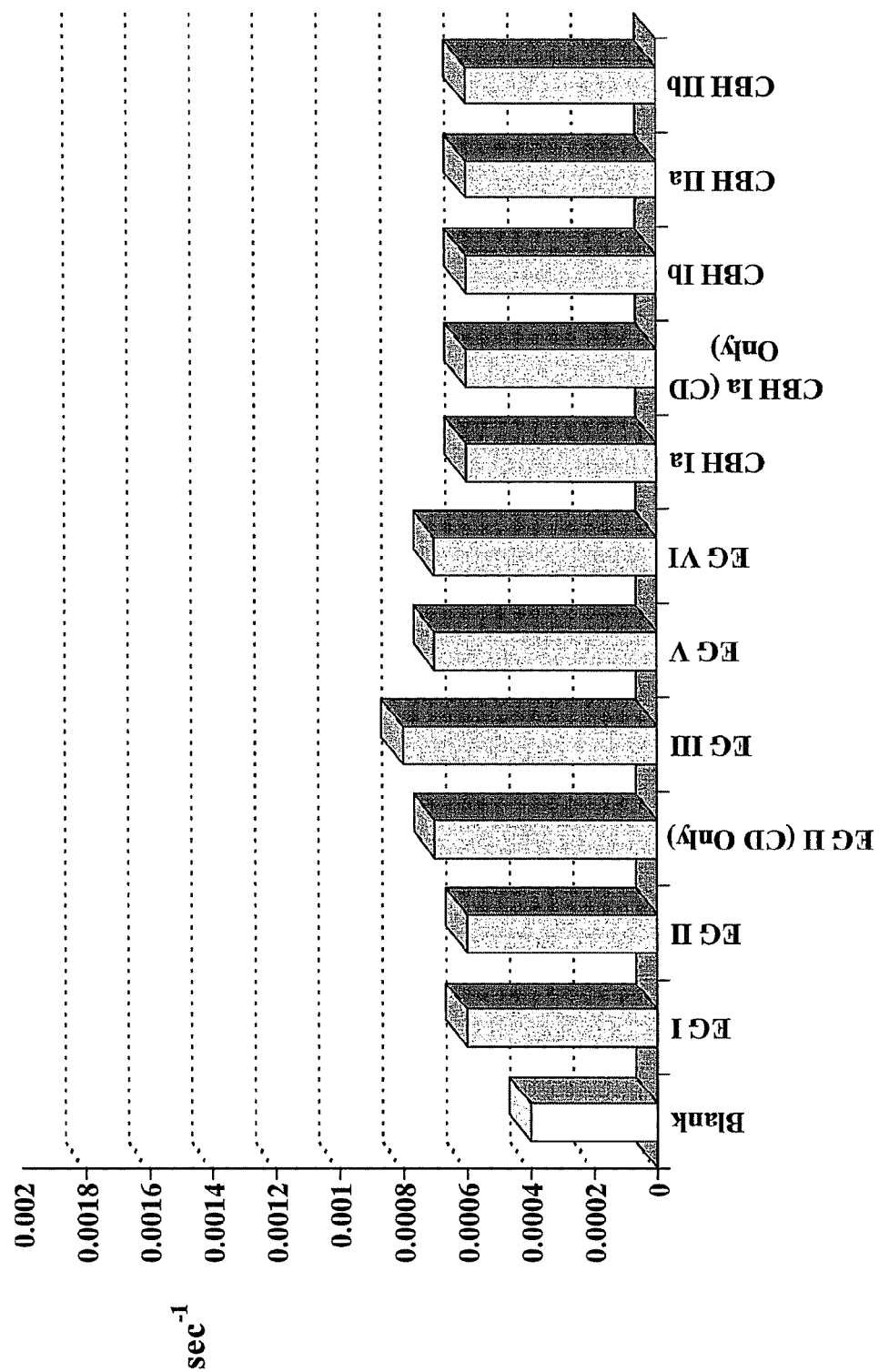
FIG. 20 illustrates the bioscouring ability of cellobiohydrolases and endoglucanases of the present invention. The reciprocal of the time (1/time; $sec^{-1}$) of water drop adsorption on a textile after treatment at pH 5.0 with 0.6 mg/l of enzyme followed by heating is shown. The water drop adsorption time for the untreated control sample is 2400 sec (1/time=0.0004).

Table 28 and FIG. 20 show the bioscouring ability of cellobiohydrolases and endoglucanases of the present invention. The reciprocal of the time (1/time; sec$^{-1}$) of water drop adsorption on a textile after treatment at pH 5.0 with 0.6 mg/l of enzyme followed by heating is shown. The water drop adsorption time for the untreated control sample is 2400 sec (1/time=0.0004).

TABLE 28

Bioscouring Abilities of C1 Cellobiohydrolases and Endoglucanases

| Enzyme | 1/Time (sec$^{-1}$) |
|---|---|
| Blank | 0.0004 |
| EG I | 0.0006 |
| EG II | 0.0006 |
| EG II (CD) | 0.0007 |
| EG III | 0.0008 |
| EG V | 0.0007 |
| EG VI | 0.0007 |
| CBH Ia | 0.0006 |
| CBH Ia (CD) | 0.0006 |
| CBH Ib | 0.0006 |
| CBH IIa | 0.0006 |
| CBH IIb | 0.0006 |

Qualitative Method for Determination (Staining) of Remaining Pectic Substances in a Scoured Fabric Ruthenium Red Dye (Sigma, R-2751) is used for specifically staining pectic substances in fabric, by forming a complex with charged carboxyl groups of pectins.

Small swatches (2.5×6 or 2.5×2.5 cm) of scoured fabric are marked using a textile marker. The scoured samples remaining after the wettability analyses described above can be used.

The following controls are included:
1) desized unscoured fabric,
2) control treated with buffer (without an enzyme),
3) alkaline scoured fabric.

All the samples are dyed in one bath and weighed together. The volume of the solution is calculated using the following formula:

$V(ml) = m \text{ samples}(g) \times 30$.

The desired volume of 1 g/l solution of the dye is prepared. The dye solution is stirred and warmed in a boiling water bath for 5 minutes until the dye dissolves completely. The dye solution is warmed in a glass vessel on a water bath shaker set at 50° C., 200 rpm. The samples are then placed in the solution and some surfactant is added if the samples are not wetted. The samples are dyed for 30 minutes at 50° C. with shaking at about 200 rpm for even dying.

Then, the samples are rinsed under tap water followed 3-4 rinses (about 5 minutes each) with hot water (about 70° C. in a glass vessel). After this, the samples are dried overnight at room temperature. The samples should not be iron dried as it may destroy the dye. The samples are generally compared visually, although quantitative calorimetric evaluation can be used.

Figure 21:
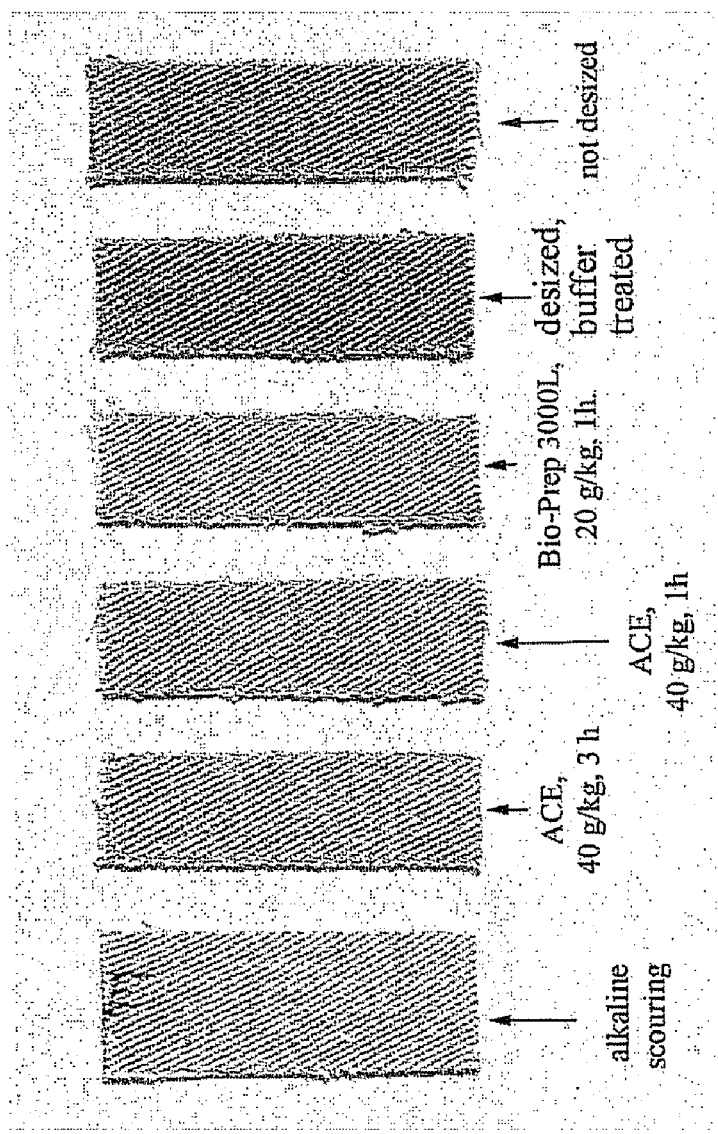
FIG. 21 illustrates a comparison of the pectin content in an unscoured sample, an alkaline scoured sample, and bio-scoured samples.

Example of stained strips are presented in FIG. 21. FIG. 21 illustrates a comparison of the pectin content in an unscoured sample, an alkaline scoured sample, a sample bioscoured by BioPrep (Novo Nordisk, Denmark) at 20 g preparation per 1 kg fabric, and samples bioscoured by ACE at 40 g/kg for 1 or 3 hours.

The unscoured sample and control (treated without enzyme) are stained at high and equal intensity—that means no pectins are removed during buffer treatment. Alkaline scoured sample is very faint stained—100% pectin removed (by definition). All three enzyme scoured samples are also faint, but little bit more intensive than alkaline scoured. This means that cellulase scouring and scouring by BioPrep removes the majority of surface (stainable) pectins from the primary wall, similar to alkaline scouring.

Other positively charged dyes can be used for staining pectins due to the negatively charged polymer in cotton. We have tested methylene blue, but it resulted in less distinction between scoured and unscoured fabric.

Method for Determination of Remaining Waxes in Scoured Textiles

The presence of remaining waxes in scoured textiles is determined using an extraction procedure. 3-12 g of scoured fabric is weighed and then extracted with boiling benzene in a Soxlet apparatus for 4 hours. The extract is evaporated in a rotary evaporator. Then, a flask containing the evaporated, extracted waxes is brought to a constant weight at 105° C. (0.75-1 hour of incubation time is usually necessary). The weight of extracted waxes is then determined and the wax content is calculated.

We compared bioscouring (ACE preparation) and alkaline scouring. Desized cotton strips were treated, dried at room conditions overnight and divided into two parts: one part was evaluated for wicking height, another part were heated to 105° C. for 1 hour, equilibrated at room conditions overnight and then evaluated for wicking height.

Wax content was determined by the method described above, and the results are presented in Table 29 below.

Bioscouring by ACE and by the alkaline procedure gave comparable results based on wicking height changes, but bioscouring removed less wax. Alkaline scouring, however, did not remove all of the wax.

TABLE 29

Bioscouring by ACE versus alkaline scouring.

| Type of treatment | Wicking height, cm Room drying | Wicking height, cm heating 105° C., 1 h | Waxes, % |
|---|---|---|---|
| Untreated cotton | 6.0 | 0 | 0.62 ± 0.03 |
| Alkaline scouring | 13.0 | 8.4 | 0.37 ± 0.03 |
| Bioscouring (ACE) | 12.4 | 8.6 | 0.57 ± 0.03 |

Example 16

The following example illustrates a method of biopolishing (biofinishing) textiles using enzymes of the present invention.

The method allows for testing small amount of enzymes (mini-testing in the range of 0.5-5 mg of enzyme sample). The method for testing of pure enzymes and crude enzyme preparations is carried out in specially designed cells (essentially a micro-washing machine) also used for the mini-denim washing assay (see FIG. 22B).

Sample preparation: Circular pieces of textile (diameter of 28 mm) are excised from TIC-460 cotton interlock dyed Red 80 fabric. The samples are marked with a textile marker on the side that will be treated with an enzyme and mechanical stress. Each sample is then weighed to an accuracy 1 mg. One piece generally weighs 160 to 180 mg.

Treatment procedure: The sample is fixed in the cell and three metal cylinders are placed into it. When all cells are assembled, 3 ml of enzyme solution are added to each cell. The enzyme solutions contain 0.1M Na-acetate buffer, pH 5.0, to control the pH. The cells are placed into a preheated Elpan water bath shaker (50° C., 300 rpm, amplitude 4) and the samples are treated for 1 hour.

The efficiency of biopolishing is assayed by measuring the optical density of the reaction solution. Immediately after the treatment, the solution should be thoroughly mixed, using a pipette, to resuspend any possible sediment of removed fuzz. A 1-1.5 ml aliquot of reaction solution is then taken from each cell. The optical density of the solution is then measured on a spectrophotometer at 400 nm in a 1 ml cuvette (1 cm optical path). The solution is resuspended and dosed into the cuvette and the optical density determined rapidly (within 10 seconds), as the suspension sediments gradually and the optical density changes due to sedimentation. If the value of $A_{400}$ exceeds 1 unit, the sample is diluted 2-4 times carefully and the optical density determined once again. If a sample was diluted, the resultant value should be multiplied by the dilution factor.

Rinse and drying: The circular pieces of textile should be rinsed immediately after taking the aliquots of reaction solution, since the enzymatic reaction will proceed otherwise. The sample is removed from the cell, and washed briefly in distilled water. All the samples are then rinsed together thoroughly in distilled water for 3-5 min, stirring gently and changing water periodically. After rinsing, the samples are blotted using filter paper and dried at room temperature for at least 24 hours.

Measurement of the efficiency of biopolishing by determination of the weight loss: Each sample is weighed to a 1 mg accuracy. The resulting values are compared with that of the same sample before the treatment and weight loss is calculated as below:

Weight loss(mg)=$m$ before treatment(mg)−$m$ after treatment(mg)

% Weight loss=Weight loss/$m$ before treatment(mg)× 100%

Qualitative evaluation of the surface appearance: The image of the edge of the folded fabric is taken using suitable device at a magnification about ×60. Images of the samples treated by different enzymes and blank runs are compared visually.

In detail, the circular piece is folded (for all samples in a same manner—e.g., so that the surface threads are perpendicular to the edge line). All samples should be folded so that the treated surface is up. The samples can be stapled to a piece of paper for more convenient operation. Images are then taken using a QX3 Intel Play microscope at ×60 magnification and recorded in JPEG format.

The samples should be run in series up to 8 samples in each. In each series, there should be a control treatment (without an enzyme) and a treatment with a standard preparation. For each preparation under investigation, at least 2 repetitions should be made.

Weight determination is influenced by the drying conditions. Drying of the samples before the treatment and after in reproducible conditions is recommended (e.g., heating in an oven and drying in a dessicator). Drying at room conditions can result in slight deviations between series run on different days.

The effect of enzymatic treatment along with mechanical stress in our test is similar to the widely used Launderometer and other laboratory testing machines, but it has different geometry. Due to this geometry, the system is amenable to further miniaturization and require less than 1 mg quantities of an enzyme.

Evaluation of the biopolished fabric can be problematic. The most important (and direct) parameters are pilling resistance and fuzziness of a treated fabric. Weight loss, color clarification, and improvement of softness are less direct but valuable parameters. Greater pilling resistance correlates with greater weight losses and gives less fuzz, clarification of color and softer feel. Fuzziness is evaluated qualitatively in our method on 3 levels: good, moderate and poor. Optical density should correlate directly both to weight loss (weight loss is due mainly to the removed fuzz making turbid suspension in a solution) and fuzziness of fabric.

Figure 23:
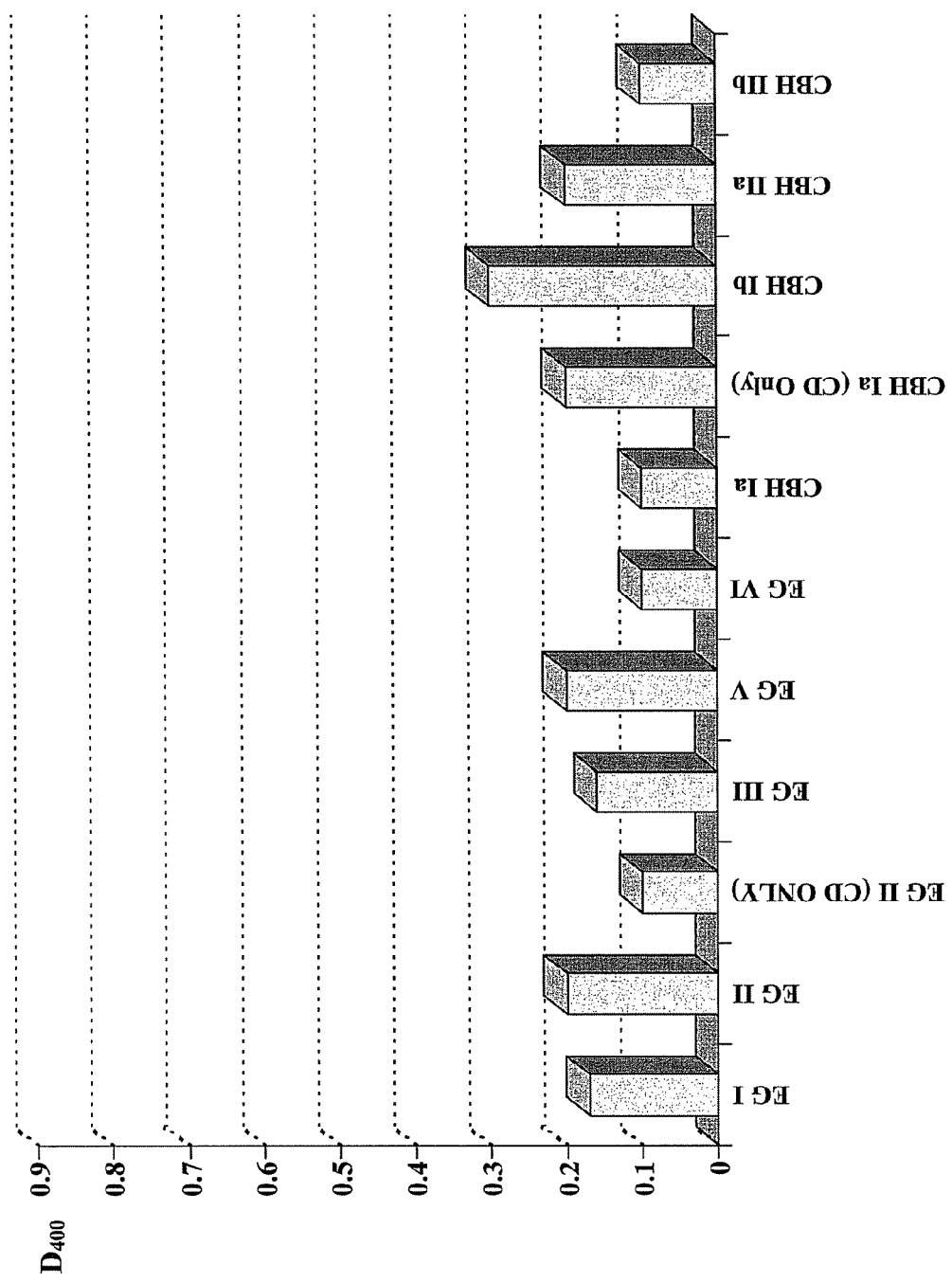
FIG. 23 illustrates the biopolishing ability of cellobiohydrolases and endoglucanases of the present invention. The dye release (D 400 nm) after treatment with 0.2 g/l enzyme at pH 5.0, 50° C. is shown.

Table 30 and FIG. 23 illustrate the biopolishing ability of cellobiohydrolases and endoglucanases of the present invention. The dye release (D 400 nm) after treatment with 0.2 g/l enzyme at pH 5.0 and 50° C. is shown.

TABLE 30

Biopolishing Abilities of C1 Cellobiohydrolases and Endoglucanases

| Enzyme | % Dye Release |
|---|---|
| EG I | 0.17 |
| EG II | 0.2 |
| EG II (CD) | 0.1 |
| EG III | 0.16 |
| EG V | 0.2 |
| EG VI | 0.1 |
| CBH Ia | 0.1 |
| CBH Ia (CD) | 0.2 |
| CBH Ib | 0.3 |
| CBH IIa | 0.2 |
| CBH IIb | 0.1 |

Example 17

The following example illustrates methods of biostoning (abrasion) textiles using enzymes of the present invention.

The method allow for testing small amount of enzymes (mini-testing in the range of 0.5-5 mg of enzyme sample). The method is available in two scales, requiring approximately 10 and 1 mg of protein, respectively (Method A and Method B). Both scales utilize the same principle and gives comparable results. Method B requires specially designed cells but proved easier when assaying pure enzymes.

Figure 22:
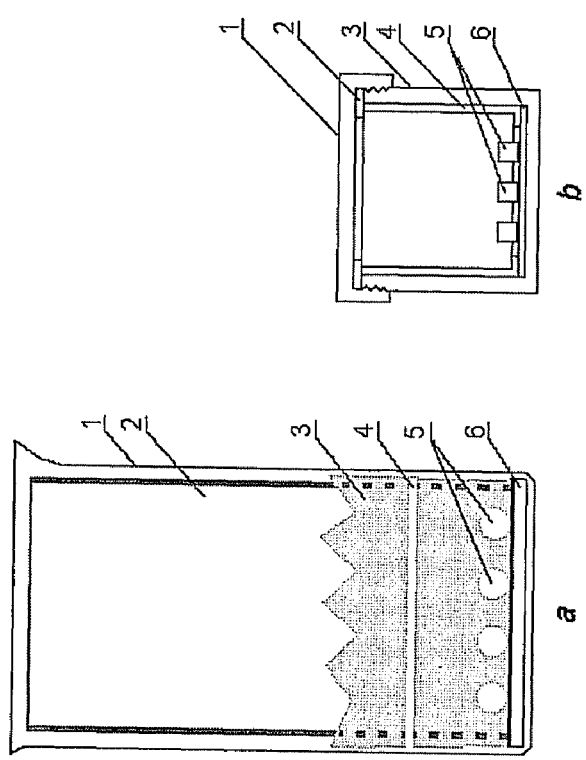
FIG. 22 shows a diagram of cells for the enzymatic and mechanical stress treatment of fabric.

Method A 250 ml vessels (internal diameter 56 mm, height 110 mm) with Teflon disks at the bottom (thickness 4 mm) are used for the treatment of denim fabric with cellulase (see FIG. 22A). A swatch of desized denim fabric (10×10 cm) is pulled over the butt of a plastic tube (diameter 50 mm, height 100 mm) and fixed with a rubber ring. The tube is inserted into the 250 ml vessel so that the swatch attaches tightly and uniformly to the Teflon disk at the bottom of the glass. Ten metal buck-shot balls (diameter 7 mm) are placed inside the tube to provide mechanical stress to the surface of fabric, and 30 ml of enzyme solution in the appropriate buffer is added. The vessel is placed onto a ELPAN water bath shaker type 357 (Poland) at 50° C. The enzymatic treatment of the denim is carried out for 1 hour at the shaker speed of 300 rpm and amplitude of vibrations adjusted to 4 units. The swatch is then removed and washed for 1 minute with running water. An excess of water on the surface of the swatch is removed by squeezing it between two sheets of blotting paper, and then the swatch is dried overnight in the open air at room temperature. In a separate experiment, a control assay is carried out as described above, but in the absence of enzyme. For the control, 30 ml of the same buffer used for enzyme dilution is added to the vessel.

Method B

This assay procedure uses specially designed cylindrical cells (external diameter 35 mm, internal diameter 30 mm, height 48 mm) made of stainless steel and equipped with tightened lids (see FIG. 22B). This method also uses 10-fold less enzyme than Method A. A circular swatch of denim fabric (diameter of 30 mm) is placed at the bottom of a cell, and a stainless steel cylindrical cartridge is inserted to clamp the swatch. Three metal cylinders (7×7 mm), made of stainless steel, are placed into the cell to provide mechanical stress, and 3 ml of enzyme solution in the appropriate buffer is added. A lid, equipped with a rubber ring inside, is quickly tightened to seal the cell hermetically, and the cell is placed in a water bath on a shaker. Then, the procedure is carried under the same conditions as described above for Method A. In the control assay, afacric swatch is treated under the same conditions but in the absence of enzyme. To this end, 3 ml of the same buffer used for enzyme dilution is added to the cell.

Both assays (Method A or Method B) are carried out at least in two repetitions for each particular enzyme (usually three repetitions). Typically, when different cellulase preparations are compared, the conditions in the reaction system are equalized by the CMCase activity (1-3 U/ml). Acid cellulase samples are assayed at pH 5.0 using 0.1 M acetate buffer. Neutral cellulases are assayed at pH 6.0 using 0.1 M phosphate buffer.

Analysis of color intensity on denim swatches is carried out using a Mustek MFS-12000SP (USA) scanner. A circular area on the swatch, subjected to the combined enzyme and mechanical action as above, is scanned at 300 dpi resolution. This area is usually more light than the denim surface near the swatch edges. Each swatch is scanned twice: first, when the threads on the surface of the fabric are parallel to the movement of the light source on scanning, and second, when the threads are directed perpendicular to the movement of the light source on scanning.

Figures 24A, 24B:
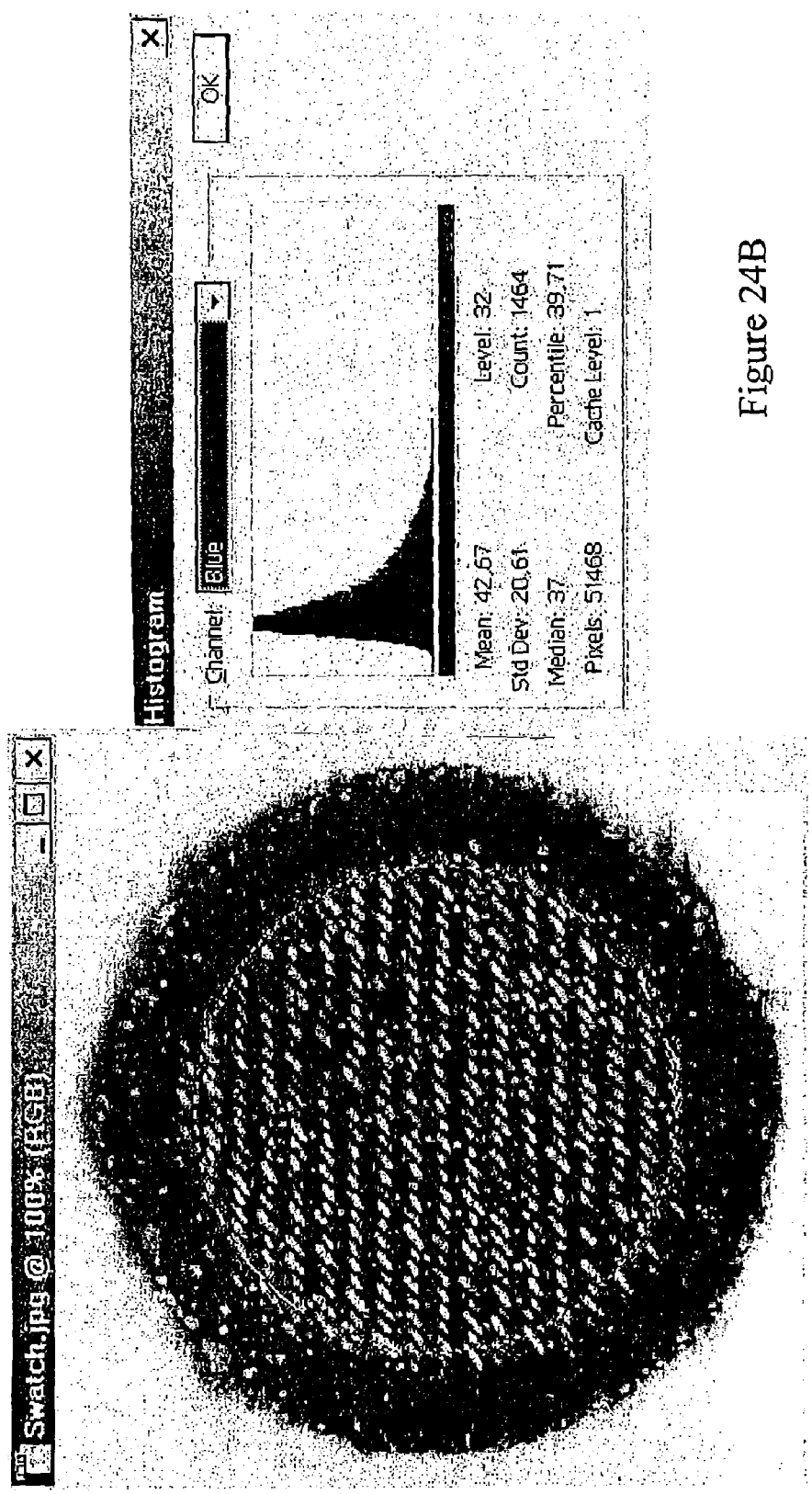
FIGS. 24A and 24B show an example histogram generated from the color intensity analysis of a denim swatch.

The JPG images obtained as a result of scanning are analyzed using Adobe Photoshop software (versions 3.0 or later can be used). For each particular scan, a histogram is opened. The blue channel is selected and the percentile at level 32 (P32) is read. This parameter shows the percentage of image pixels having the intensity of color higher than at the level 32 of histogram (a total of 256 shades (levels) of blue color as the abscissa axis). The higher is the P32, the darker is the denim swatch. On the contrary, the parameter (100- P32, %) shows the percentage of pixels having the intensity of color lower than at the level 32 of the histogram. FIGS. 24A and 24B shows an example histogram generated from the color intensity analysis of a denim swatch.

For each particular enzyme tested, an average value of the P32 and standard deviation are calculated using the data of all scans for this enzyme. For example, if the assay is performed in two repetitions, four P32 values are taken into account, since for each repetition two scans are carried out.

The difference between the average value of P32 obtained in the control (without cellulase) and the average value of P32 for the enzyme is taken as a criterion of the abrasive activity of the enzyme.

Figure 25:
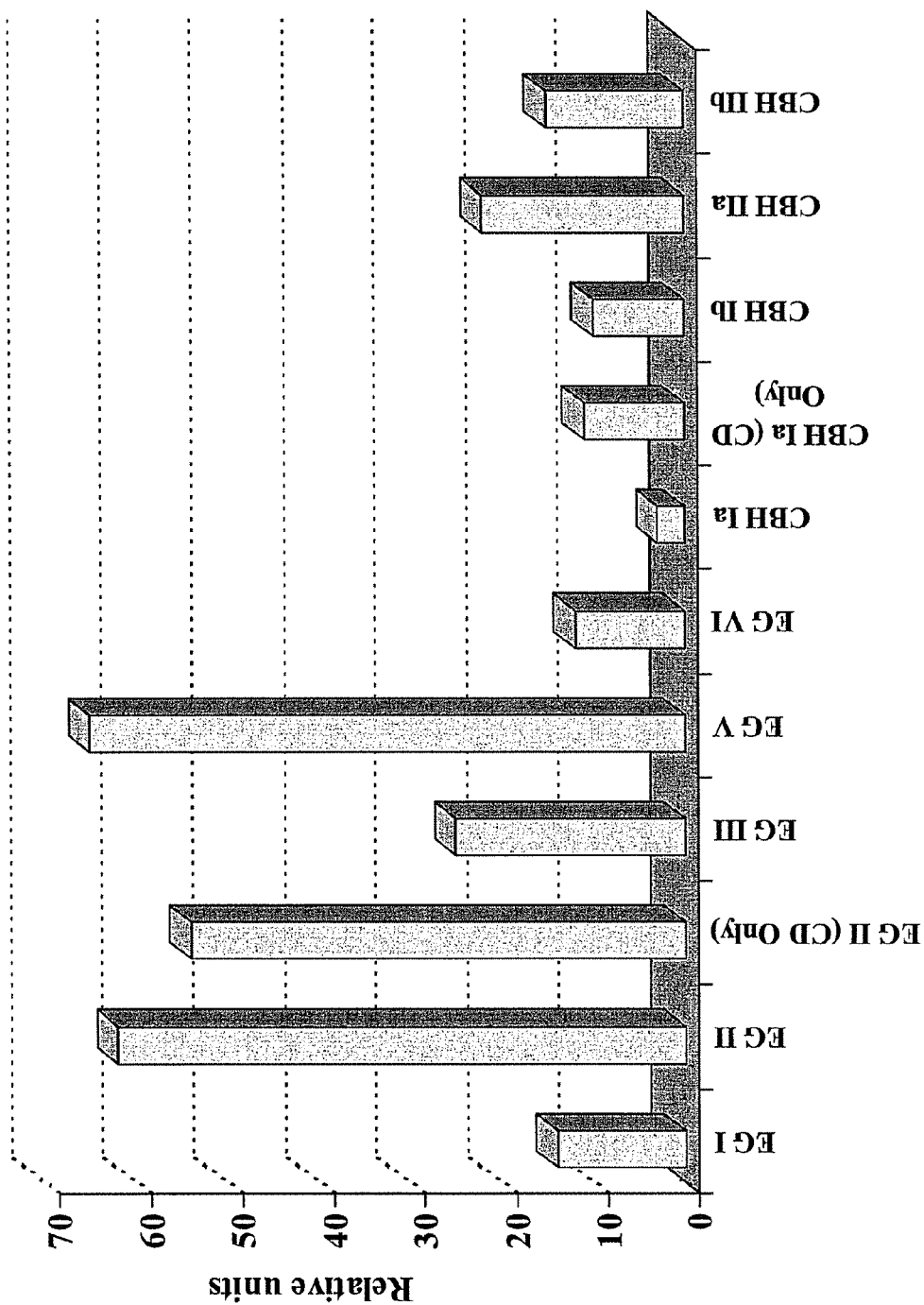
FIG. 25 illustrates the denim-washing (abrasion) ability of cellobiohydrolases and endoglucanases of the present invention. The relative units per mg of enzyme determined at 50° C., pH 5.0 is shown.

Table 31 and FIG. 25 illustrate the denim-washing (abrasion) ability of cellobiohydrolases and endoglucanases of the present invention using Assay B above. The relative units per mg of enzyme determined at 50° C., pH 5.0 is shown.

TABLE 31

Abrasion Abilities of C1 Cellobiohydrolases and Endoglucanases

| Enzyme | Relative Units per mg |
|---|---|
| EG I | 14 |
| EG II | 62 |
| EG II (CD) | 54 |
| EG III | 25 |
| EG V | 65 |
| EG VI | 12 |
| CBH Ia | 3 |
| CBH Ia (CD) | 11 |
| CBH Ib | 10 |
| CBH IIa | 22 |
| CBH IIb | 15 |

Additional examples and discussion concerning methods A and B are presented in A. Gusakov, A. Sinitsyn, S. Grishutin, D. Tikhomirov, D. Shook, D. Sheer, M. Emalfarb Microassays to control the results of cellulase treatment of denim fabrics; Textile Chemist and Colorist and American Dyestuff Reporter, (2000), V.32, N. 5, P.42, the contents of which are hereby incorporated by reference in their entirety.

Example 18

The following example illustrates methods of backstaining textiles using enzymes of the present invention.

The methods allow for testing small amount of enzymes (mini-testing in the range of 0.5-5 mg of enzyme sample).

Standard Indigo backstaining Method A requires larger enzyme quantities (typically 2-5 mg of protein for one assay performed with 3.5×3.5 cm swatches in 2-3 repetitions). When purification of enzyme components is performed on a laboratory scale and it is necessary to assay the backstaining index (BSI) for the purified enzyme, much lower quantities of an enzyme are typically available. In such case, a modification of this method (Method B) should be used, where smaller swatches of standard garment (1.4×1.4 cm) are used, and the total volume of Indigo suspension is 2 ml. This minimized microassay procedure requires ten times lower amounts of protein (0.2-0.5 mg).

Method A

Indigo reagent preparation: 250 mg of indigo is added to 50 ml of distilled water in a flask and stirred vigorously for 15-20 minutes on a magnetic stirrer. Before taking aliquots for staining experiments, the suspension is placed into a Bandelin SONOREX TK52 ultrasonic bath for 5 minutes to disrupt large indigo aggregates and to make the suspension more uniform.

2 ml aliquots are used for staining experiments (see below) under magnetic stirring in order to provide a uniform indigo suspension in the reaction mixture.

Assay procedure: A piece of white fabric (3.5×3.5 cm) is added to 18 ml of 0.1 M Na-acetate buffer (pH 5.0) in a 250 ml glass vessel and incubated at room temperature for 10 minutes (control). A solution of enzyme preparation in the same amount of the buffer is used in the enzyme assay procedure. 2 ml of indigo suspension (5 mg/ml) is then added, and the vessel is placed into a water bath (50° C.) on a shaker (300 rpm) and agitated for 30 min. The piece of fabric is removed with tweezers and washed twice for 5 minutes with 50 ml of distilled water (on a shaker at 300 rpm) and then dried at room temperature overnight. For each enzyme sample and control, the assay procedure is carried out at least in 3 repetitions.

Samples of stained fabric are scanned at 300 dpi resolution on a "Paragon" ("Muztek", USA) scanner. Two images of the front side and two images of the back side (one direct and one rotated 90°) are obtained for each sample. Images are processed using an Adobe Photoshop software. A histogram of colour intensities is calculated for each sample using a blue channel, and a percentile at level 120 is used as a criterion of staining. An average value and standard deviation are calculated for each enzyme preparation and control.

*T. reesei* (ACE) is usually used as a control (internal standard) for analyzing backstaining properties of a particular enzyme sample, since ACE is characterized by a high backstaining index. If possible, a IndiAge Super GX sample should be used as a second internal standard since it has a low backstaining index.

Method B

The Indigo stock suspension (5 g/l) is prepared and the image processing is carried out as described above.

Assay procedure: A piece of white fabric (1.4×1.4 cm) is placed in a small cylindrical vial ("penicillin vial", 2.2 cm diameter and 5 cm height) containing 1.8 ml of enzyme solution in 0.1 M Na-acetate buffer (pH 5.0) and incubated at room temperature for 10 min. 0.2 ml of Indigo suspension is then added, and the vial is placed into a water bath (50° C.) on a shaker (300 rpm) and agitated for 30 minutes. The fabric swatch is removed with tweezers and washed twice for 5 minutes with 5 ml of distilled water at 50° C. (on a shaker at 300 rpm), then dried at room temperature overnight. For each enzyme sample and control (internal standard), the assay procedure is typically carried out in 3 repetitions. In most experiments, 1.5 CMCase units per ml of reaction system are used. In cases where specific CMCase activity is very low (or absent), 0.05-0.1 mg of protein per ml of reaction system is used.

It is convenient to place three vials (3 repetitions) into a 250 ml vessel containing 15-20 ml of water at the bottom and then to place the vessel into a water bath on a shaker.

Additional examples and discussion concerning methods A and B are presented in A. Gusakov, A. Sinitsyn, S. Grishutin, D. Tikhomirov, D. Shook, D. Sheer, M. Emalfarb Microassays to control the results of cellulase treatment of denim fabrics; Textile Chemist and Colorist and American Dyestuff Reporter, (2000), V.32, N. 5, P.42, the contents of which are hereby incorporated by reference in their entirety.

Example 19

The following example illustrates assays used to measure acetyl esterase enzymatic activity.

Activity Towards p-Nitrophenyl Acetate Substrate

This assay measures the release of p-nitrophenol by the action of an acetyl esterase on p-nitrophenyl acetate (PNPAc). One acetyl esterase unit of activity is the amount of enzyme that liberates 1 micromole of p-nitrophenol in one minute at 37° C. and pH 7.2.

Phosphate buffer (0.01 M, pH 7.2) is prepared as follows: 0.124 g of $NaH_2PO_4*H_2O$ and 0.178 g $Na_2HPO_4$ are dissolved in distilled water so that the final volume of the solution 500 ml and the pH of the resulting solution is 7.2.

PNPAc (Fluka Chemie, Switzerland, cat. # 46021) is used as the assay substrate. 3.6 mg of PNPAc is dissolved in 10 ml of 0.01 M phosphate buffer using a magnetic stirrer to obtain a 2 mM stock solution. The solution is stable for 2 days with storage at 4° C.

The stop reagent (0.25 M Tris-HCl, pH 8.5) is prepared as follows: 30.29 g of Tris is dissolved in 900 ml of distilled water (Solution A). The final 0.25 M Tris-HCl pH 8.5 is prepared by mixing solution A with 37% HCl until the pH of the resulting solution is equal to 8.5. The solution volume is then adjusted to 1000 ml. This reagent is used to terminate the enzymatic reaction. Using the above reagents, the assay is performed as detailed below.

For the enzyme sample, 0.10 ml of 2 mM PNPAc stock solution is mixed with 0.01 ml of an enzyme sample and incubated at 37° C. for 5 minutes (Axe2 and Axe3) or 10 minutes (Axe1). After exactly 5 or 10 minutes of incubation, 0.1 ml of 0.25 M Tris-HCl solution is added and then the absorbance at 405 nm ($A_{405}$) is measured in microtiter plates as $A_S$.

For the substrate blank, 0.10 mL of 2 mM PNPAc stock solution is mixed with 0.01 ml of 0.01 M phosphate buffer, pH 7.2. 0.1 mL of 0.25 M Tris-HCl solution is then added and the absorbance at 405 nm ($A_{405}$) is measured in microtiter plates as $A_{SB}$.

Activity is calculated as follows:

$$\text{Activity (IU/ml)} = \frac{\Delta A_{405} * DF * 21 * 1.33}{13.700 * 5}$$

where $\Delta A_{405} = A_S - A_{SB}$, DF is the enzyme dilution factor, 21 is the dilution of 10 µl enzyme solution in 210 µl reaction volume, 1.33 is the conversion factor of microtiter plates to cuvettes, 13.700 is the extinction coefficient (13700 $M^{-1}$ $cm^{-1}$ of p-nitrophenol released corrected for mol/L to µmol/ mL), and 5 minutes is the reaction time.

Using the assay above, acetyl esterase activity of Axe1 was found to be 0.23 IU/mL ($\Delta A_{405}$=1.11, DF=1), Axe2 was found to be 2.80 U/ml (($\Delta A_{405}$=0.1714, DF=40), and Axe3 was found to be 39.97 U/ml ($\Delta A_{405}$=0.4901, DF=200).

Activity Towards Arabinoxylan Oligosaccharide Substrates

This assay measures the release of acetate by the action of a xylan acetyl esterase on the arabinoxylan oligosaccharides from *Eucalyptus* wood.

0.01 M sodium hydroxide is prepared as follows: 0.4 g of sodium hydroxide is dissolved in distilled water so that the final volume of the solution to be 1000 ml Arabinoxylan oligosaccharides from *Eucalyptus* wood were prepared by dissolving 5 mg of arabinoxylan oligosaccharides in 1 ml distilled water using a magnetic stirrer as described in Kabel et al. *Carbohdr. Polym.* 50:191 (2002).

For the enzyme sample, 1.0 mL of arabinoxylan oligosaccharides stock solution is mixed with 0.005 mg of the enzyme sample and incubated at 35° C. The pH was maintained at 5.0 by the addition of 0.01 M NaOH. The added volume of 0.01 M NaOH is proportional to the breakdown of ester linkage and release of acetate.

For the substrate blank, 1.0 ml of arabinoxylan oligosaccharides stock solution is mixed with 0.005 mg of distilled water and incubated at 35° C. The pH was maintained at 5.0 by addition of 0.01 M NaOH. The added volume of 0.01 M NaOH is proportional to the breakdown of ester linkage and release of acetate.

Using the assay above, both Axe2 and Axe3 were found to exhibit xylan acetyl esterase activity, as measured by the release of acetate from eucalyptus wood arabinoxylan oligosaccharides. For Axe2, 0.7 ml NaOH was used after 200 minutes of incubation. For Axe3, 0.35 ml was used after 200 minutes.

Example 20

The following example illustrates assays used to measure ferulic acid esterase enzymatic activity.

Activity Towards p-Nitrophenyl Butyrate Substrate

This assay measures the release of p-nitrophenol by the action of a ferulic acid esterase on p-nitrophenyl butyrate (PNPBu). One acetyl esterase unit of activity is the amount of enzyme that liberates 1 micromole of p-nitrophenol in one minute at 37° C. and pH 7.2.

Phosphate buffer (0.01 M, pH 7.2) is prepared as follows: 0.124 g of $NaH_2PO_4*H_2O$ and 0.178 g $Na_2HPO_4$ are dissolved in distilled water so that the final volume of the solution is 500 ml and the pH of the resulting solution is equal to 7.2.

PNPBu (Sigma, USA, cat. # N9876-5G) is used as the assay substrate. 10 µl of PNPBu is mixed with 25 ml of 0.01 M phosphate buffer using a magnetic stirrer to obtain a 2 mM stock solution. The solution is stable for 2 days with storage at 4° C.

The stop reagent (0.25 M Tris-HCl, pH 8.5) is prepared as follows: 30.29 g of Tris is dissolved in 900 ml of distilled water (Solution A). The final 0.25 M Tris-HCl pH 8.5 is prepared by mixing solution A with 37% HCl until the pH of the resulting solution is equal to 8.5. The solution volume is adjusted to 1000 ml. This reagent is used to terminate the enzymatic reaction. Using the above reagents, the assay is performed as detailed below.

For the enzyme sample, 0.10 ml of 2 mM PNPBu stock solution is mixed with 0.01 ml of the enzyme sample and incubated at 37° C. for 10 minutes. After exactly 10 minutes of incubation, 0.1 ml of 0.25 M Tris-HCl solution is added and then the absorbance at 405 nm ($A_{405}$) is measured in microtiter plates as $A_S$.

For the substrate blank, 0.10 ml of 2 mM PNPBu stock solution is mixed with 0.01 ml of 0.01 M phosphate buffer, pH 7.2. 0.1 ml of 0.25 M Tris-HCl solution is then added and the absorbance at 405 nm ($A_{405}$) is measured microtiter plates as $A_{SB}$.

Activity is calculated as follows:

$$\text{Activity (IU/ml)} = \frac{\Delta A_{405} * DF * 21 * 1.33}{13.700 * 10}$$

where $\Delta A_{405}=A_S-A_{SB}$, DF is the enzyme dilution factor, 21 is the dilution of 10 µl enzyme solution in 210 µl reaction volume, 1.33 is the conversion factor of microtiter plates to cuvettes, 13.700 is the extinction coefficient (13700 $M^{-1}$ $cm^{-1}$ of p-nitrophenol released corrected for mol/l to µmol/ml), and 10 minutes is the reaction time.

Using the assay above, the ferulic acid esterase activity of FaeA1 was found to be 18.5 IU/ml ($\Delta A_{405}=0.906$, DF=10), FaeA2 was found to be 0.40 U/ml ($\Delta A_{405}=1.976$, DF=1) and FaeB2 was found to be 0.02 U/ml ($\Delta A_{405}=0.111$, DF=1).

Activity Towards p-Nitrophenyl Butyrate Substrate

The following assay is used to measure the enzymatic activity of a ferulic acid esterase towards wheat bran (WB) oligosaccharides by measuring the release of ferulic acid.

Wheat bran oligosaccharides are prepared by degradation of wheat bran (obtained from Nedalco, The Netherlands) by endo-xylanase III from *A. niger* (enzyme collection Laboratory of Food Chemistry, Wageningen University, The Netherlands). 50 mg of WB is dissolved in 10 ml of 0.05 M acetate buffer pH 5.0 using a magnetic stirrer. 1.0 ml of WB stock solution is mixed with 0.0075 mg of the enzyme and incubated at 35° C. for 24 hours. The reaction is stopped by heating the samples for 10 minutes at 100° C. The residual material is removed by centrifugation (15 minutes at 14000 rpm), and the supernatant is used as the substrate in the assay detailed below.

For the enzyme sample, 1.0 ml of wheat bran oligosaccharides stock solution is mixed with 0.005 mg of the enzyme sample and incubated at 35° C. for 24 hours. The reaction is stopped by heating the samples for 10 minutes at 100° C. The release of ferulic acid is analyzed by measuring the absorbance at 335 nm.

For the substrate blank, 1.0 ml of wheat bran oligosaccharides stock solution is mixed with 0.005 mg of 0.05 M acetate buffer, pH 5.0, and incubated at 35° C. for 24 hours. The reaction is stopped by heating the samples for 10 minutes at 100° C. The release of ferulic acid is analyzed by measuring the absorbance at 335 nm.

Using the assay above, FaeA1 was found to release ferulic acid from wheat bran arabinoxylan oligosaccharides, releasing 75% of the ferulic acid present in wheat bran. FaeA1 also exhibited activity towards sugar beet pulp oligosaccharides (20% hydrolysis). FaeB2 was found to release 80% of the ferulic acid present in wheat bran. FaeB2 also exhibited activity towards sugar beet pulp oligosaccharides (16% hydrolysis).

Example 21

The following example illustrates an assay used to measure α-arabinofuranosidase enzymatic activity.

This assay measures the release of arabinose by the action of the α-arabinofuranosidase on wheat arabinoxylan oligosaccharides (WAX).

Acetate buffer (0.05 M, pH 5.0) is prepared as follows: 4.1 g of anhydrous sodium acetate or 6.8 g of sodium acetate*$3H_2O$ is dissolved in distilled water so that the final volume of the solution to be 1000 ml (Solution A). In a separate flask, 3.0 g (2.86 mL) of glacial acetic acid is mixed with distilled water to make the total volume 1000 ml (Solution B). The final 0.05 M acetate buffer, pH 5.0, is prepared by mixing Solution A with Solution B until the pH of the resulting solution is equal to 5.0.

Wheat arabinoxylan oligosaccharides are prepared by degradation of Wheat arabinoxylan (Megazyme, Bray Ireland, Cat. # P-WAXYI) by endo-xylanase I from *A. niger* (enzyme collection Laboratory of Food Chemistry, Wageningen University, The Netherlands). 50 mg of WAX is dissolved in 10 ml 0.05 M acetate buffer, pH 5.0, using a magnetic stirrer. 1.0 ml of WAX stock solution is mixed with 0.0075 mg of the enzyme and incubated at 35° C. for 24 hours. The reaction is stopped by heating the samples for 10 minutes at 100° C. The residual material is removed by centrifugation (15 minutes at 14000 rpm), and the supernatant is used as the substrate in the assay detailed below.

For the enzyme sample, 1.0 ml of wheat arabinoxylan oligosaccharides stock solution is mixed with 0.0075 mg of the enzyme sample and incubated at 35° C. for 24 hours. The reaction is stopped by heating the samples for 10 minutes at 100° C. The release of arabinose and formation of new arabinoxylan oligosaccharides were analyzed by High Performance Anion Exchange Chromatography.

For the substrate blank, 1.0 ml of wheat arabinoxylan oligosaccharides stock solution is mixed with 0.0075 mg of the 0.05 M acetate buffer, pH 5.0, and incubated at 35° C. for 24 hours. The reaction is stopped by heating the samples for 10 minutes at 100° C. The release of arabinose and formation of new arabinoxylan oligosaccharides were analyzed by High Performance Anion Exchange Chromatography.

High Performance Anion Exchange Chromatography analysis is performed using a Dionex HPLC system equipped with a Dionex CarboPac PA-1 (2 mm ID×250 mm) column in combination with a CarboPac PA guard column (1 mm ID×25 mm) and a Dionex EDet1 PAD-detector (Dionex Co., Sunnyvale, Calif., USA). A flow rate of 0.3 ml/min was used with the following gradient of sodium acetate in 0.1 M NaOH: 0-5 min, 0-100 mM; 5-45 min, 100-400 mM. Each elution was followed by a washing step of 5 minutes 1,000 mM sodium acetate in 0.1 M NaOH and an equilibration step of 15 minutes 0.1 M NaOH.

Using the above assay, both Abf1 and Abf2 were found to release arabinose from wheat arabinoxylan oligosaccharides. Both enzymes removed arabinose residues, which were monosubstituted to the xylose backbone. Arabinose residues linked to O2 and O3 position of the xylose residue were released by both Abf1 and Abf2.

Example 22

The following example illustrates an assay used to measure pectin methyl esterase enzymatic activity.

The following assay is used to measure the enzymatic activity of a pectin methyl esterase towards highly methylated citrus pectin (DM 65) in combination with methyl red. The assay measures the release of methanol by the action of pectin methyl esterases on methylated citrus pectin. The release of methanol will acidify a solution (non-esterified galacturonic acid), which makes the methyl red indicator change color at a pH of less than 4.4.

Pectin-methyl red solution is prepared as follows: 0.5 g of methylated citrus pectin (DM 65, Sigma, USA, Cat. # P9436-5G), 2 mg methyl red (Sigma, USA) and 0.435 g NaCl is dissolved in distilled water so that the final volume of the solution is 50 ml. The final pH is adjusted to 5.0 by adding 0.1 M NaOH.

For the enzyme sample, 0.1 ml of pectin-methyl red stock solution is mixed with 0.01 ml of the enzyme sample and incubated at 37° C. overnight. The absorbance at 520 nm ($A_{520}$) is measured as $A_S$.

For the substrate blank, 0.1 ml of pectin/methyl red stock solution is mixed with 0.01 ml of distilled water and incubated at 37° C. overnight. The absorbance at 520 nm ($A_{520}$) is measured as $A_{SB}$.

Using the assay above, the $\Delta A_{520}$ of Pme1 was found to be 0.401, demonstrating that Pme1 is active towards highly methylated pectin.

Example 23

The following example illustrates an assay used to measure endo-arabinase enzymatic activity.

The assay is used to measure the enzymatic activity of an endo-arabinase towards AZCL-arabinan (debranched). This substrate is insoluble in buffered solutions, but rapidly hydrates to form gel particles that are hydrolysed by specific endo-hydrolases, releasing soluble dye-labeled fragments.

Acetate buffer (0.05 M, pH 5.0) is prepared as follows: 4.1 g of anhydrous sodium acetate or 6.8 g of sodium acetate*3H$_2$O is dissolved in distilled water so that the final volume of the solution is 1000 ml (Solution A). In a separate flask, 3.0 g (2.86 ml) of glacial acetic acid is mixed with distilled water to yield a total volume of 1000 ml (Solution B). The final 0.05 M acetate buffer, pH 5.0, is prepared by mixing Solution A with Solution B until the pH of the resulting solution is equal to 5.0.

AZCL-arabinan (debranched) from Megazyme (Bray, Ireland, Cat. # I-AZDAR) is used as the assay substrate. 50 mg of AZCL-arabinan is dissolved in 10 ml of 0.05 acetate buffer, pH 5.0, using a magnetic stirrer. 96% Ethanol is used to terminate the enzymatic reaction.

For the enzyme sample, 0.2 ml of 5 mg/ml AZCL-arabinan stock solution is preheated to 40° C. for 10 minutes. This preheated stock solution is mixed with 200 µl of the enzyme sample (preheated at 40° C. for 10 minutes) and incubated at 40° C. for 10 minutes. After exactly 10 minutes of incubation, 1.0 ml of 96% ethanol is added and the absorbance at 590 nm ($A_{590}$) is then measured as $A_S$.

For the substrate blank, 1.2 ml of 5 mg/ml AZCL-arabinan stock solution is preheated at 40° C. for 10 minutes. This preheated stock solution is mixed with 200 µl of 0.05 M acetate buffer pH 5.0 (preheated at 40° C. for 10 minutes) and incubated at 40° C. for 10 minutes. After exactly 10 minutes of incubation, 1.0 ml of 96% ethanol is added and the absorbance at 590 nm ($A_{590}$) is then measured as $A_{SB}$.

Endo-arabinase activity is determined using a standard curve produced from an endo-arabinase with known activity towards AZCL-arabinan. Activity (IU/ml)=$\Delta A_{595}$*DF, where $\Delta A_{595} = A_S - A_{SB}$ and DF is the enzyme dilution factor.

Using the above assay, the $\Delta A_{595}$ was found to be 1.53 with a DF of 1, indicating that Abn1 exhibits endo-arabinase activity towards AZCL-arabinan.

Example 24

The following example illustrates an assay used to measure β-xylosidase enzymatic activity.

This assay measures the release of p-nitrophenol by the action of a β-xylosidase on p-nitrophenyl β-D-xylopyranoside (PNPX). One β-xylosidase unit of activity is the amount of enzyme that liberates 1 micromole of p-nitrophenol in one minute at 37° C. and pH 5.0.

Acetate buffer (0.1 M, pH 5.0) is prepared as follows: 8.2 g of anhydrous sodium acetate or 13.6 g of sodium acetate*3H$_2$O is dissolved in distilled water so that the final volume of the solution is 1000 ml (Solution A). In a separate flask, 6.0 g (5.72 ml) of glacial acetic acid is mixed with distilled water to make the total volume of 1000 ml (Solution B). The final 0.1 M acetate buffer, pH 5.0, is prepared by mixing Solution A with Solution B until the pH of the resulting solution is equal to 5.0.

PNPX (Extrasynthese, France, Cat. # 4244) is used as the assay substrate. 16.5 mg of PNPX is dissolved in 5 ml of distilled water and 5 ml 0.1 M acetate buffer using a magnetic stirrer to obtain 2 mM stock solution. The solution is stable for 2 days with storage at 4° C.

The stop reagent (0.25 M sodium carbonate solution) is prepared as follows: 26.5 g of anhydrous sodium carbonate is dissolved in 800 ml of distilled water, and the solution volume is adjusted to 1000 ml. This reagent is used to terminate the enzymatic reaction.

For the enzyme sample, 0.10 ml of 2 mM PNPX stock solution is mixed with 0.01 ml of the enzyme sample and incubated at 37° C. for 30 minutes. After exactly 30 minutes of incubation, 0.1 ml of 0.25 M sodium carbonate solution is added and the absorbance at 405 nm ($A_{405}$) is then measured in microtiter plates as $A_S$.

For the substrate blank, 0.10 ml of 2 mM PNPX stock solution is mixed with 0.01 ml of 0.05 M acetate buffer, pH 5.0. 0.1 mL of 0.25 M sodium carbonate solution is then added and the absorbance at 405 nm ($A_{405}$) is measured microtiter plates as $A_{SB}$.

Activity is calculated as follows:

$$\text{Activity (IU/ml)} = \frac{\Delta A_{405} * DF * 21 * 1.33}{13.700 * 30}$$

where $\Delta A_{405}=A_S-A_{SB}$, DF is the enzyme dilution factor, 21 is the dilution of 10 μl enzyme solution in 210 μl reaction volume, 1.33 is the conversion factor of microtiter plates to cuvettes, 13.700 is the extinction coefficient 13700 $M^{-1}$ $cm^{-1}$ of p-nitrophenol released corrected for mol/l to μmol/ml, and 30 minutes is the reaction time.

Using the above assay, Bxl2 was found to exhibit a β-xylosidase activity of 0.09 IU/ml ($\Delta A_{405}$=1.36, DF=1).

Example 25

The following example illustrates an assay used to measure the saccharification ability of enzymes of the present invention.

The hydrolysis of 5 g/l Avicel catalyzed by purified cellulases was performed for 120 hours at 40° C. and pH 5.0. Avicel substrate (10 mg) was mixed with 1.0 ml of 0.1 M Na-acetate buffer, pH 5.0, containing 1 mM of sodium azide to prevent microbial growth, in a 2 ml vial. The vial was incubated in a thermostatic water bath equipped with a magnetic stirrer. The enzyme solution (1 ml), diluted as needed to reach a particular concentration, was added and the mixture was stirred. Equal protein concentrations (0.1 mg/ml) were used for all enzyme preparations. To convert cellooligosaccharides, which are soluble products of cellulose hydrolysis catalyzed by endoglucanases and cellobiohydrolases, into a final hydrolysis product (glucose) and thus simplify the analysis of hydrolyzate, highly purified beta-glucosidase from *A. japonicus* (0.2 U/ml; see below) was added to the reaction mixture. Aliquots of the suspension (0.1 ml) were collected from the reaction mixture and centrifuged after fixed time intervals. Glucose concentration in the supernatant was determined by the glucose oxidase-peroxidase method (see Example 6).

Beta-glucosidase was purified from *A. japonicus* culture filtrates using anion-exchange chromatography on SOURCE Q media (pH 5.5, gradient of NaCl; GE Healthcare, USA) followed by hydrophobic chromatography on Phenyl SUPEROSE media (GE Healthcare, USA) in a gradient of ammonium sulfate.

Figure 26:
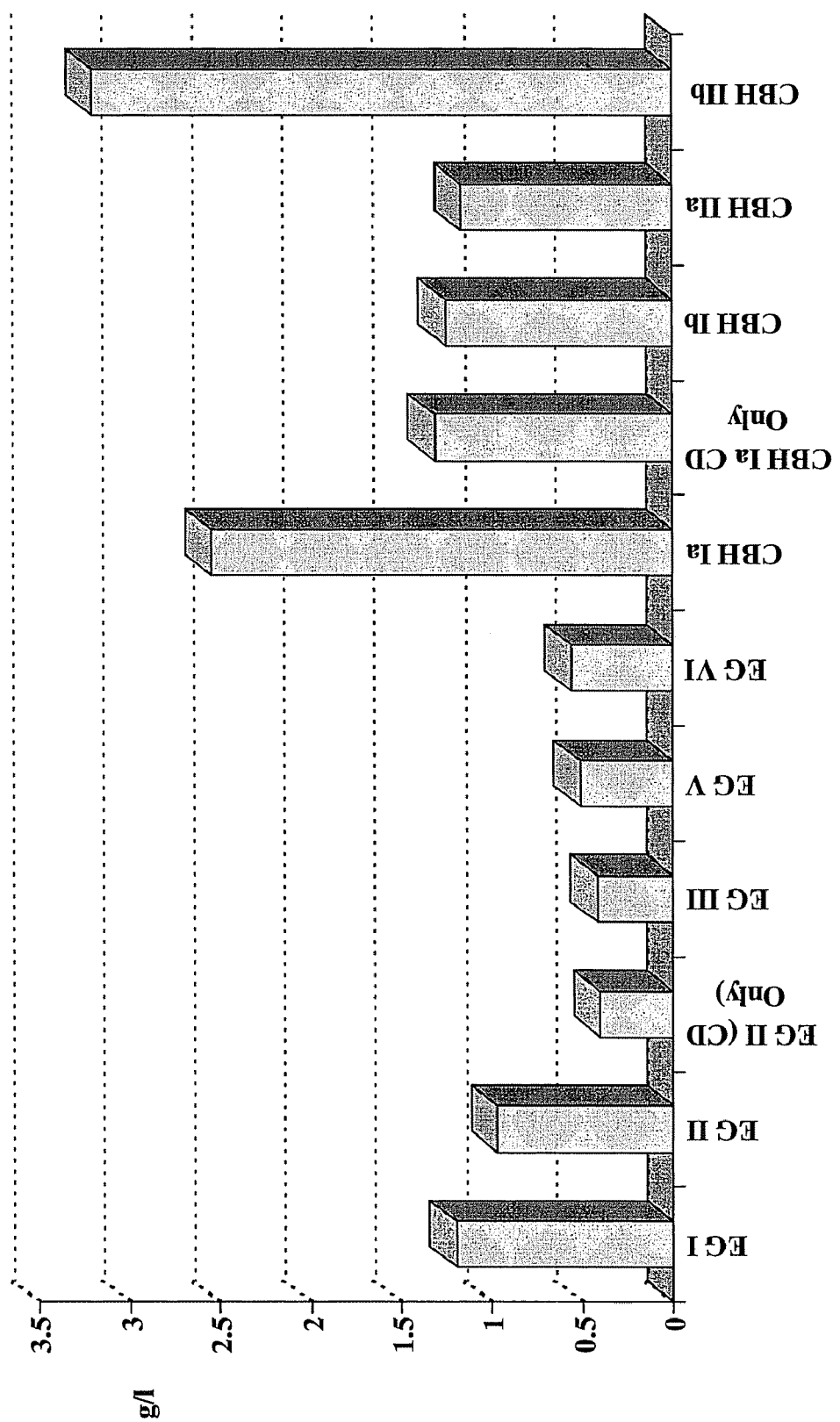
FIG. 26 shows a graph of the saccharification ability of cellobiohydrolases and endoglucanases of the present invention. The amount of glucose (g/l) produced after the hydrolysis of 5 g/l Avicel at pH 5.0, 40° C. for 120 hours in the presence of 0.1 mg/ml enzyme and 0.2 U/ml cellobiase is shown.

Table 32 and FIG. 26 show a graph of the saccharification ability of cellobiohydrolases and endoglucanases of the present invention. The amount of glucose (g/l) produced after the hydrolysis of 5 g/l Avicel at pH 5.0, 40° C. for 120 hours in the presence of 0.1 mg/ml enzyme and 0.2 U/ml beta-glucosidase is shown.

TABLE 32

Saccharification Abilities of C1 Cellobiohydrolases and Endoglucanases

| Enzyme | Glucose Yield (g/l) |
|---|---|
| EG I | 1.2 |
| EG II | 0.97 |
| EG II (CD) | 0.4 |
| EG III | 0.42 |
| EG V | 0.51 |
| EG VI | 0.56 |
| CBH Ia | 2.54 |
| CBH Ia (CD) | 1.31 |
| CBH Ib | 1.25 |
| CBH IIa | 1.16 |
| CBH IIb | 3.2 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein comprising an amino acid sequence that is at least 95% identical to the amino acid sequence of SEQ ID NO:44 and having β-glucosidase activity or a catalytic domain of SEQ ID NO:44, wherein the catalytic domain comprises from about amino acid 87 to about amino acid 643 of SEQ ID NO:44 and having β-glucosidase activity.

2. An isolated fusion protein comprising the isolated protein of claim 1 fused to a protein comprising an amino acid sequence that is heterologous to the isolated protein of claim 1.

3. A kit for degrading a lignocellulosic material to fermentable sugars comprising at least one isolated protein of claim 1.

4. A detergent comprising at least one isolated protein of claim 1.

5. A composition for the degradation of a lignocellulosic material comprising at least one isolated protein of claim 1.

6. A recombinant enzyme isolated from a genetically modified microorganism, wherein the recombinant enzyme comprises an amino acid sequence of claim 1.

7. The recombinant enzyme of claim 6, wherein the enzyme has been subjected to a purification step.

8. A crude fermentation product produced by culturing a genetically modified microorganism, wherein the crude fermentation product contains at least one protein of claim 1.

9. A multi-enzyme composition comprising at least one protein of claim 1, and at least one additional protein for degrading a lignocellulosic material or a fragment thereof that has biological activity.

10. The multi-enzyme composition of claim 9, wherein the composition comprises at least one cellobiohydrolase, at least one xylanase, at least one endoglucanase, at least one β-glucosidase, at least one β-xylosidase, and at least one accessory enzyme.

11. The multi-enzyme composition of claim 9, wherein between about 50% and about 70% of the enzymes in the composition are cellobiohydrolases.

12. The multi-enzyme composition of claim 9, wherein between about 10% and about 30% of the enzymes in the composition are xylanases.

13. The multi-enzyme composition of claim 9, wherein between about 5% and about 15% of the enzymes in the composition are endoglucanases.

14. The multi-enzyme composition of claim 9, wherein between about 1% and about 5% of the enzymes in the composition are β-glucosidases.

15. The multi-enzyme composition of claim 9, wherein between about 1% and about 3% of the enzymes in the composition are β-xylosidases.

16. The multi-enzyme composition of claim 9, wherein the composition comprises about 60% cellobiohydrolases, about 20% xylanases, about 10% endoglucanases, about 3% β-glucosidases, about 2% β-xylosidases, and about 5% accessory enzymes.

17. The multi-enzyme composition of claim 10, wherein the xylanases are selected from the group consisting of: endoxylanases, exoxylanases, and β-xylosidases.

18. The multi-enzyme composition of claim 10, wherein the accessory enzymes include an enzyme selected from the group consisting of: ligninase, glucuronidase, arabinofuranosidase, arabinogalactanase, furilic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase.

19. A multi-enzyme composition comprising:
   a) at least one protein comprising an amino acid sequence that is at least 95% identical to the amino acid sequence of SEQ ID NO:44 and having β-glucosidase activity or a catalytic domain of SEQ ID NO:44, wherein the catalytic domain comprises from about amino acid 87 to about amino acid 643 of SEQ ID NO:44 and having β-glucosidase activity;
   b) at least one protein, or a fragment thereof that has cellobiohydrolase activity;
   c) at least one protein, or a fragment thereof that has endoglucanase activity; and
   d) at least one protein, or a fragment thereof that has xylanase activity.

20. The multi-enzyme composition of claim 19, further comprising at least one protein that has β-xylosidase activity, or a fragment thereof that has β-xylosidase activity.

21. The multi-enzyme composition of claim 9, wherein the multi-enzyme composition comprises at least one hemicellulase.

22. The multi-enzyme composition of claim 21, wherein the hemicellulase is selected from the group consisting of a xylanase, an arabinofuranosidase, an acetyl xylan esterase, a glucuronidase, and endo-galactanase, a mannanase, an endo arabinase, an exo arabinase, an exo-galactanase, a ferulic acid esterase, a galactomannanase, a xylogluconase, and mixtures thereof.

23. The multi-enzyme composition of claim 22, wherein the xylanase is selected from the group consisting of endoxylanases, exoxylanase, and β-xylosidase.

24. The multi-enzyme composition of claim 9, wherein the multi-enzyme composition comprises at least one cellulase.

25. The multi-enzyme composition of claim 9, wherein the composition is a crude fermentation product.

26. The multi-enzyme composition of claim 9, wherein the composition is a crude fermentation product that has been subjected to a purification step.

27. The multi-enzyme composition of claim 9, further comprising one or more accessory enzymes.

28. The multi-enzyme composition of claim 27, wherein the accessory enzymes includes at least one enzyme selected from the group consisting of: cellulase, xylanase, ligninase, glucuronidase, arabinofuranosidase, arabinogalactanase, furilic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase.

29. The multi-enzyme composition of claim 27, wherein the accessory enzyme is selected from the group consisting of a glucoamylase, a pectinase, and a ligninase.

30. The multi-enzyme composition of claim 27, wherein the accessory enzyme is a glucoamylase.

31. The multi-enzyme composition of claim 27, wherein the accessory enzyme is added as a crude or a semi-purified enzyme mixture.

32. The multi-enzyme composition of claim 27, wherein the accessory enzyme is produced by culturing an organism on a substrate to produce the enzyme.

33. A method for degrading a lignocellulosic material to fermentable sugars, comprising contacting the lignocellulosic material with the multi-enzyme composition of claim 9.

34. A method for producing an organic substance, comprising:
   a) saccharifying a lignocellulosic material with the multi-enzyme composition of claim 9;
   b) fermenting the saccharified lignocellulosic material obtained with one or more fermentating microoganisms; and
   c) recovering the organic substance from the fermentation.

35. The method of claim 34, wherein the steps of saccharifying and fermenting are performed simultaneously.

36. The method of claim 34, wherein the organic substance is an alcohol, organic acid, ketone, amino acid, or gas.

37. The method of claim 34, wherein the organic substance is an alcohol.

38. The method of claim 37, wherein the alcohol is ethanol.

39. A method for degrading a lignocellulosic material consisting of distiller's dried grains or distiller's dried grains with solubles to sugars, the method comprising contacting the distiller's dried grains or distiller's dried grains with solubles with a multi-enzyme composition, whereby at least 10% of the fermentable sugars are liberated, wherein the multi-enzyme composition is the multi-enzyme composition of claim 9.

40. The method of claim 39, whereby at least 15% of the sugars are liberated.

41. The method of claim 39, whereby at least 20% of the sugars are liberated.

42. The method of claim 39, whereby at least 23% of the sugars are liberated.

43. The method of claim 39, wherein the distiller's dried grains or distiller's dried grains with solubles is derived from corn.

44. A method for stonewashing a fabric, comprising contacting the fabric with at least one isolated protein of claim 1.

45. A method for stonewashing a fabric, comprising contacting the fabric with at least one multi-enzyme composition of claim 9.

46. The method of claim 44 or claim 45, wherein the fabric is denim.

47. A method for enhancing the softness or feel of a fabric or depilling a fabric, comprising contacting the fabric with at least one isolated protein of claim 1.

48. A method for enhancing the softness or feel of a fabric or depilling a fabric, comprising contacting the fabric with at least one multi-enzyme composition of claim 9.

49. A method for restoring color to or brightening a fabric, comprising contacting the fabric with at least one isolated protein of claim 1.

50. A method for restoring color to or brightening a fabric, comprising contacting the fabric with at least one multi-enzyme composition of claim 9.

51. A method of biopolishing, defibrillating, bleaching, dyeing or desizing a fabric, comprising contacting the fabric with at least one isolated protein of claim 1.

52. A method of biopolishing, defibrillating, bleaching, dyeing or desizing a fabric, comprising contacting the fabric with at least one multi-enzyme composition of claim 9.

53. A method of treating, biorefining, deinking or biobleaching paper or pulp, comprising contacting the paper or pulp with at least one isolated protein of claim 1.

54. A method of treating, biorefining, deinking or biobleaching paper or pulp, comprising contacting the paper or pulp with at least one multi-enzyme composition of claim 9.

55. A method for enhancing the cleaning ability of a detergent composition, comprising adding at least one isolated protein of claim 1 to the detergent composition.

56. A method for enhancing the cleaning ability of a detergent composition, comprising adding the multi-enzyme composition claim 9 to the detergent composition.

57. A detergent composition, comprising at least one isolated protein of claim 1 and at least one surfactant.

58. A detergent composition, comprising at least one multi-enzyme composition of claim 9 and at least one surfactant.

* * * * *